US008568766B2

(12) United States Patent  (10) Patent No.: US 8,568,766 B2
Anantharamaiah et al.  (45) Date of Patent: Oct. 29, 2013

(54) PEPTIDES AND PEPTIDE MIMETICS TO TREAT PATHOLOGIES ASSOCIATED WITH EYE DISEASE

(76) Inventors: Gattadahalli M. Anantharamaiah, Birmingham, AL (US); Alan M. Fogelman, Beverly Hills, CA (US); Mohamad Navab, Los Angeles, CA (US); Martin Rudolf, Lubeck (DE)

(*) Notice: Subject to any disclaimer, the term of this patent is extended or adjusted under 35 U.S.C. 154(b) by 1334 days.

(21) Appl. No.: 12/027,728

(22) Filed: Feb. 7, 2008
(Under 37 CFR 1.47)

(65) Prior Publication Data
US 2010/0143444 A1 Jun. 10, 2010

Related U.S. Application Data

(63) Continuation-in-part of application No. 11/407,390, filed on Apr. 18, 2006, now Pat. No. 7,723,303, which is a continuation-in-part of application No. 10/423,830, filed on Apr. 25, 2003, now Pat. No. 7,199,102, which is a continuation-in-part of application No. 10/273,386, filed on Oct. 16, 2002, now Pat. No. 7,166,578, and a continuation-in-part of application No. 10/187,215, filed on Jun. 28, 2002, now Pat. No. 7,144,862, which is a continuation-in-part of application No. PCT/US01/26457, filed on Aug. 24, 2001, which is a continuation-in-part of application No. 09/896,841, filed on Jun. 29, 2001, now Pat. No. 6,933,279, which is a continuation-in-part of application No. 09/645,454, filed on Aug. 24, 2000, now Pat. No. 6,664,230.

(60) Provisional application No. 60/697,495, filed on Jul. 7, 2005, provisional application No. 60/676,431, filed on Apr. 29, 2005.

(51) Int. Cl.
*A61K 38/00* (2006.01)
*A61K 9/00* (2006.01)

(52) U.S. Cl.
USPC ........................................................ 424/429

(58) Field of Classification Search
None
See application file for complete search history.

(56) References Cited

U.S. PATENT DOCUMENTS

| | | | |
|---|---|---|---|
| 3,687,808 A | 8/1972 | Englisch et al. |
| 3,767,040 A | 10/1973 | Tushaus |
| 4,155,913 A | 5/1979 | Hellerbach et al. |
| 4,342,566 A | 8/1982 | Theofilopoulos et al. |
| 4,428,938 A | 1/1984 | Kisfaludy et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,643,988 A | 2/1987 | Segrest et al. |
| 4,667,025 A | 5/1987 | Miyoshi et al. |
| 4,684,520 A | 8/1987 | Bertelli |
| 4,762,779 A | 8/1988 | Snitman |
| 4,789,737 A | 12/1988 | Miyoshi et al. |
| 4,816,567 A | 3/1989 | Cabilly et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,868,116 A | 9/1989 | Morgan et al. |
| 4,876,335 A | 10/1989 | Yamane et al. |
| 4,877,611 A | 10/1989 | Cantrell |
| 4,897,355 A | 1/1990 | Eppstein et al. |
| 4,904,582 A | 2/1990 | Tullis |
| 4,946,778 A | 8/1990 | Ladner et al. |
| 4,948,882 A | 8/1990 | Ruth |
| 4,958,013 A | 9/1990 | Letsinger |
| 4,980,286 A | 12/1990 | Morgan et al. |
| 4,981,957 A | 1/1991 | Lebleu et al. |
| 5,023,243 A | 6/1991 | Tullis |
| 5,034,506 A | 7/1991 | Summerton et al. |
| 5,082,830 A | 1/1992 | Brakel et al. |

(Continued)

FOREIGN PATENT DOCUMENTS

| | | |
|---|---|---|
| AU | 2001286732 | 3/2002 |
| AU | 2005287004 | 3/2006 |
| CA | 2420222 | 2/2002 |
| CA | 2580501 | 3/2006 |
| CN | 1739787 A | 3/2006 |
| CN | 1469754 | 4/2007 |
| CN | 1943781 | 4/2007 |
| EP | 1186299 | 3/2002 |
| EP | 1318828 | 6/2003 |
| EP | 1562624 | 8/2005 |

(Continued)

OTHER PUBLICATIONS

Datta et al. Effects of increasing hydrophobicity on the physical-chemical and biological properites of a class A amphiphatic helical peptide. J Lipid Research. Jul. 2001. vol. 42, pp. 1096-1104.*
Roscoe et al. Lipid Changes in the Eye Concomitant with the Development of Atherosclerosis in the Aorta in the Rabbit. 1968. Circulation Research, vol. XXIII. pp. 633-643.*
U.S. Appl. No. 10/269,755, filed Oct. 11, 2002, Fogelman et al.
U.S. Appl. No. 11/541,481, filed Sep. 29, 2006, Fogelman et al.
U.S. Appl. No. 11/541,482, filed Sep. 29, 2006, Fogelman et al.
U.S. Appl. No. 11/541,494, filed Sep. 29, 2006, Fogelman et al.

(Continued)

*Primary Examiner* — Marcela M Cordero Garcia
(74) *Attorney, Agent, or Firm* — Ballard Spahr LLP

(57) ABSTRACT

This invention provides novel active agents (e.g. peptides, small organic molecules, amino acid pairs, etc.) peptides that ameliorate one or more symptoms of eye disease and/or other pathologies characterized by an inflammatory response. In certain embodiment, the peptides resemble a G* amphipathic helix of apolipoprotein J. The agents are highly stable and readily administered via an oral route or via intraocular injection.

24 Claims, 23 Drawing Sheets

(56) References Cited

U.S. PATENT DOCUMENTS

| | | |
|---|---|---|
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,135,917 A | 8/1992 | Burch |
| 5,138,045 A | 8/1992 | Cook et al. |
| 5,166,315 A | 11/1992 | Summerton et al. |
| 5,168,053 A | 12/1992 | Altman et al. |
| 5,175,273 A | 12/1992 | Bischofberger et al. |
| 5,176,996 A | 1/1993 | Hogan et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,294,533 A | 3/1994 | Lupski et al. |
| 5,298,490 A | 3/1994 | Heavner et al. |
| 5,317,098 A | 5/1994 | Shizuya et al. |
| 5,319,080 A | 6/1994 | Leumann et al. |
| 5,321,131 A | 6/1994 | Agrawal et al. |
| 5,334,711 A | 8/1994 | Sproat et al. |
| 5,344,822 A | 9/1994 | Levine et al. |
| 5,358,934 A | 10/1994 | Schmickel |
| 5,359,044 A | 10/1994 | Cook et al. |
| 5,367,066 A | 11/1994 | Urdea et al. |
| 5,371,241 A | 12/1994 | Brush |
| 5,391,377 A | 2/1995 | Barnwell et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,436,330 A | 7/1995 | Taira et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,135 A * | 10/1995 | Baranowitz et al. .......... 514/725 |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,766 A | 12/1995 | Gold et al. |
| 5,476,925 A | 12/1995 | Letsinger et al. |
| 5,480,869 A | 1/1996 | Wei et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,503,978 A | 4/1996 | Schneider et al. |
| 5,508,060 A | 4/1996 | Perman et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,293 A | 8/1996 | Gold et al. |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,332 A | 10/1996 | Hoogenboom et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,579,250 A | 11/1996 | Balaji et al. |
| 5,580,731 A | 12/1996 | Chang et al. |
| 5,580,737 A | 12/1996 | Polisky et al. |
| 5,580,967 A | 12/1996 | Joyce |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,873 A | 1/1997 | Joyce |
| 5,595,973 A | 1/1997 | Bogden |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,612,895 A | 3/1997 | Balaji et al. |
| 5,614,617 A | 3/1997 | Cook et al. |
| 5,616,466 A | 4/1997 | Cantor et al. |
| 5,618,704 A | 4/1997 | Sanghvi et al. |
| 5,623,070 A | 4/1997 | Cook et al. |
| 5,624,824 A | 4/1997 | Yuan et al. |
| 5,625,050 A | 4/1997 | Beaton et al. |
| 5,627,053 A | 5/1997 | Usman et al. |
| 5,627,158 A | 5/1997 | Cho-Chung |
| 5,631,115 A | 5/1997 | Ohtsuka et al. |
| 5,631,146 A | 5/1997 | Szostak et al. |
| 5,631,280 A | 5/1997 | Ciccarone et al. |
| 5,633,133 A | 5/1997 | Long et al. |
| 5,633,360 A | 5/1997 | Bischofberger et al. |
| 5,639,873 A | 6/1997 | Barascut et al. |
| 5,641,754 A | 6/1997 | Iversen |
| 5,645,985 A | 7/1997 | Froehler et al. |
| 5,646,020 A | 7/1997 | Swiggen et al. |
| 5,646,031 A | 7/1997 | DeYoung et al. |
| 5,646,042 A | 7/1997 | Stinchcomb et al. |
| 5,646,265 A | 7/1997 | McGee |
| 5,650,316 A | 7/1997 | Aggarwal et al. |
| 5,652,094 A | 7/1997 | Usman et al. |
| 5,652,107 A | 7/1997 | Lizardi et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |

(56) References Cited

U.S. PATENT DOCUMENTS

| | | |
|---|---|---|
| 5,677,439 A | 10/1997 | Weis et al. |
| 5,681,941 A | 10/1997 | Cook et al. |
| 5,683,873 A | 11/1997 | George et al. |
| 5,683,874 A | 11/1997 | Kool |
| 5,683,902 A | 11/1997 | Hampel et al. |
| 5,688,670 A | 11/1997 | Szostak et al. |
| 5,688,941 A | 11/1997 | Cook et al. |
| 5,691,317 A | 11/1997 | Cho-Chung |
| 5,693,535 A | 12/1997 | Draper et al. |
| 5,693,773 A | 12/1997 | Kandimalla et al. |
| 5,700,920 A | 12/1997 | Altmann et al. |
| 5,700,922 A | 12/1997 | Cook |
| 5,712,384 A | 1/1998 | Symonds et al. |
| 5,714,331 A | 2/1998 | Buchardt et al. |
| 5,719,262 A | 2/1998 | Buchardt et al. |
| 5,721,138 A | 2/1998 | Lawn |
| 5,721,367 A | 2/1998 | Kay et al. |
| 5,728,521 A | 3/1998 | Yuan et al. |
| 5,731,295 A | 3/1998 | Draper et al. |
| 5,731,424 A | 3/1998 | Toothman et al. |
| 5,733,549 A | 3/1998 | Yamada et al. |
| 5,733,879 A | 3/1998 | Rosseneu et al. |
| 5,770,576 A * | 6/1998 | Morozov et al. .............. 514/19.1 |
| 5,770,715 A | 6/1998 | Sugiyama et al. |
| 5,780,228 A | 7/1998 | Parma et al. |
| 5,780,607 A | 7/1998 | Goodnow, Jr. et al. |
| 5,786,138 A | 7/1998 | Swenson |
| 5,786,462 A | 7/1998 | Schneider et al. |
| 5,792,613 A | 8/1998 | Schmidt et al. |
| 5,795,721 A | 8/1998 | Rabin et al. |
| 5,800,758 A | 9/1998 | Topolkaraev et al. |
| 5,804,440 A | 9/1998 | Burton et al. |
| 5,807,718 A | 9/1998 | Joyce et al. |
| 5,811,300 A | 9/1998 | Sullivan et al. |
| 5,814,467 A | 9/1998 | Curtiss et al. |
| 5,834,185 A | 11/1998 | Ts'o et al. |
| 5,837,243 A | 11/1998 | Deo et al. |
| 5,837,855 A | 11/1998 | Chowrira et al. |
| 5,843,708 A | 12/1998 | Hardman et al. |
| 5,846,713 A | 12/1998 | Pagratis et al. |
| 5,849,903 A | 12/1998 | Pietrzkowski et al. |
| 5,854,238 A | 12/1998 | Kempen |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schneider et al. |
| 5,861,288 A | 1/1999 | Usman et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,153 A | 3/1999 | Harris et al. |
| 5,877,162 A | 3/1999 | Werner et al. |
| 5,891,683 A | 4/1999 | Usman et al. |
| 5,891,684 A | 4/1999 | Usman et al. |
| 5,910,408 A | 6/1999 | Szostak et al. |
| 5,919,772 A | 7/1999 | Szyf et al. |
| 5,939,598 A | 8/1999 | Kucherlapati et al. |
| 5,955,590 A | 9/1999 | Levina et al. |
| 5,958,691 A | 9/1999 | Pieken et al. |
| 5,962,426 A | 10/1999 | Glazer |
| 5,972,699 A | 10/1999 | Draper |
| 5,972,704 A | 10/1999 | Draper et al. |
| 5,985,621 A | 11/1999 | Usman et al. |
| 5,989,906 A | 11/1999 | Thompson |
| 5,989,908 A | 11/1999 | Scanlon |
| 5,990,081 A | 11/1999 | Ageland et al. |
| 5,990,088 A | 11/1999 | Ensoli et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence et al. |
| 6,001,988 A | 12/1999 | Parma et al. |
| 6,004,925 A | 12/1999 | Dasseux et al. |
| 6,005,013 A | 12/1999 | Suh et al. |
| 6,005,095 A | 12/1999 | Capaccioli et al. |
| 6,007,995 A | 12/1999 | Baker et al. |
| 6,011,002 A | 1/2000 | Pastan et al. |
| 6,011,020 A | 1/2000 | Gold et al. |
| 6,013,443 A | 1/2000 | Heilig et al. |
| 6,013,522 A | 1/2000 | Monia et al. |
| 6,017,756 A | 1/2000 | Draper |
| 6,017,898 A | 1/2000 | Pietrzkowski et al. |
| 6,018,042 A | 1/2000 | Mett et al. |
| 6,444,230 B1 | 1/2000 | Flavahan et al. |
| 6,019,739 A | 2/2000 | Rhee et al. |
| 6,020,130 A | 2/2000 | Gold et al. |
| 6,022,962 A | 2/2000 | Chowrira et al. |
| 6,025,198 A | 2/2000 | Bennett et al. |
| 6,028,186 A | 2/2000 | Tasset et al. |
| 6,030,776 A | 2/2000 | Eaton et al. |
| 6,033,910 A | 3/2000 | Monia et al. |
| 6,037,323 A | 3/2000 | Dasseux et al. |
| 6,040,147 A | 3/2000 | Ridker et al. |
| 6,040,296 A | 3/2000 | Nyce |
| 6,046,004 A | 4/2000 | Wu et al. |
| 6,046,166 A | 4/2000 | Dasseux et al. |
| 6,046,319 A | 4/2000 | Power et al. |
| 6,051,698 A | 4/2000 | Janjic et al. |
| 6,057,437 A | 5/2000 | Kamiya et al. |
| 6,086,918 A | 7/2000 | Stern et al. |
| 6,090,921 A | 7/2000 | Winge et al. |
| 6,107,457 A | 8/2000 | Arlinghaus et al. |
| 6,113,898 A | 9/2000 | Anderson et al. |
| 6,130,364 A | 10/2000 | Jakobovits et al. |
| 6,180,377 B1 | 1/2001 | Morgan et al. |
| 6,191,151 B1 | 2/2001 | Zik |
| 6,201,165 B1 | 3/2001 | Grant et al. |
| 6,228,989 B1 | 5/2001 | Traugh et al. |
| 6,265,377 B1 | 7/2001 | Dasseux et al. |
| 6,287,590 B1 | 9/2001 | Dasseux et al. |
| 6,303,619 B1 | 10/2001 | Linden |
| 6,329,341 B1 | 12/2001 | Dasseux et al. |
| 6,367,479 B1 | 4/2002 | Williams et al. |
| 6,376,464 B1 | 4/2002 | Dasseux et al. |
| 6,383,808 B1 | 5/2002 | Monia et al. |
| 6,410,802 B1 | 6/2002 | Dasseux et al. |
| 6,423,511 B1 | 7/2002 | Nakamura et al. |
| 6,423,830 B1 | 7/2002 | Winge et al. |
| 6,444,111 B1 | 9/2002 | Montgomery |
| 6,444,681 B1 | 9/2002 | Flavahan et al. |
| 6,455,088 B1 | 9/2002 | Dasseux et al. |
| 6,458,592 B1 | 10/2002 | Jakobovitz et al. |
| 6,459,003 B1 | 10/2002 | Dasseux et al. |
| 6,464,975 B2 | 10/2002 | Millis |
| 6,472,184 B1 | 10/2002 | Hegemann |
| 6,498,038 B1 | 12/2002 | Ghosh et al. |
| 6,506,799 B1 | 1/2003 | Dasseux et al. |
| 6,506,879 B1 | 1/2003 | Ageland et al. |
| 6,506,880 B2 | 1/2003 | Anantharamaiah |
| 6,514,523 B1 | 2/2003 | Sparks |
| 6,518,412 B1 | 2/2003 | Dasseux et al. |
| 6,555,651 B2 | 4/2003 | Stern et al. |
| 6,559,284 B1 | 5/2003 | Ageland et al. |
| 6,573,239 B1 | 6/2003 | Dasseux et al. |
| 6,602,854 B1 | 8/2003 | Dasseux et al. |
| 6,617,134 B1 | 9/2003 | Sirtori et al. |
| 6,630,450 B1 | 10/2003 | Dasseux et al. |
| 6,635,623 B1 | 10/2003 | Hoogeveen et al. |
| 6,646,170 B1 | 11/2003 | Dasseux et al. |
| 6,664,230 B1 | 12/2003 | Fogelman et al. |
| 6,673,780 B2 | 1/2004 | Dasseux et al. |
| 6,680,203 B2 | 1/2004 | Dasseux et al. |
| 6,696,545 B1 | 2/2004 | Buelow et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |

(56) References Cited

U.S. PATENT DOCUMENTS

| | | |
|---|---|---|
| 6,716,816 B1 | 4/2004 | Dasseux et al. |
| 6,717,031 B2 | 4/2004 | Games et al. |
| 6,727,063 B1 | 4/2004 | Lander et al. |
| 6,734,169 B2 | 5/2004 | Dasseux et al. |
| 6,753,313 B1 | 6/2004 | Dasseux et al. |
| 6,773,719 B2 | 8/2004 | Rodrigueza et al. |
| 6,790,953 B2 | 9/2004 | Dasseux et al. |
| 6,831,105 B2 | 12/2004 | Dasseux et al. |
| 6,846,636 B1 | 1/2005 | Argraves et al. |
| 6,849,714 B1 | 2/2005 | Bridon et al. |
| 6,869,568 B2 | 3/2005 | Fogelman et al. |
| 6,887,470 B1 | 5/2005 | Bridon et al. |
| 6,909,014 B2 | 6/2005 | Dasseux et al. |
| 6,930,085 B2 | 8/2005 | Fogelman et al. |
| 6,933,279 B2 | 8/2005 | Fogelman et al. |
| 6,936,691 B2 | 8/2005 | Fiscella et al. |
| 6,982,348 B2 | 1/2006 | Kori et al. |
| 7,144,862 B2 | 12/2006 | Fogelman et al. |
| 7,148,197 B2 | 12/2006 | Fogelman et al. |
| 7,148,199 B2 * | 12/2006 | Neu et al. ............... 514/13.3 |
| 7,166,578 B2 | 1/2007 | Fogelman et al. |
| 7,189,689 B2 | 3/2007 | Dasseux et al. |
| 7,192,940 B2 | 3/2007 | Dasseux et al. |
| 7,199,102 B2 | 4/2007 | Fogelman et al. |
| 7,211,565 B2 | 5/2007 | Dasseux et al. |
| 7,217,785 B2 | 5/2007 | Bielicki |
| 7,291,590 B2 | 11/2007 | Kisilevsky et al. |
| 7,312,190 B2 | 12/2007 | Dasseux et al. |
| 7,427,662 B2 | 9/2008 | Hornick et al. |
| 7,470,660 B2 | 12/2008 | Schwartz et al. |
| 7,531,514 B2 | 5/2009 | Fogelman et al. |
| 7,563,771 B2 | 7/2009 | Anantharamiah et al. |
| 7,579,319 B2 | 8/2009 | Fogelman et al. |
| 7,638,494 B2 | 12/2009 | Fogelman et al. |
| 7,723,303 B2 | 5/2010 | Fogelman et al. |
| 8,084,423 B2 | 12/2011 | Anantharamaiah et al. |
| 2001/0005714 A1 | 6/2001 | Boffelli et al. |
| 2002/0042441 A1 | 4/2002 | Acton et al. |
| 2002/0071862 A1 | 6/2002 | Williams et al. |
| 2002/0142369 A1 | 10/2002 | Fersht |
| 2003/0027769 A1 | 2/2003 | Scialdone et al. |
| 2003/0040505 A1 | 2/2003 | Fogelman et al. |
| 2003/0045460 A1 | 3/2003 | Fogelman et al. |
| 2003/0077641 A1 | 4/2003 | Laskowitz et al. |
| 2003/0087819 A1 | 5/2003 | Bielicki |
| 2003/0109442 A1 | 6/2003 | Bisgaier et al. |
| 2003/0125260 A1 | 7/2003 | Haviv et al. |
| 2003/0203842 A1 | 10/2003 | Dasseux et al. |
| 2003/0229015 A1 | 12/2003 | Fogelman et al. |
| 2004/0059110 A1 | 3/2004 | Nakano et al. |
| 2004/0122091 A1 | 6/2004 | Dasseux et al. |
| 2004/0136989 A1 | 7/2004 | Banerjee et al. |
| 2004/0152623 A1 | 8/2004 | Varadhachary et al. |
| 2004/0186057 A1 | 9/2004 | Anantharamiah et al. |
| 2004/0224011 A1 | 11/2004 | Rodrigueza et al. |
| 2004/0266663 A1 | 12/2004 | Schwartz et al. |
| 2004/0266671 A1 | 12/2004 | Fogelman et al. |
| 2005/0070996 A1 | 3/2005 | Dinh et al. |
| 2005/0154046 A1 | 7/2005 | Wang et al. |
| 2005/0164950 A1 | 7/2005 | Fogelman et al. |
| 2005/0197381 A1 | 9/2005 | Wang et al. |
| 2005/0239136 A1 | 10/2005 | Hazen et al. |
| 2006/0069030 A1 | 3/2006 | Bachovehin |
| 2006/0172919 A1 | 8/2006 | Hornick et al. |
| 2006/0173067 A1 | 8/2006 | Fogelman et al. |
| 2006/0205634 A1 | 9/2006 | Varadhachary et al. |
| 2006/0205669 A1 | 9/2006 | Fogelman et al. |
| 2006/0217298 A1 | 9/2006 | Srivastava |
| 2006/0217307 A1 | 9/2006 | Takashi et al. |
| 2006/0234908 A1 | 10/2006 | Fogelman et al. |
| 2007/0032430 A1 | 2/2007 | Fogelman et al. |
| 2007/0060527 A1 | 3/2007 | Fogelman et al. |
| 2007/0071756 A1 | 3/2007 | Peyman |
| 2007/0101448 A1 | 5/2007 | Anantharamiah et al. |
| 2007/0254839 A1 | 11/2007 | Fogelman et al. |
| 2008/0045459 A1 | 2/2008 | Fogelman et al. |
| 2008/0095821 A1 | 4/2008 | Fogelman et al. |
| 2008/0096814 A1 | 4/2008 | Fogelman et al. |
| 2008/0096815 A1 | 4/2008 | Fogelman et al. |
| 2008/0096816 A1 | 4/2008 | Fogelman et al. |
| 2008/0293639 A1 | 11/2008 | Fogelman et al. |
| 2009/0163408 A1 | 6/2009 | Fogelman et al. |
| 2009/0286741 A1 | 11/2009 | Fogelman |

FOREIGN PATENT DOCUMENTS

| | | |
|---|---|---|
| EP | 1799242 | 6/2007 |
| JP | 2000-136202 | 6/1905 |
| JP | 61-126099 | 6/1986 |
| JP | 7-507554 | 8/1995 |
| JP | 2006-312650 | 11/2006 |
| WO | WO 93/25581 | 12/1993 |
| WO | WO 97/36927 | 10/1997 |
| WO | WO 98/09602 | 3/1998 |
| WO | WO 99/16408 | 4/1999 |
| WO | WO 99/16409 | 4/1999 |
| WO | WO 99/47566 | 9/1999 |
| WO | WO 01/75067 | 10/2001 |
| WO | WO 01/75168 | 10/2001 |
| WO | WO 01/75170 | 10/2001 |
| WO | WO 02/15923 | 2/2002 |
| WO | WO 02/098446 | 12/2002 |
| WO | WO 03/086326 | 10/2003 |
| WO | WO 2004/027027 | * 4/2004 |
| WO | WO 2004/034977 | 4/2004 |
| WO | WO 2004/043396 | 5/2004 |
| WO | WO 2005/016280 | 2/2005 |
| WO | WO 2006/020652 | 2/2006 |
| WO | WO 2006/063132 | 6/2006 |
| WO | WO 2006/118805 | 11/2006 |
| WO | WO 2008/021088 | 2/2008 |
| WO | WO 2009/073725 | 6/2009 |

OTHER PUBLICATIONS

Abrahmsen et al. (1991) Engineering Subtilisin and Its Substrates for Efficient Ligation of Peptide Bonds in Aqueous Solution, Biochemistry, 30: 4151 (1991).

Acsadi G et al. (1991) Human dystrophin expression in mdx mice after intramuscular injection of DNA constructs. Nature, 352(6338): 815-8.

Adachi, T., et al., (2003) Binding of human xanthine oxidase to sulphated glycosaminoglycans on the endothelial-cell surface Biochem. J. 289(2):523-527.

Aikawa, M., et al., Lipid Lowering Reduces Oxidative Stress and Endothelial Cell Activation in Rabbit Atheroma. Circulation (2002) 106:1390-1396.

Ajees et al. (2006) Crystal structure of human apolipoprotein A-1: Insights into its protective effect against cariodvascular diseases. PNAS 103:2126-2131.

Ali, et al. (2005). Apolipoprotein E suppresses the Type I inflammatory response in vivo. Circ. Res. 97:922-927.

Ambati, J. et al. (2003) Age-related macular degeneration: etiology, pathogenesis, and therapeutic strategies. Surv Ophthalmol. 48(3): 257-293.

Anantharamaiah et al. (1985) Studies of Synthetic Peptide of the Amphipathic Helix. The Journal of Biological Chemistry 260:10248-10255.

Anantharamaiah et al. (1988) Effect of Oxidation on the Properties of Apolipoproteins A-I and A-II. J. Lipid Res. 29:309-318.

Anantharamaiah et al. (1990) Use of Synthetic Peptide Analogues to Localize Lecithin: Cholseterol Acyltransf erase Activating Domain in Apolipoprotein A-I. Arteriosclerosis 10: 95-105.

Anantharamaiah G et al., (2006) Synthetic peptides: managing lipid disorders. Curr Opin Lipidol. 17(3): 233-237.

Anantharamaiah et al. (2007) Structural requirements for antioxidative and a enti-inflammatory properties of apolipoprotein A-I mimetic peptides. J Lipid Res. 48(9): 1915-1923.

Anantharamaiah, G.M. et al., (2001) Toward the design of peptide mimics of antiatherogenic apolipoproteins A-I and E., Current Science 81:53-65.

(56) References Cited

OTHER PUBLICATIONS

Aoyagi H et al. (1988) Synthesis of antibacterial peptides-gramicidin S analogs and designed amphiphilic oligopeptides. Tetrahedron; 44:877-886.

Aravinda, S. et al., (2003) Aromatic—Aromatic Interactions in Crystal Structures of Helical Peptide Scaffolds Containing Projecting Phenylalinine Residues, J. Am Chem Soc.; 125:5308 5315.

Arisaph Pharmaceuticals Reports on Promising Results Presented at American Heart Association: Novel Apo A-I Mimetic Peptide Significantly Inhibits Atherosclerosis in Preclinical Animal Study, http://www.biospace.com/news_print.aspx?NewsEntityID=2610, [online] retrieved on Jan. 5, 2011, pp. 1-2.

Armitage et al., (1997) Peptide nucleic acid—DNA duplexes: Long range hole migration from an internally linked anthraquinone. Proc Natl Acad Sci USA.; 94(23):12320-5.

Ashby D, (2001) Lack of effect of serum amyloid A (SAA) on the ability of high-density lipoproteins to inhibit endothelial cell adhesion molecule expression. Atherosclerosis. 154:113-121.

Ashby et al., (1998) Factors influencing the ability of HDL to inhibit expression of vascular cell adhesion molecule-1 in endothelial cells. Arteriosclerosis. Thrombosis and Vascular Biology, 18:1450-1455.

Badimon et al., (1990) Regression of Atherosclerotic Lesions by High Density Lipoprotein lasma Fraction in the Cholesterol-fed Rabbit. J. Clinical Investigation 85:1234-1241.

Baggiolini et al. Interleukin-8, a chemotactic and inflammatory cytokine FEBS Lett. 307: 97-101, (1992).

Bailey et al. (2001) Clusterin, a binding protein with a molten globule-like region. Biochemistry. 40(39): 11828-11840.

Baker et al. (1999) Ability of reconstituted high density lipoproteins to inhibit cytokine-induced expression of vascular cell adhesion molecule-1 in human umbilical cell endothelial cells. J Lipid Res, 1999, 40:345-353.

Baker et al. (2000) Phospholipid composition of reconstituted high density lipoproteins influences their ability to inhibit endothelial cell adhesion molecule expression. J Lipid Res, 2000;41:1261-1267.

Barengolts et al. (1998) Osteoporosis and coronary atherosclerosis in asymptomatic postmenopausal women. Calcif Tissue Int. 62(3): 209-213.

Barter, P.J. and Rye, K-A. High density lipoproteins and coronary heart disease. Atherosclerosis, 1996, 121:1-12.

Baumbach et al. (2002) Structure of Cerebral Arterioles in Cystathionine B-SynthaseDeficient Mice, Circulation Res., 91: 931-937.

Baumbach et al. (2003) Cerebral Arteriolar Structure in Mice Overexpressing Human Renin and Angiotensinogen, Hypertension, 41: 50-55.

Beatty S, Koh H, Phil M, Henson D, Boulton M. (2000) The role of oxidative stress in the pathogenesis of age-related macular degeneration. Surv Ophthalmol. 45(2): 115-134.

Bechinger B. (2000) Understanding peptide interactions with the lipid bilayer: a guide to membrane protein engineering. Curr Opin Chem Biol. 4(6):639-644.

Beisiegel, U. et al. The LDL-receptor-related protein, LRP, is an apolipoprotein E-binding protein. Nature 341: 162-164 (1989).

Berkner et al. (1987) Abundant Expression of Polyomavirus Middle T Antigen and Dihydrofolate Reductase in an Adenovirus Recombinant. J. Virology 61:1213-1220.

Besiegel, U. et al. (1991) Lipoprotein lipase enhances the binding of chylomicrons to low density lipoprotein receptor-related protein Proc. Natl. Acad. Sci. U.S.A. 88:8342-8346.

Betteridge, D.J., Long-term risk reduction: Who needs treatment?, Diabetes Research and Clinical Practice. (2005) 68S2:S15-2.

Bisoendial et al. (2003) Restoration of Endothelial Function by Increasing High-Density Lipoprotein in Subjects With Isolated Low High-Density Lipoprotein Circulation 107: 2944-2948.

Blackburn WD Jr, et al. (1991) Apolipoprotein A-I decreases neutrophil degranulation and superoxide production. J Lipid Res. 32(12): 1911-1918.

Blankenberg et al. (2001) Circulating cell adhesion molecules and death in patients with coronary artery disease. Circulation 2001;104:1336-1342.

Boerner et al. (1991) Production of Antigen-Specific Human Monoclonal Antibodies from in Vitro-Primed Human Splenocytes. J. Immunol., 147(1):86-95.

Boffa et al., Isolation of active genes containing CAG repeats by DNA strand invasion by a peptide nucleic acid. Proc Natl Acad Sci USA. Mar. 14, 1995; 92(6):1901-5.

Boffelli et al. (1997) Reconstitution and Further Characterization of the Cholesterol Transport Activity of the Small-Intestinal Brush Border Membrane Biochemistry 36:10784-10792.

Boffelli et al., (1997) The uptake of cholesterol at the small-intestinal brush border membrane is inhibited by apolipoproteins. FEBS Letters, 411: 7-11.

Borhani et al. (1999) Crystal structure of truncated human apolipoprotein A-1 suggests a lipid bound conformation. Proc. Natl. Acad. Sci. USA. 94:12291-12296.

Bourdillon et al. (2000) ICAM 1 deficiency reduces atherosclerotic lesions in double-knockout mice (ApoE(-/ ) IICAM-1(-/-)) fed a fat or a chow diet. Arterioscler Thromb Vasc Biol 2000;20:2630-2635.

Bowry et al. (1992) High density lipoprotein is the major carrier of lipid hydroperoxides in human blood plasma from fasting donors. Proc Natl Acad Sci USA. 1992;89:10316-10320.

Braddock. D. T., et al., (1996) Conformationally Specific Enhancement of Receptor-ediated LDL Binding and Internalization by Peptide Models of a Conserved Anionic N-Termina Domain of Human Apolipoprotein E. Biochemistry 35, 13975-13984.

Bradley, W.A., et al., (1986) ApoE is necessary and sufficient for the binding of large triglyceride-rich lipoproteins to the LDL receptor; apoB is unnecessary. J. Lipid Res. 27, 40-48.

Bradley et al. (1982) Apolipoprotein E degradation in human very low density lipoproteins by protease(s): chemical and biological consequences. Biochim. Biophys. Res. Commun. 109:1360-1367.

Brigham et al. (1989) Expression of a prokaryotic gene in cultured lung endothelial cells after lipofection with a plasmid vector. Am. J. Resp. Cell. Mol. Biol. 1: 95-100.

Brousseau, M.E. (2005) Emerging role of high-density lipoprotein in the prevention of cardiovascular disease. Drug Discovery Today. 10:1095-1099.

Brousseau, M.E., and Hoeg, J.M. (1999) Transgenic rabbits as models for atherosclerosis research. J. lipid Res. 40:365-375.

Brown, D.T. and Burlingham, B.T., (1973) Penetration of Host Cell Membranes by Adenovirus 2 J. Virology 12:386-396.

Brown, B.G. et al. (2001) Simvastatin and Niacin, Antioxidant Vitamins, or the Combination for the Prevention of Coronary Disease. N Engl J Med. 345(22):1583-92.

Brown M.L., et al. (2000) A Macrophage Receptor for Apolipoprotein B48: Clining, Expression, and Atherosclerosis. Proc. Natl. Acad. Sci. USA 97:7488-7493.

Burger et al. (2002) High-density lipoprotein-associated apolipoprotein A-I: the missing link between infection and chronic inflammation? Autoimmunity Reviews 2002;1:111-117.

Burnett, J.R. and Vasikaran, S.D. (2002) Cardiovascular disease and osteoporosis: is there a link between lipids and bone? Ann Clin Biochem. 39(Pt 3): 203-210.

Calabresi L, et al. (2002) Elevated cellular adhesion molecules in subjects with low ML-cholesterol. Arterioscler Thromb Vasc Biol. ;22:656-661.

Calabresi L, Franceschini G, Sirtoh CR, De Palma A, Saresella M, Ferrante P, Taramelli D Inhibition of VCAM-1 expression in endothelial cells by reconstituted high density lipoproteins. Biochem Biophys Res Commun. (1997) 238:61-65.

Calabresi, L., et al., (2003) Entothelial Protection by High-Denisty Lipoproteins. Athero. Thromb. Vasc. Biol. 23:1724-1731.

Campbell, E.J. Human leukocyte elastase, cathepesin G and lactoferrin: family of neutrophil granule glycoproteins that bind to an alveolar macrophage receptor. Proc Natl Acad Sci USA (1982) 79:6941-6945.

Cardillo, C. et al., (1997) Xanthine Oxidase Inhibition With Oxypurinol Improves Endothelial Vasodilator Function in Hypercholesterolemic but Not in Hypertensive Patients. Hypertension 30:57-63.

(56) References Cited

OTHER PUBLICATIONS

Carlos TM, et al. (1990) Vascular cell adhesion molecule-1 mediates lymphocyte adherence to cytokine-activated cultured human endothelial cells. Blood;76:965-970.

Carr, A.C. et al. (2000) Oxidation of LDL by myeloperoxidase and reactive nitrogen species oxidation of LDL by myeloperoxidase and reactive nitrogen species. Arterioscler Thromb Vasc Biol; 20:1716-1723.

Carrara et al., Two helices plus a linker: A small model substrate for eukaryotic RNase P Proc. Natl. Acad. Sci. (USA) 92:2627-2631 (1995).

Casserly, I. and Topol, E. (2004) Convergence of atherosclerosis and Alzheimer's disease: inflammation, cholesterol, and misfolded proteins Lancet 363:1139-1146.

Castelli, W.P. et al., Incidence of coronary heart disease and lipoprotein cholesterol levels. The Framingham study. JAMA. 1986; 256:2835-2838. Abstract.

Catapano, A.L. et al. Suppression of 3-hydroxy-3-methylglutaryl-CoA reductase by low density lipoproteins produced in vitro by lipoprotein lipase action on nonsuppressive very low density lipoproteins. J. Biol. Chem. 254: 1007-1009 (1979).

Charles-Schoeman C, Banquerigo ML, Hama S, Navab M, Park GS, Van Lenten BJ, Wagner AC, Fogelman AM, Brahn E. (2008) Treatment with an apolipoprotein A-1 mimetic peptide in combination with pravastatin inhibits collagen-induced arthritis. Clin Immunol. 127(2): 234-244.

Chiesa G, et al., Recombinant apolipoprotein A-I(Milano) infusion into rabbit carotid artery rapidly removes lipid from fatty streaks. Circ Res. 2002;90:974-980.

Chillon, J. and Baumbach, G.L. (1999) Effects of an Angiotensin—Converting Enzyme Inhibitor and a b-Blocker on Cerebral Arterioles in Rats Hypertension, 33: 856-861.

Chorev, M. and Goodman, M. (1995) Recent developments in retro peptides and proteins—an ongoing topochemical exploration. Trends Biotechnol. 13(10): 438-445.

Christison J, (1996) Rapid reduction and removal of HDL- but not LDL-associated cholesteryl ester hydroperoxides by rat liver in situ. Biochem J.; 314:739-742.

Chung, B.H. et al. Liposome-like Particles Isolated From Human Atherosclerotic Plaques Are Structurally and Compositionally Similar to Surface Remnants of Triglyceride-Rich Lipoproteins. Arterio. Thromb. 14:622-635 (1994).

Chung et al., (1985) Studies of Synthetic Peptide Analogs of the Amphipathic Helix. J. Biol. Chem. 60(18): 10256-10262.

Chung, B.H., et al. (1996) Probing structure and function of VLDL by synthetic amphipathic helical peptides. J. Lipid Res. 37:1099-1112.

Clark-Lewis et al. (1991) Chemical Synthesis, Purification, and Characterization of Two Inflammatory Proteins, Neutrophil Activating Peptide 1 (Interleukin-8) and Neutrophil Activating Peptide 2. Biochemistry 30: 3128-3135.

Clark-Lewis I, et al. (1994) Structural requirements for interleukin-8 function identified by design of analogs and CXC chemokine hybrids. J Biol Chem. 269(23): 16075-16081.

Clay, M.A., et al. (2001) Time sequence of the inhibition of endothelial adhesion molecule expression by reconstituted high density liproteins, Atherosclerosis 157: 23-29.

Clay, M.A. et al. (1995) Localization of a domain in apolipoprotein E with both cytostatic and cytotoxic activity. Biochemistry. 34:11142-11151.

Clee, S.M., et al. (2000) Age and residual cholesterol efflux affect HDL cholesterol levels and coronary artery disease in ABCA1 hetrozygotes. J. Clin. Invest. 106:1263-1270.

Clubb, F.J., et al. (2001) Development of atherosclerotic plaque with endothelial disruption in Watanabe heritable hyperlipidemic rabbit aortas. Cardiovasc. Pathol. 9:1-11.

Cockerill, G.W. et al. (2001) Elevation of plasma high-density lipoprotein concentration reduces interleukin-I induced expression of E-selectin in an in vivo model of acute inflammation. Rculation;103:108-112.

Cockerill, G.W. et al. (1999) High-density lipoproteins differentially modulate cytokine induced expression of E-selectin and cyclooxygenase-2. Arterioscler Thromb Vasc Biol.;19:910-917.

Cockerill, G.W. et al. (1995) High-density lipoproteins inhibit crone-induced expression of endothelial cell adhesion molecules. Arterioscler Thromb Vasc Biol. 15:1987-1994.

Collard, M.W. and Griswold, M.D. (1987) Biosynthesis and molecular cloning of sulfated glycoprotein 2 secreted by rat Sertoli cells. Biochemistry. 26(12): 3297-3303.

Colles, S.M., Masson, J.M., Carlson, S.G., and Chisom, G.M., Oxidized LDL-induced injury and apoptosis in atherosclerosis. Potential roles for oxysterols. Trends Cardiovasc. Med. 11:131-138 (2001).

Berg, C. et al., (2004) The myeloperoxidase product hypochlorous acid oxidizes HDL in the human artery wall and impairs ABCA1-dependent cholesterol transport Natl.. Acad. Sci. U.S.A. 101:13032-13037.

Corey, D.R. Peptide nucleic acids: expanding the scope of nucleic acid recognition. Trends Biotechnol Jun. 1997; 15(6):224-9.

Coyne, E.F. et al. (2002) Methods for isolation and characterization of intracerebral arterioles in the C57/13L6 wild-type mouse, J. Neurosci. Meth., 120: 145-153.

Curcio, C.A. et al. (2001) Accumulation of cholesterol with age in human Bruch's membrane. Invest Ophthalmol Vis Sci. 42(1): 265-274.

Curcio CA, et al. (2005) Esterified and unesterified cholesterol in drusen and basal deposits of eyes with age-related maculopathy. Exp Eye Res. 81(6): 731-741.

Cybulsky MI, et al., (2001) A major role for VCAM-1, but not ICAM-I, in early atherosclerosis. Journal of Clinical Investigation;107:1255-1262.

Cyrus, et al., (2001) Absence of 12/15-lipoxygenase expression decreases lipid peroxidation and atherogenesis in apolipoprotein E-deficient mice. Circulation;103 :2277-2282.

Dai et al. (2004) Implantation of Immature Neonatal Cardiac Cells Into the Wall of the Aorta in Rats: A Novel Model for Studying Morphological and Functional Development of Heart Cells in an Extracardiac Environment. Circulation. 110(3): 324-329.

Dai et al. (2005) Allogeneic mesenchymal stem cell transplantation in postinfarcted rat myocardium: short- and long-term effects. Circulation 112(2): 214-223.

Dansky HM, et al., Adhesion of monocytes to arterial endothelium and initiation of atherosclerosis are critically dependent on vascular cell adhesion molecule-1 gene dosage. Arterioscler Thromb Vasc Biol 2001; 21:1662-1667.

Dansky HM, et al. (1999), Apo A-I inhibits foam cell formation in Apo E-deficient mice after monocyte adherence to endothelium. J Clin Invest.;104:31-39.

Dashti et al. (2004) Model class A and class L peptides increase the production of apoA-I-containing lipoproteins in HepG2 cells. Journal of Lipid Res. 45: 1919-1928.

Datta et al. (2001) Effects of Increasing Hydrophobicity on the Physical-Chemical and Biological Properties of a Class A Amphipathic Helical Peptide. J Lipid Research 42:1096-1104.

Datta et al. The Receptor Binding Domain of Apolipoprotein E, Linked to a Model Class A Amphipathic Helix, Enhances Internalization and Degradation of LDL by Fibroblasts. Biochemistry 30: 213-220 (2000).

Datta et al., (2001) Cationic Domain (141-150) of Apo E Linked to a Class A Amphipathic Helix Enhances th e Metabolism of Apo a-Containing Lipoproteins in Hepatocytes. Arterio. Thromb. Vasc. Biol. 21:651.

Datta et al. (2001) Cationic domain 141-150 of apoE covalently linked to a class A amphipathic helix enhances atherogenic lipoprotein metabolism in vitro and in vivo. Journal of Lipid Research 42:959-966.

Datta G, et al. (2009) Anti-inflammatory and recycling properties of an apolipoprotein mimetic peptide, Ac-hE18A-NH(2). Atherosclerosis Epub ahead of print. Volume and page TBA.

Datta, G. et al. (2004) Aromatic Residue Position on the Nonpolar Face of Class A Amphipathic Helical Peptides Determines Biological Activity. J. Biol. Chem. 279:26509-26517.

(56) References Cited

OTHER PUBLICATIONS

Davenport, P. and Tipping, P.G. (2003) The role of interleukin-4 and interleukin-12 in the progression of atherosclerosis in apolipoprotein E-deficient mice. Am J Pathol 163:1117-1125.
Davidson, D. et al. Overproduction of Polyomavirus Middle T Antigen in Mammalian Cells through the Use of an Adenovirus Vector. J. Virology 61:1226-1239 (1987).
Davidson, et al. (1994) The Influence of Apolipoprotein Structure on the Efflux of Celluar Free Cholesterol to High Density Lipoprotein. J. Biol. Chem. 269(37): 22975-22982.
Dawson, P.E. et al. Synthesis of Proteins by Native Chemical Ligations. Science 266: 776-779 (1994).
De Caterina R, et al., (1998) Structural requirements for inhibition of cytokine-induced endothelial activation by unsaturated fatty acids. J. Lipid Res.;39:1062-1070.
Diederich et al. (2001) Apolipoprotein AI and HDL3 Inhibit Spreading of Primary Human Monocytes through a Mechanism that Involves Cholesterol Depletion and Regulation of CD42, Atherosclerosis. 159:313-324.
Dimayuga, P. et al., Reconstituted HDL containing human apolipoprotein A-1 reduces VCAM-1 expression and neointima formation following periadventitial cuffinduced carotid injury in apoE null mice. Biochem Biophys Res Commun. 1999;264:465-468.
Dithmar S, et al. (2000) Ultrastructural changes in Bruch's membrane of apolipoprotein E-deficient mice. Invest Ophthalmol Vis Sci. 41(8): 2035-2042.
Dooley, C.T. et al. (1994) An All D-Amino Acid Opioid Peptide with Central Analgesic Activity from a Combinatorial Library. Science. 2019-2022.
Dunlop, D.S. and Neidle, A. (1997) The Origin and Turnover of D-Serine in Brain. Biochemical and Biophysical Research Communication 235:26-30.
Duong, P. T., et al. (2006). Characterization of nascent HDL particles and macroparticles formed by ABC A1-mediated cholesterol efflux of cellular lipids to apo A-I. J. Lipid Res. 47:832-843.
Dyer, C. A., et al., (1991) Only multimers of a synthetic peptide of human apolipoprotein E are biologically active. J. Biol. Chem. 266, 15009-15015.
Dyer, C. A., et al., (1991) Only Multimers of a Synthetic Peptide of Human Apolipoprotein E Are Biologically Active. J. Biol. Chem. 266, 22803-22806.
Dyer, C. A., et al., (1995) Structural features of synthetic peptides of apolipoprotein E that bind the LDL receptor. J. Lipid Res. 36, 80-8.
Ehara et al. (2001) Elevated Levels of Oxidized Low Density Lipoprotein Show a Positive Relationship With the Severity of Acute Coronary Syndromes. Circulation. 103:1955-1960.
Eisenberg et al. Lipoprotein lipase enhances binding of lipoproteins to heparan sulfate on cell surfaces and extracellular matrix. J. Clin Invest. 90: 2013-2021 (1992).
Epand et al. (1987) Studies Synthetic Peptide Analog of the Amphipathic Helix J. Biol. Chem. 262(19): 9389-9396.
Epand RM, Stafford A, Leon B, Lock PE, Tytler EM, Segrest JP, Anantharamaiah GM. (1994) HDL and apolipoprotein A-I protect erythrocytes against the generation of procoagulant activity. Arterioscler Thromb. 14(11): 1775-1783.
Epand, et al. (2004) An Apolipoprotein AI Mimetic Peptide: Membrane Interactions and the Role of Cholesterol. Biochemistry. 43:5073-5083.
Epand, et al. (2004) Two Homologous Apolipoprotein AI Mimetic Peptides: Relationship Between Membrane Interactions and Biological Activity. J. of Biol. Chem. 279:51404-51415.
Farkas, M.H. et al., (2004) The recycling of apolipoprotein E and its amino-terminal 22kDA fragment: evidence for multiple redundant pathways. J. Lipid Res. 45:1546-1554.
Felgner et al. Lipofection: a highly efficient, lipid-mediated DNA-transfection procedure. PNAS, 84: 7413-7417 (1987).
Field et al. (2001) Gene expression of sterol regulatory element-binding proteins in hamster small intestine, Journal of Lipid Research. 42:1-9.

Keech, A. et al. Effects of long-term fenofibrate therapy on cardiovascular events in 9795 people with type 2 diabetes (the Field study): randomised controlled trial. Lancet. (2005) 366: 1849-1861.
Fielding and Fielding (1995) Molecular physiology of reverse cholesterol transport. J. Lipid Res. 36: 211-228.
Fleisher et al., Stimulation of arterial endothelial cell prostacyclin synthesis by high density lipoproteins. J Biol. Chem. 1982; 257:6653-6655.
Fogelman et al., Malondialdehyde alteration of low density lipoproteins leads to cholesteryl ester accumulation in human monocyte-macrophages. Proc Natl Acad Sci USA. 1980; 77:2214-2218.
Fogelman, A.M., When good cholesterol goes bad. Nat Med. 2004; 10:902-903.
Folch, J. et al., (1957) A simple method for isolation and purification of total lipides from animal tissues. J. Biol. Chem. 226:497-509.
Footer et al. (1996) Biochemical evidence that a D-Loop is part of a four-strandedPNA-DNA bundle. Nickel-mediated cleavage of duplex DNA by a Gly-Gly-His-Bis-PNA, Biochemistry. 35(33): 10673-9.
Forte et al., Altered activities of anti-atherogenic enzymes LCAT, paraoxonase, and platelet-activating factor acetylhydrolase in atherosclerosis susceptible mice. J. Lipid Res., 2002; 43:477-485.
Fritz, I.B. (1992) What is clusterin? Clin Exp Immunol. 88(3): 375.
Fukuda, et al., Bilayer forming ion-pair amphi-philes from single chain surfactants. J Am Chem Soc., 1990, 112:1635-1637.
Futterman, L.G and Lemberg, L. (2004) Statin pleiotropy: fact or fiction? Am J Crit Care. 13(3): 244-249.
Gabay C. and Kushner I., Acute-phase proteins and other systemic responses to inflammation, N. Engl. I Med. 1999; 340; 448-454.
Gambacorti-Passerini et al., In Vitro Transcription and Translation Inhibition by Anti-PromyelocyticLeukemia (PML)/Retinoic Acid Receptor α and Anti-PML Peptide Nucleic Acid. Blood. 1996; 88(4):1411-7.
Garber DW, Handattu S, Aslan I, Datta G, Chaddha M, Anantharamaiah GM. (2003) Effect of an arginine-rich amphipathic helical peptide on plasma cholesterol in dyslipidemic mice. Atherosclerosis 168(2):229-237.
Garber et al. (1992) Turnover of synthetic class A amphipathic peptide analogues of exchangeable apolipoproteins in rats. Correlation with physical properties. Arteriosclerosis and Thrombosis, 12(8): 886-894.
Garber et al. (2001) A new synthetic class A amphipathic peptide analogue protects from diet-induced atherosclerosis. Journal of Lipid Research 42:-545-552.
Garber et al. (2001) An Arginine-rich amphipathic helical peptide mediates rapid clearance of plasma cholesterol is dyslipidemic mice. Arterio. Thromb. Vasc.
Garber et al. (2006) Atherosclerosis and vascular disease: effects of peptide mimetics of apolipoproteins. Curr. Pharm. Biotechnol. 7:235-240.
Garber, D.W., Kulkarni, K.R., and Anantharamaiah, G.M. A sensitive and convenient method for lipoprotein profile analysis of individual mouse plasma samples. J. Lipid Res. 41:1020-1026, (2000).
Garner et al. (1998) Oxidation of high density lipoproteins. I. Formation of methionine sulfoxide in apolipoproteins AI and AII is an early event that accompanies lipid peroxidation and can be enhanced by alpha-tocopherol. J Biol Chem. 1998; 273:6080-6087.
Garner et al. (1998) Oxidation of high density lipoproteins. II. Evidence for direct reduction of lipid hydroperoxides by methionine residues of apolipoproteins AI and AII. J Biol Chem. 1998; 273:6088-6095.
Gaut, et al. (2002) Myeloperoxidase produces nitrating oxidants in vivo. J Clin Invest 2002; 109: 1311-1319.
Geetanjali, B. et al. Changes in heat shock protein 70 localization and its content in rabbit aorta at various stages of experimental atherosclerosis Cardiovascular Pathology 11: 97-103 (2002).
Gehrs KM, Anderson DH, Johnson LV, Hageman GS. (2006) Age-related macular degeneration—emerging pathogenetic and therapeutic concepts. Ann Med. 38(7): 450-471.
George et al. (2001) 12/15-lipoxygenase gene disruption attenuates atherogenesis in LDL, receptor-deficient mice. Circulation, 2001: 104:1646-1650.

(56) References Cited

OTHER PUBLICATIONS

Geysen HM, Mason TJ, Rodda SJ. (1988) Cognitive features of continuous antigenic determinants. J Mol Recognit. 1(1): 32-41.
Ghandi et al. (2004) Apolipoprotein B-containing Lipoprotein Particle Assembly: Lipid Capacity of the Nascent Lipoprotein Particle. J. Biol. Chem. 279:39757-39766.
Ghersi-Egea et al. (1996) Fate of Cerebrospinal Bluid-Borne Amyloid B-Peptide: Rapid Clearance into Blood and Appreciable Accumulation by Cerebral Arteries, J. Neurochem., 67: 880-883.
Gianturco et al., Receptor-mediated uptake of hypertriglyceridemic very low density lipoproteins by normal human fibroblasts. Journal of Lipid Research. 23: 984-993 (1982).
Gianturco, S.H. et al. Apolipoprotein E mediates uptake of Sf 100-400 hypertriglyceridemic very low density lipoproteins by the low density lipoprotein receptor pathway in normal human fibroblasts. J. Biol. Chem. 258:4526-4533 (1983).
Gianturco, S.H. et al. Control of 3-hydroxy 3-methylglutaryl CoA reductase activity in cultured human fibroblasts by VLDL of subjects with hypertriglyceredemia. J. Clin Invest. 61:320-328 (1978).
Gillote et al. (1999) Apolipoprotein-mediated plasma membrane microsolubilization. Role of lipid affinity and membrane penetration in the efflux of cellular cholesterol and phospholipid. J Biol. Chem. 274(4):2021-8.
Glomset, J.A. (1968) The Plasma lecithin: cholesterol acytransferase reaction. J. Lipid Res. 9:155-167.
Gomez-Foix, A.M. et al. Adenovirus-mediated Transfer of the Muscle Glycogen Phosphorylase Gene into Hepatocytes Confers Altered Regulation of Glycogen Metabolism. J. Biol. Chem. 267:25129-25134 (1992).
Gong et al., (1994) Structural and functional properties of human and mouse apolipoprotein A-I. Biochim. Biophys. Acta. 1213:335-342; Abstract.
Graf R, Schachman HK. (1996) Random circular permutation of genes and expressed polypeptide chains: application of the method to the catalytic chains of aspartate transcarbamoylase. Proc Natl Acad Sci U S A. 93(21): 11591-11596.
Greenway, P.J. et al. Human cytomegalovirus DNA: BumHI, EcoRI and Pst I restriction endonuclease cleavage maps Gene 18: 355-360 (1982).
Greten FR, Eckmann L, Greten TF, Park JM, Li ZW, Egan LJ, Kagnoff MF, Karin M. IKKbeta links inflammation and tumorigenesis in a mouse model of colitis-associated cancer. Cell. Aug 6, 2004;118(3):285-96.
Griendling, K.K. et al. (2000) NAD(P)H Oxidase : Role in Cardiovascular Biology and Disease Circulation Research. 86:494-501.
Grundy S.M., et al. Implications of Recent Clinical Trials for the National Cholesterol Education Program Adult Treatment Panel III Guidelines Circulation. 110:227-239 (2004).
Gupta et al. (2004) Calculation of Creatinine Clearance Based on Unadjusted Body Weight Leads to Errors in Renal and Heart Failure Patients Circulation 110:III-243.
Gupta H, et al. (2005) Inhibition of lipopolysaccharide-induced inflammatory responses by an apolipoprotein AI mimetic peptide. Circ Res. 97(3): 236-243.
Gupta H, et al. (2005) Apolipoprotein E mimetic Peptide dramatically lowers plasma cholesterol and restores endothelial function in watanabe heritable hyperlipidemic rabbits. Circulation. 111(23): 3112-3118.
Gurfinkel et al (2002) Influenza Vaccine Pilot Study in Acute Coronary Syndromes and Planned Percutaneous Coronary Interventions. The FLU Vaccination Acute Coronary Syndromes (FLUVACS) Study. Circulation 105 :2143-2147.
Guzman, R.J. et al. Efficient Gene Transfer Into Myocardium by Direct Injection of Adenovirus Vectors Circulation Research 73:1201-1207 (1993).
Haimovici R, Gantz DL, Rumelt S, Freddo TF, Small DM. (2001) The lipid composition of drusen, Bruch's membrane, and sclera by hot stage polarizing light microscopy. Invest Ophthalmol Vis Sci. 42(7): 1592-1599.

Haj-Ahmad et al. Development of a Helper-Independent Human Adenovirus Vectorand Its Use in the Transfer of the Herpes Simplex Virus Thymidine Kinase Gene. J. Virology. 57:267-274 (1986).
Halcox, J.P. et al. (2002) Prognostic Value of Coronary Vascular Endothelial Dysfunction. Circulation. 106:653-658.
Hamase et al. (2001) Determination of Free D-ProIine and D-Leucine in the Brains of Mutant Mice Lacking D-Amino Acid Oxidase Activity. Analytical Biochemistry. 298:253-258.
Handattu et al. (2006) Physical, Chemical, and Structural Studies of Apolipoprotein A-I Mimetics Correlate Well with the Efficacy for Inhibiting Atherosclerosis Atheroscler. Thromb. Vasc. Biol. 26(5):e64.
Handattu, S., P.,Garber, D.W., Beno, B., Bain, A.D., Mishra, V.K., Palgunachari, M.N., Datta, G., Anantharamaiah, G.M., and Epand, R.M. ApoA-I Mimetic Peptides with Differing Ability to Inhibit Atherosclerosis Also Exhibit Differences in Their Interactions with Membrane Bilayers. J. Biol. Chem. 282:1980-1988 (2007).
Handwerger, et al. (1999) Pre-β-HDL stimulates placental lactogen release from human trophoblast cells. Am. J. Physiol. 276:E384-E389.
Hanvey et al. Antisense and Antigene properties of Peptide Nucleic Acids. Science. 1992; 258(5087):1481-5.
Harats, et al., Overexpression of 15-lipoxygenase in vascular endothelium accelerates early atherosclerosis in LDL receptor-deficient mice. Arterioscler Thromb Vasc Biol. 2000; 20:2100-2105.
Hardy et al. (2001) An Automated High-Performance Liquid Chromatography Procedure for the Quantitation of L- and D-Amino Acids by Means of Stepwise Precolumn Derivatization Analytical Biochemistry 291:297-299.
Harkin et al. (1997) The Effects of hyper-and hypocarbia on intraparenchymal arterioles in rat brian slices, Neuroreport, 8: 1841-1844.
Hashimoto (2000) Improvement of intestinal absorption of peptides: absorption of BI-Phe monoglucosylated insulin to rat intestinal brush-border membrane vesicles. J. Pharmaceutics & Therapeutics 50(2): 197-204.
Hasty, A.H., Linton, M.R., Sanan, D., Swift, L.L., and Fazio, S. Determination of lower threshold of apolipoprotein E resulting in lipoprotein remnant clearance. J. Lipid Res. 40:1529-1538 (1999).
Hauser et al.. (1998) Identification of a Receptor Mediating Absorption of Dietary Cholesterol in the Intestine Biochemistry 178423-17850.
Havel, R. J. George Lyman Duff memorial lecture. Role of the liver in atherosclerosis. Arteriosclerosis 5: 569-580 (1985).
Hayry et al., (1995) Stabile D peptide analog of insulin-like growth factor-1 inhibits smooth muscle cell proliferation after carotid balooning injury in the rat. FASEB J. 9(13): 1336-1344.
Hein TW, Platts SH, Waitkus-Edwards KR, Kuo L, Mousa SA, Meininger GA. (2001) Integrin-binding peptides containing RGD produce coronary arteriolar dilation via cyclooxygenase activation. Am J Physiol Heart Circ Physiol. 281(6): H2378-H2384.
Henricksen et al., Enhanced macrophage degradation of low density lipoprotein prevously incubated with cultured endolelial cells; recognition by receptor for acetylated low density lipoproteins. Proc Natl Acad Sci USA., 1981; 78:6499-6503.
Hermanowski-Vosatka A, Balkovec JM, Cheng K, Chen HY, Hernandez M, Koo GC, Le Grand CB, Li Z, Metzger JM, Mundt SS, Noonan H, Nunes CN, Olson SH, Pikounis B, Ren N, Robertson N, Schaeffer JM, Shah K, Springer MS, Strack AM, Strowski M, Wu K, Wu T, Xiao J, Zhang BB, Wright SD, Thieringer R.11beta-HSD1 inhibition ameliorates metabolic syndrome and prevents progression of atherosclerosis in mice., J Exp Med. Aug. 15, 2005;202(4):517-27.
Hessler et al. (1979) LDL-induced cytotoxicity and its inhibition by 1-DL in human vascular smooth muscle and endothelial cells in culture. Atherosclerosis, 32:213-229, Abstract.
Hoffman et al. (1997) Isoprostanes: Free Radical-Generated Prostaglandins with constrictor Effects on cerebral Arterioles, Stroke, 28: 844-849.
Holvoet, P. et al. (1997) β-VLDL Hypercholesterolemia Relative to LDL Hypercholesterolemia Is Associated With Higher Levels of Oxidized Lipoproteins and a More Rapid Progression of Coronary Atherosclerosis in Rabbits Arterioscl. Thromb. Vasc. Biol. 17:2376-2382.

(56) References Cited

OTHER PUBLICATIONS

Hoogenboom et al. By-passing immunisation: Human antibodies from synthetic repertoires of germline VH gene segments rearranged in vitro J. Mol. Biol., 227:381-388, 1992.

Houstis, N., Rosen, E.D., and Lander E.S. Reactive oxygen species have a causal role in multiple forms of insulin resistance. Nature 440:944-948 (2006).

Hristova et al. (1999) An Amphipathic α-Helix at a Membrane Interface: A Structural Study using a Novel X-ray Diffraction Method. J. Mol. Biol. 290:99-117.

Huber MA, Azoitei N, Baumann B, Grünert S, Sommer A, Pehamberger H, Kraut N, Beug H, Wirth T. (2004) NF-kappaB is essential for epithelial-mesenchymal transition and metastasis in a model of breast cancer progression. J Clin Invest. 114(4): 569-581.

Hussain et al. High affinity binding between lipoprotein lipase and lipoproteins involves multiple ionic and hydrophobic interactions, does not require enzyme activity, and is modulated by glycosaminoglycans. J. Biol. Chem. 275: 29324-29330 (2000).

Hwang SJ, Ballantyne CM, Sharrett AR, Smith LC, Davis CE, Gotto AM Jr, Boerwinkle E. Circulating adhesion molecules VCAM-I, ICAM-1, and E-selectin in carotid therosclerosis and incident coronary heart disease cases. The atherosclerosis risk in communities (AMC) study. Circulation 1997;96:4219-4225.

Hyka et al. (2001) Apolipoprotein A-I Inhibits the Production of Interleukin-10 and Tumor Necrosis Factor-a by Blocking Contact-Mediated Activation of Monocytes by T Lymphocytes Blood 97:2381-2389.

Hyrup, B. and Nielsen, P.E. Peptide Nucleic Acids (PNA): Synthesis, Properties and Potential Applications Bioorg Med Chem. Jan. 1996; 4(1):5-23.

Ishigami, M., Swertfeger, D.K., Hui, M.S., Granholm, N. A. and Hui, D.Y. Apolipoprotein E inhibition of vascular smooth muscle cell proliferation but not the inhibition of migration is mediated through activation of inducible nitric oxide synthase. Arterio. Thromb. Vasc. Biol. 20:1020-1026 (2000).

Jaeger et al. Improved predictions of secondary structures for RNA Proc. Natl. Acad. Sci. USA 86:7706-7710, 1989.

Jakobovits et al. Germ-line transmission and expression of a human-derived yeast artificial chromosome. Nature, 362:255-258 (1993).

Jakobovits et al. Analysis of homozygous mutant chimeric mice: Deletion of the immunoglobulin heavy-chain joining region blocks B-cell development and antibody production Proc. Natl. Acad. Sci. USA, 90:2551-255 (1993).

Jamaluddin, et al. (1987) Aggregatory reactions of blood platelets in ustirred dilute suspensions and their monitoring by spectrophotometry. Curr Sci; 56:254-256.

Jamieson et al. (2001) Detection of Lipoprotein(a) in Intraparenchymal Cerebral Vessels: Correlation with Vascular Pathology and Clinical History, Exp. Mol Pathol., 71: 99-105.

Jensen et al. Kinetics for Hybridization of Peptide Nucleic Acids (PNA) with DNA and RNA Studied with the BIAcore Technique Biochemistry. 1997; 36(161:5072-7.

Jin et al. (2003) Inhibition of endothelial lipase causes increased ML cholesterol levels in vivo. J Clin Invest 2003; 111:357-362.

Jones. et al. Computer programs to identify and classify amphipathic of domains. J. Lipid. Res. 33: 287-296 (1992).

Jong, M.C., Dahlmans, V.E., van Gorp, P. J., Brewer, M. L. Mol, M. J., van der Ze, A., Frants, R. R., Hofker, M. H., and Havekes, L. M. Both lipolysis and hepatic uptake of VLDL are impaired in transgenic mice coexpressing human apolipoprotein E*3Leiden human apolipoprotein C-I. Arteriosc. Thromb. Vasc. Biol. 16:934-940 (1996).

Kabanov et al. A new class of antivirals: antisense oligonucleotides combined with a hydrophobic substituent effectively inhibit influenza virus reproduction and synthesis of virus-specific proteins in MDCK cells. FEBS Lett., 1990, 259, 327-330.

Kaler et al (1989) Spontaneous vesicle formation in aqueous mixtures of single-tailed surfactants, Science, 245:1371-1374.

Kandel ER, Schwartz JH, Jessell TM (Eds.) (1991) Principles of Neural Science, Third Edition. Elsevier: New York, pp. 188-189.

Karle et al. (2004) A combined extented and helical backbone for Boc-(Ala-Leu-Ac7C)2-OME, Peptides Res., 63:174-180.

Karle, et al. (1998) Crystal structure of the channel-forming polypeptide antiamoebin in a membrane-mimetic environment. Proc. Natl. Acad. Sci. 95:5501-5504.

Karle, et al. (2003) Crystal structure of hydrophobic 19-residue peptide helix containing three centrally located D amino acids, PNAS, 100:24:13946-13951.

Kaul, S., et al. (2004) Rapid Reversal of Endothelial Dysfunction in Hypercholesterolemic Apolipoprotein E-Null Mice by Recombinant Apolipoprotein A-I$_{Milano}$-Phospholipid Complex. J. Am. Coll. Cardiol. 44:1311-1319.

Kirshenbaum, L.A. et al. Highly Efficient Gene Transfer into Adult Ventricular Myocytes by Recombinant Adenovirus. J Clin. Invest. 92:381-387 (1993).

Kissinger C, Skinner MK, Griswold MD. (1982) Analysis of Sertoli cell-secreted proteins by two-dimensional gel electrophoresis. Biol Reprod. 27(1): 233-240.

Kita, T., Brown, M.S., Watanabe, Y., and Goldstein, J.L. Deficiency of low density lipoprotein receptors in liver and adrenal gland of the WHHL rabbit, an animal model of familial hypercholesterolemia. Proc Natl. Acad. Sci, USA 78: 2268-2272 (1981).

Knowler, W.C. et al. Reduction in the incidence of type 2 diabetes with lifestyle intervention or metformin. N Engl J Med. (2002) 346(6):393-403.

Ko, et al. (1993) A. Highdensity lipoprotein reduces epidermal growth factor-induced DNA synthesis in vascular smooth muscle cells. Atherosclerosis, 99: 253-259, Abstract.

Kockx, et al. (2004) Apolipoprotein A-I-stimulated Apolipoprotein E Secretion from Human Macrophages Is Independent of Cholesterol Efflux. J. Biol. Chem. 279:25966-25970.

Kolodgie, F.D., Katocs, A.S., Largis, E.E., Wrenn, S.M., Cornhill, J.F., Herdrick, E.E., Lee, S.J., and Virmani, R. Hypercholesterolemia in the rabbit induced by feeding graded amounts of low-level cholesterol. Arterioscler. Thromb. Vasc. Biol. 16:1454-1464 (1996).

Kontos, H.A. and Wei, E.P. (1998) Cerebral arteriolar dilations by KATP channelactivators need L-lysine or L-arginine Am. J. Physiol. 274 (Heart Circ. Physiol. 43): H974-H981, 1998.

Kowal, R.C., Herz, J., Goldstein, J.L., Esser, V., and Brown, M.S. Low density lipoprotein receptor related protein mediates uptake of cholesteryl ester derived from apolipoprotein E enriched lipoproteins. Proc. Natl. Acad. Sci. U.S.A. 86:5810-5814 (1989).

Kozbor D, Lagarde AE, Roder JC. (1982) Human hybridomas constructed with antigen-specific Epstein-Barr virus-transformed cell lines. Proc Natl Acad Sci USA, 79(21): 6651-55.

Kreiger (1999) Charting the Fate of the Good Cholesterol: Identifcation and Characterization of the High-Density Lipoprotein Receptor Sr-Bi. Ann Rev. Biochem. 68: 523-558.

Kullman et al. (1999) Evaluation of the Enantiomeric Composition of Amino Acids in Tobacco, Chirality, 11:669-673.

Kumar et al. (2002) A novel peptide derivative exhibits anti inflammatory and antioxidant activity in adjuvant induced arthritis in rats. Mol Cell Biochem, Jan.; 229 (1-2):9-17.

Kume et al. (1992) Lysophosphatidylcholine, a component of atherogenic lipoproteins, induces mononuclear leukocyte adhesion molecules in cultured human and rabbit arterial endothelial cells. J Clin Invest. 90:1138-1144.

Kwiterovich, P.O. State-of-the-art update and review: clinical trials of lipid-lowering agents. Am. J. Cardiol. 82: 3U-17U (1998).

La Salle, G. et al, An adenovirus vector for gene transfer into neurons and glia in the brain. Science. 259:988-990 (1993).

Lalazar, A. et al. (1988) Site-specific Mutagenesis of Human Apolipoprotein E: Receptor Binding Activity of Variants With Single Amino Acid Substitutions. J. Biol. Chem. 263, 3542-2545.

Lawrence, M.B. and Springer, T.A. (1991) Leukocytes roll on a selectin at physiologic flow rates: distinction from and prerequisite for adhesion through integrins. Cell. 65:859-873.

Lee, S. et al. (2001) Vitamin C-induced decomposition of lipid hydroperoxides to endogenous genotoxins. Science. 292:2083-2086.

(56) References Cited

OTHER PUBLICATIONS

Legrand et al. (1992) Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin, Biochemistry, 31, 9243-9251.

Letsinger et al. Cholesteryl-conjugated oligonucleotides: Synthesis, properties, and activity as inhibitors of replication of human immunodeficiency virus in cell culture. Proc. Natl. Acad. Sci. USA, 1989, 86, 6553-6556.

Levine, et al. (1993) In vivo protection against endotoxin by plasma high density lipoprotein. Proc. Natl. Acad. Sci. USA, 90:12040-12044.

Li et al. (1993) An atherogenic diet rapidly induces VCAM-1, a cytokine-regulatable mononuclear leukocyte adhesion molecule, in rabbit aortic endothelium. Arteriosclerosis and Thrombosis, 13:197-204.

Li, et al. (2004) Double Belt Structure of Discoidal High Density Lipoproteins: Molecular Basis for Size Heterogeneity. J. Mol. Biol. 343:1293-1311.

Libby et al. (2002) Inflammation and atherosclerosis. Circulation. 105:1135-1143.

Linsel-Nitschke, P. et al. HDL as a target in the treatment of atherosclerotic cardiovascular disease. Nat Rev Drug Discov. (2005) 4(3):193-205.

Mach et al. (1998) Reduction of atherosclerosis in mice by inhibition of CD40 signalling. Nature, 394:200-203.

Mahley et al. Remnant lipoprotein metabolism: key pathways involving cell-surface heparan sulfate proteoglycans and apolipoprotein E. J. Lipid Res. 40: 1-16. (1999).

Mahley et al. Pathogenesis of type III hyperlipoproteinemia (dysbetalipoproteinemia): questions, quandaries, and paradoxes. J. Lipid Res. 40: 1933-1949. (1999).

Mahley, R.W., Weisgraber, K.H., Hussain, M.M., Greenman, B., Fishe, M., Vogel, T., and Gorecki, M. Intravenous infusion of apolipoprotein E accelerates clearance of plasma lipoproteins in rabbits. J. Clin. Invest. 83: 2125-2130 (1989).

Mala, John Geraldine Sandana et al., (Aug. 2001) "Strain improvement of Aspergillus niger for enhanced lipase production", J Gen Appl Microbiol, 47(4):181-186.

Manikandan et al. (2002) Antioxidant potential of a novel tetrapeptide derivative in isoproterenol-induced myocardial. Pharmacology, 65:105-109.

Manoharan et al. Cholic acid-oligonucleotide conjugates for antisense applications Bioorg. Med. Chem. Let., 1994, 4, 1053-1060.

Manoharan et al. Lipidic nucleic acids. Tetrahedron Lett., 1995, 36, 3651-3654.

Marks et al. By-passing immunization. Human antibodies from V-gene libraries displayed on phage. J. Mol. Biol., 222:581, 1991.

Massie et al. Construction of a Helper-Free Recombinant Adenovirus That Expresses Polyomavirus Large T Antigen Mol. Cell. Biol. 6:2872-2883 (1986).

Mato et al. (1996) Involvement of specific macrophage-lineage cells surrounding arterioles in barrier and scavenger function in brain cortex, Proc. Natl. Acad. Sci. USA, vol. 93, pp. 3269-3274, Apr. 1996.

Mazoyer E, Levy-Toledano S, Rendu F, Hermant L, Lu H, Fiat AM, Jolles P, Caen J. KRDS, a new peptide derived from human lactotransferrin, inhibits platelet aggregation and release reaction. Eur J Biochem 1990;194:43-49.

McGarry JD. Banting lecture 2001: dysregulation of fatty acid metabolism in the etiology of type 2 diabetes.Diabetes. 2002; 51(1):7-18.

Meera et al. (1999) Inhibition of neutrophil derived lysosomal enzymes and reactive oxygen species by a novel tetrapeptide. Inflamm Res. Sep. 1999, 48(9):479-84.

Mehrabian et al. (2002) Identification of 5-lipoxygenase as a major gene contributing to atherosclerosis susceptibility in mice. Circ Res. 91:120-126.

Mendez et al. (1994) Synthetic Amphipathic Helical Peptides that Mimic Apolipoprotein A-I in Clearing Cellular Cholesterol. J Clin Invest 94: 1698-1705.

Merrifield et al. (1995) Retro and Retroenantio Analogs of Cecropin-Melittin Hybrids Proc Natl Acad Sci USA 92: 3449-3453.

Mertens, A., et al. (2003) Increased Low-Density Lipoprotein Oxidation and Impaired High-Density Lipoprotein Antioxidant Defense Are Associated With Increased Macrophage Homing and Atherosclerosis in Dyslipidemic Obese Mice: LCAT Gene Transfer Decreases Atherosclerosis. Circulation. 107:1640-1646.

Miller et al. Redesign of Retrovirus Packaging Cell Lines to Avoid Recombination Leading to Helper Virus Production Mol. Cell. Biol. 6: 2895 (1986).

Mims, M. P., et al. (1994) A Nonexchangeable Apolipoprotein E Peptide That Mediates Binding to the Low Density Lipoprotein Receptor. J. Biol. Chem. 269, 20539-20647.

Mishra et al. (1994) Interaction of Synthetic Peptide Analogs of the Class A Amphipathic Helix with Lipids: Evidence for the Snorkel Hypothesis. J Biol. Chem. 269: 7185-7191.

Mishra et al. (1995) Effect of the Arrangement of Tandem Repeating Units of Class A Amphipathic a-Helixes on Lipid Interaction. J. Biol. Chem. 270: 1602-1611.

Mishra et al. (1996) Interaction of Model Class A1, Class A2, and Class Y Amphipathic Helical Peptides with Membranes. Biochemistry 35:11210-11220.

Mishra et al. (1998) Studies of Synthetic Peptides of Human Apolipoprotein A-I Containing Tandem Amphipathic a-Helixes Biochemistry 37: 10313-10324.

Mishra et al. (2001) Solution NMR structure of a model class A (apolipoprotein) amphipathic a helical peptide Peptides 22:567-573.

Mishra et al. (2006) Association of a model class A (apolipoprotein) amphipathic alpha helical peptide with lipid: high resolution NMR studies of peptide.lipid discoidal complexes. J. Biol. Chem. 281:6511-6519.

Miyazaki et al. (1995) Intravenous Injection of Rabbit Apolipoprotein A-I Inhibits the Progression of Atherosclerosis in Cholesterol-Fed Rabbits Arterioscler. Thromb. Vasc. Biol. 15:1882-1888.

Chiesa, G., Monteggia, E., Marchesi, M., Lorenson, L., Laucello, M., Loruso, V., DiMario, C., Karvouni, E., Newton, R.S., Bisgaier, C.L., Franceshini, G. and Sirtori, C.R. Recombinant apolipoprotein A-I(Milano) infusion into rabbit carotid artery rapidly removes lipid from fatty streaks. Circ. Res. 90:974-980, 2002.

Moore DJ, Hussain AA, Marshall J. (1995) Age-related variation in the hydraulic conductivity of Bruch's membrane. Invest Ophthalmol Vis Sci. 36(7): 1290-1297.

Morrison et al. Chimeric human antibody molecules: Mouse antigen-binding domains with human constant region domains Proc. Natl. Acad. Sci. USA, 81:6851-6855 (1984).

Morsy et al. Efficient Adenoviral-mediated Ornithine Transcarbamylase Expression in Deficient Mouse and Human Hepatocytes. J. Clin. Invest. 92:1580-1586 (1993).

Moullier et al. Correction of lysosomal storage in the liver and spleen of MPS VII mice by implantation of genetically madified skin fibroblast. Nature Genetics. 4:154-159 (1993).

Mulder et al. (2004) Low-density lipoprotein receptor-knockout mice display impaired spatial memory associated with a decreased synaptic density in the hippocampus, Neurobiology of Disease 16: 212-219.

Mulligan, R.C. The basic science of gene therapy. Science. 260:926-932 (1993).

Murugesan et al. (1994) High-density lipoprotein stimulates endothelial cell movement by a mechanism distinct from basic fibroblast growth factor. Circ. Res. 74 : 1149-1156.

Nag et al. (1997) Cerebrovascular Changes in Chronic Hypertension Protective Effects of Enalapril in Rats, Stroke, 28: 1028-1034.

Nagata et al. (1994) Distribution of free D-serine in vertebrate brains, Brain Res., 634: 291-295.

Nagata et al. (1995) Free D-serine concentration in normai and Alzheimer human brain, Brain Res. Bull., 38(2): 181-183.

Nagata et al. (2002) Hemodynamic Aspects of Alzheimer's Disease, Ann. N. Acad. Sci., 977: 391-402.

(56) References Cited

OTHER PUBLICATIONS

Naghavi M, Wyde P, Litovsky S, Madjid M, Akhtar A, Naguib S, Siadaty MS, Sanati S, Casscells W. (2003) Influenza infection exerts prominent inflammatory and thrombotic effects on the atherosclerotic plaques of apolipoprotein E-deficient mice. Circulation. 107(5): 762-768.
Nakamura et al. (1997) Deposition of amyloid B protein (AB) subtypes [AB40 and AB42(43)] in canine senile plaques and cerebral amyoloid angiopathy Acta Neuropathot 94: 323-328.
Nanjee et al. (1999) Acute effects of intravenous infusion of apoA-Uphosphos-phatidycholine discs on plasma lipoproteins in humans. Arterioscler Thromb Vase Biol, 19:979-989.
Nanjee et al. (2001) Intravenous apoA-1/lecithin discs increase preconcentration in tissue fluid and stimulate reverse cholesterol transport in humans. J Lipid Res, 42:1586-1593.
Navab et al. (1991) Monocyte transmigration induced by modification of low density lipoprotein in cocultures of human aortic wall cells is due to induction of monocyte chemotactic protein 1 synthesis and is abolished by high density lipoprotein. Journal of Clinical Investigation 1991;88:2039-2046.
Navab et al. (1997) Mildly oxidized LDL induces an increased apolipoprotein J/paraoxonase ratio. J Clin.Invest. 99: 2005-2019.
Navab et al. (2000) Normal high density lipoprotein inhibits three steps in the formation of midly oxidized low density lipoprotein: step 1. J Lipid Res. 41: 1481-1494.
Navab et al. (2000) Normal high density lipoprotein inhibits three steps in the formation of mildly oxidized low density lipoprotein: steps 2 and 3. J. Lipid Res. 41:1495-1508.
Navab et al. (2001) A cell-free assay for detecting HDL that is dysfunctional in preventing the formation of or inactivating oxidized phospholipids. J Lipid Res 2001; 42:1308-1317.
Navab et al. (2001) HDL and the inflammatory response induced by LDL-derived oxidized phospholipids. Arterioscler Thromb Vasc Bio. 21:481-488.
Navab et al. (2003) Oral synthetic phospholipids (DMPC) raises high-density lipoprotein cholesterol levels, improves high-density lipoprotein function, and markedly reduces atherosclerosis in apolipoprotein E-null mice. Circulation 2003; 108:1735-1739.
Navab et al. (2004) Oral D-4F causes formation of pre-high-density lipoprotein and improves high-density lipoprotein-mediated cholesterol efflux and reverse cholesterol transport from macrophages in apoE-null mice, Circulation 109:r120-r125.
Navab et al. (2004) The oxidation hypothesis of atherogenesis: the role of oxidized phospholipids and L. J. Lipid Res. 45: 993-1007.
Navab et al. (2005) The double jeopardy of HDL. Annals of Medicine 37:173-178.
Navab et al. (2005) Apolipoprotein A-I Mimetic Peptides. Arterioscler Thromb Vasc Biol 25:1325-1331.
Navab et al. (2005) D-4F and Statins Synergize to Render HDL Antiinflammatory in Mice and Monkeys and Cause Lesion Regression in Old Apolipoprotein E-Null Mice. Arterioscler Thromb Vasc Biol 25:1426-1432.
Navab et al. (2005) An oral ApoJ peptide renders HDL anti-inflammatory in Mice and Monkeys and dramatically reduces atherosclerosis in Apolipoprotein E-null mice. Arterioscler Thromb Vasc Biol 25:1932-1937.
Navab et al. (2005) The Role of High-Density Lipoprotein in Inflammation Cardiovascular Medicine 15:158-161.
Navab et al. (2005) An Apolipoprotein A-I Mimetic Works Best in the Presence of Apolipoprotein A-I Circ. Res. 97:1085-1086.
Navab et al. (2005) Oral Small Peptides render HDL antiinflammatory in mice, and monkeys and reduce atherosclerosis in ApoE null mice. Circ Res. 2005, 97:524-532.
Navab M, et al. (2002) Oral administration of an Apo A-I mimetic Peptide synthesized from D-amino acids dramatically reduces atherosclerosis in mice independent of plasma cholesterol. Circulation. 105(3): 290-292.
Navab, M., et al. (2004) Oral D-4F causes formation of pre-beta high-density lipoprotein and improves high-density lipoprotein-mediated cholesterol efflux and reverse cholesterol transport from macrophages in apolipoprotein E-null mice. Circulation 109:3215-3220.
Navab, M., et al., (2004) Apparent Paradox of Low-Fat "Healthy" Diets Increasing Plasma Levels of Oxidized Low-Density Lipoprotein and Lipoprotein(a). Arterioscler Thromb Vasc Biol 24:392-393.
Nguyen et al. (2006) Apolipoprotein A-I-mimetic peptides with antioxidant actions Arch Biochem. Biophys. 451:34-42.
Houstis, N. et al. (2006) Reactive oxygen species have a causal role in multiple forms of insulin resistance. Nature. 440:944-948 (2006).
Nicholls, S.J. et al. Relationship Between Atheroma Regression and Change in Lumen Size After Infusion of Apolipoprotein A-I Milano. J Am Coll Cardiol. (2006) 47(5):992-7.
Nicholls, S.J., Zeng, L., and Hazen, S.L. Formation of dusfunctional high-density lipoprotein by myeloperoxidase. Trrends Crdiovasc. Med. 15: 212-219 (2005).
Nikoulin, I.R. et al. (1998) An Apolipoprotein E Synthetic Peptide Targets to Lipoproteins in Plasma and Mediates Both Cellular Lipoprotein Interactions in Vitro and Acute Clearance of Cholesterol-rich Lipoproteins. In Vivo. J. Clin Invest. 101, 223-234.
Nielsen et al., Sequence-Selective Recognition of DNA by Strand Displacement with a Thymine-Substituted Polyamide. Science, 254, 1497-1500 (1991).
Nievelstein et al. (1991) Lipid accumulation in rabbit aortic intima two hours after bolus infusion of low density lipoprotein: A deep-etch and immuno-localization study of ultra-rapidly frozen tissue. Arteriosclerosis and Thrombosis, 11: 1795-1805.
Nirmala, C. and Puvanakrishnan, R. (1996) Effect of curcumin on certain lysosomal hydrolases in isoproterenol-induced myocardial infarction in rats. Biochem Pharmacol. Jan. 12, 1996;51(1):47-51.
Nirmala et al. (1999) Curcumin treatment modulates collagen metabolism in isoproterenol induced myocardial necrosis in rats. Mol Cell Bioche, Jul. 1999; 197 (1-2):31-37.
Nissen, S.E., et al. Effect of Recombinant ApoA-I Milano on Coronary Atherosclerosis in Patients With Acute Coronary Syndromes: A Randomized Controlled Trial. (2003) JAMA 290:2292-2300.
Nofer, J.R., van der Giet, M., Tolle, M., Wolinska, I., von Wnuck Lipinski, K., Baba, H.A., Tietge, U.J., Godecke, A., Ishii, I., Kleuser, B., Schafers, M., Fobker, M., Zidek, W., Assmann, G., Chun, J., and Levkau, B. HDL induces NO-dependent vasorelaxation via the lysophosphoreceptor S1P3. J. Clin. Invest. 113:569-581 (2004).
Nomoto et al. (1998) Improvement of Intestinal Absorption of Peptide Drugs by Glycosylation: Transport of Tetrapeptide by the Sodium Ion-Dependent D-Glucose Transporter, Jrnl of Phar, Sci, vol. 87, No. 3, Mar. 1998, pp. 326-332.
Norton et al., Targeting Peptide Nucleic Acid-Protein Conjugates to Structural Features Within Duplex DNA Bioorg Med Chem. Apr. 1995; 3(4):437-45.
Nuttall ME, Gimble JM. (2000) Is there a therapeutic opportunity to either prevent or treat osteopenic disorders by inhibiting marrow adipogenesis? Bone. 27(2): 177-184.
Oberhauser et al., Effective incorporation of 2'-O-methyl-oligoribonucleotides into liposomes and enhanced cell association through modification with thiocholesterol. Nucl. Acids Res., 1992, 20, 533-538.
O'Brien et al. (1996) Neovascular expression of E-selectin, intercellular adhesion molecule-1, and vascular cell adhesion molecule-1 in human atherosclerosis and their relation to intimal leukocyte content. Circulation 1996; 93: 672-82.
Obunike, J.C., Pillarasetti, S., Paka, L., Kako, Y., Butteri, M.J., Ho, Y-Y., Wagner, W.D., Yamada, N., Mazzone, T., Deckelbaum, R.J., and Goldberg, I. (2000) The heparin-binding proteins apolipoprotein E and lipoprotein lipase enhance cellular proteoglycan production. Arterio. Thromb. Vasc. Biol. 20:111-118 (2000).
0'Connell BJ, Genest J Jr. High-density lipoproteins and endothelial function. Circulation. 2001;104:1978-1983.
Oguchi et al. (2000) Monoclonal antibody against vascular cell adhesion molecule-1 inhibits neointimal formation after periadventitial carotid artery injury in genetically hypercholesterolemic mice. Arterioscler Thromb Vasc Biol; 20:1729-1736.

(56) References Cited

OTHER PUBLICATIONS

Oram and Heinecke (2005) ATP-Binding Cassette Transporter A1: A Cell Cholesterol Exporter That Protects Against Cardiovascular Disease. Physiol Rev. 85: 1343-1372.
Oram and Yokoyama (1996) Apolipoprotein mediated removal of cellular cholesterol and phospholipids. J Lipid Res. 37: 2473-2491.
Otvos, J.D. et al. Low-density lipoprotein and high-density lipoprotein particle subclasses predict coronary events and are favorably changed by gemfibrozil therapy in the Veterans Affairs High-Density Lipoprotein Intervention Trial. Circulation. (2006);113(12):1556-63.
Ou et al. (2003) AP-4F, antennapedia peptide linked to an amphipathic a helical peptide, increases the efficiency of lipofectamine-mediated gene transfection in endothelial cells. Biochem Biophys Res Commun 2003;305:605-610.
Ou et al. (2003) L-4F, an apolipoprotein A-1 mimetic, dramatically improves vasodilation in hypercholesterolemic and sickle cell disease. Circulation 2003; 107:2337-2341.
Ou et al. (2005) Effects of D-4F on Vasodilation and Vessel Wall Thickness in Hyperholesterolemic LDL Receptor—Null and LDL Receptor/Apolipoprotein A-I Double-Knockout Mice on Western Diet. Circ. Res. 97;1190-1197.
Ou et al., L-4F, an apolipoprotein A-I mimetic, restores nitric oxide and superoxide anion balance in low-density lipoprotein-treated endothelial cells. Circulation 2003; 107:1520-1524.
Owens BJ, Anantharamaiah GM, Kahlon JB, Srinivas RV, Compans RW, Segrest JP. (1990) Apolipoprotein A-I and its amphipathic helix peptide analogues inhibit human immunodeficiency virus-induced syncytium formation. J Clin Invest. 86(4): 1142-1150.
Paigen et al. (1990) Atherosclerosis Susceptibility Differences among Progenitors of Recombinant Inbred Strains of Mice. Arteriosclerosis 10: 316-323.
Paka et al. Apolipoprotein E Containing High Density Lipoprotein Stimulates Endothelial Production of Heparan Sulfate Rich in Biologically Active Heparin-like Domains J. Biol. Chem. 274: 4816-4823 (1999).
Palgunachari et al. (1996) Only the Two End Xelises of Eight Tandem Amphipathic Helical Domaine of Human Apo A-I Have Significant Lipid Affinity. Arteriosclerosis, Thrombosis, & Vascular Biology 16: 328-338.
Palinski et al. (1994) ApoE-Deficient Mice Are a Model of Lipoprotein Oxidation in Atherogenesis: Demonstration of Oxidation-Specific Epitopes in Lesions and High Titers of Autoantibodies to Malondialdehyde-Lysine in Serum. Arteriosclerosis & Thrombosis. 14(4):605-616.
Pan, T.C., et al. Rabbit apolipoprotein A-I mRNA and gene: Evidence that rabbit apolipoprotein A-I is synthesized in the intestine but not in the liver. Eur. J. Biochem. 30:99-104, 1987.
Panizzutti et al. (2001) A New Strategy to Decrease N-methyl-D-aspartate (NMDA) Receptor Coactivation. Inhibition of D-serine Synthesis by Converting Serine Racemase into an Eliminase PNAS 98:5294-5299.
Papo et al. (2002) The consequence of sequence alteration of an amphipathic a-helical antimicrobial peptide and its diastereomers. J. Biol. Chem.2002;277(37): 33913-33921.
Pappenheimer et al. (1994) Intestinal Absorption and Excretion of Octapeptides Composed of D Amino Acids Proc Nail Acad Sci USA 91: 1942-1945.
Pappenheimer et al. (1997) Absorption and Excretion of Undegradable Peptides: Rols of Lipid Solubility and Net Charge. J. Pharmacology & Experimental Therapeutics 280(1):292-300.
Pardridge et al., Vector-mediated delivery of a polyamide ("peptide") nucleic acid analogue through the blood-brain barrier in vivo. Proc Natl Acad Sci USA. 1995; 92(12):5592-6.
Parhami F, Morrow AD, Balucan J, Leitinger N, Watson AD, Tintut Y, Berliner JA, Demer LL. (1997) Lipid oxidation products have opposite effects on calcifying vascular cell and bone cell differentiation. A possible explanation for the paradox of arterial calcification in osteoporotic patients. Arterioscler Thromb Vasc Biol. 17(4): 680-687.

Pasceri et al. Direct proinflammatory effect of C-reactive protein on human endothelial cells. Circulation. 2000;102:2165-2168.
Pasceri etl al. (2001) Modulation of Creactive protein-mediated monocyte chemoattractant protein-1 induction in human endothelial cells by anti-atherosclerosis drugs, Circulation. 2001;103:2531-2534.
Pasqui AL, Puccetti L, Di Renzo M, Bruni F, Camarri A, Palazzuoli A, Biagi F, Servi M, Bischeri D, Auteri A, Pastorelli M. (2005) Structural and functional abnormality of systemic microvessels in cardiac syndrome X. Nutr Metab Cardiovasc Dis. 15(1): 56-64.
Pastan et al. A retrovirus carrying an MDR1 cDNA confers multidrug resistance and polarized expression of P-glycoprotein in MDCK cells. PNAS, 85: 4486 (1988).
Patszty et al., (1994) Apolipoprotein A1 Transgene Corrects Apolipoprotein E Deficiency-induced Atherosclerosis in Mice. J. Clinical Investigation 94:899-903.
Pilone (2000) D-amino acid oxidase: new findings. CMLS, Cell. Mol Life Sci, 57: 1732-1747.
Plump et al. (1994) Human apolipoprotein A-I gene expression increases high density lipoprotein and suppresses stherosclerosis in the apolipoprotein E-deficient mouse. Proc. Natl. Acad. Sci. USA 91:9607-9611.
Pohle K, Mäffert R, Ropers D, Moshage W, Stilianakis N, Daniel WG, Achenbach S. (2001) Progression of aortic valve calcification: association with coronary atherosclerosis and cardiovascular risk factors. Circulation. 104(16): 1927-1932.
Presta, Antibody engineering. Curr. Opin. Struct. Biol., 2:593-596 (1992).
Purdue News (Oct. 2000) 'Microspheres' Offer Promise for Oral Drug Delivery (pp. 1-3).
Purdue News (Sep. 12, 1997) New Oral Insulin Delivery System Shows Promise (pp. 1-3).
Quyyumi, A.A. (1998) Endothelial Function in Health and Disease: New Insights into the Genesis of Cardiovascular Disease Am. J. Med. 105:32S-39S.
Rader, D.J. (2003) Regulation of Reverse Cholesterol Transport and Clinical Implications. Am. J. Cardiology. 92:42J-49J.
Ragot, T. et al. Replication-defective recombinant adenovirus expressing the Epstein-Barr virus (EBV) envelope glycoprotein gp340]220 induces protective immunity against EBV-induced lymphomas in the cottontop tamarin. J Gen. Virology 74:501-507 (1993).
Raha et al. (1988) KRDS a tetra peptide derived from lactotransferrin inhibits binding of monoclonal antibody against glycoprotein Iib-IIIa on ADP-stimulated platelets and megakaryocytes. Blood 1988;72: 172-178.
Rajarathnam et al. 1H NMR studies of interleukin 8 analogs: characterization of the domains essential for function. Biochemistry 33: 6623-6630 (1994).
Rajashree, S. and Puvanakrishnan, R. (1999) Dexamethasone induced alterations in the levels of proteases involved in blood pressure homeostasis and blood coagulation in rats. Mol Cell Biochem. 1999; 197(1-2):203-8.
Rajashree, S. and Puvanakrishnan, R. (1996) Alterations in certain lysosomal glycohydrolases and cathepsins in rats on dexamethasone administration. Mol Cell Biochem. 154(2):165-70.
Rajashree, S. and Puvanakrishnan, R. (1998) Dexamethasone induced alterations in enzymatic and nonenzymatic antioxidant status in heart and kidney of rats, Mol Cell Biochem. 181(1-2):77-85.
Rall, S. C., Jr., et al. (1982) Structural basis for receptor binding heterogeneity of apolipoprotein E from type III hyperlipoproteinemic subjects. PNAS USA. 79, 4696-4700.
Ram et al. In Situ Retroviral-mediated Gene Transfer for the Treatment of Brain Tumors in Rats. Cancer Res. 53:83-88, (1993).
Ramesh et al. (1998) A novel surface-active peptide derivative exhibits in vitro inhibition of platelet aggregation. Peptides. 19:1695-1702.
Ramesh et al. (1998) Effect of a novel tetrapeptide derivative in a model of isoproterenol induced myocardial necrosis. Mol Cell Biochem. 187(1-2):173-82.
Ramprasad et al. Sustained-delivery of an apolipoproteinE-peptidomimetic using multivesicular liposomes lowers serum cholesterol levels. J. Controlled Release, 79: 207-218 (2002).

(56) References Cited

OTHER PUBLICATIONS

Ranganathan et al. (2000) Channel-forming, self-assembling, bishelical amphiphilic peptides: design, synthesis and crystal structure of Py(Aibn)21 n=2, 3, 4. J Peptide Res. 2000 56:416-426.
Rapp, J.H., Lespine, A., Hamilton, R.L., Colyvas, N., Chaumenton, A.H., Tweedie-Hardman, J. Kotite, L., Kunitake, S.T., Havel, R.J., and Kane, J.P. Triglyceride rich lipoproteins isolated by selected affinity antiapolipoprotein B immunosorption from human atherosclerotic plaque. Athero. Thromb. 14:1767-1774 (1994).
Reape and Groot (1999) Chemokines and atherosclerosis. Atherosclerosis. 147:213-225.
Reddy et al. (2001) Human paraoxonase-3 is an HDLassociated enzyme with biological activity similar to paraoxonase-1 protein but is not regulated by oxidized lipids. Arterioscler Thromb Vasc Biol. 21:542-547.
Reddy et al. (2004) Potential role for mitogen-activated protein kinase phosphatase-1 in the development of atherosclerotic lesions in mouse models. Arterioscler Thromb Vasc Biol 2004;24:1676-1681.
Remaley et al. (2003) Synthetic amphipathic helical peptides promote lipid efflux from cells by an ABCA1-dependent and an ABCA1-independent pathway. J. Lipid. Res. 44:828-836.
Rencurel, F., Foretz, M., Kaufmann, M. R., Stroka, D., Looser, R., Leclerc, I., de Silva G., Rutter, G.A., Viollet, B., and Meyer, S.A. Stimulation of AMP-activated protein kinase is essential for the induction of drug metabolizing enzymes by Phenobarbital in human and mouse liver. Molecular Pharmacol. 70:1925-1934, (2006).
Rensen, P.C., and van Berkel, T.J. Apolipoprotein E effectively inhibits lipoprotein lipase-mediated lipolysis of chylomicron-like triglyceride-rich lipid emulsions in vitro and in vivo. J. Biol. Chem. 271:14791-14799 (1996).
Ridker, P. M. (2002) On evolutionary biology, inflammation, infection, and the causes of atherosclerosis. Circulation 2002;105:2-4.
Roessler, J. et al. Adenoviral-mediated gene transfer to rabbit synovium in vivo. Clin. Invest. 92:1085-1092 (1993).
Rogers, et al. The lipid-free structure of apolipoprotein A-I: effects of amino-terminal deletions. (1998) Biochemistry 37:11714-11725.
Roher et al. (1993) 18-Amyloid-(142) is a major component of cerebrovascular amyloid deposits: Implications for the pathology of Alzheimer disease Proc. Natl. Acad. Sci., USA, 90: 10836-10840.
Rohlmann, A., Gotthardt, M., Hammer, R.E., and Herz, J. Inducible activation of hepatic LRP gene by cell mediated recombination confirms role of LRP in clearance of chylomicron remnants. J. Clin. Invest. 101:689-695 (1998).
Roman et al. (2002) Subcortical ischaemic vascular dementia, Lancet Neurol., 1: 426-436.
Rong et al. (2001) Elevating high-density lipoprotein cholesterol in apolipoprotein E-eficient mice remodels advanced atherosclerotic lesions by decreasing macrophage and increasing smooth muscle cell content. Circulation. 104:2447-2452.
Rose, D.J. Characterization of antisense binding properties of peptide nucleic acids by capillary gel electrophoresis. Anal Chem. 1993; 65(24):3545-9.
Rubin et al. (1991) Inhibition of early atherogenesis in transgenic mice by human apolipoprotein AI. Nature 353:265-267.
Sabbatini et al. (2001) Microanatomical changes of intracerebral arteries in spontaneously hypertensive rats: a model of cerebrovascular disease of the elderly Mech. Aging & Dev., 122: 1257-1268.
Saison-Behmoaras et al., Short modified antisense oligonucleotides directed against Ha-ras point mutation induce selective cleavage of the mRNA and inhibit T24 cells proliferation. EMBO J., 1991, 10, 1111-1118.
Sandana Mala JG, Kamini NR, Puvanakrishnan R. Strain improvement of *Aspergillus niger* for enhanced lipase production. J Gen Appl Microbiol. Aug. 2001; 47 (4):181-186.
Sattler W, Stocker R. Greater selective uptake by Hep G2 cells of highdensity lipoprotein cholesteryl ester hydroperoxides than of unoxidized cholesterylesters. Biochem J. 1993;294:771-778.

Schmitz-Peiffer C. Signaling aspects of insulin resistance in skeletal muscle: mechanisms induced by lipid oversupply. Cell Signal. Oct. 2000;12(9-10):583- 94. Review.
Schnolzer et al. Constructing proteins by dovetailing unprotected synthetic peptides: backbone-engineered HIV protease. Science 256: 221 (1992).
Schonbeck, U. and Libby, P. (2004) Inflamation, Immunity, and HMG-CoA Reductase Inhibitors, Statins as Anti inflammatory Agents? Circulation 109(21 Suppl 1): II18-II26.
Schonfeld et al. Lipolysis produces changes in the immunoreactivity and cell reactivity of very low density lipoproteins. J. Clin. Invest. 64: 1288-1297 (1979).
Segrest et al, (1974) A Molecular Theory of Lipid-Protein Interaction in the Plasma Lipoproteins. FEBS Left. 38: 247-253.
Segrest et al. (1992) The Amphipathic Helix in the Exchangeable Apolipoproteins: A Review of Secondary Structure and Function J Lipid Research 33:141-166.
Segrest et al. (1990) Proteins: Structure, Function and Genetics, 8: 103-117.
Segrest et al., Apolipoprotein B-100: conservation of lipid-associating amphipathic secondary structural motifs in nine species of vertebrates. J. Lipid. Res. 39:85-102 (1998).
Segrest et al., Structure of apolipoprotein B-100 in low density lipoproteins. J. Lipid. Res. 42, pp. 1346-1367 (2001).
Segrest et al. apoB-100 has a pentapartite structure composed of three amphipathic alpha-helical domains alternating with two amphipathic beta-strand domains. Detection by the computer program LOCATE. (1994) Arteriosclerosis and Thrombosis 14:1674-1685.
Senior (1999) New options developed for needle-free drug delivery. Lancet, 1998:354:1102.
Seth, et al., Role of a low-pH environment in adenovirus enhancement of the toxicity of a Pseudomonas exotoxin-epidermal growth factor conjugate. J. Virol. 51:650-655 (1984).
Seth, et al., Evidence that the Penton Base of Adenovirus Is Involved in Potentiation of Toxicity of Pseudomonas Exotoxin Conjugated to Epidermal Growth Factor. Mol. Cell. Biol. 4:1528-1533 (1984).
Shah et al. (1998) Effects of recombinant apolipoprotein A-I(Mi.lano) on aortic atherosclerosis in apolipoprotein E-deficient mice. Circulation, 1998:97(8): 780-785.
Shah et al. (2001) High-dose recombinant apolipoproteins A-Imilano mobilizes tissue cholesterol and rapidly reduces plaque lipid and macrophase content in apolipoprotein Edeficient mice: potential implications ofr acute plaque stabilization. Circulation. 2001; 103:3047-3050.
Shah, P.K. et al. Apolipoprotein A-I mimetic peptides: potential role in atherosclerosis management. . (2005) Trends Cardiovasc. Med. 15:291-296.
Shea et al., Synthesis, hybridization properties and antiviral activity of lipid-oligodeoxynucleotide conjugates. Nucl. Acids Res., 1990, 18, 3777-3783.
Shen, B.W., Scanu, A.M., and Kezdy, F.J. Structure of human serum lipoproteins inferred from compositional analysis. Proc. Natl. Acad. Sci. U.S.A. 74:837-841 (1977).
Shih et al. (1999) Minimally modified low-density lipoprotein induces monocyte adhesion to endothelial connecting segment-1 by activating beta integrin. J Clin Invest 1999; 103:613-625.
Shih et al. (2000) Combined serum paraoxonase/apolipoprotein E knockout mice exhibit increased lipoprotein oxidation and atherosclerosis. I Biol. Chem., 2000; 275:17527-17535.
Shimono, H. N., et al., Plasma lipoprotein metabolism in transgenic mice overexpressing apolipoprotein E. Accelerated clearance of lipoproteins containing apolipoprotein B. (1992) Eur. J. Clin. Invest. 90, 2084-2991.
Shishehbor et al. (2003) Association of nitrotyrosine levels with cardiovascular disease and modulation by statin therapy. JA 2003:289:1675-1680.
Silkensen et al., Identification of clusterin sequences mediating renal tubular cell interactions; J Peptide Res., 1999,54:449-547.
Singh et al. (2000) Innate defences against viremia, Rev Med Virol 2000, 10:395-403.
Sonntag et al. (1997) Decreases in Cerebral Microvasculature with Age Are Associated with the Decline in Growth Hormone and insulin-Like Growth Factorl, Endocrinol 138(8): 3515-3520.

(56) References Cited

OTHER PUBLICATIONS

Sorescu et al. NAD(P)H oxidases and their relevance to atherosclerosis. Trends Cardiovas Med 2001;11:124-131.
Sparrow, C.P., Baffle, J., Lam, M.H., Lund, E.G., Adams, A.D., Fu, X, Haynes, N., Jones, A.B., Macnaul, K.L., Ordeyka, J., Singh, S., Wang, J., Zhou, G., Moller, D.E., Wright, S.D., and Menke, J.G. A potent synthetic LXR agonist is more effective than cholesterol loading at inducing ABC A1-mRNA and stimulating cholesterol efflux. J. Biol. Chem. 277:10021-10027 (2002).
Spieker et al. (2002) High-density lipoprotein restores endothelial function in hypercholesterolemic men. Circulation. 2002;105:1399-1402.
Sprecher et al. (1993) The Low HDL Cholesterol/ High Triglyceride Trait Arterioscler. Thromb. 13: 495-504.
Springer, T.A. (1990) Adhesion receptors of the immune system. Nature 1990; 346:425-434.
Srinivas et al. (1990) Antivrial Effects of Apolipoprotein A-I and Its Synthetic Amphipathic Peptide Analogs. Virology. 176:48-57.
Stannard et al. (2001) Inability of plasma high-density lipoproteins to inhibit cell adhesion molecule expression in human coronary artery endothelial cells. Atherosclerosis. 2001;154:31-38.
Steplewski et al. Isolation and characterization of anti-monosialoganglioside monoclonal antibody 19-9 class-switch variants. PNAS 82: 8653 (1985).
Sugatani et al. (1996) High-density lipoprotein inhibits the synthesis of platelet-activating factor in human vascular endothelial cells. J Lipid Mediators Cell Signal. 1996:13:73-88.
Sumitra et al. (2001) Experimental myocardial necrosis in rats: role of arjunolic acid on platelet aggregation, coagulation and antioxidant status. Mol Cell Biochem. 2001; 224(1-2).
Suresh, R. et al. (1992) Alterations in human gingival glycosaminoglycan pattern in inflammation and in phenytoin induced overgrowth. Mol Cell Biochem. Oct. 7, 1992; 115(2):149-54.
Svensson, U. Role of vesicles during adenovirus 2 internalization into HeLa cells. J. Virology 55:442-449 (1985).
Swain, J. et al. Prooxidant iron and copper, with ferroxidase and xanthine oxidase activities in human atherosclerotic material. (1995) FEBS Lett. 368(3):513-515.
Swarnakar et al. The apolipoprotein E-dependent low density lipoprotein cholesteryl ester selective uptake pathway in murine adrenocortical cells involves chondroitin sulfate proteoglycans and an alpha 2-macroglobulin receptor. J. Biol. Chem. 276: 21121-21126 (2001).
Swift, L.L. et al., A recycling pathway for resecretion of internalized apolipoprotein E in liver cells. (2001) J. Biol. Chem. 276:22965-22970.
Takahashi, S.Y., Kawarabayasi, T., Nakai, J., Sakai, and Yamamoto, T. Rabbit very low density lipoprotein receptor-a low density receptor like protein with distinct ligand specificity. Proc. Natl. Acad. Sci. U.S.A. 89: 9252-9256 (1992).
Tan et al. (1997) A Novel, highly Efficient Peptide-HLA Class TH:ca Binding Assay using unfolded heavy change molecules: Identification of HIV-1 Derived Peptides that Bind to FILA-A 0201 and HLA-A 0301, J Immunol Methods, 205:201-209.
Thomas, Eric C. (1999) Brain macrophages: on the role of pericytes and perivascular cells, Brain Res. Rev., 31: 42-57.
Throngate, F.E. et al., Low levels of extrahepatic nonmacrophage ApoE inhibit atherosclerosis without correcting hypercholesterolemia in ApoE-deficient mice. (2000) Arterio. Thromb. Vasc. Biol. 20:1939-1945.
Tian et al. (2002) Structure-affinity relationships in the gp41 ELDKWA epitope for the HIV-1 neutralizing monoclonal antibody 2F5: effects of side-chain and backbone modifications and conformational constraints, J. Peptide Res. 59, 2002, 264-276.
Toyoda, Kazunori et al (1997) Effect of Aging on Regulation of Brain Stem Circulation During hypotension, J. Cerebral Blood Flow & Metab., 17(6): 680-685.
Triaggiai et al., An efficient method to make human monoclonal antibodies from memory B cells: potent neutralization of SARS coronavirus, Nat Med. Aug. 2004;10(8):871-5 (2004).
Tsai et al. (1998) D-serine added to antipsychotics for the treatment of schizophrenia. Biol. Psychiatry, 44: 1081-1089.
Tsao et al. (2001) Hibernation-induction Peptide and Cell Death: [D-Ala2, D-Leulenkephalin Blocks Bax-related Apoptotic Processes. European Journal of Pharmacology 428:149-151.
Tsimikas et al. (2001) Measuring Circulating Oxidized Low-Density Lipoprotein to Evaluate Coronary Risk. Circulation 103:1930-1932.
Tward et al. (2002) Decreased atherosclerotic lesion formation in human serum paraoxonase transgenic mice, Circulation 2002;106:484-490.
Tytler et al. Reciprocal effects of apolipoprotein and lytic peptide analogs on membranes. Cross-sectional molecular shapes of amphipathic alpha helixes control membrane stability. J. Biol. Chem. 268: 2212-2218 (1993).
Valabhji, J., et al., (2001) High-density lipoprotein composition and paraoxonase activity in Type I diabetes. Clinical Science. 101:659-670.
Van Leeuwen R, Klaver CC, Vingerling JR, Hofman A, de Jong PT. (2003) Epidemiology of age-related maculopathy: a review. Eur J Epidemiol. (9): 845-854.
Van Lenten et al. (2002) Influenza infection promotes macrophage traffic into arteries of mice that is prevented by D-4F, an apolipoprotein A-I mimetic peptide. Cir 2002, 106:1127-1132.
Van Lenten, BJ. et al. (2001) High-density lipoprotein loses its anti-inflammatory properties during acute influenza A infection, Circulation 2001; 103:2283-2288.
Van Lenten, et al. (1995) Anti-inflammatory HDL Becomes Pro-inflammatory during the Acute Phase Response, J. Clin. Invest., vol. 96, Dec. 1995, 2758-2767.
Van Lenton et al. (2004). D-4F an ApoA-I mimetic peptide inhibits the inflammatory response induced by influenza A infection of human type II pneumocytes, Circulation: 110:3252-3258.
Varga et al., Infectious entry pathway of adenovirus type 2. J. Virology. 65:6061-6070 (1991).
Venugopal et al. (2002) Demonstration that C-reactive protein decreases eNOS expression and bioactivity in human aortic endothelial cells. Circulation. 2002; 106:1439-41.
Verhoeyen et al., Reshaping human antibodies: grafting an antilysozyme activity. Science, 239:1534-1536 (1988).
Vinters et al. (1998) Secondary microvascular degeneration in amyloid angiopathy of patients with hereditary cerebral hemorrhage with amyloidosis, Dutch type (HCHWA-D), Acta Neuropathol. 95: 235-244.
Vovenko, Eugene (1999) Distribution of oxygen tension on the surface of arterioles, capillaries and venules of brain cortex and in tissue in normoxia; an experimental study on rats. Eur. J. Physiol., 437: 617-623.
Wake AK, Datta G, Palgunachari MN, Mishra VK, Anatharamaiah GM, White RG. Apolipoprotein A-1 mimetic peptide retains function after oxidant exposure. Proc ASME 2008 Summer Bioenginerring Conference (Marco Island, Florida), Jun. 25-29, 2008, SBC2008-189660.
Walpola et al. (1995) Expression of ICAM-1 and VCAM-1 and monocyte adherence in arteries exposed to altered shear stress. Arterioscler Thromb Vasc Biol, 15:2-10.
Watson et al. (1995) Effect of platelet activating factor-acetylhydrolase on the formation and action of minimally oxidized-low gensitylipoprotein. J Clin Invest. 1995; 95:774-782.
Watson et al. (1995) Protective effect of high density lipoprotein associated paraoxonase. Inhibition of the biological activity of minimally oxidized low density lipoprotein. J Clin Invest 1995;96:2882-2891.
Watts et al. Dyslipoproteinaemia and hyperoxidative stress in the pathogenesis of endothelial dysfunction in non-insulin dependent diabetes mellitus: an hypothesis. Atherosclerosis 141: 17-30 (1998).
Weers PM, Narayanaswami V, Ryan RO. (2001) Modulation of the lipid binding properties of the N-terminal domain of human apolipoprotein E3. Eur J Biochem. 268(13): 3728-3735.
Wei et al. (1998) Antioxidants Inhibit ATP-Sensitive Potassium Channels in Cerebral Arterioles, Stroke, 29: 817-823.

(56) References Cited

OTHER PUBLICATIONS

White, C. R., et al., Superoxide and peroxynitrite in atherosclerosis. (1994) Proc. Natl. Acad. Sci. USA. 91:1044-1048.

White, C.R., et al., Circulating plasma xanthine oxidase contributes to vascular dysfunction in hypercholesterolemic rabbits. (1996) Proc. Natl. Acad. Sci. (USA) 93: 8745-8749.

Wickham et al., Integrins alpha v beta 3 and alpha v beta 5 promote adenovirus internalization but not virus attachment. Cell 73:309-319 (1993).

Wilson et al. Three-dimensional structure of the LDL receptor-binding domain of human apolipoprotein E. Science 252: 1817-1822 (1991).

Witztum, J.L. et al. Role of oxidized low density lipoprotein in atherogenesis. J. Clin Invest. 88:1785-1792 (1991).

Wolff JA, Malone RW, Williams P, Chong W, Acsadi G, Jani A, Felgner PL. (1990) Direct gene transfer into mouse muscle in vivo. Science, 247(4949 Pt 1): 1465-8.

Wool GD, Reardon CA, Getz GS. (2008) Apolipoprotein A-I mimetic peptide helix number and helix linker influence potentially anti-atherogenic properties. J Lipid Res. 49(6): 1268-1283.

Wool GD, Vaisar T, Reardon CA, Getz GS. (2009) An apoA-I mimetic peptide containing a proline residue has greater in vivo HDL binding and anti-inflammatory ability than the 4F peptide. J Lipid Res. 50(9): 1889-1900.

Wu, G., Yuan, J., and Hunninghake, D.B. Effect of human apolipoprotein E isoforms on plasma lipids, lipoproteins and apolipoproteins in apolipoprotein E deficient mice. Atherosclerosis. 141:287-296 (1998).

Xia et al. (1999) High density lipoproteins (HDL) interrupt the sphingosine kinase signaling pathway. A possible mechanism for protection against atherosclerosis by HDL. J Biol Chem. 274:33143-33147.

Yamada, et al., Increased clearance of plasma cholesterol after injection of apolipoprotein E into Watanabe heritable hyperlipidemic rabbits. (1989) Proc. Natl. Acad. Sci. U.S.A. 86, 665-669.

Yamashita et al. (2000) Molecular mechanisms, lipoprotein abnormalities and atherogenicity of hyperalphalipoproteinemia. Atherosclerosis. 152:271-285.

Yan et al. (2004) PLTP deficiency improves the anti-inflammatory properties of HDL and reduces the ability of LDL to induce monocyte chemotactic activity. J Lipid Res. 45:1852-1858.

Yancey et al. (1995) Efflux of Cellular Cholesterol and Phospholipid to Lipid-free Apolipoproteins and Class A Amphipathic Peptides. Biochemistry, 34: 7955-7965.

Yip KP, Marsh DJ. (1997) An Arg-Gly-Asp peptide stimulates constriction in rat afferent arteriole. Am J Physiol. 273(5 Pt 2): F768-F776.

Yla-Herttuala, S. et al. Macrophages and smooth muscle cells express lipoprotein lipase in human and rabbit atherosclerotic lesions. (1991) Proc. Natl. Acad. Sci. U.S.A. 88:10143-10147.

Yokoyama, et al. The mechanism of activation of lecithin:cholesterol acyltransferase by apolipoprotein A-I and an amphiphilic peptide. J. Biol. Chem. 255:7333-7339, 1980.

Yu et al. Tissue Doppler imaging is superior to strain rate imaging and postsystolic shortening on the prediction of reverse remodeling in both ischemic and nonischemic heart failure after cardiac resynchronization therapy. (2004) Circulation. 110:66-73.

Yuan and Altman, Substrate recognition by human RNase P: identification of small, model substrates for the enzyme. EMBO J. 14:159-168 (1995).

Yuan et al., Targeted cleavage of mRNA by human RNase P. Proc. Natl. Acad. Sci. USA 89:8006-8010 (1992).

Yui et al. (1988) Serum prostacyclin stabilizing factor is identical to apolipoprotein A-I (Apo A-I). A novel function of Apo A-1, J. Clin. Invest. 82: 803-807.

Zabner et al., Adenovirus-mediated gene transfer transiently corrects the chloride transport defect in nasal epithelia of patients with cystic fibrosis. Cell 75:207-216 (1993).

Zabner et al., Safety and efficacy of repetitive adenovirus-mediated transfer of CFTR cDNA to airway epithelia of primates and cotton rats. Nature Genetics. 6:75-83 (1994).

Zaiou et al., Apolipoprotein E;-low density lipoprotein receptor interaction. Influences of basic residue and amphipathic alpha-helix organization in the ligand. Journal of Lipid Research. 41: 1087-1095 (2000).

Zeiher at al. (1994) Coronary atherosclerotic wall thickening and vascular reactivity in humans. Elevated high-density lipoprotein levels ameliorate abnormal vasoconstriction in early atherosclerosis. Circulation. 89;25252532.

Zhang Z, et al. (2007) D-4F, An Apolipoprotein A-I Mimetic Peptide, Prevents Endothelial Dysfunction Induced by Myeloperoxidase-Derived Hypochlorous Acid. Meeting Abstract 21: 706.11, FASEB J.

Zhang, C., et al. L-arginine chlorination products inhibit endothelial nitric oxide production. J. Biol. Chem. 276: 27159-27165 (2001).

Zhang, Renliang et al (2002) Myeloperoxidase functions as a major enzymatic catalyst for initiation of lipid peroxidation at sites of inflammation. J Biol Chem 2002;277:46116-46122.

Zhang, S. H., et al., Spontaneous hypercholesterolemia and arterial lesions in mice lacking apolipoprotein E. Science, 1992, 258, 468-471.

Zhang, Wei-Jian et al. (2002) Lack of inhibitory effect of HDL on TNFalpha-induced adhesion molecule expression in human aortic endothelial cells. Atherosclerosis 2002; 165:241-249.

Zhao et al. (2002) Selective interleukin-12 synthesis defect in 12/15-lipoxygenase deficient macrophages associated with reduced atherosclerosis in a mouse model of familial hypercholesterolemia. J Biol Chem. 277:35350-35356.

Zhu, B., Kubel, D.G., Witte, D.P., and Hui, D.Y. Apolipoprotein E inhibits neointimal hyperplasia after arterial injury in mice. Am. J. Pathol. 157:1839-48 (2000).

Zhu, Y., and Hui, D.Y. Apolipoprotein E binding to low density lipoprotein receptor related protein-1 inhibits cell migration via activation of cAMP dependent protein kinase A. J. Biol. Chem. 278:36257-63 (2003).

Zilversmit, D.E. (1979) Atherogenesis: a postprandial phenomenon.. Circulation 60:473-485.

Zuker, M. On finding all suboptimal foldings of an RNA molecule. Science 244:48-52, 1989.

Restriction Requirement issued Sep. 12, 2002 for U.S. Appl. No. 09/645,454.

Response to Restriction Requirement filed Dec. 12, 2002 for U.S. Appl. No. 09/645,454.

Non-Final Office Action issued Jan. 22, 2003 for U.S. Appl. No. 09/645,454.

Response to Non-Final Office Action filed May 27, 2003 for U.S. Appl. No. 09/645,454.

Notice of Allowance issued Jun. 25, 2003 for U.S. Appl. No. 09/645,454.

Restriction Requirement issued Feb. 20, 2003 for U.S. Appl. No. 09/896,841.

Response to Restriction Requirement filed Aug. 25, 2003 for U.S. Appl. No. 09/896,841.

Non-Final Office Action issued Oct. 21, 2003 for U.S. Appl. No. 09/896,841.

Response to Non-Final Office Action filed Apr. 23, 2004 for U.S. Appl. No. 09/896,841.

Final Office Action issued May 7, 2004 for U.S. Appl. No. 09/896,841.

RCE/Response to Final Office Action filed Nov. 15, 2004 for U.S. Appl. No. 09/896,841.

Notice of Allowance issued Dec. 20, 2004 for U.S. Appl. No. 09/896,841.

International Search Report issued May 17, 2002 for PCT App. No. PCT/US01/26457.

International Preliminary Examination Report issued Mar. 4, 2003 for PCT App. No. PCT/US01/26457.

Restriction Requirement issued Jul. 15, 2003 for U.S. Appl. No. 10/187,215.

Response to Restriction Reqirement filed Nov. 19, 2003 for U.S. Appl. No. 10/187,215.

(56) References Cited

OTHER PUBLICATIONS

Non-Final Office Action issued Jan. 8, 2004 for U.S. Appl. No. 10/187,215.
Response to Non-Final Office Action filed Jul. 12, 2004 for U.S. Appl. No. 10/187,215.
Non-Final Office Action issued Aug. 26, 2004 for U.S. Appl. No. 10/187,215.
Response to Non-Final Office Action filed Feb. 28, 2005 for U.S. Appl. No. 10/187,215.
Final Office Action issued Apr. 11, 2005 for U.S. Appl. No. 10/187,215.
RCE/Response to Final Office Action filed Oct. 7, 2005 for U.S. Appl. No. 10/187,215.
Non-Final Office Action issued Oct. 28, 2005 for U.S. Appl. No. 10/187,215.
Response to Non-Final Office Action filed Mar. 20, 2006 for U.S. Appl. No. 10/187,215.
Notice of Allowance issued May 1, 2006 for U.S. Appl. No. 10/187,215.
Restriction Requirement issued Feb. 19, 2004 for U.S. Appl. No. 10/273,386.
Response to Restriction Requirement filed May 3, 2004 for U.S. Appl. No. 10/273,386.
Non-Final Office Action issued Jun. 21, 2004 for U.S. Appl. No. 10/273,386.
Response to Non-Final Office Action filed Dec. 21, 2004 for U.S. Appl. No. 10/273,386.
Final Office Action issued Feb. 2, 2005 for U.S. Appl. No. 10/273,386.
RCE/Response to Final Office Action filed Aug. 15, 2005 for U.S. Appl. No. 10/273,386.
Non-Final Office Action issued Sep. 7, 2005 for U.S. Appl. No. 10/273,386.
Response to Non-Final Office Action filed Jan. 20, 2006 for U.S. Appl. No. 10/273,386.
Final Office Action issued Mar. 31, 2006 for U.S. Appl. No. 10/273,386.
Response to Final Office Action filed Jul. 3, 2006 for U.S. Appl. No. 10/273,386.
Notice of Allowance issued Aug. 20, 2006 for U.S. Appl. No. 10/273,386.
Restriction Requirement issued Nov. 9, 2004 for U.S. Appl. No. 10/423,830.
Response to Restriction Requirement filed Mar. 1, 2005 for U.S. Appl. No. 10/423,830.
Non-Final Office Action issued Apr. 18, 2005 for U.S. Appl. No. 10/423,830.
Response to Non-Final Office Action filed Oct. 19, 2005 for U.S. Appl. No. 10/423,830.
Final Office Action issued Nov. 15, 2005 for U.S. Appl. No. 10/423,830.
RCE/Response to Final Office Action filed Oct. 18, 2006 for U.S. Appl. No. 10/423,830.
Notice of Allowance issued Nov. 21, 2006 for U.S. Appl. No. 10/423,830.
Restriction Requirement issued Aug. 21, 2007 for U.S. Appl. No. 11/407,390.
Response to Restriction Requirement filed Nov. 23, 2007 for U.S. Appl. No. 11/407,390.
Non-Final Office Action issued Jan. 17, 2008 for U.S. Appl. No. 11/407,390.
Response to Non-Final Office Action filed Jul. 7, 2008 for U.S. Appl. No. 11/407,390.
Final Office Action issued Sep. 11, 2008 for U.S. Appl. No. 11/407,390.
RCE/Response to Final Office Action filed Jul. 13, 2009 for U.S. Appl. No. 11/407,390.
*Ex Parte Quayle* Action issued Aug. 14, 2009 for U.S. Appl. No. 11/407,390.
Response to *Ex Parte Quayle* Action filed Oct. 14, 2009 for U.S. Appl. No. 11/407,390.
Notice of Allowance issued Dec. 2, 2009 for U.S. Appl. No. 11/407,390.
International Search Report and Written Opinion issued Sep. 1, 2009 for PCT App. No. PCT/US2009/033415.
International Preliminary Opinion on Patentability issued Aug. 19, 2010 for PCT App. No. PCT/US2009/033415.
Preliminary Amendment filed Nov. 13, 2003 for U.S. Appl. No. 10/712,447.
Preliminary Amendment filed May 14, 2004 for U.S. Appl. No. 10/712,447.
Restriction Requirement issued Oct. 14, 2005 for U.S. Appl. No. 10/712,447.
Restriction Requirement issued Feb. 16, 2006 for U.S. Appl. No. 10/712,447.
Response to Restriction Requirement filed Mar. 16, 2006 for U.S. Appl. No. 10/712,447.
Non-Final Office Action issued May 31, 2006 for U.S. Appl. No. 10/712,447.
Response to Non-Final Office Action filed Nov. 29, 2006 for U.S. Appl. No. 10/712,447.
Final Office Action issued Mar. 2, 2007 for U.S. Appl. No. 10/712,447.
Response to Final Office Action filed Jul. 31, 2007 for U.S. Appl. No. 10/712,447.
Advisory Action issued Aug. 13, 2007 for U.S. Appl. No. 10/712,447.
Response to Advisory Action and Final Office Action filed Sep. 4, 2007 for U.S. Appl. No. 10/712,447.
Non-Final Office Action issued Nov. 19, 2007 for U.S. Appl. No. 10/712,447.
Response after Non-Final Office Action filed Mar. 12, 2008 for U.S. Appl. No. 10/712,447.
Non-Final Office Action issued Jun. 13, 2008 for U.S. Appl. No. 10/712,447.
Response to Non-Final Office Action filed Sep. 3, 2008 for U.S. Appl. No. 10/712,447.
Terminal Disclaimer filed Sep. 3, 2008 for U.S. Appl. No. 10/712,447.
Terminal Disclaimer accepted Feb. 12, 2009 for U.S. Appl. No. 10/712,447.
Notice of Allowance with Interview Summary and Examiner's Amendment issued Feb. 24, 2009 for U.S. Appl. No. 10/712,447.
Issue Notification issued Jul. 1, 2009 for U.S. Appl. No. 10/712,447.
Request for Certificate of Correction filed Aug. 3, 2009 for U.S. Appl. No. 10/712,447.
Certificate of Correction issued Sep. 8, 2009 for U.S. Appl. No. 10/712,447.
Restriction Requirement issued Jun. 26, 2008 for U.S. Appl. No. 11/405,601.
Response to Restriction Requirement filed Jul. 25, 2008 for U.S. Appl. No. 11/405,601.
Miscellaneous Action issued Oct. 24, 2008 for U.S. Appl. No. 11/405,601.
Response to Restriction Requirement filed Mar. 17, 2009 for U.S. Appl. No. 11/405,601.
Non-Final Office Action issued Jun. 10, 2009 for U.S. Appl. No. 11/405,601.
Response to Non-Final Rejection filed Oct. 9, 2009 for U.S. Appl. No. 11/405,601.
Final Office Action issued Jan. 29, 2010 for U.S. Appl. No. 11/405,601.
Response to Final Office Action filed Sep. 28, 2010 for U.S. Appl. No. 11/405,601.
Notice of Allowance issued Sep. 9, 2011 for U.S. Appl. No. 11/405,601.
International Search Report issued Nov. 17, 2005 for PCT Application No. PCT/US2003/036268.
Examiner's First Report issued Apr. 30, 2008 for Australian Application No. 200390825.
First Statement of Proposed Amendments filed Sep. 18, 2008 for Australian Application No. 200390825.

(56) References Cited

OTHER PUBLICATIONS

Notice of Acceptance issued Oct. 14, 2008 for Australian Application No. 200390825.
Grant of Request for Leave to Amend issued Jul. 3, 2009 for Australian Application No. 200390825.
First Examination Report issued Sep. 18, 2007 for New Zealand Application No. 541504.
Response to Examination Report filed Jul. 16, 2008 for New Zealand Application No. 541504.
Examination Report issued for Aug. 5, 2008 New Zealand Application No. 541504.
Response to Examination Report filed Dec. 23, 2008 for New Zealand Application No. 541504.
Examination Report issued Jan. 22, 2009 for New Zealand Application No. 541504.
Response to Examination Report filed Mar. 18, 2009 for New Zealand Application No. 541504.
Examination Report and Notice of Acceptance of Completed Specification issued Apr. 7, 2009 for New Zealand Application No. 541504.
Letters Patent issued Aug. 13, 2009 for New Zealand Application No. 541504.
Office Action issued Aug. 10, 2009 for Canadian Application No. 2,514,303.
Response to Office Action filed Feb. 10, 2010 for Canadian Application No. 2,514,303.
Office Action issued Oct. 6, 2010 for Canadian Application No. 2,514,303.
Response to Office Action filed Mar. 29, 2011 for Canadian Application No. 2,514,303.
Preliminary Amendment filed Mar. 16, 2010 for U.S. Appl. No. 12/675,073.
Preliminary Amendment filed Mar. 12, 2010 for U.S. Appl. No. 12/675,089.

\* cited by examiner

PEPTIDES AND PEPTIDE MIMETICS TO TREAT PATHOLOGIES ASSOCIATED WITH EYE DISEASE

This application claims priority to and benefit of U.S. Ser. No. 60/697,495, filed Jul. 7, 2005 and to U.S. Ser. No. 60/676,431 filed on Apr. 29, 2005, both of which are incorporated herein by reference in their entirety for all purposes.

This application is a Continuation-in-Part of U.S. Ser. No. 11/407,390, filed on Apr. 18, 2006, now U.S. Pat. No. 7,723,303, which is a Continuation-in-Part of U.S. Ser. No. 10/423,830 filed on Apr. 25, 2003, now issued U.S. Pat. No. 7,199,102, which is a Continuation-in-Part of U.S. Ser. No. 10/273,386 filed on Oct. 16, 2002, now issued U.S. Pat. No. 7,166,578, which is a Continuation-in-Part of PCT/US01/26457 filed on Aug. 24, 2001 and a Continuation-in-Part of U.S. Ser. No. 10/187,215, filed on Jun. 28, 2002, now issued U.S. Pat. No. 7,144,862, which is a Continuation-in-Part of U.S. Ser. No. 09/896,841, filed on Jun. 29, 2001, now issued U.S. Pat. No. 6,933,279, which is a Continuation-in-Part of U.S. Ser. No. 09/645,454, filed on Aug. 24, 2000, now issued U.S. Pat. No. 6,664,230, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No: HL30568 and GrantNo: ey 06109 awarded by the National Heart Blood Lung Institute of the National Institutes of Health and the National Eye Institute. The Government of the United States of America has certain rights in the invention.

FIELD OF THE INVENTION

This invention relates to the field of atherosclerosis and other conditions characterized by inflammation and/or the formation of various oxidized species. In particular, this invention pertains to the identification of classes of active agents that are orally administrable and that ameliorate one or more symptoms of conditions characterized by an inflammatory response and/or the formation of various oxidized species. This invention also relates to the field of macular degeneration. In particular, this invention pertains to methods of treating macular degeneration as well as methods of ameliorating a symptom of macular degeneration.

BACKGROUND OF THE INVENTION

The introduction of statins (e.g., Mevacor®, Lipitor®, etc.) has reduced mortality from heart attack and stroke by about one-third. However, heart attack and stroke remain the major cause of death and disability, particularly in the United States and in Western European countries. Heart attack and stroke are the result of a chronic inflammatory condition, which is called atherosclerosis.

Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include the amount and type of fat (saturated and polyunsaturated fatty acids), the amount of cholesterol, amount and type of fiber, and perhaps the amounts of vitamins such as vitamin C and D and minerals such as calcium.

Low density lipoprotein (LDL) oxidation has been strongly implicated in the pathogenesis of atherosclerosis. High density lipoprotein (HDL) has been found to be capable of protecting against LDL oxidation, but in some instances has been found to accelerate LDL oxidation. Important initiating factors in atherosclerosis include the production of LDL-derived oxidized phospholipids.

Normal HDL has the capacity to prevent the formation of these oxidized phospholipids and also to inactivate these oxidized phospholipids once they have formed. However, under some circumstances HDL can be converted from an anti-inflammatory molecule to a pro-inflammatory molecule that actually promotes the formation of these oxidized phospholipids.

It has been suggested that HDL and LDL function as part of the innate immune system (Navab et al. (2001) Arterioscler. Thromb. Vasc. Biol., 21: 481-488). The generation of anti-inflammatory HDL has been achieved using class A amphipathic helical peptides that mimic the major protein of HDL, apolipoprotein A-I (apo A-I) (see, e.g., WO 02/15923).

Age-related macular degeneration (AMD) is the most frequent cause of legal blindness in the elderly in industrial countries (Van Leeuwen et al. (2003) European Journal of Epidemiology 18: 845-854). It is a heterogeneous disease, which is characterized by progressive loss of central, high acuity vision. For the patient it compromises dramatically quality of life, since they lose their ability to read, to recognize faces and day-to-day tasks become major obstacles. According to the WHO a total of 30-50 million individuals are affected and about 14 million people are blind or severely visually impaired due to AMD (Gehrs et al., (2006) Annals of Medicine 38:450-471).

The most prominent clinical and histopathological lesions of AMD involve the choriocapillaris, Bruch's membrane, and the retinal pigment epithelium (RPE) (Ambati et al. (2003) Survey of Opthalmology 48:257-293). The choriocapillaris is a highly specialized capillary plexus with the highest blood flow rate in the body which interacts with the highly metabolic active RPE. The RPE forms the outer blood-retina barrier and supplies the photoreceptors, the sensory cells in the eye, with nutriments as well as phagocytes daily shed outer photoreceptor segments which are degraded and partially recycled. Under normal conditions unrecycled end products are rendered into the choriocapillaris. Bruch's membrane is a five layer connective tissue between the RPE and choriocapillaris resembling an arterial intima in its function (Curcio et al. (2001) Invest Opthalmol Vis Sci 42:265-274). With age Bruch's membrane undergoes distinctive degenerative changes. One major characteristic feature next to thickening is the accumulation of neutral lipids, which build up a diffusion barrier between the RPE and choriocapillaris compromising RPE and photoreceptor function (Curcio et al. (2001) Invest Opthalmol Vis Sci 42:265-274; Pauleikhoff et al. (1990) Opthalmology 97:171-178; Moore et al. (1995) Invest Opthalmol Vis Sci 36:1290-1297).

In early stages of AMD an additional deposition of debris is observed between the basal membrane of the RPE ($1^{st}$ layer of Bruch's membrane) and the inner collagenous layer ($2^{nd}$ layer of Bruch's membrane). This debris is called basal linear deposits and drusen, both rich in lipids and hallmarks of AMD, impairing even more the diffusion along Bruch's membrane (Gehrs et al, (2006) Annals of Medicine 38:450-471; Curcio et al. (1999) Arch Opthalmol 117:329-339; Curcio et al. (2005) Experimental Eye Research 81: 731-741; Haimovici et al. (2001) Invest Opthalmol Vis Sci 42:1592-1599). Furthermore, cytotoxic and lipid rich, metabolic end products, called lipofuscin, accumulate in the RPE cells (Beatty et al. (2000) Surv Opthalmol 45:115-134). All these conditions together cause oxidative stress and inflammation resulting in RPE atrophy and successively photoreceptor degeneration (Kopitz et al. (2004) Biochimie 86: 825-831). This atrophy of RPE and photoreceptors is called the dry form of AMD and progresses slowly and irreversibly. Currently a treatment or prevention of this form of AMD, which affect about 85-90% of all AMD patients, does not exist (Van Leeuwen et al. (2003) European Journal of Epidemiology 18: 845-854).

The second form of AMD is called wet AMD and can arise from the dry form. It affects about 10-15% of all AMD patients and is marked by the growth of a pathological vessel from the choriocapillaris into the subretinal space, called choroidal neovascularization (CNV) (Gehrs et al. (2006) Annals of Medicine 38:450-471 and Ambati et al. (2003) Survey of Opthalmology 48:257-293). It causes a rapid, irreversible vision loss due to leakage, bleeding, and scaring (Ambati et al. (2003) Survey of Opthalmology 48:257-293). In the last 5 years antiangiogentic therapies were developed targeting vascular endothelial growth factor, which could show success in slowing down the progression of vision loss (Michels et al. (2006) Expert Opin Investig Drugs 15:779-793).

In general, current therapies use antibodies or antibody fragments against VEGF, which are injected into the vitreous body of the eye (Michels et al. (2006)). A prevention therapy of wet AMD does not exist (Gehrs et al. (2006)), which would be especially desirable when the vision in one eye is already largely compromised and the second eye shows definite risk factors for a progression like e.g. large soft drusen (Ambati et al. (2003)).

Lipids are hydrophobic and cannot simply dissolve in an aqueous medium such as blood. In order to be transported in blood lipids have to be assembled in particles called lipoproteins. Specialized proteins called apolipoproteins help to form and stabilize these particles. There are several classes of apolipoproteins (A-JM, a). Basically their functional structures are comparable which are amphipathic helices.

Apolipoprotein mimetic peptides are synthetic helical lipid accepting peptides mimicking the function of an apolipoprotein (Mendez et al. (1994) J. Clin. Invest 94:1698-1705). One of the best known is the ApoA-I mimetic peptide 4F, has been shown to treat atherosclerosis (Anantharamaiah et al. (2006) Current Opinion in Lipidology 17:233-237). It is available as L-4F and as its stereoisomer D-4F. It consists of 18 amino acids, is well water-soluble, a high potent lipid acceptor, and acts as a highly anti-inflammatory (Navab et al. (2006) Nat. Clin. Pract. Cardiovasc. Med. 3:540-547). D-4F is based on D-amino acids and is compared to L-4F more resistant to degradation and can be taken orally (Anantharamaiah et al. (2006)). A phase I clinical trial with D-4F already started. So far no side effects of D-4F are described.

SUMMARY OF THE INVENTION

This invention provides novel compositions and methods to ameliorate one or more symptoms of a vascular condition and/or a condition characterized by an inflammatory response and/or a condition characterized by the formation of oxidized reactive species in a mammal.

Thus, in certain embodiments, this invention provides a peptide that ameliorates a symptom of atherosclerosis, where the peptide comprises the amino acid sequence or the retro amino acid sequence of a peptide listed in Table 6. In another embodiment this invention provides a peptide that ameliorates a symptom of atherosclerosis, where the peptide: consists of 18 amino acids, the 18 amino acids consisting of 3 alanines (A), 2 aspartates (D), 2 glutamates (E), 4 phenylalanines (F), 4 lysines (K), 1 valine (V), 1 tryptophan (W), and 1 tyrosine (Y); where the peptide forms a class A amphipathic helix; comprises at least one "D" amino acid residue; and protects a phospholipid against oxidation by an oxidizing agent. In certain embodiments these peptides include but are not limited to a peptide having the amino acid sequence or the retro amino acid sequence of a peptide listed in Table 4. In still another embodiment, this invention provides a peptide that ameliorates a symptom of atherosclerosis, where the peptide: ranges in length from about 18 to 37 amino acids and comprises at least 3 alanines (A), 2 aspartates (D), 2 glutamates (E), 4 phenylalanines (F), 4 lysines (K), 1 valine (V), 1 tryptophan (W), 1 tyrosine (Y); where the peptide forms a class A amphipathic helix; comprises at least one "D" amino acid residue; and protects a phospholipid against oxidation by an oxidizing agent. In certain embodiments these peptides comprise an amino acid sequence selected from the group consisting of D-W-F-K-A-F-Y-D-K-V-A-E-K-F-K-E-A-F (SEQ ID NO: 1191), -D-W-L-K-A-F-Y-D-K-V-A-E-K-L-K-E-A-F-P-D-W-L-K-A-F-Y-D-K-V-A-E-K-L-K-E-A-F (SEQ ID NO: 1192), -D-W-L-K-A-F-Y-D-K-V-A-E-K-L-K-E-F-F-P-D-W-L-K-A-F-Y-D-K-V-A-E-K-L-K-E-F-F (SEQ ID NO: 1193), -D-W-F-K-A-F-Y-D-K-V-A-E-K-L-K-E-A-F-P-D-W-F-K-A-F-Y-D-K-V-A-E-K-L-K-E-A-F (SEQ ID NO: 1194), D-K-L-K-A-F-Y-D-K-V-F-E-W-A-K-E-A-F-P-D-K-L-K-A-F-Y-D-K-V-F-E-W-L-K-E-A-F (SEQ ID NO: 1195), D-K-W-K-A-V-Y-D-K-F-A-E-A-F-K-E-F-L-P-D-K-W-K-A-V-Y-D-K-F-A-E-A-F-K-E-F-L (SEQ ID NO: 1196), D-W-F-K-A-F-Y-D-K-V-A-E-K-F-K-E-A-F-P-D-W-F-K-A-F-Y-D-K-V-A-E-K-F-K-E-A-F-(SEQ ID NO: 1197), or the reverse of any of these sequences. In still yet another embodiment this invention provides a peptide that forms a class A amphipathic helix or a class Y amphipathic helix and is described by the formula: $D^1-X^1-X^1-K^1-Y^1-X^3-X^4-D^2-K_2-X-^5-Y-D^3-K^3-X^6-K^4-D^4-Y^2-X^7$ (SEQ ID NO:402) where $X^1$, $X^2$, $X^3$, $X^4$, $X^5$, and $X^6$ are independently selected from the group consisting of Leu, norLeu, Val, Ile, Trp, Phe, Tyr, β-Nal, and α-Nal, and all X residues are on the non-polar face of the peptide, except for one that can be on the polar face between two K residues; $K^1$, $K^2$, $K^3$, and $K^4$ are independently Lys or Arg, and no more than two K's are adjacent to each other in a helical wheel diagram of the peptide; $Y^1$ and $Y^2$ are independently selected from the group consisting of Ala, His, Ser, Gln, Asn, and Thr, when present on the non-polar face of the molecule; when one of $Y^1$ or $Y^2$ are present on the polar face of the molecule, the $Y^1$ or $Y^2$ on the polar face of the molecule is selected from the group consisting of Ala, His, Ser, Gln, Asn, and Thr; $D^1$, $D^2$, $D^3$, and $D^4$ are independently Asp or Glu, and no more than 3 Ds are contiguous in a helical wheel diagram of the peptide, and the remaining D is separated from the other D's by a Y. In certain embodiments these peptides comprise the amino acid sequence or the retro amino acid sequence of a peptide listed in Table 5.

In certain embodiments any one or more of these peptides further comprise a protecting group coupled to the amino or carboxyl terminus. In certain embodiments the peptides comprise a first protecting group coupled to the amino terminus and a second protecting group coupled to the carboxyl terminus. In certain embodiments the protecting groups can be independently selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

In certain embodiments the peptide comprises a protecting group coupled to the amino terminal and the amino terminal protecting group is a protecting group selected from the group consisting of acetyl, propeonyl, and a 3 to 20 carbon alkyl. In certain embodiments the peptide comprises a protecting group coupled to the carboxyl terminal and the carboxyl terminal protecting group is an amide. In certain embodiments the peptide comprises: a first protecting group coupled to the amino terminus where the protecting group is a protecting group selected from the group consisting of acetyl, propeonyl, and a 3 to 20 carbon alkyl; and a second protecting group coupled to the carboxyl terminal and the carboxyl terminal protecting group is an amide.

In various embodiments one or more amino acids comprising the peptide are "D" amino acids. In various embodiments all amino acids comprising the peptide "D" amino acids. The peptide(s) can, optionally, be mixed/combined with a pharmacologically acceptable excipient. In certain embodiments the excipient is an excipient suitable for oral administration to a mammal.

In certain embodiments this invention provides methods of treating a vascular condition and/or a condition characterized by an inflammatory response and/or a condition characterized by the formation of oxidized reactive species in a mammal. The methods typically involve administering to a mammal in need thereof one or more of the active agents described in Tables 2-18, and/or a small organic molecule as described herein in an amount sufficient to ameliorate one or more symptoms of the condition. In certain embodiments the active agent is a polypeptide comprising the amino acid sequence of 4F (SEQ ID NO:5). In certain embodiments the administration is by a route selected from the group consisting of oral administration, nasal administration, rectal administration, intraperitoneal injection, and intravascular injection, intraocular injection, intravitreal injection, subconjutival injection, peri-/retrobulbar injection, subcutaneous injection, eye drops, eye gel, eye ointment, spray, emulsion, suspension, transcutaneous administration, and intramuscular injection, via any drug carriers as sponges, contact lenses, polymers, microspheres, implants, pellets, and genetically engineered cells. In certain embodiments the active agent is administered in conjunction with a drug selected from the group consisting of CETP inhibitors, FTY720, Certican, DPP4 inhibitors, Calcium channel blockers, ApoA1 derivative or mimetic or agonist, PPAR agonists, Steroids, Gleevec, Cholesterol Absorption blockers (Zetia), Vytorin, Any Renin Angiotensin pathway blockers, Angiotensin II receptor antagonist (Diovan etc), ACE inhibitors, Renin inhibitors, MR antagonist and Aldosterone synthase inhibitor, Beta-blockers, Alpha-adrenergic antagonists, LXR agonist, FXR agonist, Scavenger Receptor B1 agonist, ABCA1 agonist, Adiponectic receptor agonist or adiponectin inducers, Stearoyl-CoA Desaturase I (SCD1) inhibitor, Cholesterol synthesis inhibitors (non-statins), Diacylglycerol Acyltransferase I (DGAT1) inhibitor, Acetyl CoA Carboxylase 2 inhibitor, PAI-1 inhibitor, LP-PLA2 inhibitor, GLP-1, Glucokinase activator, CB-1 agonist, AGE inhibitor/breaker, PKC inhibitors, Anti-thrombotic/coagulants: Aspirin, ADP receptor blockers e.g. Clopidigrel, Factor Xa inhibitor, GPIIb/IIIa inhibitor, Factor VIIa inhibitor, Warfarin, Low molecular weight heparin, Tissue factor inhibitor, Anti-inflammatory drugs: Probucol and derivative e.g. AGI-1067 etc, CCR2 antagonist, CX3CR1 antagonist, IL-1 antagonist, Nitrates and NO donors, and Phosphodiesterase inhibitors.

In various embodiments this invention provides for the use of an active agent described in Tables 2-18, and/or a small organic molecule as described herein in a treatment of a condition selected from the group consisting of atherosclerotic plaque formation, atherosclerotic lesion formation, myocardial infarction, stroke, congestive heart failure, arteriole function, arteriolar disease, arteriolar disease associated with aging, arteriolar disease associated with Alzheimer's disease, arteriolar disease associated with chronic kidney disease, arteriolar disease associated with hypertension, arteriolar disease associated with multi-infarct dementia, arteriolar disease associated with subarachnoid hemorrhage, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, rheumatoid arthritis, polyarteritis nodosa, polymyalgia rheumatica, lupus erythematosus, multiple sclerosis, Wegener's granulomatosis, central nervous system vasculitis (CNSV), Sjogren's syndrome, scleroderma, polymyositis, AIDS inflammatory response, bacterial infection, fungal infection, viral infection, parasitic infection, influenza, avian flu, viral pneumonia, endotoxic shock syndrome, sepsis, sepsis syndrome, trauma/wound, organ transplant, transplant atherosclerosis, transplant rejection, corneal ulcer, chronic/non-healing wound, ulcerative colitis, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer, osteoarthritis, inflammatory bowel disease, allergic rhinitis, cachexia, diabetes, Alzheimer's disease, implanted prosthesis, biofilm formation, Crohns' disease, dermatitis, acute and chronic, eczema, psoriasis, contact dermatitis, scleroderma, Type I Diabetes, Type II Diabetes, juvenile onset diabetes, prevention of the onset of diabetes, diabetic nephropathy, diabetic neuropathy, diabetic retinopathy, erectile dysfunction, macular degeneration, multiple sclerosis, nephropathy, neuropathy, Parkinson's Disease, peripheral vascular disease, and meningitis.

This invention additionally provides for the use of active agent described in Tables 2-18, and/or a small organic molecule as described herein for the manufacture of a medicament for the treatment of a condition selected from the group consisting of atherosclerotic plaque formation, atherosclerotic lesion formation, myocardial infarction, stroke, congestive heart failure, arteriole function, arteriolar disease, arteriolar disease associated with aging, arteriolar disease associated with Alzheimer's disease, arteriolar disease associated with chronic kidney disease, arteriolar disease associated with hypertension, arteriolar disease associated with multi-infarct dementia, arteriolar disease associated with subarachnoid hemorrhage, peripheral vascular disease, chronic obstructive pulmonary disease (COPD), emphysema, asthma, idiopathic pulmonary fibrosis, pulmonary fibrosis, adult respiratory distress syndrome, osteoporosis, Paget's disease, coronary calcification, rheumatoid arthritis, polyarteritis nodosa, polymyalgia rheumatica, lupus erythematosus, multiple sclerosis, Wegener's granulomatosis, central nervous system vasculitis (CNSV), Sjogren's syndrome, scleroderma, polymyositis, AIDS inflammatory response, bacterial infection, fungal infection, viral infection, parasitic infection, influenza, avian flu, viral pneumonia, endotoxic shock syndrome, sepsis, sepsis syndrome, trauma/wound, organ transplant, transplant atherosclerosis, transplant rejection, corneal ulcer, chronic/non-healing wound, ulcerative colitis, reperfusion injury (prevent and/or treat), ischemic reperfusion injury (prevent and/or treat), spinal cord injuries (mitigating effects), cancers, myeloma/multiple myeloma, ovarian cancer, breast cancer, colon cancer, bone cancer osteoarthritis, inflammatory bowel disease, allergic rhinitis, cachexia, diabetes, Alzheimer's disease, implanted prosthesis, biofilm formation, Crohns' disease, dermatitis, acute and chronic, eczema, psoriasis, contact dermatitis, scleroderma, Type I Diabetes, Type II Diabetes, juvenile onset diabetes, prevention of the onset of diabetes, diabetic nephropathy, diabetic neuropathy, diabetic retinopathy, erectile dysfunction, macular degeneration, multiple sclerosis, nephropathy, neuropathy, Parkinson's Disease, peripheral vascular disease, and meningitis.

In certain embodiments this invention provides a stent for delivering drugs to a vessel in a body. The stent typically comprises a stent framework including a plurality of reservoirs formed therein, and a peptide comprising the amino acid sequence or the retro amino acid sequence of a peptide listed in Tables 2-18 (e.g., Table 4, Table 5, or Table 6) and/or the inverse thereof. In certain embodiments the stent comprises a peptide comprising the amino acid sequence of 4F (SEQ ID NO:5) or the inverse thereof. In certain embodiments the active agent is contained within a polymer. In certain embodiments the stent framework comprises one of a metallic base or a polymeric base. In certain embodiments the stent framework base comprises a material selected from the group consisting of stainless steel, nitinol, tantalum, MP35N alloy, platinum, titanium, a suitable biocompatible alloy, a suitable biocompatible polymer, and a combination thereof. The reservoir(s) comprising said stent can, in some embodiments, comprise micropores (e.g. having a diameter of about 20 microns or less). In certain embodiments the micropores have a diameter in the range of about 20 microns to about 50 microns. In various embodiments the micropores have a depth in the range of about 10 to about 50 microns. The micropores, in certain embodiments, extend through the stent framework having an opening on an interior surface of the stent and an opening on an exterior surface of the stent. In various embodiments the stent can further comprise a cap layer disposed on the interior surface of the stent framework, the cap layer covering at least a portion of the through-holes and providing a barrier characteristic to control an elution rate of a drug in the drug polymer from the interior surface of the stent framework. In various embodiments the reservoirs comprise channels along an exterior surface of the stent framework. In various embodiments the polymer comprises a first layer of a first drug polymer having a first pharmaceutical characteristic and the polymer layer comprises a second drug polymer having a second pharmaceutical characteristic. In certain embodiments the stent further comprises a barrier layer positioned between the polymer comprising the active agent. In various embodiments a catheter can be coupled to the stent framework. In certain embodiments the catheter can include a balloon used to expand the stent. In certain embodiments the catheter includes a sheath that retracts to allow expansion of the stent.

Also provided is a method of manufacturing a drug-polymer stent. The method typically involves providing a stent framework; cutting a plurality of reservoirs in the stent framework; applying a composition comprising one or more peptides comprising the amino acid sequence or the retro amino acid sequence of a peptide listed in any of Tables 2-18 to at least one reservoir; and drying the composition. The method can further involve applying a polymer layer to the dried composition; and drying the polymer layer.

This invention also provides a method of treating a vascular condition. The method involves positioning a stent as described above, within a vessel of a body; expanding the stent; and eluting at least one active agent (e.g., an active agent from any of Tables 2-18) from at least a surface of the stent.

In certain embodiments, this invention expressly excludes one or more of the peptides described in U.S. Pat. Nos. 6,037,323; 4,643,988; 6,933,279; 6,930,085; 6,664,230; 3,767,040; 6,037,323; U.S. Patent Publications 2005/0164950; 2004/0266671; 2004/0254120; 2004/0057871; 2003/0229015; 2003/0191057; 2003/0171277; 2003/0045460; 2003/0040505; PCT Publications WO 2002/15923; WO 1999/16408; WO 1997/36927; and/or in Garber et al. (1992) Arteriosclerosis and Thrombosis, 12: 886-894, which are incorporated herein by reference.

Also disclosed herein are methods for treating a subject with eye disease, the method comprising administering to the subject in need thereof an effective amount of one or more of the active agents described in Tables 2-18, and/or a small organic molecule as described herein in an amount sufficient to ameliorate one or more symptoms of said condition. The active agent can be a polypeptide comprising the amino acid sequence of 4F (SEQ ID NO:5). Administration can be by a route selected from the group consisting of oral administration, nasal administration, rectal administration, intraperitoneal injection, and intravascular injection, intraocular injection, intravitreal injection, subconjuctival injection, peri-/retrobulbar injection, subcutaneous injection, eye drops, eye gel, eye ointment, spray, emulsion, suspension, transcutaneous administration, and intramuscular injection, via any drug carriers as sponges, contact lenses, polymers, microspheres, implants, pellets, and genetically engineered cells.

Also disclosed herein are methods for treating a subject with eye disease, the method comprising administering to the subject in need thereof an effective amount of one or more of the active agents described in Tables 2-18, and/or a small organic molecule as described herein in an amount sufficient to ameliorate one or more symptoms of said condition, wherein said active agent is administered in conjunction with an antiangiogenic agent.

Also disclosed herein are methods of ameliorating a symptom of eye disease, the method comprising administering to the subject to the subject in need thereof an effective amount of one or more of the active agents described in Tables 2-18, and/or a small organic molecule as described herein in an amount sufficient to ameliorate one or more symptoms of said condition. Symptoms of eye disease can include, but are not limited to accumulation of extracellular lipids in Bruch's membranes, accumulation of lipid rich debris, vision loss, formation of choriocapillaris, thickening of the Bruch's membrane, accumulation of neutral lipids in the Bruch's membrane, formation of a diffusion barrier between the retinal pigment epithelium and choriocapillaris, deposition of debris (basal linear deposits and drusen) between the basal membrane of the RPE, and the inner collagenous layer, accumulation of lipofuscin in the RPE cells, RPE atrophy, photoreceptor degeneration, choroidal neovascularization, as well as leakage, bleeding, scarring of the eye Also disclosed herein are methods of ameliorating a symptom of eye disease, the method comprising administering to the subject an effective amount of a peptide wherein said peptide: ranges in length from about 18 to 37 amino acids and comprises at least 3 alanines (A), 2 aspartates (D), 2 glutamates (E), 4 phenylalanines (F), 4 lysines (K), 1 valine (V), 1 tryptophan (W), 1 tyrosine (Y); wherein said peptide forms a class A amphipathic helix; comprises at least one "D" amino acid residue; and protects a phospholipid against oxidation by an oxidizing agent.

Also disclosed herein are methods of ameliorating a symptom of eye disease, the method comprising administering to the subject an effective amount of a peptide wherein said peptide: ranges in length from about 18 to 37 amino acids and comprises at least 3 alanines (A), 2 aspartates (D), 2 glutamates (E), 4 phenylalanines (F), 4 lysines (K), 1 valine (V), 1 tryptophan (W), 1 tyrosine (Y); wherein said peptide forms a class A amphipathic helix; comprises at least one "D" amino acid residue; and protects a phospholipid against oxidation by an oxidizing agent, wherein said peptide further comprises a protecting group coupled to the amino or carboxyl terminus.

Also disclosed herein are methods of ameliorating a symptom of eye disease, the method comprising administering to the subject an effective amount of a peptide wherein said peptide: ranges in length from about 18 to 37 amino acids and comprises at least 3 alanines (A), 2 aspartates (D), 2 glutamates (E), 4 phenylalanines (F), 4 lysines (K), 1 valine (V), 1 tryptophan (W), 1 tyrosine (Y); wherein said peptide forms a class A amphipathic helix; comprises at least one "D" amino acid residue; and protects a phospholipid against oxidation by an oxidizing agent, wherein said peptide comprises an amino acid sequence selected from the group consisting of D-W-F-K-A-F-Y-D-K-V-A-E-K-F-K-E-A-F (SEQ ID NO: 1191), -D-W-L-K-A-F-Y-D-K-V-A-E-K-L-K-E-A-F-P-D-W-L-K-A-F-Y-D-K-V-A-E-K-L-K-E-A-F (SEQ ID NO: 1192), -D-W-L-K-A-F-Y-D-K-V-A-E-K-L-K-E-F-F-P-D-W-L-K-A-F-Y-D-K-V-A-E-K-L-K-E-F-F (SEQ ID NO: 1193), -D-W-F-K-A-F-Y-D-K-V-A-E-K-L-K-E-A-F-P-D-W-F-K-A-F-Y-D-K-V-A-E-K-L-K-E-A-F (SEQ ID NO: 1194), D-K-L-K-A-F-Y-D-K-V-F-E-W-A-K-E-A-F-P-D-K-L-K-A-F-Y-D-K-V-F-E-W-L-K-E-A-F (SEQ ID NO: 1195), D-K-W-K-A-V-Y-D-K-F-A-E-A-F-K-E-F-L-P-D-K-W-K-A-V-Y-D-K-F-A-E-A-F-K-E-F-L (SEQ ID NO: 1196), D-W-F-K-A-F-Y-D-K-V-A-E-K-F-K-E-A-F-P-D-W-F-K-A-F-Y-D-K-V-A-E-K-F-K-E-A-F- (SEQ ID NO: 1197), or the reverse of any of these sequences.

Also discloses is the use of an active agent described in Tables 2-18, and/or a small organic molecule as described herein in a treatment of macular degeneration.

Also disclose are methods of treating a subject with eye disease, the method comprising administering to the subject in need thereof an effective amount of one or more of the active agents described in Tables 2-18, and/or a small organic molecule as described herein in an amount sufficient to ameliorate one or more symptoms of said condition in combination with an anti-angiogenic therapy.

Also disclosed are methods of ameliorating a symptom of eye disease, the method comprising administering to the subject to the subject in need thereof an effective amount of one or more of the active agents described in Tables 2-18, and/or a small organic molecule as described herein in an amount sufficient to ameliorate one or more symptoms of said condition in combination with an anti-angiogenic therapy.

DEFINITIONS

The term "treat" when used with reference to treating, e.g. a pathology or disease refers to the mitigation and/or elimination of one or more symptoms of that pathology or disease, and/or a reduction in the rate of onset or severity of one or more symptoms of that pathology or disease, and/or the prevention of that pathology or disease.

The terms "isolated", "purified", or "biologically pure" when referring to an isolated polypeptide refer to material that is substantially or essentially free from components that normally accompany it as found in its native state. With respect to nucleic acids and/or polypeptides the term can refer to nucleic acids or polypeptides that are no longer flanked by the sequences typically flanking them in nature. Chemically synthesized polypeptides are "isolated" because they are not found in a native state (e.g. in blood, serum, etc.). In certain embodiments, the term "isolated" indicates that the polypeptide is not found in nature.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "an amphipathic helical peptide" refers to a peptide comprising at least one amphipathic helix (amphipathic helical domain). Certain amphipathic helical peptides of this invention can comprise two or more (e.g., 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) Proteins: Structure, Function, and Genetics 8: 103-117).

"Apolipoprotein J" (apo J) is known by a variety of names including clusterin, TRPM2, GP80, and SP 40 (see, e.g., Fritz (1995) Pp 112 In: Clusterin: Role in Vertebrate Development, Function, and Adaptation (Harmony J A K Ed.), R. G. Landes, Georgetown, Tex.). It was first described as a heterodimeric glycoprotein and a component of the secreted proteins of cultured rat Sertoli cells (see, e.g., Kissinger et al. (1982) Biol. Reprod.; 27: 233240). The translated product is a single-chain precursor protein that undergoes intracellular cleavage into a disulfide-linked 34 kDa α-subunit and a 47 kDa β-subunit (see, e.g., Collard and Griswold (1987) Biochem., 26: 3297-3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) Biochem., 40: 11828-11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, e.g., Segrest et al. (1990) Proteins: Structure, Function, and Genetics. 8: 103-117; Erratum (1991) Proteins: Structure, Function and Genetics, 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see, e.g., Segrest et al. (1992) J. Lipid Res., 33: 141-166; Anantharamaiah et al. (1993) Pp. 109-142 In: The Amphipathic Helix, Epand, R. M. Ed CRC Press, Boca Raton, Fla.). Computer programs to identify and classify amphipathic helical domains have been described by Jones et al. (1992) J. Lipid Res. 33: 287-296) and include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "eye disease" as used herein includes diseases associated or compromised with/by a reduced hydraulic conductivity and metabolic exchange via Bruch's membrane, diseases characterized by an accumulation of extra-/intracellular lipids in the eye, diseases that use lipid-derived mediators of inflammation or benefit from oxidized lipid removal as well as diseases that benefit from Bruch's membrane remodeling. "eye disease" as used herein includes, but is not limited to, macular degeneration, age related maculopathy (ARM), age related macular degeneration (AMD) including both the dry and wet forms of age related macular degeneration, glaucoma, ocular hypertension, macular edema, retinal pigment epithelium detachments, coats disease, uveitis, sicca syndrome, hereditary diseases associated with increased extra-/intracellular lipid storage/accumulation, and juvenile macular degeneration as well as all risk factors for each mentioned disease The term "ameliorating" when used with respect to "ameliorating one or more symptoms of eye disease" refers to a reduction, prevention, or elimination of one or more symptoms characteristic of eye disease and/or associated pathologies. Such a reduction includes, but is not limited to a reduction or elimination of oxidized phospholipids, accumulation of extracellular lipids in Bruch's membranes, accumulation of lipid rich debris in Bruch's membranes, vision loss, formation of choriocapillaris, thickening of the Bruch's membrane, accumulation of neutral lipids in the Bruch's membrane, formation of a diffusion barrier between the retinal pigment epithelium, deposition of debris (basal linear deposits and drusen) between the basal membrane of the RPE and the inner collagenous layer, accumulation of lipofuscin in the RPE cells, RPE atrophy, photoreceptor degeneration, choroidal neovascularization, trapped fluid accumulation in the retina and retinal pigment epithelial cells, elevated intraocular pressure, as well as leakage, bleeding, scarring of the eye, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art. Amino acids are designated herein using standard 1-letter or three-letter codes, e.g. as designated in Standard ST.25 in the Handbook On Industrial Property Information and Documentation.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propeonyl, formyl and others. Preferred carboxyl terminal protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)-HPODE, 15-(S)-HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations may be used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phosphocholine; ChCl8: 2: cholesteryl linoleate; ChCl8:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; BL/6:C57BL/6J; C3H:C3H/HeJ.

The term "conservative substitution" is used in reference to proteins or peptides to reflect amino acid substitutions that do not substantially alter the activity (specificity (e.g. for lipoproteins)) or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) J. Mol. Biol. 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Natl. Acad. Sci. USA, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "in conjunction with" when used in reference to the use of one or more drugs in conjunction with one or more active agents described herein indicates that the drug(s) and the active agent(s) are administered so that there is at least some chronological overlap in their physiological activity on the organism. Thus the drug(s) and active agent(s) can be administered simultaneously and/or sequentially. In sequential administration there may even be some substantial delay (e.g., minutes or even hours or days) before administration of the second moiety as long as the first administered drug/agent has exerted some physiological alteration on the organism when the second administered agent is administered or becomes active in the organism.

The phrases "adjacent to each other in a helical wheel diagram of a peptide" or "contiguous in a helical wheel diagram of a peptide" when referring to residues in a helical peptide indicates that in the helical wheel representation the residues appear adjacent or contiguous even though they may not be adjacent or contiguous in the linear peptide. Thus, for example, the residues "A, E, K, W, K, and F" are contiguous in the helical wheel diagrams shown in FIG. 15 even though these residues are not contiguous in the linear peptide.

BRIEF DESCRIPTION OF THE DRAWINGS

FIG. 10A: $V^2W^3A^5F^{10, 17}$-D-4F (SEQ ID NO. 1168); FIG. 10B: $W^3$-D-4F (SEQ ID NO. 1132); FIG. 10C: $V^2W^3F^{10}$-D-4F (SEQ ID NO. 1169).

DETAILED DESCRIPTION

I. Methods of Treatment

The active agents (e.g. peptides, small organic molecules, amino acid pairs, etc.) described herein are effective for mitigating one or more symptoms and/or reducing the rate of onset and/or severity of one or more indications described herein. In particular, the active agents (e.g. peptides, small organic molecules, amino acid pairs, etc.) described herein are effective for mitigating one or more symptoms of atherosclerosis and/or eye disease. Without being bound to a particular theory, it is believed that the peptides bind the "seeding molecules" required for the formation of pro-inflammatory oxidized phospholipids such as Ox-PAPC, POVPC, PGPC, and PEIPC.

In addition, since many inflammatory conditions and/or other pathologies are mediated at least in part by oxidized lipids, we believe that the peptides of this invention are effective in ameliorating conditions that are characterized by the formation of biologically active oxidized lipids. In addition, there are a number of other conditions for which the active agents described herein appear to be efficacious.

A number of pathologies for which the active agents described herein appear to be a palliative and/or a preventative are described below.

A) Atherosclerosis and Associated Pathologies.

We discovered that normal HDL inhibits three steps in the formation of mildly oxidized LDL. In particular, we demonstrated that treating human LDL in vitro with apo A-I or an apo A-I mimetic peptide (37 pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers after injection/infusion of apo A-I was resistant to oxidation by human artery wall cells and did not induce monocyte chemotactic activity in the artery wall cell cocultures.

Figure 1:
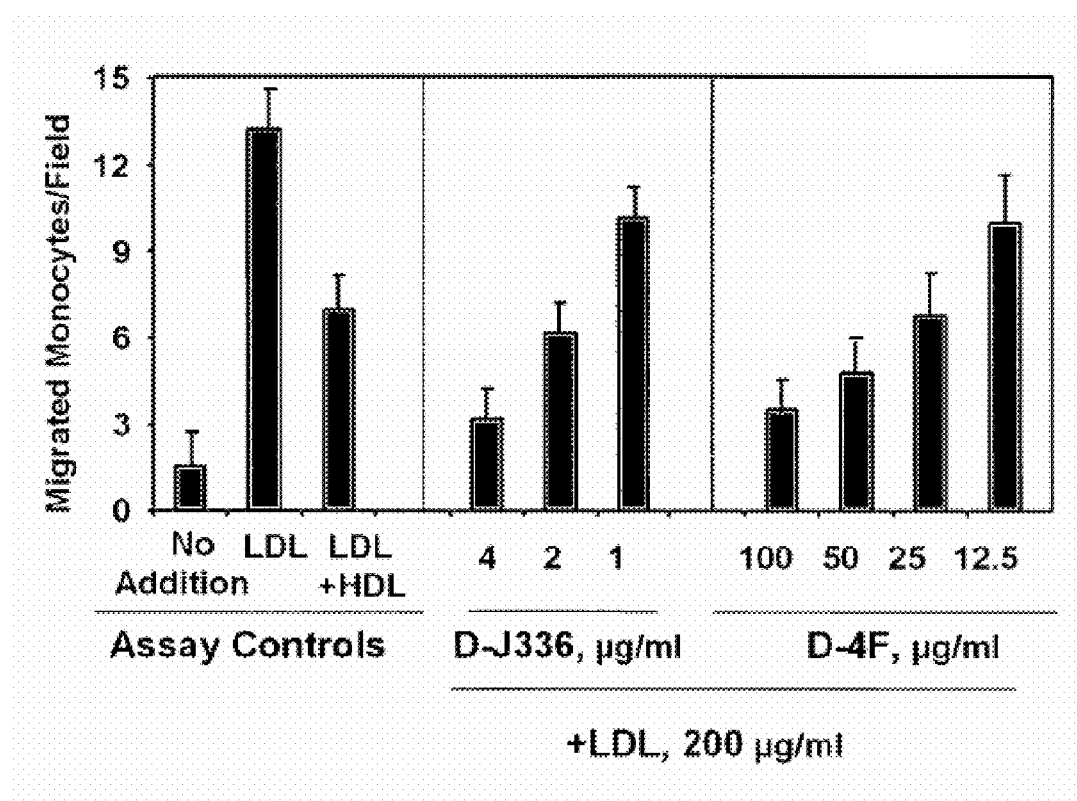
FIG. 1 shows a comparison of the effect of D4F (Navab, et al. (2002) Circulation, 105: 290-292) and apo-J peptide 336 made from D amino acids (D-J336*) on the prevention of LDL-induced monocyte chemotactic activity in vitro in a co-incubation experiment. The data are mean±SD of the number of migrated monocytes in nine high power fields in quadruple cultures. (D-J336=Ac-LLEQLNEQFNWVSR-LANLTQGE-NH$_2$, SEQ ID NO:1011).
Figure 2:
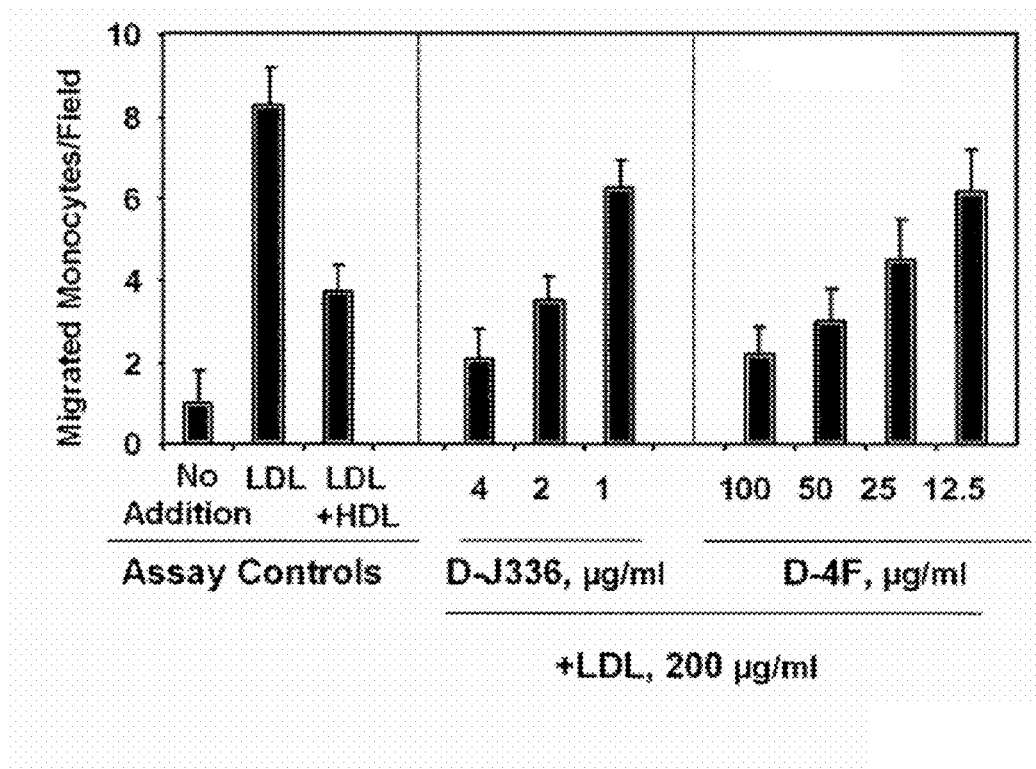
FIG. 2 illustrates the prevention of LDL-induced monocyte chemotactic activity by pre-treatment of artery wall cells with D-J336 as compared to D-4F. The data are mean±SD of the number of migrated monocytes in nine high power fields in quadruple cultures.
Figure 3:
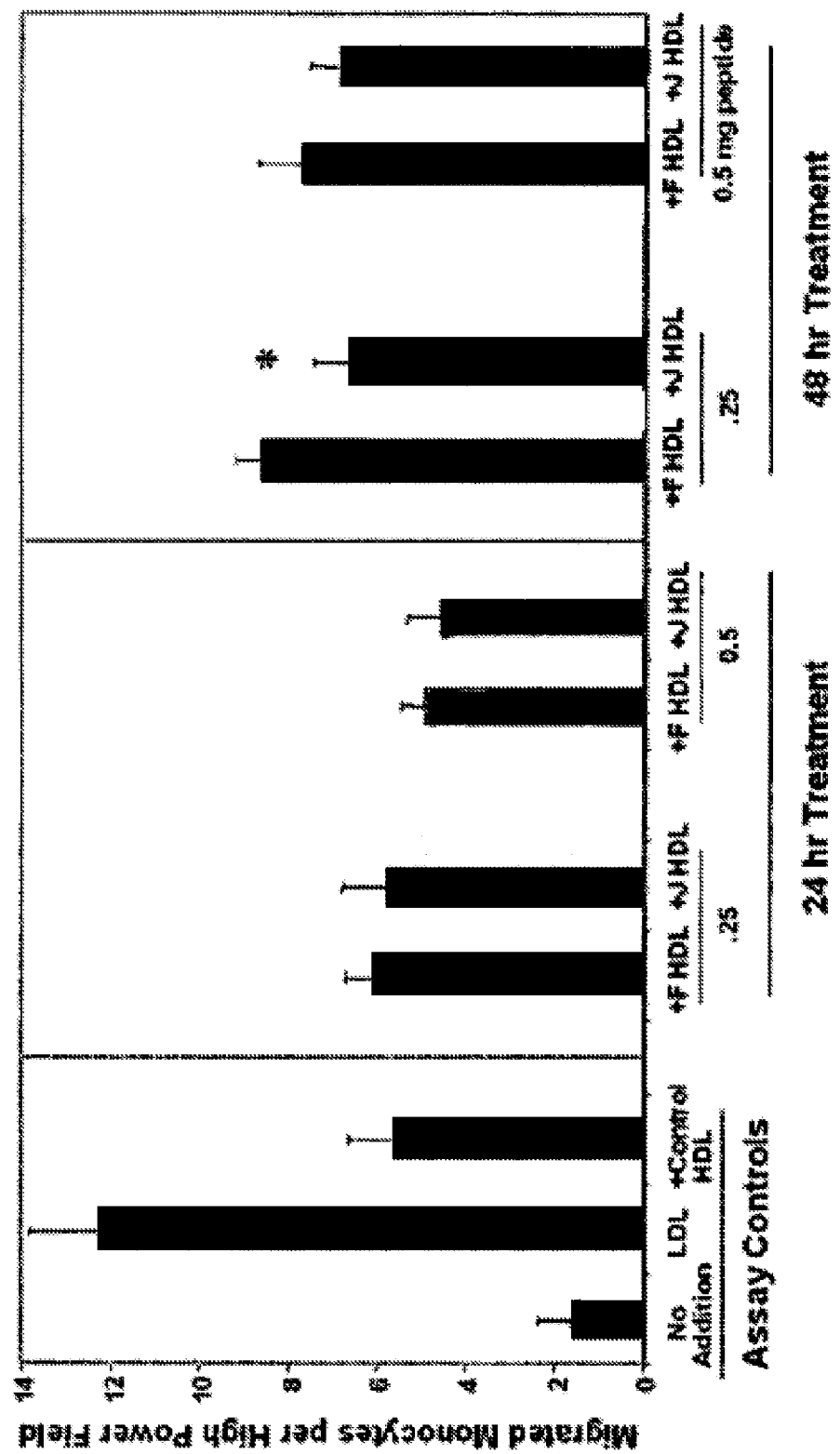
FIG. 3 illustrates the effect of apo J peptide mimetics on HDL protective capacity in LDL receptor null mice. The values are the mean±SD of the number of migrated monocytes in 9 high power fields from each of quadruple assay wells.
Figure 4:
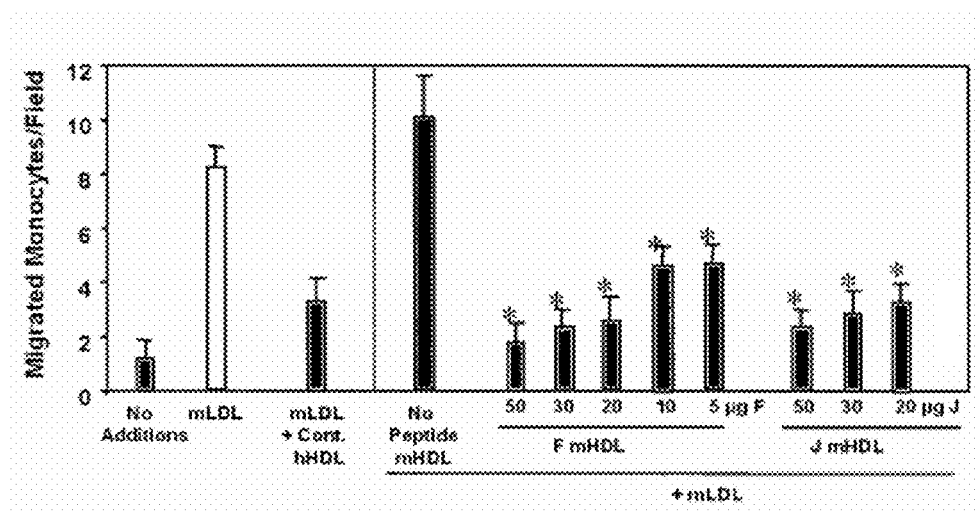
FIG. 4 illustrates protection against LDL-induced monocyte chemotactic activity by HDL from apo E null mice given oral peptides. The values are the mean±SD of the number of migrated monocytes in 9 high power fields from each of quadruple assay wells. Asterisks indicate significant difference (p<0.05) as compared to No Peptide mHDL.

The protective function of various active agents of this invention is illustrated in the parent applications (Ser. No. 09/645,454, filed Aug. 24, 2000, Ser. No. 09/896,841, filed Jun. 29, 2001, and WO 02/15923 (PCT/US01/26497), filed Jun. 29, 2001, see, e.g., FIGS. 1-5 in WO 02/15923. FIG. 1, panels A, B, C, and D in WO 02/15923 show the association of 14C-D-5F with blood components in an ApoE null mouse). It is also demonstrated that HDL from mice that were fed an atherogenic diet and injected with PBS failed to inhibit the oxidation of human LDL and failed to inhibit LDL-induced monocyte chemotactic activity in human artery wall cocultures. In contrast, HDL from mice fed an atherogenic diet and injected daily with peptides described herein was as effective in inhibiting human LDL oxidation and preventing LDL-induced monocyte chemotactic activity in the cocultures as was normal human HDL (FIGS. 2A and 2B in WO 02/15923). In addition, LDL taken from mice fed the atherogenic diet and injected daily with PBS was more readily oxidized and more readily induced monocyte chemotactic activity than LDL taken from mice fed the same diet but injected with 20 .mu.g daily of peptide 5F. The D peptide did not appear to be immunogenic (FIG. 4 in WO 02/15923).

Figure 5:
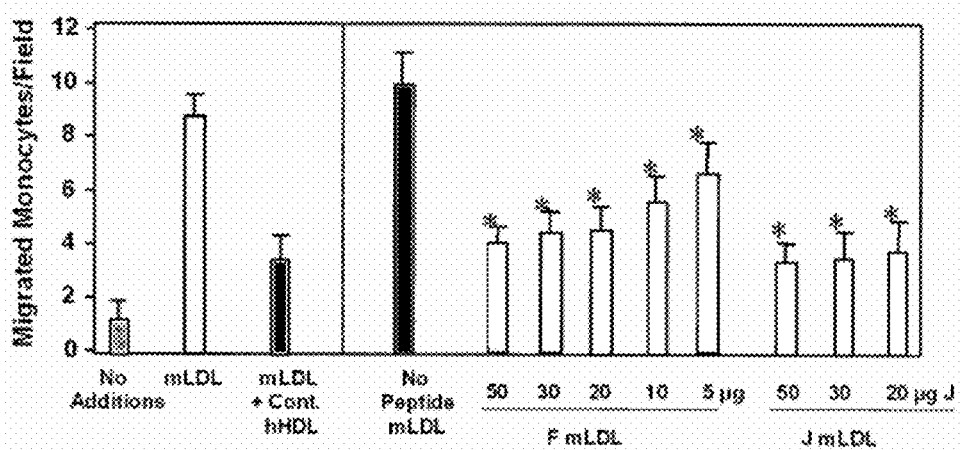
FIG. 5 illustrates the effect of oral apo A-1 peptide mimetic and apoJ peptide on LDL susceptibility to oxidation. The values are the mean±SD of the number of migrated monocytes in 9 high power fields from each of quadruple assay wells. Asterisks indicate significant difference (p<0.05) as compared to No Peptide LDL.

The in vitro responses of human artery wall cells to HDL and LDL from mice fed the atherogenic diet and injected with a peptide according to this invention are consistent with the protective action shown by such peptides in vivo. Despite, similar levels of total cholesterol, LDL-cholesterol, IDL+ VLDL-cholesterol, and lower HDL-cholesterol as a percent of total cholesterol, the animals fed the atherogenic diet and injected with the peptide had significantly lower lesion scores (FIG. 5 in WO 02/15923). The peptides of this invention thus prevented progression of atherosclerotic lesions in mice fed an atherogenic diet.

Thus, in one embodiment, this invention provides methods for ameliorating and/or preventing one or more symptoms of atherosclerosis by administering one or more of the active agents described herein.

It is also noted that c-reactive protein, a marker for inflammation, is elevated in congestive heart failure. Also, in congestive heart failure there is an accumulation of reactive oxygen species and vasomotion abnormalities. Because of their effects in preventing/reducing the formation of various oxidized species and/or because of their effect in improving vasoreactivity and/or arteriole function (see below) the active agents described herein will be effective in treating congestive heart failure.

B) Arteriole/Vascular Indications.

Vessels smaller than even the smallest arteries (i.e., arterioles) thicken, become dysfunctional and cause end organ damage to tissues as diverse as the brain and the kidney. It is believed the active agents described herein can function to improve areteriole structure and function and/or to slow the rate and/or severity of arteriole dysfunction. Without being bound to a particular theory, it is believed that arteriole dysfunction is a causal factor in various brain and kidney disorders. Use of the agents described herein thus provides a method to improve the structure and function of arterioles and preserve the function of end organs such as the brain and kidney.

Thus, for example, administration of one or more of the active agents described herein is expected to reduce one or more symptoms or to slow the onset or severity of arteriolar disease associated with aging, and/or Alzheimer's disease, and/or Parkinson's disease, and/or with multi-infarct dementia, and/or subarachnoid hemorrhage, and the like. Similarly, administration of one or more agents described herein is expected to mitigate one or more symptoms and/or to slow the onset and/or severity of chronic kidney disease, and/or hypertension.

Similarly, the agents described herein appear to improve vasoreactivity. Because of the improvement of vasoreactivity and/or arteriole function, the agents described herein are suitable for the treatment of peripheral vascular disease, erectile dysfunction, and the like.

C) Pulmonary Indications.

The agents described herein are also suitable for treatment of a variety of pulmonary indications. These include, but are not limited to chronic obstructive pulmonary disease (COPD), emphysema, pulmonary disease, asthma, idiopathic pulmonary fibrosis, and the like.

D) Mitigation of a Symptom or Condition Associated with Coronary Calcification and Osteoporosis.

Vascular calcification and osteoporosis often co-exist in the same subjects (Ouchi et al. (1993) Ann NY Acad. Sci., 676: 297-307; Boukhris and Becker (1972) JAMA, 219: 1307-1131; Banks et al. (1994) Eur J Clin Invest., 24: 813-817; Laroche et al. (1994) Clin Rheumatol., 13: 611-614; Broulik and Kapitola (1993) Endocr Regul., 27: 57-60; Frye et al. (1992) Bone Mine., 19: 185-194; Barengolts et al. (1998) Calcif Tissue Int., 62: 209-213; Burnett and Vasikaran (2002) Ann Clin Biochem., 39: 203-210. Parhami et al. (1997) Arterioscl Thromb Vasc Biol., 17: 680-687, demonstrated that mildly oxidized LDL (MM-LDL) and the biologically active lipids in MM-LDL [i.e. oxidized 1-palmitoyl-2-arachidonoyl-sn-glycero-3-phosphorylcholine) (Ox-PAPC)], as well as the isoprostane, 8-iso prostaglandin $E_2$, but not the unoxidized phospholipid (PAPC) or isoprostane 8-iso progstaglandin $F_2\alpha$ induced alkaline phosphatase activity and osteoblastic differentiation of calcifying vascular cells (CVCs) in vitro, but inhibited the differentiation of MC3T3-E1 bone cells.

The osteon resembles the artery wall in that the osteon is centered on an endothelial cell-lined lumen surrounded by a subendothelial space containing matrix and fibroblast-like cells, which is in turn surrounded by preosteoblasts and osteoblasts occupying a position analogous to smooth muscle cells in the artery wall (Id.). Trabecular bone osteoblasts also interface with bone marrow subendothelial spaces (Id.). Parhami et al. postulated that lipoproteins could cross the endothelium of bone arteries and be deposited in the subendothelial space where they could undergo oxidation as in coronary arteries (Id.). Based on their in vitro data they predicted that LDL oxidation in the subendothelial space of bone arteries and in bone marrow would lead to reduced osteoblastic differentiation and mineralization which would contribute to osteoporosis (Id.). Their hypothesis further predicted that LDL levels would be positively correlated with osteoporosis as they are with coronary calcification (Pohle et al. (2001) Circulation, 104: 1927-1932), but HDL levels would be negatively correlated with osteoporosis (Parhami et al. (1997) Arterioscl Thromb Vasc Biol., 17: 680-687).

In vitro, the osteoblastic differentiation of the marrow stromal cell line M2-10B4 was inhibited by MM-LDL but not native LDL (Parhami et al. (1999) J Bone Miner Res., 14: 2067-2078). When marrow stromal cells from atherosclerosis susceptible C57BU6 (BL6) mice fed a low fat chow diet were cultured there was robust osteogenic differentiation (Id.). In contrast, when the marrow stromal cells taken from the mice after a high fat, atherogenic diet were cultured they did not undergo osteogenic differentiation (Id.). This observation is particularly important since it provides a possible explanation for the decreased osteogenic potential of marrow stromal cells in the development of osteoporosis (Nuttall and Gimble (2000) Bone, 27: 177-184). In vivo the decrease in osteogenic potential is accompanied by an increase in adipogenesis in osteoporotic bone (Id.).

It was found that adding D-4F to the drinking water of apoE null mice for 6 weeks dramatically increased trabecular bone mineral density and it is believed that the other active agents of this invention will act similarly.

Our data indicate that osteoporosis can be regarded as an "atherosclerosis of bone". It appears to be a result of the action of oxidized lipids. HDL destroys these oxidized lipids and promotes osteoblastic differentiation. Our data indicate that administering active agent (s) of this invention to a mammal (e.g., in the drinking water of apoE null mice) dramatically increases trabecular bone in just a matter of weeks.

This indicates that the active agents, described herein are useful for mitigation one or more symptoms of osteoporosis (e.g., for inhibiting decalcification) or for inducing recalcification of osteoporotic bone. The active agents are also useful as prophylactics to prevent the onset of symptom(s) of osteoporosis in a mammal (e.g., a patient at risk for osteoporosis).

We believe similar mechanisms are a cause of coronary calcification, e.g., calcific aortic stenosis. Thus, in certain embodiments, this invention contemplates the use of the active agents described herein to inhibit or prevent a symptom of a disease such as coronary calcification, calcific aortic stenosis, osteoporosis, and the like.

E) Inflammatory and Autoimmune Indications.

Chronic inflammatory and/or autoimmune conditions are also characterized by the formation of a number of reactive oxygen species and are amenable to treatment using one or more of the active agents described herein. Thus, without being bound to a particular theory, we also believe the active agents described herein are useful, prophylactically or therapeutically, to mitigate the onset and/or more or more symptoms of a variety of other conditions including, but not limited to rheumatoid arthritis, lupus erythematous, polyarteritis nodosa, polymyalgia rheumatica, scleroderma, multiple sclerosis, and the like.

In certain embodiments, the active agents are useful in mitigating one or more symptoms caused by, or associated with, an inflammatory response in these conditions.

Also, in certain embodiments, the active agents are useful in mitigating one or more symptoms caused by or associated with an inflammatory response associated with AIDS.

F) Infections/Trauma/Transplants.

We have observed that a consequence of influenza infection and other infections is the diminution in paraoxonase and platelet activating acetylhydrolase activity in the HDL. Without being bound by a particular theory, we believe that, as a result of the loss of these HDL enzymatic activities and also as a result of the association of pro-oxidant proteins with HDL during the acute phase response, HDL is no longer able to prevent LDL oxidation and is no longer able to prevent the LDL-induced production of monocyte chemotactic activity by endothelial cells.

We observed that in a subject injected with very low dosages of certain agents of this invention (e.g., 20 micrograms for mice) daily after infection with the influenza A virus paraoxonase levels did not fall and the biologically active oxidized phospholipids were not generated beyond background. This indicates that 4F, D4F (and/or other agents of this invention) can be administered (e.g. orally or by injection) to patients (including, for example with known coronary artery disease during influenza infection or other events that can generate an acute phase inflammatory response, e.g. due to viral infection, bacterial infection, trauma, transplant, various autoimmune conditions, etc.) and thus we can prevent by this short term treatment the increased incidence of heart attack and stroke associated with pathologies that generate such inflammatory states.

In addition, by restoring and/or maintaining paroxonase levels and/or monocyte activity, the agent(s) of this invention are useful in the treatment of infection (e.g., viral infection, bacterial infection, fungal infection) and/or the inflammatory pathologies associated with infection (e.g. meningitis) and/or trauma.

In certain embodiments, because of the combined anti-inflammatory activity and anti-infective activity, the agents described herein are also useful in the treatment of a wound or other trauma, mitigating adverse effects associated with organ or tissue transplant, and/or organ or tissue transplant rejection, and/or implanted prostheses, and/or transplant atherosclerosis, and/or biofilm formation. In addition, we believe that L-4F, D-4F, and/or other agents described herein are also useful in mitigating the effects of spinal cord injuries.

G) Diabetes and Associated Conditions.

Various active agents described herein have also been observed to show efficacy in reducing and/or preventing one or more symptoms associated with diabetes. Thus, in various embodiments, this invention provides methods of treating (therapeutically and/or prophylactically) diabetes and/or associated pathologies (e.g., Type I diabetes, Type II diabetes, juvenile onset diabetes, diabetic nephropathy, nephropathy, diabetic neuropathy, diabetic retinopathy, and the like.

H) Cancer.

NFκB is a transcription factor that is normally activated in response to proinflammatory cytokines and that regulates the expression of more than 200 genes. Many tumor cell lines show constitutive activation of NFκB signaling. Various studies of mouse models of intestinal, and mammary tumors conclude that activation of the NFκB pathway enhances tumor development and may act primarily in the late stages of tumorigenesis (see, e.g., (2004) Cell 118: 285; (2004) J. Clin. Invest., 114: 569). Inhibition of NFκB signaling suppressed tumor development. Without being bound to a particular theory, mechanisms for this suppression are believed to include an increase in tumor cell apoptosis, reduced expression of tumor cell growth factors supplied by surrounding stromal cells, and/or abrogation of a tumor cell dedifferentiation program that is critical for tumor invasion/metastasis.

Without being bound by a particular theory, it is believed the administration of one or more active agents described herein will inhibit expression and/or secretion, and/or activity of NFκB. Thus, in certain embodiments, this invention provides methods of treating a pathology characterized by elevated NFκB by administering one or more active agents described herein. Thus, In various embodiments this invention contemplates inhibiting NFκB activation associated with cancer by administering one or more active agents described herein, optionally in combination with appropriate cancer therapeutics.

I) Biochemical Activity.

The active agent(s) described herein have been shown to exhibit a number of specific biological activities. Thus, for example, they increase heme oxygenase 1, they increase extracellular superoxide dismutase, they reduce or prevent the association of myeloperoxidase with apoA-I, they reduce or prevent the nitrosylation of tyrosine in apoA-I, they render HDL Anti-inflammatory or more anti-inflammatory, and they increase the formation cycling of pre-βHDL, they promote reverse cholesterol transport, in particular, reverse cholesterol transport from macrophages, and they synergize the activity of statins. The active agents described herein can thus be administered to a mammal to promote any of these activities, e.g. to treat a condition/pathology whose severity, and/or likelihood of onset is reduced by one or more of these activities.

J) Mitigation of a Symptom of Atherosclerosis Associated with an Acute Inflammatory Response.

The active agents, of this invention are also useful in a number of contexts. For example, we have observed that cardiovascular complications (e.g., atherosclerosis, stroke, etc.) frequently accompany or follow the onset of an acute phase inflammatory response, e.g., such as that associated with a recurrent inflammatory disease, a viral infection (e.g., influenza), a bacterial infection, a fungal infection, an organ transplant, a wound or other trauma, and so forth.

Thus, in certain embodiments, this invention contemplates administering one or more of the active agents described herein to a subject at risk for, or incurring, an acute inflammatory response and/or at risk for or incurring a symptom of atherosclerosis and/or an associated pathology (e.g., stroke).

Thus, for example, a person having or at risk for coronary disease may prophylactically be administered a one or more active agents of this invention during flu season. A person (or animal) subject to a recurrent inflammatory condition, e.g., rheumatoid arthritis, various autoimmune diseases, etc., can be treated with a one or more agents described herein to mitigate or prevent the development of atherosclerosis or stroke. A person (or animal) subject to trauma, e.g., acute injury, tissue transplant, etc. can be treated with a polypeptide of this invention to mitigate the development of atherosclerosis or stroke.

In certain instances such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPS) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase response, or risk therefore is evaluated by measuring one or more APPs. Measuring such markers is well known to those of skill in the art, and commercial companies exist that provide such measurement (e.g., AGP measured by Cardiotech Services, Louisville, Ky.).

K) Eye Disease

Also disclosed are methods for ameliorating and/or preventing one or more symptoms of eye disease by administering one or more of the active agents described herein. As described above, the "eye disease" includes, but is not limited to, age related maculopathy (ARM), age related macular degeneration (AMD) including both the dry and wet forms of age related macular degeneration, glaucoma, ocular hypertension, macular edema, retinal pigment epithelium detachments, coats disease, uveitis, sicca syndrome, hereditary diseases associated with increased extra-/intracellular lipid storage/accumulation, juvenile macular degeneration as well as all risk factors for each mentioned disease.

For example the active agents disclosed herein can mobilize and remove accumulated intra-/extracellular lipid deposits in all eye structures. The active agents can also structurally remodel essential transport passages and supply structures and/or they have the highest affinity to oxidized lipids, which removal of such oxidized lipids can causes an anti-inflammatory effect.

The active agents can be used prophylactically in both the treatment and prevention of eye diseases if risk factors are present. Risk factors for eye disease are described elsewhere herein.

1) Macular Degeneration

Age-related macular degeneration sometimes begins with characteristic yellow deposits in the macula (central area of the retina which provides detailed central vision) called drusen between the retinal pigment epithelium and the underlying choroid. Most people with these early changes (sometimes referred to as age-related maculopathy) have good vision. People with drusen can go on to develop advanced macular degeneration. The risk is considerably higher when the drusen are large and numerous and associated with disturbance in the pigmented cell layer under the macula. Recent research suggests that large and soft drusen are related to elevated cholesterol deposits and may respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, lutein and zeaxanthin, have been demonstrated by the National Eye Institute and others to slow the progression of dry macular degeneration and in some patients, improve visual acuity.

Neovascular or exudative AMD, the wet form of advanced AMD, causes vision loss due to abnormal blood vessel growth in the choriocapillaries, through Bruch's membrane, ultimately leading to blood and protein leakage below the macula. Bleeding, leaking, and scarring from these blood vessels eventually cause irreversible damage to the photoreceptors and rapid vision loss if left untreated.

Until recently, no effective treatments were known for wet macular degeneration. However, new drugs, called anti-angiogenics or anti-VEGF (anti-Vascular Endothelial Growth Factor) agents, when injected directly into the vitreous humor of the eye using a small, painless needle, can cause regression of the abnormal blood vessels and improvement of vision. The injections frequently have to be repeated on a monthly or bi-monthly basis. Examples of these agents include Lucentis, Avastin and Macugen. Only Lucentis and Macugen are FDA approved as of April 2007. Macugen has been found to have only minimal benefits in neovascular AMD and is no longer used. Worldwide, Avastin has been used extensively despite its "off label" status. The cost of Lucentis is approximately $2000 US while the cost of Avastin is approximately $150.

2) AMD: Dry Form: Geographic Atrophy

The remodeling of Bruch's membrane provides an undisturbed passage between retinal pigment epithelium and choriocapillaris, which is essential for the health of the retina. The retinal pigment epithelium stands with the choriocapillaris in a close relationship and they are dependent on each other. An uncompromised communication between these structures improves the blood supply for the outer retina by the choriocapillaris and the retinal pigment epithelium layer integrity by improved anchorage on Bruch's membrane via water soluble proteins.

3) AMD: Wet Form: Choroidal Neovascularization

The same mechanism as for dry AMD applies. Due to the improved environmental conditions retinal pigment epithelium cells also reduce the secretion of pro-angiogenic factors, which normally keeps a neovascularization active for a longer period. In combination with anti-angiogenic treatments (elsewhere herein) pro-angiogenic mechanisms are not just temporarily blocked but the secretion stimulus can be long-term reduced.

4) Glaucoma/Ocular Hypertension

One main characteristic of glaucoma/ocular hypertension is elevated intraocular pressure (TOP). The treatment of the age-related "lipid wall" in Bruch's membrane increases the hydraulic conductivity along Bruch's membrane again and facilitates fluid transport from the vitreous to the choroid (vitreoretinal-choroidal outflow, uveoscleral outflow), which can normalize the IOP.

5) Macular Edema, Retinal Pigment Epithelium Detachments

Macular edema is characterized by trapped fluid accumulations in the retina and RPE detachments by fluid accumulations under the retinal pigment epithelium. The normal fluid transport is directed across Bruch's membrane into the choriocapillaris. An improved transport across Bruch's membrane after lipid clean up ("lipid wall") and remodeling due to ApoA-I/ApoE mimetic peptide treatment facilitates the natural fluid transport and helps to resolve the sight-threatening macular edema and RPE detachment.

L) Mitigation of a Symptom of Macular Degeneration.

The active agents, of this invention are also useful in a number of contexts. For example, we have observed that eye disease (e.g., macular degeneration, etc.) are frequently associated with drusen, basal linear deposit, basal laminar deposit, lipid accumulation in Bruch's membrane, and/or positive genetic risk profiles, and so forth.

Thus, in certain embodiments, this invention contemplates administering one or more of the active agents described herein to a subject at risk for, or incurring, one or more of the symptoms and/or at risk for or incurring a symptom of an eye disease and/or an associated pathology (e.g., blindness).

Thus, for example, a person having or at risk for eye disease may prophylactically be administered a one or more active agents of this invention during flu season. A person (or animal) subject to an eye disease, e.g., macular degeneration, glaucoma, etc., can be treated with a one or more agents described herein to mitigate or prevent the development of eye disease. A person (or animal) subject to trauma, e.g., acute injury, tissue transplant, etc. can also be treated with a polypeptide of this invention to mitigate the development of eye disease.

In certain instances such methods will entail a diagnosis of the occurrence or risk of an eye disease. The eye disease typically involves alterations in drusen, basal linear deposit, basal laminar deposit, lipid accumulation in and/or Bruch's membrane.

M) Other Indications.

In various embodiments it is contemplated that the active agents described herein are useful in the treatment (e.g. mitigation and/or prevention) of corneal ulcers, endothelial sloughing, Crohn's disease, acute and chronic dermatitis (including, but not limited to eczema and/or psoriasis), macular degeneration, neuropathy, scleroderma, and ulcerative colitis.

A summary of indications/conditions for which the active agents have been shown to be effective and/or are believed to be effective is shown in Table 1.

TABLE 1

Summary of conditions in which the active agents (e.g., D-4F) have been shown to be or are believed to be effective.

atherosclerosis/symptoms/consequences thereof
    plaque formation
    lesion formation
    myocardial infarction
    stroke
    congestive heart failure
    vascular function:
        arteriole function
        arteriolar disease
            associated with aging
            associated with alzheimer's disease
            associated with chronic kidney disease
            associated with hypertension
            associated with multi-infarct dementia
            associated with subarachnoid hemorrhage peripheral vascular disease
        peripheral vascular disease
    pulmonary disease:
        chronic obstructive pulmonary disease (COPD)
        emphysema
        asthma
        idiopathic pulmonary fibrosis
        pulmonary fibrosis
        adult respiratory distress syndrome
    osteoporosis
    Paget's disease
    coronary calcification
    autoimmune:

TABLE 1-continued

Summary of conditions in which the active agents (e.g., D-4F) have been shown to be or are believed to be effective.

rheumatoid arthritis
        polyarteritis nodosa
        polymyalgia rheumatica
        lupus erythematosus
        multiple sclerosis
        Wegener's granulomatosis
        central nervous system vasculitis (CNSV)
        Sjogren's syndrome
        Scleroderma
        polymyositis
AIDS inflammatory response
infections:
    bacterial
    fungal
    viral
    parasitic
    influenza
        avian flu
    viral pneumonia
    endotoxic shock syndrome
    sepsis
    sepsis syndrome
    (clinical syndrome where it appears that the patient is septic but no organisms are recovered from the blood)
trauma/wound:
    organ transplant
    transplant atherosclerosis
    transplant rejection
    corneal ulcer
    chronic/non-healing wound
    ulcerative colitis
    reperfusion injury (prevent and/or treat)
    ischemic reperfusion injury (prevent and/or treat)
    spinal cord injuries (mitigating effects)
cancers
    myeloma/multiple myeloma
    ovarian cancer
    breast cancer
    colon cancer
    bone cancer
osteoarthritis
inflammatory bowel disease
allergic rhinitis
cachexia
diabetes
Alzheimer's disease
implanted prosthesis
biofilm formation
Crohns' disease
dermatitis, acute and chronic
    eczema
    psoriasis
    contact dermatitis
    scleroderma
diabetes and related conditions
        Type I Diabetes
        Type II Diabetes
        Juvenile Onset Diabetes
        Prevention of the onset of diabetes
        Diabetic Nephropathy
        Diabetic Neuropathy
        Diabetic Retinopathy
    erectile dysfunction
    macular degeneration
    multiple sclerosis
    nephropathy
    neuropathy
    Parkinson's Disease
    peripheral Vascular Disease
    meningitis
    Specific biological activities:
        increase Heme Oxygenase 1
        increase extracellular superoxide dismutase
        prevent endothelial sloughing
        prevent the association of myeloperoxidase with ApoA-I
        prevent the nitrosylation of tyrosine in ApoA-I
        render HDL anti-inflammatory TABLE 1-continued Summary of conditions in which the active agents (e.g., D-4F) have been shown to be or are believed to be effective.

improve vasoreactivity
increase the formation of pre-beta HDL
promote reverse cholesterol transport
promote reverse cholesterol transport from macrophages
synergize the action of statins It is noted that the conditions listed in Table 1 are intended to be illustrative and not limiting.

It is noted that the conditions listed in Table 1 are intended to be illustrative and not limiting.

N) Administration.

Typically the active agent(s) will be administered to a mammal (e.g., a human) in need thereof. Such a mammal will typically include a mammal (e.g. a human) having or at risk for one or more of the pathologies described herein.

The active agent(s) can be administered, as described herein, according to any of a number of standard methods including, but not limited to injection, suppository, nasal spray, time-release implant, transdermal patch, eye drops, gels, ointments, orally, intraocular injection, parenterally (e.g., intravenously or subcutaneous administration), by intramuscular injection, by intraperitoneal injection, subconjuctival injection, peri-/retrobulbar injection, transdermally, extracorporeally, by intracavity administration, transdermally, or topically or the like, including topical intranasal administration or administration by inhalant, and the like, spray, emulsion, suspension, via any drug carriers as sponges, contact lenses, polymers, microspheres, implants, pellets, and genetically engineered cells. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or vector used, its mode of administration and the like. An appropriate amount for a particular composition and a particular subject can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

The active agent(s) can also be administered, as described herein, for immediate delivery or extended release. The active agent(s) can also be administered as dilutions, suspensions, emulsions, polymers, microspheres, gels, crèmes, and/or pellets. The active agents can also be administered in the form of drug carriers, sponges, polymers encapsulated cells, engineered cells, implants, and the like.

In one particularly preferred embodiment, the peptide(s) are administered orally (e.g. as a syrup, capsule, or tablet).

The methods involve the administration of a single active agent of this invention or the administration of two or more different active agents. The active agents can be provided as monomers (e.g., in separate or combined formulations), or in dimeric, oligomeric or polymeric forms. In certain embodiments, the multimeric forms may comprise associated monomers (e.g., ionically or hydrophobically linked) while certain other multimeric forms comprise covalently linked monomers (directly linked or through a linker).

While the invention is described with respect to use in humans, it is also suitable for animal, e.g. veterinary use. Thus certain preferred organisms include, but are not limited to humans, non-human primates, canines, equines, felines, porcines, ungulates, largomorphs, and the like.

The methods of this invention are not limited to humans or non-human animals showing one or more symptom(s) of the pathologies described herein, but are also useful in a prophylactic context. Thus, the active agents of this invention can be administered to organisms to prevent the onset/development of one or more symptoms of the pathologies described herein (e.g., atherosclerosis, stroke, macular degeneration, etc.). Particularly preferred subjects in this context are subjects showing one or more risk factors for the pathology. Thus, for example, in the case of atherosclerosis risk factors include family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.

In the case of eye disease, factors can include, but are not limited to age, family history, genetic predisposition, hypertension, obesity, cardiovascular health, fat intake, plasma lipids, oxidative stress, race, and exposure to sunlight.

P) Dosages

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products. For example, disclosed herein are methods comprising administering one or more of the disclosed synthetic apolipoprotein E-mimicking peptides to a subject, whereby plasma LDL, plasma VLDL, or both, are affected, wherein said synthetic apolipoprotein E-mimicking peptide is administered in an amount of about 0.01 mg/kg to about 5 mg/kg.

Dosages also suitable for administration of the active agents disclosed herein include, but are not limited to dosages of 10 µg/ml to 400 µg/ml. For example, For example, disclosed herein are methods comprising administering one or more of the disclosed synthetic apolipoprotein E-mimicking peptides to a subject, whereby plasma LDL, plasma VLDL, or both, are affected, wherein said synthetic apolipoprotein E-mimicking peptide is administered in an amount of about 200 ug/ml to 800 ug/ml.

II. Active Agents

A wide variety of active agents are suitable for the treatment of one or more of the indications discussed above. These agents include, but are not limited to class A amphipathic helical peptides, class A amphipathic helical peptide mimetics of apoA-I having aromatic or aliphatic residues in the non-polar face, small peptides including pentapeptides, tetrapeptides, tripeptides, dipeptides and pairs of amino acids, Apo-J (G* peptides), and peptide mimetics, e.g., as described below.

A) Class A Amphipathic Helical Peptides.

In certain embodiments, the activate agents for use in the method of this invention include class A amphipathic helical peptides, e.g. as described in U.S. Pat. No. 6,664,230, and PCT Publications WO 02/15923 and WO 2004/034977. It was discovered that peptides comprising a class A amphipathic helix ("class A peptides"), in addition to being capable of mitigating one or more symptoms of atherosclerosis are also useful in the treatment of one or more of the other indications described herein.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) Meth. Enzymol, 128: 626-668). It is noted that the fourth exon of apo A-I, when folded into 3.667 residues/turn produces a class A amphipathic helical structure.

One class A peptide, designated 18A (see, e.g., Anantharamaiah (1986) Meth. Enzymol, 128: 626-668) was modified as described herein to produce peptides orally administrable and highly effective at inhibiting or preventing one or more symptoms of atherosclerosis and/or other indications described herein. Without being bound by a particular theory, it is believed that the peptides of this invention may act in vivo by picking up seeding molecule(s) that mitigate oxidation of LDL.

Another theory could be that with macular degeneration, where the presence of lipids in the Bruch's membrane causes the transfer of blood from the eye vessels through the Bruch's membrane to the retinal pigment cells and then to the photoreceptors to decrease. The decrease in blood flow leads to a decrease in oxygen getting to the photoreceptors. The body then responds by creating more vasculature that invades the Bruch's membrane and into the retinal pigment epithelial cells to compensate for the decrease in oxygen supply to the photoreceptors and retinal pigment epithelial cells. By providing one or more of the active agents described herein, the lipid accumulation could be removed and/or prevented, thereby relieving the need for increased vasculature. In addition, by providing one or more of the active agents described herein in combination with an anti-angiogenic factor, not only could the lipid accumulation be removed and/or prevented, the revascularization could be prevented as well, thereby relieving the need for increased vasculature and preventing detrimental vascular growth.

We determined that increasing the number of Phe residues on the hydrophobic face of 18A would theoretically increase lipid affinity as determined by the computation described by Palgunachari et al. (1996) Arteriosclerosis, Thrombosis, & Vascular Biol. 16: 328-338. Theoretically, a systematic substitution of residues in the nonpolar face of 18A with Phe could yield six peptides. Peptides with an additional 2, 3 and 4 Phe would have theoretical lipid affinity (λ) values of 13, 14 and 15 units, respectively. However, the λ values jumped four units if the additional Phe were increased from 4 to 5 (to 19λ units). Increasing to 6 or 7 Phe would produce a less dramatic increase (to 20 and 21λ units, respectively).

A number of these class A peptides were made including, the peptide designated 4F, D4F, 5F, and D5F, and the like. Various class A peptides inhibited lesion development in atherosclerosis-susceptible mice. In addition, the peptides show varying, but significant degrees of efficacy in mitigating one or more symptoms of the various pathologies described herein. A number of such peptides are illustrated in Table 2.

TABLE 2

| Peptide Name | Amino Acid Sequence | SEQ ID NO. |
|---|---|---|
| 18F | D-W-L-K-A-F-Y-D-K-V-A-E-K-L-K-E-A-F | 1 |
| 2F | Ac-D-W-L-K-A-F-Y-D-K-V-A-E-K-L-K-E-A-F-NH$_2$ | 2 |
| 3F | Ac-D-W-F-K-A-F-Y-D-K-V-A-E-K-L-K-E-A-F-NH$_2$ | 3 |
| 3F14 | Ac-D-W-L-K-A-F-Y-D-K-V-A-E-K-F-K-E-A-F-NH$_2$ | 4 |
| 4F | Ac-D-W-F-K-A-F-Y-D-K-V-A-E-K-F-K-E-A-F-NH$_2$ | 5 |
| 5F | Ac-D-W-L-K-A-F-Y-D-K-V-F-E-K-F-K-E-F-F-NH$_2$ | 6 |
| 6F | Ac-D-W-L-K-A-F-Y-D-K-F-F-E-K-F-K-E-F-F-NH$_2$ | 7 |
| 7F | Ac-D-W-F-K-A-F-Y-D-K-F-F-E-K-F-K-E-F-F-NH$_2$ | 8 |
|  | Ac-D-W-L-K-A-F-Y-D-K-V-A-E-K-L-K-E-F-F-NH$_2$ | 9 |
|  | Ac-D-W-L-K-A-F-Y-D-K-V-F-E-K-F-K-E-A-F-NH$_2$ | 10 |
|  | Ac-D-W-L-K-A-F-Y-D-K-V-F-E-K-L-K-E-F-F-NH$_2$ | 11 |
|  | Ac-D-W-L-K-A-F-Y-D-K-V-A-E-K-F-K-E-F-F-NH$_2$ | 12 |
|  | Ac-D-W-L-K-A-F-Y-D-K-V-F-E-K-F-K-E-F-F-NH$_2$ | 13 |

TABLE 2-continued

| Peptide Name | Amino Acid Sequence | SEQ ID NO. |
|---|---|---|
| | Ac-E-W-L-K-L-F-Y-E-K-V-L-E-K-F-K-E-A-F-NH₂ | 14 |
| | Ac-E-W-L-K-A-F-Y-ID-K-V-A-E-K-F-K-E-A-F-NH₂ | 15 |
| | Ac-E-W-L-K-A-F-Y-D-K-V-A-E-K-L-K-E-F-F-NH₂ | 16 |
| | Ac-E-W-L-K-A-F-Y-D-K-V-F-E-K-F-K-E-A-F-NH₂ | 17 |
| | Ac-E-W-L-K-A-F-Y-D-K-V-F-E-K-L-K-E-F-F-NH₂ | 18 |
| | Ac-E-W-L-K-A-F-Y-D-K-V-A-E-K-F-K-E-F-F-NH₂ | 19 |
| | Ac-E-W-L-K-A-F-Y-D-K-V-F-E-K-F-K-E-F-F-NH₂ | 20 |
| | Ac-A-F-Y-D-K-V-A-E-K-L-K-E-A-F-NH₂ | 21 |
| | Ac-A-F-Y-D-K-V-A-E-K-F-K-E-A-F-NH₂ | 22 |
| | Ac-A-F-Y-D-K-V-A-E-K-F-K-E-A-F-NH₂ | 23 |
| | Ac-A-F-Y-D-K-F-F-E-K-F-K-E-F-F-NH₂ | 24 |
| | Ac-A-F-Y-D-K-F-F-E-K-F-K-E-F-F-NH₂ | 25 |
| | Ac-A-F-Y-D-K-V-A-E-K-F-K-E-A-F-NH₂ | 26 |
| | Ac-A-F-Y-D-K-V-A-E-K-L-K-E-F-F-NH₂ | 27 |
| | Ac-A-F-Y-D-K-V-F-E-K-F-K-E-A-F-NH₂ | 28 |
| | Ac-A-F-Y-D-K-V-F-E-K-L-K-E-F-F-NH₂ | 29 |
| | Ac-A-F-Y-D-K-V-A-E-K-F-K-E-F-F-NH₂ | 30 |
| | Ac-K-A-F-Y-D-K-V-F-E-K-F-K-E-F-NH₂ | 31 |
| | Ac-L-F-Y-E-K-V-L-E-K-F-K-E-A-F-NH₂ | 32 |
| | Ac-A-F-Y-D-K-V-A-E-K-F-K-E-A-F-NH₂ | 33 |
| | Ac-A-F-Y-D-K-V-A-E-K-L-K-E-F-F-NH₂ | 34 |
| | Ac-A-F-Y-D-K-V-F-E-K-F-K-E-A-F-NH₂ | 35 |
| | Ac-A-F-Y-D-K-V-F-E-K-L-K-E-F-F-NH₂ | 36 |
| | Ac-A-F-Y-D-K-V-A-E-K-F-K-E-F-F-NH₂ | 37 |
| | Ac-A-F-Y-D-K-V-F-E-K-F-K-E-F-F NH₂ | 38 |
| | Ac-D-W-L-K-A-L-Y-D-K-V-A-E-K-L-K-E-A-L-NH₂ | 39 |
| | Ac-D-W-F-K-A-F-Y-E-K-V-A-E-K-L-K-E-F-F-NH₂ | 40 |
| | Ac-D-W-F-K-A-F-Y-E-K-F-F-E-K-F-K-E-F-F-NH₂ | 41 |
| | Ac-E-W-L-K-A-L-Y-E-K-V-A-E-K-L-K-E-A-L-NH₂ | 42 |
| | Ac-E-W-L-K-A-F-Y-E-K-V-A-E-K-L-K-E-A-F-NH₂ | 43 |
| | Ac-E-W-F-K-A-F-Y-E-K-V-A-E-K-L-K-E-F-F-NH₂ | 44 |
| | Ac-E-W-L-K-A-F-Y-E-K-V-F-E-K-F-K-E-F-F-NH₂ | 45 |
| | Ac-E-W-L-K-A-F-Y-E-K-F-F-E-K-F-K-E-F-F-NH₂ | 46 |
| | Ac-E-W-F-K-A-F-Y-E-K-F-F-E-K-F-K-E-F-F-NH₂ | 47 |
| | Ac-D-F-L-K-A-W-Y-D-K-V-A-E-K-L-K-E-A-W-NH₂ | 48 |
| | Ac-E-F-L-K-A-W-Y-E-K-V-A-E-K-L-K-E-A-W-NH₂ | 49 |
| | Ac-D-F-W-K-A-W-Y-D-K-V-A-E-K-L-K-E-W-W-NH₂ | 50 |
| | Ac-E-F-W-K-A-W-Y-E-K-V-A-E-K-L-K-E-W-W-NH₂ | 51 |
| | Ac-D-K-L-K-A-F-Y-D-K-V-F-E-W-A-K-E-A-F-NH₂ | 52 |

TABLE 2-continued

| Peptide Name | Amino Acid Sequence | SEQ ID NO. |
| --- | --- | --- |
| | Ac-D-K-W-K-A-V-Y-D-K-F-A-E-A-F-K-E-F-L-NH$_2$ | 53 |
| | Ac-E-K-L-K-A-F-Y-E-K-V-F-E-W-A-K-E-A-F-NH$_2$ | 54 |
| | Ac-E-K-W-K-A-V-Y-E-K-F-A-E-A-F-K-E-F-L-NH$_2$ | 55 |
| | Ac-D-W-L-K-A-F-V-D-K-F-A-E-K-F-K-E-A-Y-NH$_2$ | 56 |
| | Ac-E-K-W-K-A-V-Y-E-K-F-A-E-A-F-K-E-F-L-NH$_2$ | 57 |
| | Ac-D-W-L-K-A-F-V-Y-D-K-V-F-K-L-K-E-F-F-NH$_2$ | 58 |
| | Ac-E-W-L-K-A-F-V-Y-E-K-V-F-K-L-K-E-F-F-NH$_2$ | 59 |
| | Ac-D-W-L-R-A-F-Y-D-K-V-A-E-K-L-K-E-A-F-NH$_2$ | 60 |
| | Ac-E-W-L-R-A-F-Y-E-K-V-A-E-K-L-K-E-A-F-NH$_2$ | 61 |
| | Ac-D-W-L-K-A-F-Y-D-R-V-A-E-K-L-K-E-A-F-NH$_2$ | 62 |
| | Ac-E-W-L-K-A-F-Y-E-R-V-A-E-K-L-K-E-A-F-NH$_2$ | 63 |
| | Ac-D-W-L-K-A-F-Y-D-K-V-A-E-R-L-K-E-A-F-NH$_2$ | 64 |
| | Ac-E-W-L-K-A-F-Y-E-K-V-A-E-R-L-K-E-A-F-NH$_2$ | 65 |
| | Ac-D-W-L-K-A-F-Y-D-K-V-A-E-K-L-R-E-A-F-NH$_2$ | 66 |
| | Ac-E-W-L-K-A-F-Y-E-K-V-A-E-K-L-R-E-A-F-NH$_2$ | 67 |
| | Ac-D-W-L-K-A-F-Y-D-R-V-A-E-R-L-K-E-A-F-NH$_2$ | 68 |
| | Ac-E-W-L-K-A-F-Y-E-R-V-A-E-R-L-K-E-A-F-NH$_2$ | 69 |
| | Ac-D-W-L-R-A-F-Y-D-K-V-A-E-K-L-R-E-A-F-NH$_2$ | 70 |
| | Ac-E-W-L-R-A-F-Y-E-K-V-A-E-K-L-R-E-A-F-NH$_2$ | 71 |
| | Ac-D-W-L-R-A-F-Y-D-R-V-A-E-K-L-K-E-A-F-NH$_2$ | 72 |
| | Ac-E-W-L-R-A-F-Y-E-R-V-A-E-K-L-K-E-A-F-NH$_2$ | 73 |
| | Ac-D-W-L-K-A-F-Y-D-K-V-A-E-R-L-R-E-A-F-NH$_2$ | 74 |
| | Ac-E-W-L-K-A-F-Y-E-K-V-A-E-R-L-R-E-A-F-NH$_2$ | 75 |
| | Ac-D-W-L-R-A-F-Y-D-R-V-A-E-R-L-K-E-A-F-NH$_2$ | 76 |
| | Ac-E-W-L-R-A-F-Y-E-K-V-A-E-R-L-K-E-A-F-NH$_2$ | 77 |
| | D-W-L-K-A-F-Y-D-K-V-A-E-K-L-K-E-A-F-<u>P</u>-D-W<br>L-K-A-F-Y-D-K-V-A-E-K-L-K-E-A-F | 78 |
| | D-W-L-K-A-F-Y-D-K-V-A-E-K-L-K-E-F-F-<u>P</u>-D-W<br>L-K-A-F-Y-D-K-V-A-E-K-L-K-E-F-F | 79 |
| | D-W-F-K-A-F-Y-D-K-V-A-E-K-L-K-E-A-F-<u>P</u>-D-W<br>F-K-A-F-Y-D-K-V-A-E-K-L-K-E-A-F | 80 |
| | D-K-L-K-A-F-Y-D-K-V-F-E-W-A-K-E-A-F-<u>P</u>-D-K<br>L-K-A-F-Y-D-K-V-F-E-W-L-K-E-A-F | 81 |
| | D-K-W-K-A-V-Y-D-K-F-A-E-A-F-K-E-F-L-<u>P</u>-D-K<br>W-K-A-V-Y-D-K-F-A-E-A-F-K-E-F-L | 82 |
| | D-W-F-K-A-F-Y-D-K-V-A-E-K-F-K-E-A-F-<u>P</u>-D-W<br>F-K-A-F-Y-D-K-V-A-E-K-F-K-E-A-F | 83 |
| | D-W-L-K-A-F-V-Y-D-K-V-F-K-L-K-E-F-F-<u>P</u>-D-W<br>L-K-A-F-V-Y-D-K-V-F-K-L-K-E-F-F | 84 |
| | D-W-L-K-A-F-Y-D-K-F-A-E-K-F-K-E-F-F-<u>P</u>-D-W<br>L-K-A-F-Y-D-K-F-A-E-K-F-K-E-F-F | 85 |
| | Ac-E-W-F-K-A-F-Y-E-K-V-A-E-K-F-K-E-A-F-NH$_2$ | 86 |
| | Ac-D-W-F-K-A-F-Y-D-K-V-A-E-K-F-NH$_2$ | 87 |

TABLE 2-continued

| Peptide Name | Amino Acid Sequence | SEQ ID NO. |
|---|---|---|
| | Ac-F-K-A-F-Y-D-K-V-A-E-K-F-K-E-NH$_2$ | 88 |
| | Ac-F-K-A-F-Y-E-K-V-A-E-K-F-K-E-NH$_2$ | 89 |
| | NMA-F-K-A-F-Y-D-K-V-A-E-K-F-K-E-NH$_2$ | 90 |
| | NMA-F-K-A-F-Y-E-K-V-A-E-K-F-K-E-NH$_2$ | 91 |
| | NMA-D-W-F-K-A-F-Y-D-K-V-A-E-K-F-K-E-A-F-NH$_2$ | 92 |
| | NMA-E-W-F-K-A-F-Y-E-K-V-A-E-K-F-K-E-A-F-NH$_2$ | 93 |
| | NMA-A-F-Y-D-K-V-A-E-K-F-K-E-A-F-NH$_2$ | 94 |
| | NMA-D-W-F-K-A-F-Y-D-K-V-A-E-K-F-NH$_2$ | 95 |
| | Ac-D-W-L-K-A-F-Y-D-K-V-F-E-K-F-K-E-F-F-NH$_2$ | 96 |
| | NMA-D-W-L-K-A-F-Y-D-K-V-F-E-K-F-K-E-F-F-NH$_2$ | 1198 |
| | Ac-E-W-L-K-A-F-Y-E-K-V-F-E-K-F-K-E-F-F-NH$_2$ | 97 |
| | NMA-E-W-L-K-A-F-Y-E-K-V-F-E-K-F-K-E-F-F-NH$_2$ | 1199 |
| | Ac-A-F-Y-D-K-V-F-E-K-F-K-E-F-F-NH$_2$ | 98 |
| | NMA-A-F-Y-D-K-V-F-E-K-F-K-E-F-F-NH$_2$ | 1200 |
| | Ac-A-F-Y-E-K-V-F-E-K-F-K-E-F-F-NH$_2$ | 99 |
| | NMA-A-F-Y-E-K-V-F-E-K-F-K-E-F-F-NH$_2$ | 1201 |
| | Ac-D-W-L-K-A-F-Y-D-K-V-F-E-K-F-NH$_2$ | 100 |
| | NMA-D-W-L-K-A-F-Y-D-K-V-F-E-K-F-NH$_2$ | 1202 |
| | Ac-E-W-L-K-A-F-Y-E-K-V-F-E-K-F-NH$_2$ | 101 |
| | NMA-E-W-L-K-A-F-Y-E-K-V-F-E-K-F-NH$_2$ | 1203 |
| | Ac-L-K-A-F-Y-D-K-V-F-E-K-F-K-E-NH$_2$ | 102 |
| | NMA-L-K-A-F-Y-D-K-V-F-E-K-F-K-E-NH$_2$ | 1204 |
| | Ac-L-K-A-F-Y-E-K-V-F-E-K-F-K-E-NH$_2$ | 103 |
| | NMA-L-K-A-F-Y-E-K-V-F-E-K-F-K-E-NH$_2$ | 1205 |

*Linkers are underlined.
NMA is N-Methyl Anthranilyl.

In certain preferred embodiments, the peptides include variations of 4F ((SEQ ID NO:5 in Table 2), also known as L-4F, where all residues are L form amino acids) or D-4F where one or more residues are D form amino acids). In any of the peptides described herein, the C-terminus, and/or N-terminus, and/or internal residues can be blocked with one or more blocking groups as described herein.

While various peptides of Table 2, are illustrated with an acetyl group or an N-methylanthranilyl group protecting the amino terminus and an amide group protecting the carboxyl terminus, any of these protecting groups may be eliminated and/or substituted with another protecting group as described herein. In particularly preferred embodiments, the peptides comprise one or more D-form amino acids as described herein. In certain embodiments, every amino acid (e.g., every enantiomeric amino acid) of the peptides of Table 2 is a D-form amino acid.

It is also noted that Table 2 is not fully inclusive. Using the teachings provided herein, other suitable class A amphipathic helical peptides can routinely be produced (e.g., by conservative or semi-conservative substitutions (e.g., D replaced by E), extensions, deletions, and the like). Thus, for example, one embodiment utilizes truncations of any one or more of peptides shown herein (e.g., peptides identified by SEQ ID Nos:2-20 and 39—in Table 2). Thus, for example, SEQ ID NO:21 illustrates a peptide comprising 14 amino acids from the C-terminus of 18A comprising one or more D amino acids, while SEQ ID NOS:22-38 illustrate other truncations.

Longer peptides are also suitable. Such longer peptides may entirely form a class A amphipathic helix, or the class A amphipathic helix (helices) can form one or more domains of the peptide. In addition, this invention contemplates multimeric versions of the peptides (e.g., concatamers). Thus, for example, the peptides illustrated herein can be coupled together (directly or through a linker (e.g., a carbon linker, or one or more amino acids) with one or more intervening amino acids). Illustrative polymeric peptides include 18A-Pro-18A and the peptides of SEQ ID NOs:78-85, in certain embodiments comprising one or more D amino acids, more preferably with every amino acid a D amino acid as described herein and/or having one or both termini protected.

It will also be appreciated in addition to the peptide sequences expressly illustrated herein, this invention also contemplates retro and retro-inverso forms of each of these peptides. In retro forms, the direction of the sequence is reversed. In inverse forms, the chirality of the constituent amino acids is reversed (i.e., L form amino acids become D form amino acids and D form amino acids become L form amino acids). In the retro-inverso form, both the order and the chirality of the amino acids is reversed. Thus, for example, a retro form of the 4F peptide (DWFKAFYDKVAEKFKEAF, SEQ ID NO:5), where the amino terminus is at the aspartate (D) and the carboxyl terminus is at the phenylalanine (F), has the same sequence, but the amino terminus is at the phenylalanine and the carboxy terminus is at the aspartate (i.e., FAEKFKEAVKDYFAKFWD, SEQ ID NO:104). Where the 4F peptide comprises all L amino acids, the retro-inverso form will have the sequence shown above (SEQ ID NO:104) and comprise all D form amino acids. As illustrated in the helical wheel diagrams of FIG. 15, 4F and retroinverso (Rev-4F) are mirror images of each other with identical segregation of the polar and nonpolar faces with the positively charged residues residing at the polar-nonpolar interface and the negatively charged residues residing at the center of the polar face. These mirror images of the same polymer of amino acids are identical in terms of the segregation of the polar and nonpolar faces with the positively charged residues residing at the polar-nonpolar interface and the negatively charged residues residing at the center of the polar face. For a discussion of retro- and retro-inverso peptides see, e.g., Chorev and Goodman, (1995) TibTech, 13: 439-445.

Where reference is made to a sequence and orientation is not expressly indicated, the sequence can be viewed as representing the amino acid sequence in the amino to carboxyl orientation, the retro form (i.e., the amino acid sequence in the carboxyl to amino orientation), the retro form where L amino acids are replaced with D amino acids or D amino acids are replaced with L amino acids, and the retro-inverso form where both the order is reversed and the amino acid chirality is reversed.

C) Class a Amphipathic Helical Peptide Mimetics of apoA-I Having Aromatic or Aliphatic Residues in the Non-Polar Face.

In certain embodiments, this invention also provides modified class A amphipathic helix peptides. Certain preferred peptides incorporate one or more aromatic residues at the center of the nonpolar face, e.g., $3F^{C\pi}$, (as present in 4F), or with one or more aliphatic residues at the center of the non-polar face, e.g., $3F^{I\pi}$, see, e.g., Table 3. Without being bound to a particular theory, we believe the central aromatic residues on the nonpolar face of the peptide $3F^{C\pi}$, due to the presence of π electrons at the center of the nonpolar face, allow water molecules to penetrate near the hydrophobic lipid alkyl chains of the peptide-lipid complex, which in turn would enable the entry of reactive oxygen species (such as lipid hydroperoxides) shielding them from the cell surface. Similarly, we also believe the peptides with aliphatic residues at the center of the nonpolar face, e.g., $3F^{I\pi}$, will act similarly but not quite as effectively as $3F^{C\pi}$.

Preferred peptides will convert pro-inflammatory HDL to anti-inflammatory HDL or make anti-inflammatory HDL more anti-inflammatory, and/or decrease LDL-induced monocyte chemotactic activity generated by artery wall cells equal to or greater than D4F or other peptides shown in Table 2.

TABLE 3

| Name | Sequence | SEQ ID NO |
|---|---|---|
| ($3F^{c\pi}$) | Ac-DKWKAVYDKFAEAFKEFL-NH$_2$ | 105 |
| ($3F^{i\pi}$) | Ac-DKLKAFYDKVFEWAKEAF-NH$_2$ | 106 |

D) Other Class A and Some Class Y Amphipathic Helical Peptides.

In certain embodiments this invention also contemplates class a amphipathic helical peptides that have an amino acid composition identical to one or more of the class a amphipathic helical peptides described above. Thus, for example, in certain embodiments this invention contemplates peptides having an amino acid composition identical to 4F. Thus, in certain embodiments, this invention includes active agents that comprise a peptide that consists of 18 amino acids, where the 18 amino acids consist of 3 alanines (A), 2 aspartates (D), 2 glutamates (E), 4 phenylalanines (F), 4 lysines (K), 1 valine (V), 1 tryptophan (W), and 1 tyrosine (Y); and where the peptide forms a class A amphipathic helix; and protects a phospholipid against oxidation by an oxidizing agent. In various embodiments, the peptides comprise least one "D" amino acid residue; and in certain embodiments, the peptides comprise all "D: form amino acid residues. A variety of such peptides are illustrated in Table 4. Reverse (retro-), inverse, retro-inverso-, and circularly permuted forms of these peptides are also contemplated.

TABLE 4

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-4F analogs | | 107 |
| [Switch D-E]-1-4F | Ac-EWFKAFYEKVADKFKDAF-NH$_2$ | 108 |
| [Switch D-E]-2-4F | Ac-EWFKAFYDKVADKFKEAF-NH$_2$ | 109 |
| [Switch D-E]-3-4F | Ac-DWFKAFYEKVADKFKEAF-NH$_2$ | 110 |
| [Switch D-E]-4-4F | Ac-DWFKAFYEKVAEKFKDAF-NH$_2$ | 111 |
| [W-2, F-3 positions reversed] | | 112 |
| 4F-2 | Ac-DFWKAFYDKVAEKFKEAF-NH$_2$ | 113 |
| [Switch D-E]-1-4F-2 | Ac-EFWKAFYEKVADKFKDAF-NH$_2$ | 114 |
| [Switch D-E]-2-4F-2 | Ac-EFWKAFYDKVADKFKEAF-NH$_2$ | 115 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-3-4F-2 | Ac-DFWKAFYEKVADKFKEAF-NH$_2$ | 116 |
| [Switch D-E]-4-4F-2 | Ac-DFWKAFYEKVAEKFKDAF-NH$_2$ | 117 |
| [F-6 and Y-7 positions switched] | | 118 |
| 4F-3 | Ac-DWFKAYFDKVAEKFKEAF-NH$_2$ | 119 |
| [Switch D-E]-1-4F-5 | Ac-EWFKAYFEKVADKFKDAF-NH$_2$ | 120 |
| [Switch D-E]-2-4F-5 | Ac-EWFKAYFDKVADKFKEAF-NH$_2$ | 121 |
| [Switch D-E]-3-4F-5 | Ac-DWFKAYFEKVADKFKEAF-NH$_2$ | 122 |
| [Switch D-E]-4-4F-5 | Ac-DWFKAYFEKVAEKFKDAF-NH$_2$ | 123 |
| [Y-land 10V positions switched] | | 124 |
| 4F-4 | Ac-DWFKAFVDKYAEKFKEAF-NH$_2$ | 125 |
| [Switch D-E]-1-4F-4 | Ac-EWFKAFVEKYADKFKDAF-NH$_2$ | 126 |
| [Switch D-E]-2-4F-4 | Ac-EWFKAFVDKYADKFKEAF-NH$_2$ | 127 |
| [Switch D-E]-3-4F-4 | Ac-DWFKAFVEKYADKFKEAF-NH$_2$ | 128 |
| [Switch D-E]-4-4F | Ac-DWFKAFVEKYAEKFKDAF-NH$_2$ | 129 |
| [V-10 and A-11 switched] | | 130 |
| 4-F-5 | Ac-DWFKAFYDKAVEKFKEAF-NH$_2$ | 131 |
| [Switch D-E]-1-4F-5 | Ac-EWFKAFYEKAVDKFKDAF-NH$_2$ | 132 |
| [Switch D-E]-2-4F-5 | Ac-EWFKAFYDKAVDKFKEAF-NH$_2$ | 133 |
| [Switch D-E]-3-4F-5 | Ac-DWFKAFYEKAVDKFKEAF-NH$_2$ | 134 |
| [Switch D-E]-4-4F-5 | Ac-DWFKAFYEKAVEKFKDAF-NH$_2$ | 135 |
| [A-11 and F-14 switched] | | 136 |
| 4F-6 | Ac-DWFKAFYDKVFEKAKEAF-NH$_2$ | 137 |
| [Switch D-E]-1-4F-6 | Ac-EWFKAFYEKVFDKAKDAF-NF$_2$ | 138 |
| [Switch D-E]-2-4F-6 | Ac-EWFKAFYDKVFDKAKEAF-NH$_2$ | 139 |
| [Switch D-E]-3-4F-6 | Ac-DWFKAFYEKVFDKAKEAF-NH$_2$ | 140 |
| [Switch D-E]-4-4F-6 | Ac-DWFKAFYEKVFEKAKDAF-NH$_2$ | 141 |
| [F-14 and A-17 switched] | | 142 |
| 4F-7 | Ac-DWFKAFYDKVAEKAKEFF-NH$_2$ | 143 |
| [Switch D-E]-1-4F-7 | Ac-EWFKAFYEKVADKAKDFF-NH$_2$ | 144 |
| [Switch D-E]-2-4F-7 | Ac-EWFKAFYDKVADKAKEFF-NH$_2$ | 145 |
| [Switch D-E]-3-4F-7 | Ac-DWFKAFYEKVADKAKEFF-NH$_2$ | 146 |
| [Switch D-E]-4-4F-7 | Ac-DWFKAFYEKVAEKAKDFF-NH$_2$ | 147 |
| [A-17 and F-18 switched] | | 148 |
| 4F-8 | Ac-DWFKAFYDKVAEKFKEFA-NH$_2$ | 149 |
| [Switch D-E]-1-4F-8 | Ac-EWFKAFYEKVADKFKDFA-NH$_2$ | 150 |
| [Switch D-E]-2-4F-8 | Ac-EWFKAFYDKVADKFKEFA-NH$_2$ | 151 |
| [Switch D-E]-3-4F-8 | Ac-DWFKAFYEKVADKFKEFA-NH$_2$ | 152 |
| [Switch D-E]-4-4F-8 | Ac-DWFKAFYEKVAEKFKDFA-NH$_2$ | 153 |
| [W-2 and A-17 switched] | | 154 |
| 4F-9 | Ac-DAFKAFYDKVAEKFKEWF-NH$_2$ | 155 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-1-4F-9 | Ac-EAFKAFYEKVADKFKDWF-NH$_2$ | 156 |
| [Switch D-E]-2-4F-9 | Ac-EAFKAFYDKVADKFKEWF-NH$_2$ | 157 |
| [Switch D-E]-3-4F-9 | Ac-DAFKAFYEKVADKFKEWF-NH$_2$ | 158 |
| [Switch D-E]-4-4F-9 | Ac-DAFKAFYEKVAEKFKDWF-NH$_2$ | 159 |
| [W-2 and A-11 switched] 4F-10 | Ac-DAFKAFYDKVWEKFKEAF-NH$_2$ | 160 161 |
| [Switch D-E]-1-4F-10 | Ac-EAFKAFYEKVWDKFKDAF-NH$_2$ | 162 |
| [Switch D-E]-2-4F-10 | Ac-EAFKAFYDKVWDKFKEAF-NH$_2$ | 163 |
| [Switch D-E]-3-4F-10 | Ac-DAFKAFYEKVWDKFKEAF-NH$_2$ | 164 |
| [Switch D-E]-4-4F-10 | Ac-DAFKAFYEKVWEKFKDAF-NH$_2$ | 165 |
| [W-2 and Y-7 switched] 4F-11 | Ac-DYFKAFWDKVAEKFKEAF-NH$_2$ | 166 167 |
| [Switch D-E]-1-4F-11 | Ac-EYFKAFWEKVADKFKDAF-NH$_2$ | 168 |
| [Switch D-E]-2-4F-11 | Ac-EYFKAFWDKVADKFKEAF-NH$_2$ | 169 |
| [Switch D-E]-3-4F-11 | Ac-DYFKAFWEKVADKFKEAF-NH$_2$ | 170 |
| [Switch D-E]-4-4F-11 | Ac-DYFKAFWEKVAEKFKDAF-NH$_2$ | 171 |
| [F-3 and A-17 switched] 4F-12 | Ac-DWAKAFYDKVAEKFKEFF-NH$_2$ | 172 173 |
| [Switch D-E]-1-4F-12 | Ac-EWAKAFYEKVADKFKDFF-NH$_2$ | 174 |
| [Switch D-E]-2-4F-12 | Ac-EWAKAFYDKVADKFKEFF-NH$_2$ | 175 |
| [Switch D-E]-3-4F-12 | Ac-DWAKAFYEKVADKFKEFF-NH$_2$ | 176 |
| [Switch D-E]-4-4F-12 | Ac-DWAKAFYEKVAEKFKDFF-NH$_2$ | 177 |
| [F-6 and A-17 switched] 4F-13 | Ac-DWFKAAYDKVAEKFKEFF-NH$_2$ | 178 179 |
| [Switch D-E]-1-4F-13 | Ac-EWFKAAYEKVADKFKDFF-NH$_2$ | 180 |
| [Switch D-E]-2-4F-13 | Ac-EWFKAAYDKVADKFKEFF-NH$_2$ | 181 |
| [Switch D-E]-3-4F-13 | Ac-DWFKAAYEKVADKFKEFF-NH$_2$ | 182 |
| [Switch D-E]-4-4F-13 | Ac-DWFKAAYEKVAEKFKDFF-NH$_2$ | 183 |
| [Y-7 and A-17 switched 4F-14 | Ac-DWFKAFADKVAEKFKEYF-NH$_2$ | 184 185 |
| [Switch D-E]-1-4F-14 | Ac-EWFKAFAEKVADKFKDYF-NH$_2$ | 186 |
| [Switch D-E]-2-4F-14 | Ac-EWFKAFADKVADKFKEYF-NH$_2$ | 187 |
| [Switch D-E]-3-4F-14 | Ac-DWFKAFAEKVADKFKEYF-NH$_2$ | 188 |
| [Switch D-E]-4-4F | Ac-DWFKAFAEKVAEKFKDYF-NH$_2$ | 189 |
| [V-10 and A-17 switched] 4F-15 | Ac-DWFKAFYDKAAEKFKEVF-NH$_2$ | 190 191 |
| [Switch D-E]-1-4F-15 | Ac-EWFKAFYEKAADKFKDVF-NH$_2$ | 192 |
| [Switch D-E]-2-4F-15 | Ac-EWFKAFYDKAADKFKEVF-NH$_2$ | 193 |
| [Switch D-E]-3-4F-15 | Ac-DWFKAFYEKAADKFKEVF-NH$_2$ | 194 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-4-4F-15 | Ac-DWFKAFYEKAAEKFKDVF-NH$_2$ | 195 |
| [F3 and Y-7 switched] 4F-16 | Ac-DWYKAFFDKVAEKFKEAF-NH$_2$ | 196 197 |
| [Switch D-E]-1-4F-16 | Ac-EWYKAFFEKVADKFKDAF-NH$_2$ | 198 |
| [Switch D-E]-2-4F-16 | Ac-EWYKAFFDKVADKFKEAF-NH$_2$ | 199 |
| [Switch D-E]-3-4F-16 | Ac-DWYKAFFEKVADKFKEAF-NH$_2$ | 200 |
| [Switch D-E]-4-4F-16 | Ac-DWYKAFFEKVAEKFKDAF-NH$_2$ | 201 |
| [F-3 and V-10 switched] 4F-17 | Ac-DWVKAFYDKFAEKFKEAF-NH$_2$ | 202 203 |
| [Switch D-E]-1-4F-17 | Ac-EWVKAFYEKFADKFKDAF-NH$_2$ | 204 |
| [Switch D-E]-2-4F-17 | Ac-EWVKAFYDKFADKFKEAF-NH$_2$ | 205 |
| [Switch D-E]-3-4F-17 | Ac-DWVKAFYEKFADKFKEAF-NH$_2$ | 206 |
| [Switch D-E]-4-4F-17 | Ac-DWVKAFYEKFAEKFKDAF-NH$_2$ | 207 |
| [Y-7 and F-14 switched] 4F-18 | Ac-DWFKAFFDKVAEKYKEAF-NH$_2$ | 208 209 |
| [Switch D-E]-1-4F-18 | Ac-EWFKAFFEKVADKYKDAF-NH$_2$ | 210 |
| [Switch D-E]-2-4F-18 | Ac-EWFKAFFDKVADKYKEAF-NH$_2$ | 211 |
| [Switch D-E]-3-4F-18 | Ac-DWFKAFFEKVADKYKEAF-NH$_2$ | 212 |
| [Switch D-E]-3-4F-18 | Ac-DWFKAFFEKVADKYKEAF-NH$_2$ | 213 |
| [Y-7 and F-18 switched] 4F-19 | Ac-DWFKAFFDKVAEKFKEAY-NH$_2$ | 214 215 |
| [Switch D-E]-1-4F-19 | Ac-EWFKAFFEKVADKFKDAY-NH$_2$ | 216 |
| [Switch D-E]-2-4F-19 | Ac-EWFKAFFDKVADKFKEAY-NH$_2$ | 217 |
| [Switch D-E]-3-4F-19 | Ac-DWFKAFFEKVADKFKEAY-NH$_2$ | 218 |
| [Switch D-E]-4-4F-19 | Ac-DWFKAFFEKVAEKFKDAY-NH$_2$ | 219 |
| [V-10 and F-18 switched] 4F-20 | Ac-DWFKAFYDKFAEKFKEAV-NH$_2$ | 220 221 |
| [Switch D-E]-1-4F-20 | Ac-EWFKAFYEKFADKFKDAV-NH$_2$ | 222 |
| [Switch D-E]-2-4F-20 | Ac-EWFKAFYDKFADKFKEAV-NH$_2$ | 223 |
| [Switch D-E]-3-4F-20 | Ac-DWFKAFYEKFADKFKEAV-NH$_2$ | 224 |
| [Switch D-E]-4-4F-20 | Ac-DWFKAFYEKFAEKFKDAV-NH$_2$ | 225 |
| [W-2 and K13 switched] 4F-21 | Ac-DKFKAFYDKVAEKFWEAF-NH$_2$ | 226 227 |
| [Switch D-E]-1-4F-21 | Ac-EKFKAFYEKVADKFWDAF-NH$_2$ | 228 |
| [Switch D-E]-2-4F-21 | Ac-EKFKAFYDKVADKFWEAF-NH$_2$ | 229 |
| [Switch D-E]-3-4F-21 | Ac-DKFKAFYEKVADKFWEAF-NH$_2$ | 230 |
| [Switch D-E]-4-4F-21 | Ac-DKFKAFYEKVAEKFWDAF-NH$_2$ | 231 |
| [W-3, F-13 and K-2 4F] 4F-22 | Ac-DKWKAFYDKVAEKFFEAF-NH$_2$ | 232 233 |
| [Switch D-E]-1-4F-22 | Ac-EKWKAFYEKVADKFFDAF-NH$_2$ | 234 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-2-4F-22 | Ac-EKWKAFYDKVADKFFEAF-NH$_2$ | 235 |
| [Switch D-E]-3-4F-22 | Ac-DKWKAFYEKVADKFFEAF-NH$_2$ | 236 |
| [Switch D-E]-4-4F-22 | Ac-DKWKAFYEKVAEKFFDAF-NH$_2$ | 237 |
| [K-2, W10, V-13] | | 238 |
| 4F-23 | Ac-DKKAFYDKWAEVFKEAF-NH$_2$ | 239 |
| [Switch D-E]-4F analogs | | 240 |
| [Switch D-E]-1-4F-23 | Ac-EKFKAFYEKWADVFKDAF-NH$_2$ | 241 |
| [Switch D-E]-2-4F-23 | Ac-EKFKAFYDKWADVFKEAF-NH$_2$ | 242 |
| [Switch D-E]-3-4F-23 | Ac-DKFKAFYEKWADVFKEAF-NH$_2$ | 243 |
| [Switch D-E]-4-4F-23 | Ac-DKFKAFYEKWAEVFKDAF-NH$_2$ | 244 |
| [K-2, F-13, W-14 4F] | | 245 |
| 4F-24 | Ac-DKFKAFYDKVAEFWKEAF-NH$_2$ | 246 |
| [Switch D-E]-4F analogs | | 247 |
| [Switch D-E]-1-4F-24 | Ac-EKFKAFYEKVADFWKDAF-NH$_2$ | 248 |
| [Switch D-E]-2-4F-24 | Ac-EKF1CAFYDKVADFWKEAF-NH$_2$ | 249 |
| [Switch D-E]-3-4F-24 | Ac-DKFKAFYEKVADFWKEAF-NH$_2$ | 250 |
| [Switch D-E]-4-4F-24 | Ac-DKFKAFYEKVAEFWKDAF-NH$_2$ | 251 |
| Reverse 4F analogs | | 252 |
| Rev-4F | Ac-FAEKFKEAVKDYFAKFWD-NH$_2$ | 253 |
| [Switch D-E]-1-Rev-4F | Ac-FADKFKDAVKEYFAKFWE-NH$_2$ | |
| [Switch D-E]-2-Rev-4F | Ac-FADKFKEAVKDYFAKFWE-NH$_2$ | 255 |
| [Switch D-E]-3-Rev-4F | Ac-FAEKFKDAVKEYFAKFWD-NH$_2$ | 256 |
| [Switch D-E]-4-Rev-4F | Ac-FAEKFKDAVKDYFAKFWE-NH$_2$ | 257 |
| [A-2 and W-17 switched] | | 258 |
| Rev-4F-1 | Ac-FWEKFKEAVKDYFAKFAD-NH$_2$ | 259 |
| [Switch D-E]-1-Rev-4F-1 | Ac-FWDKFKDAVKEYFAKFAE-NH$_2$ | 260 |
| [Switch D-E]-2-Rev-4F-1 | Ac-FADKFKEAVKDYFAKFWE-NH$_2$ | 261 |
| [Switch D-E]-3-Rev-4F-1 | Ac-FAEKFKDAVKEYFAKFWD-NH$_2$ | 262 |
| [Switch D-E]-4-Rev-4F-1 | Ac-FAEKFKDAVKDYFAKFWE-NH$_2$ | 263 |
| [Switch A-2 and F-16] | | 264 |
| Rev-4F-2 | Ac-FFEKFKEAVKDYFAKAWD-NH$_2$ | 265 |
| [Switch D-E]-1-Rev-4F-2 | Ac-FFDKFKDAVKEYFAKAWE-NH$_2$ | 266 |
| [Switch D-E]-2-Rev-4F-2 | Ac-FFDKFKEAVKDYFAKAWE-NH$_2$ | 267 |
| [Switch D-E]-3-Rev-4F-2 | Ac-FFEKFKDAVKEYFAKAWD-NH$_2$ | 268 |
| [Switch D-E]-4-Rev-4F-2 | Ac-FFEKFKDAVKDYFAKAWE-NH$_2$ | 269 |
| [switch F-5 and A-8] | | 270 |
| Rev-4F-3 | Ac-FAEKAKEFVKDYFAKFWD-NH$_2$ | 271 |
| [Switch D-E]-1-Rev-4F-3 | Ac-FADKAKDFVKEYFAKFWE-NH$_2$ | 272 |
| [Switch D-E]-2-Rev-4F-3 | Ac-FADKAKEFVKDYFAKFWE-NH$_2$ | 273 |
| [Switch D-E]-3-Rev-4F-3 | Ac-FAEKAKDFVKEYFAKFWD-NH$_2$ | 274 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-4-Rev-4F-3 | Ac-FAEKAKDFVKDYFAKFWE-NH$_2$ | 275 |
| [Switch A-8 and V9] | | 276 |
| Rev-4F-4 | Ac-FAEKFKEVAKDYFAKFWD-NH$_2$ | 277 |
| [Switch D-E]-1-Rev-4F-4 | Ac-FADKFKDVAKEYFAKFWE-NH$_2$ | 278 |
| [Switch D-E]-2-Rev-4F-4 | Ac-FADKFKEVAKDYFAKFWE-NH$_2$ | 279 |
| [Switch D-E]-3-Rev-4F-4 | Ac-FAEKFKDVAKEYFAKFWD-NH$_2$ | 280 |
| [Switch D-E]-4-Rev-4F-4 | Ac-FAEKFKDVAKDYFAKFWE-NH$_2$ | 281 |
| [Switch V-9 to Y-12] | | 282 |
| Rev-4F-5 | Ac-FAEKFKEAYKDVFAKFWD-NH$_2$ | 283 |
| [Switch D-E]-1-Rev-4F-5 | Ac-FADKFKDAYKEVFAKFWE-NH$_2$ | 284 |
| [Switch D-E]-2-Rev-4F-5 | Ac-FADKFKEAYKDVFAKFWE-NH$_2$ | 285 |
| [Switch D-E]-3-Rev-4F-5 | Ac-FAEKFKDAYKEVFAKFWD-NH$_2$ | 286 |
| [Switch D-E]-4-Rev-4F-5 | Ac-FAEKFKDAYKDVFAKFWE-NH$_2$ | 287 |
| [Switch Y-12 and F-13] | | 288 |
| Rev-4F-6 | Ac-FAEKFKEAVKDFYAKFWD-NH$_2$ | 289 |
| [Switch D-E]-1-Rev-4F-6 | Ac-FADKFKDAVKEFYAKFWE-NH$_2$ | 290 |
| [Switch D-E]-2-Rev-4F-6 | Ac-FADKFKEAVKDFYAKFWE-NH$_2$ | 291 |
| [Switch D-E]-3-Rev-4F-6 | Ac-FAEKFKDAVKEFYAKFWD-NH$_2$ | 292 |
| [Switch D-E]-4-Rev-4F-6 | Ac-FAEKFKDAVKDFYAKFWE-NH$_2$ | 293 |
| [Switch K-6 and W-17] | | 294 |
| Rev-4F-7 | Ac-FAEKFWEAVKDYFAKFKD-NH$_2$ | 295 |
| [Switch D-E]-1-Rev-4F-7 | Ac-FADKFWDAVKEYFAKFKE-NH$_2$ | 296 |
| [Switch D-E]-2-Rev-4F-7 | Ac-FADKFWEAVKDYFAKFKE-NH$_2$ | 297 |
| [Switch D-E]-3-Rev-4F-7 | Ac-FAEKFWDAVKEYFAKFKD-NH$_2$ | 298 |
| [Switch D-E]-4-Rev-4F-7 | Ac-FAEKFWDAVKDYFAKFKE-NH$_2$ | 299 |
| [Switch F-1 and A-2] | | 300 |
| Rev-4F-8 | Ac-A FEKFKEAVKDYFAKFWD-NH$_2$ | 301 |
| [Switch D-E]-1-Rev-4F-8 | Ac-AFDKFKDAVKEYFAKFWE-NH$_2$ | 302 |
| [Switch D-E]-2-Rev-4F-8 | Ac-AFDKFKEAVKDYFAKFWE-NH$_2$ | 303 |
| [Switch D-E]-3-Rev-4F-8 | Ac-AFEKFKDAVKEYFAKFWD-NH$_2$ | 304 |
| [Switch D-E]-4-Rev-4F-8 | Ac-AFEKFKDAVKDYFAKFWE-NH$_2$ | 305 |
| [F-1 and V-9 are switched] | | 306 |
| Rev-F-9 | Ac-VAEKFKEAFKDYFAKFWD-NH$_2$ | 307 |
| [Switch D-E]-1-Rev-4F-9 | Ac-VADKFKDAFKEYFAKFWE-NH$_2$ | 308 |
| [Switch D-E]-2-Rev-4F-9 | Ac-VADKFKEAFKDYFAKFWE-NH$_2$ | 309 |
| [Switch D-E]-3-Rev-4F-9 | Ac-VAEKFKDAFKEYFAKFWD-NH$_2$ | 310 |
| [Switch D-E]-4-Rev-4F-9 | Ac-VAEKFKDAFKDYFAKFWE-NH$_2$ | 311 |
| [F-1 and Y-12 are switched] | | 312 |
| Rev-4F-10 | Ac-YAEKFKEAVKDFFAKFWD-NH$_2$ | 313 |
| [Switch D-E]-1-Rev-4F-10 | Ac-YADKFKDAVKEFFAKFWE-NH$_2$ | 314 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-2-Rev-4F-10 | Ac-YADKFKEAVKDFFAKFWE-NH$_2$ | 315 |
| [Switch D-E]-3-Rev-4F-10 | Ac-YAEKFKDAVKEFFAKFWD-NH$_2$ | 316 |
| [Switch D-E]-4-Rev-4F-10 | Ac-YAEKFKDAVKDFFAKFWE-NH$_2$ | 317 |
| [F-1 and A-8 are switched] Rev-4F-11 | Ac-AAEKFKEFVKDYFAKFWD-NH$_2$ | 318 319 |
| [Switch D-E]-1-Rev-4F-11 | Ac-AADKFKDFVKEYFAKFWE-NH$_2$ | 320 |
| [Switch D-E]-2-Rev-4F-11 | Ac-AADKFKEFVKDYFAKFWE-NH$_2$ | 321 |
| [Switch D-E]-3-Rev-4F-11 | Ac-AAEKFKDFVKEYFAKFWD-NH$_2$ | 322 |
| [Switch D-E]-4-Rev-4F-11 | Ac-AAEKFKDFVKDYFAKFWE-NH$_2$ | 323 |
| [A-2 and F-5 are switched] Rev-4F-12 | Ac-FFEKAKEAVKDYFAKFWD-NH$_2$ | 324 325 |
| [Switch D-E]-1-Rev-4F-12 | Ac-FFDKAKDAVKEYFAKFWE-NH$_2$ | 326 |
| [Switch D-E]-2-Rev-4F-12 | Ac-FFDKAKEAVKDYFAKFWE-NH$_2$ | 327 |
| [Switch D-E]-3-Rev-4F-12 | Ac-141-EKAKDAVKEYFAKFWD-NH$_2$ | 328 |
| [Switch D-E]-4-Rev-4F-12 | Ac-1-1-EKAKDAVKDYFAKFWE-NH$_2$ | 329 |
| [A-2 and Y12 are switched] Rev-4F-13 | Ac-FYEKFKEAVKDAFAKFWD-NH$_2$ | 330 331 |
| [Switch D-E]-1-Rev-4F-13 | Ac-FYDKFKDAVKEAFAKFWE-NH$_2$ | 332 |
| [Switch D-E]-2-Rev-4F-13 | Ac-FYDKFKEAVKDAFAKFWE-NH$_2$ | 333 |
| [Switch D-E]-3-Rev-4F-13 | Ac-FYEKFKDAVKEAFAKFWD-NH$_2$ | 334 |
| [Switch D-E]-4-Rev-4F-13 | Ac-FYEKFKDAVKDAFAKFWE-NH$_2$ | 335 |
| [A-2 and V-9 are switched] Rev-4F-14 | Ac-FVEKFKEAAKDYFAKFWD-NH$_2$ | 336 337 |
| [Switch D-E]-1-Rev-4F-14 | Ac-FVDKFKDAAKEYFAKFWE-NH$_2$ | 338 |
| [Switch D-E]-2-Rev-4F-14 | Ac-FVDKFKEAAKDYFAKFWE-NH$_2$ | 339 |
| [Switch D-E]-3-Rev-4F-14 | Ac-FVEKFKDAAKEYFAKFWD-NH$_2$ | 340 |
| [Switch D-E]-4-Rev-4F-14 | Ac-FVEKFKDAAKDYFAKFWE-NH$_2$ | 341 |
| [F-5 and Y-12 are switched] Rev-4F-15 | Ac-FAEKYKEAVKDFFAKFWD-NH$_2$ | 342 343 |
| [Switch D-E]-1-Rev-4F-15 | Ac-FADKYKDAVKEFFAKFWE-NH$_2$ | 344 |
| [Switch D-E]-2-Rev-4F-15 | Ac-FADKYKEAVKDFFAKFWE-NH$_2$ | 345 |
| [Switch D-E]-3-Rev-4F-15 | Ac-FAEKYKDAVKEFFAKFWD-NH$_2$ | 346 |
| [Switch D-E]-4-Rev-4F-15 | Ac-FAEKYKDAVKDFFAKFWE-NH$_2$ | 347 |
| [F-5 and V-9 are switched] Rev-4F-16 | Ac-FAEKVKEAFKDYFAKFWD-NH$_2$ | 348 349 |
| [Switch D-E]-1-Rev-4F-16 | Ac-FADKVKDAFKEYFAKFWE-NH$_2$ | 350 |
| [Switch D-E]-2-Rev-4F-16 | Ac-FADKVKEAFKDYFAKFWE-NH$_2$ | 351 |
| [Switch D-E]-3-Rev-4F-16 | Ac-FAEKVKDAFKEYFAKFWD-NH$_2$ | 352 |
| [Switch D-E]-4-Rev-4F-16 | Ac-FAEKVKDAFKDYFAKFWE-NH$_2$ | 353 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [A-8 and Y-12 switched] Rev-4F-17 | Ac-FAEKFKEYVKDAFAKFWD-NH₂ | 354 355 |
| [Switch D-E]-1-Rev-4F-17 | Ac-FADKFKDYVKEAFAKFWE-NH₂ | 356 |
| [Switch D-E]-2-Rev-4F-17 | Ac-FADKFKEYVKDAFAKFWE-NH₂ | 357 |
| [Switch D-E]-3-Rev-4F-17 | Ac-FAEKFKDYVKEAFAKFWD-NH₂ | 358 |
| [Switch D-E]-4-Rev-4F-17 | Ac-FAEKFKDYVKDAFAKFWE-NH₂ | 359 |
| [V-9 and F-13 are switched] Rev-4F-18 | Ac-FAEKFKEAFKDYVAKFWD-NH₂ | 360 361 |
| [Switch D-E]-1-Rev-4F-18 | Ac-FADKFKDAFKEYVAKFWE-NH₂ | 362 |
| [Switch D-E]-2-Rev-4F-18 | Ac-FADKFKEAFKDYVAKFWE-NH₂ | 363 |
| [Switch D-E]-3-Rev-4F-18 | Ac-FAEKFKDAFKEYVAKFWD-NH₂ | 364 |
| [Switch D-E]-4-Rev-4F-18 | Ac-FAEKFKDAFKDYVAKFWE-NH₂ | 365 |
| [V-9 and F-16 switched] Rev-4F-19 | Ac-FAEKFKEAFKDYFAKVWD-NH₂ | 366 367 |
| [Switch D-E]-1-Rev-4F-19 | Ac-FADKFKDAFKEYFAKVWE-NH₂ | 368 |
| [Switch D-E]-2-Rev-4F-19 | Ac-FADKFKEAFKDYFAKVWE-NH₂ | 369 |
| [Switch D-E]-3-Rev-4F-19 | Ac-FAEKFKDAFKEYFAKVWD-NH₂ | 370 |
| Switch D-E]-4-Rev-4F-19 | Ac-FAEKFKDAFKDYFAKVWE-NH₂ | 371 |
| [Y-12 and F-16 are switched Rev-4F-20 | Ac-FAEKFKEAVKDFFAKYWD-NH₂ | 372 373 |
| [Switch D-E]-1-Rev-4F-20 | Ac-FADKFKDAVKEFFAKYWE-NH₂ | 374 |
| [Switch D-E]-2-Rev-4F-20 | Ac-FADKFKEAVKDFFAKYWE-NH₂ | 375 |
| [Switch D-E]-3-Rev-4F-20 | Ac-FAEKFKDAVKEFFAKYWD-NH₂ | 376 |
| [Switch D-E]-4-Rev-4F-20 | Ac-FAEKFKDAVKDFFAKYWE-NH₂ | 377 |
| [W-1, F-6 and K-17 Rev 4F] Rev-4F-21 | Ac-WAEKFFEAVKDYFAKFKD-NH₂ | 378 379 |
| [Switch D-E]-1-Rev-4F-7 | Ac-WADKFFDAVKEYFAKFKE-NH₂ | 380 |
| [Switch D-E]-2-Rev-4F-7 | Ac-WADKFFEAVKDYFAKFKE-NH₂ | 381 |
| [Switch D-E]-3-Rev-4F-7 | Ac-WAEKFFDAVKEYFAKFKD-NH₂ | 382 |
| Switch D-E]-4-Rev-4F-7 | Ac-WAEKFFDAVKDYFAKFKE-NH₂ | 383 |
| [W-5, F-6 and K-17 Rev-4F] Rev-4F-22 | Ac-FAEKWFEAVKDYFAKFKD-NH₂ | 384 385 |
| [Switch D-E]-1-Rev-4F-22 | Ac-FADKWFDAVKEYFAKFKE-NH₂ | 386 |
| [Switch D-E]-2-Rev-4F-22 | Ac-FADKWFEAVKDYFAKFKE-NH₂ | 387 |
| [Switch D-E]-3-Rev-4F-22 | Ac-FAEKWFDAVKEYFAKFKD-NH₂ | 388 |
| [Switch D-E]-4-Rev-4F-22 | Ac-FAEKWFDAVKDYFAKFKE-NH₂ | 389 |
| [V-6, W-9, K-17 Rev-4F] Rev-4F-23 | Ac-FAEKFVEAWKDYFAKFKD-NH₂ | 390 391 |
| [Switch D-E]-1-Rev-4F-23 | Ac-FADKFVDAWKEYFAKFKE-NH₂ | 392 |
| [Switch D-E]-2-Rev-4F-23 | Ac-FADKFVEAWKDYFAKFKE-NH₂ | 393 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-3-Rev-4F-23 | Ac-FAEKFV<u>D</u>AWK<u>E</u>YFAKFKD-NH$_2$ | 394 |
| [Switch D-E]-4-Rev-4F-23 | Ac-FAEKFV<u>D</u>AWKDYFAKFK<u>E</u>-NH$_2$ | 395 |
| [Y-2, A-4, W-12, K-17 Rev-4F] | | 396 |
| Rev-4F-24 | Ac-F<u>Y</u>EKF<u>A</u>EAVKD<u>W</u>FAKF<u>K</u>D-NH$_2$ | 397 |
| [Switch D-E]-1-Rev-4F-24 | Ac-FY<u>D</u>KFA<u>D</u>AVK<u>E</u>WFAKFKE-NH$_2$ | 398 |
| [Switch D-E]-2-Rev-4F-24 | Ac-FY<u>D</u>KFAEAVKDWFAKFK<u>E</u>-NH$_2$ | 399 |
| [Switch D-E]-3-Rev-4F-24 | Ac-FYEKFA<u>D</u>AVK<u>E</u>WFAKFKD-NH$_2$ | 400 |
| [Switch D-E]-4-Rev-4F-24 | Ac-FYEKFA<u>D</u>AVKDWFAKFK<u>E</u>-NH$_2$ | 401 |

Figure 15:
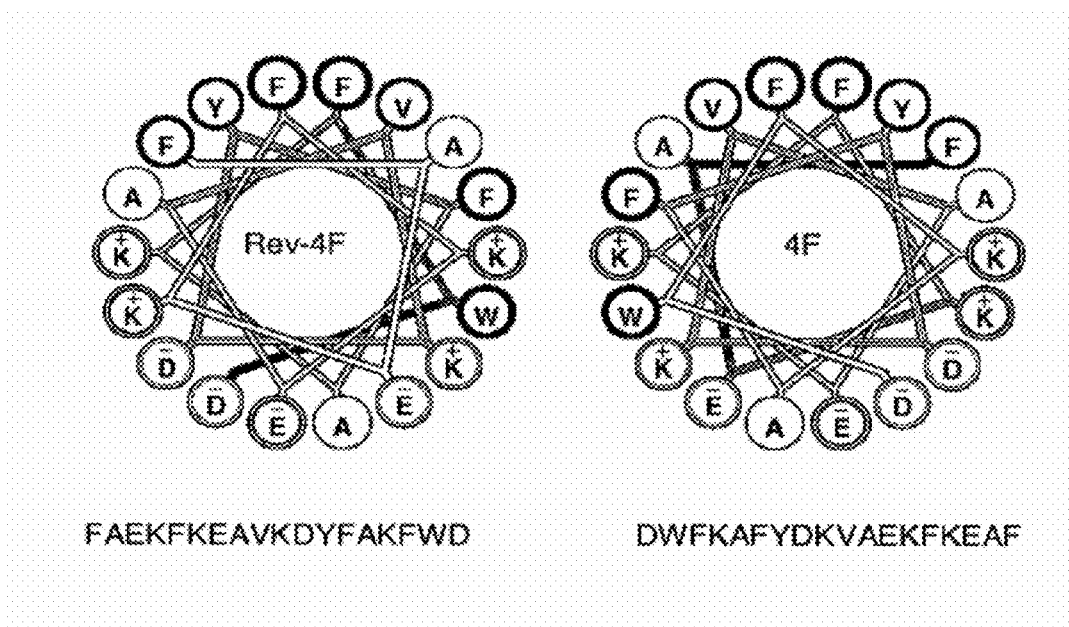
FIG. 15 illustrates a helical wheel representation of 4F and reverse (retro) 4F. Reverse-4F is a mirror image of 4F with the relative positions of the amino acids to each other and to the hydrophilic and hydrophobic faces being identical.

Based on the helical wheel diagrams shown in FIG. 15 it is possible to readily identify biologically active and useful peptides. Thus, for example, the following peptides have been accurately identified as active: 3F1; 3F2; 4F the reverse (retro) forms thereof and the retro-inverso forms thereof. Thus, in certain embodiments, this invention contemplates active agents comprising a peptide that is 18 amino acids in length and forms a class A amphipathic helix where the peptide has the amino acid composition 2 aspartates, 2 glutamates, 4 lysines, 1 tryptophan, 1 tyrosine, no more than one leucine, no more than 1 valine, no less than 1 and no more than 3 alanines, and with 3 to 6 amino acids from the group: phenylalanine, alpha-naphthalanine, beta-naphthalanine, histidine, and contains either 9 or 10 amino acids on the polar face in a helical wheel representation of the class A amphipathic helix including 4 amino acids with positive charge at neutral pH with two of the positively charged residues residing at the interface between the polar and non-polar faces and with two of the four positively charged residues on the polar face that are contiguous and on the non-polar face two of the amino acid residues from the group: phenylalanine, alpha-naphthalanine, beta-naphthalanine, histidine are also contiguous and if there are 4 or more amino acids from this group on the non-polar face there are also at least 2 residues from this group that are not contiguous.

In certain embodiments, this invention also contemplates certain class Y as well as class A amphipathic helical peptides. Class Y amphipathic helical peptides are known to those of skill in the art (see, e.g., Segrest et al. (1992) J. Lipid Res. 33: 141-166; Oram and Heinecke (2005) Physiol Rev. 85: 1343-1372, and the like). In various embodiments these peptides include, but are not limited to an 18 amino acid peptide that forms a class A amphipathic helix or a class Y amphipathic helix described by formula III (SEQ ID NO:402):

$$D\ X\ X\ K\ Y\ X\ X\ D\ K\ X\ Y\ D\ KX\ K\ D\ Y\ X \qquad III$$

where the D's are independently Asp or Glu; the Ks are independently Lys or Arg; the Xs are independently Leu, norLeu, Val, Ile, Trp, Phe, Tyr, β-Nal, or α-Nal and all X residues are on the non-polar face (e.g., when viewed in a helical wheel diagram) except for one that can be on the polar face between two K residues; the Y's are independently Ala, His, Ser, Gln, Asn, or Thr non-polar face (e.g., when viewed in a helical wheel diagram) and the Y's are independently one Ala on the polar face, one His, one Ser, one Gln one Asn, or one Thr on the polar face (e.g., when viewed in a helical wheel diagram), where no more than two K are be contiguous (e.g., when viewed in a helical wheel diagram); and where no more than 3 D's are contiguous (e.g., when viewed in a helical wheel diagram) and the fourth D is be separated from the other D's by a Y. Illustrative peptides of this kind which include peptides with histidine, and/or alpha- and/or beta-napthalanine are shown in Table 5. Reverse (retro-), inverse, retro-inverso-, and circularly permuted forms of these peptides are also contemplated.

TABLE 5

| Short Name | Peptide Sequence | SEQ ID NO. |
|---|---|---|
| [A-5 > H]4F | Ac-DWFKHFYDKVAEKFKEAF-NH$_2$ | 403 |
| [A-5 > H, D-E switched] 4F | Ac-EWFKHFYEKVADKFKDAF-NH$_2$ | 404 |
| [A-5 > H, D-1 > E]4F | Ac-EWFKHFYDKVAEKFKEAF-NH$_2$ | 405 |
| [A-5 > H, D-8 > E]4-F | Ac-DWFKHFYEKVAEKFKEAF-NH$_2$ | 406 |
| [A-5 > H, E-12 > D]4F | Ac-DWFKHFYDKVADKFKEAF-NH$_2$ | 407 |
| [A-5 > H, E-16 > D]4F | Ac-DWFKHFYDKVAEKFKDAF-NH$_2$ | 408 |
| [F-3 > H, A-5 > F]-4F | Ac-DWHKFFYDKVAEKFKEAF-NH$_2$ | 409 |
| [F-3 > H, A-5 > F, D-E switched]-4F | Ac-EWHKFFYEKVADKFKDAF-NH$_2$ | 410 |

TABLE 5-continued

| Short Name | Peptide Sequence | SEQ ID NO. |
|---|---|---|
| [F-3 > H, A-5 > F, D-1 > E]-4F | Ac-EWHKFFYDKVAEKFKEAF-NH$_2$ | 411 |
| [F-3 > H, A-5 > F, D-8 > E]-4F | Ac-DWHKFFYEKVAEKFKEAF-NH$_2$ | 412 |
| [F-3 > H, A-5 > F, E-12 > D]-4F | Ac-DWHKFFYDKVADKFKEAF-NH$_2$ | 413 |
| [F-3 > H, A-5 > F, E-16 > D]-4F | Ac-DWHKFFYDKVAEKFKDAF-NH$_2$ | 414 |
| [A-5 > F, F-6 > H]4F | Ac-DWFKPHYDKVAEKFKEAF-NH$_2$ | 415 |
| [A-5 > F, F-6 > H, D-E switched]4F | Ac-EWFKPHYEKVADKFKDAF-NH$_2$ | 416 |
| [[A-5 > F, F-6 > H, D-1 > E]4F | Ac-EWFKPHYDKVAEKFKEAF-NH$_2$ | 417 |
| [A-5 > F, F-6 > H, D-8 > E]4F | Ac-DWFKPHYEKVAEKFKEAF-NH$_2$ | 418 |
| [A-5 > F, F-6 > H, E-12 > D]4F | Ac-DWFKPHYDKVADKFKEAF-NH$_2$ | 419 |
| [A-5 > F, F-6 > H, E-16 > D]4F | Ac-DWFKPHYDKVAEKFKDAF-NH$_2$ | 420 |
| [A-5 > V, V-10 > H]4F | Ac-DWFKVFYDKHAEKFKEAF-NH$_2$ | 421 |
| [A-5 > V, V-10 > H, D-E switched]4F | Ac-EWFKVFYEKHADKFKDAF-NH$_2$ | 422 |
| [A-5 > V, V-10 > H, D-1 > E]4F | Ac-EWFKVFYDKHAEKFKEAF-NH$_2$ | 423 |
| [A-5 > V, V-10 > H, D-8 > E]4F | Ac-DWFKVFYEKHAEKFKEAF-NH$_2$ | 424 |
| [A-5 > V, V-10 > H, E-12 > D]4F | Ac-DWFKVFYDKHADKFKEAF-NH$_2$ | 425 |
| [A-5 > V, V-10 > H, E16 > D]4F | Ac-DWFKVFYDKHAEKFKDAF-NH$_2$ | 426 |
| [[A-17 > H]4F | Ac-DWFKAFYDKVAEKFKEHF-NH$_2$ | 427 |
| [A-17 > H, D-E switched]4F | Ac-EWFKAFYEKVADKFKDHF-NH$_2$ | 428 |
| [[A-17 > H, D-1 > E]4F | Ac-EWFKAFYDKVAEKFKEHF-NH$_2$ | 429 |
| [[A-17 > H, D-8 > E]4F | Ac-DWFKAFYEKVAEKFKEHF-NH$_2$ | 430 |
| [[A-17 > H, E-12 > D]4F | Ac-DWFKAFYDKVADKFKEHF-NH$_2$ | 431 |
| [[A-17 > H, E16 > D]4F | Ac-DWFKAFYDKVAEKFKDHF-NH$_2$ | 432 |
| [A-17 > F, F-18 > H]4F | Ac-DWFKAFYDKVAEKFKEFH-NH$_2$ | 433 |
| [A-17 > F, F-18 > H, D-E switched]4F | Ac-EWFKAFYEKVADKFKDFH-NH$_2$ | 434 |
| [A-17 > F, F-18 > H, D-1 > E]-4F | Ac-EWFKAFYDKVAEKFKEFH-NH$_2$ | 435 |
| [A-17 > F, F-18 > H]4F | Ac-DWFKAFYDKVAEKFKEFH-NH$_2$ | 436 |
| [A-17 > F, F-18 > H, D-8 > E]-4F | Ac-DWFKAFYEKVAEKFKEFH-NH$_2$ | 437 |
| [A-17 > F, F-18 > H, E-12 > D]4F | Ac-DWFKAFYDKVAEKFKEFH-NH$_2$ | 438 |
| [A-17 > F, F-18 > H], E-16 > D]-4F | Ac-DWFKAFYDKVAEKFKDFH-NH$_2$ | 439 |
| Rev-4F | Ac-FAEKFKEAVKDYFAKFWD-NH$_2$ | 440 |
| [A-2 > H]Rev4F | Ac-FHEKFKEAVKDYFAKFWD-NH$_2$ | 441 |
| Rev-[A-2 > H, D > E]-4F | Ac-FHEKFKEAVKEYFAKFWE-NH$_2$ | 442 |
| Rev-[A-2 > H, E > D]4F | Ac-FHDKFKDAVKDYFAKFWE-NH$_2$ | 443 |
| [A-2 > H, D-E switched]Rev-4F | Ac-FHDKFKDAVKEYFAKFWE-NH$_2$ | 444 |
| [A-2 > H, E-3 > D]Rev-4F | Ac-FHDKFKEAVKDYFAKFWD-NH$_2$ | 445 |
| [A-2 > H, E-7 > D]Rev-4F | Ac-FHEKFKDAVKDYFAKFWD-NH$_2$ | 446 |
| [A-2 > 2H, D-11 > E]Rev-4F | Ac-FHEKFKEAVKEYFAKFWD-NH$_2$ | 447 |
| [A-2 > H, D-18 > E]Rev-4F | Ac-FHEKFKEAVKDYFAKFWE-NH$_2$ | 448 |
| [F-1 > H, A-2 > F]Rev-4F | Ac-HFEKFKEAVKDYFAKFWD-NH$_2$ | 449 |

TABLE 5-continued

| Short Name | Peptide Sequence | SEQ ID NO. |
|---|---|---|
| [F-1 > H, A-2 > F, D-E switched]Rev-4F | Ac-HFDKFKDAVKEYFAKFWE-NH$_2$ | 450 |
| [F-1 > H, A-2 > F, D > E]Rev-4F | Ac-HFEKFKEAVKEYFAKFWE-NH$_2$ | 451 |
| [F-1 > H, A-2 > F, E-3 > D]Rev-4F | Ac-HFDKFKEAVKDYFAKFWD-NH$_2$ | 452 |
| [F-1 > H, A-2 > F, E-7 > D]Rev-4F | Ac-HFEKFKDAVKDYFAKFWD-NH$_2$ | 453 |
| [F-1 > H, A-2 > F, D-11 > E]Rev-4F | Ac-HFEKFKEAVKEYFAKFWD-NH$_2$ | 454 |
| [F-1 > H, A-2 > F, D-18 > E]Rev-4F | Ac-HFEKFKEAVKDYFAKFWE-NH$_2$ | 455 |
| [A-2 > F, F-5 > H] Rev D-4F | Ac-FFEKHKEAVKDYFAKFWD-NH$_2$ | 456 |
| [A-2 > F, F-5 > H, D-E switched]Rev D-4F | Ac-FFDKHKDAVKEYFAKFWE-NH$_2$ | 457 |
| [A-2 > F, F-5 > H, D > E]Rev D-4F | Ac-FFEKHKEAVKEYFAKFWE-NH$_2$ | 458 |
| [A-2 > F, F-5 > H, E > D]Rev D-4F [ | Ac-FFDKHKDAVKDYFAKFWD-NH$_2$ | 459 |
| A-2 > F, F-5 > H, E-3 > D]Rev D-4F | Ac-FFDKHKEAVKDYFAKFWD-NH$_2$ | 460 |
| [A-2 > F, F-5 > H, D-11 > E]Rev D-4F | Ac-FFEKHKEAVKEYFAKFWD-NH$_2$ | 461 |
| [A-2 > F, F-5 > H, D-18 > E]Rev D-4F | Ac-FFEKHKEAVKDYFAKFWE-NH$_2$ | 462 |
| [A-2 > V, V-9 > H]Rev D-4F | Ac-FVEKFKEAHKDYFAKFWD-NH$_2$ | 463 |
| [A-2 > V, V-9 > H, D-E switched]Rev D-4F | Ac-FVDKFKDAHKEYFAKFWE-NH$_2$ | 464 |
| [A-2 > V, V-9 > H, D > E]Rev D-4F | Ac-FVEKFKEAHKEYFAKFWE-NH$_2$ | 465 |
| [A-2 > V, V-9 > H, E > D]Rev D-4F | Ac-FVDKFKDAHKDYFAKFWD-NH$_2$ | 466 |
| [A-2 > V, V-9 > H, E-3 > D]Rev D-4F | Ac-FVDKFKEAHKDYFAKFWD-NH$_2$ | 467 |
| [A-2 > V, V-9 > H, E-7 > D]Rev D-4F | Ac-FVEKFKDAHKDYFAKFWD-NH$_2$ | 468 |
| [A-2 > V, V-9 > H, D-11 > E]Rev D-4F | Ac-FVEKFKEAHKEYFAKFWD-NH$_2$ | 469 |
| [A-2 > V, V-9 > H, D-18 > E]Rev D-4F | Ac-FVEKFKEAHKDYFAKFWE-NH$_2$ | 470 |
| [A-8 > H]Rev-4F | Ac-FAEKFKEHVKDYFAKFWD-NH$_2$ | 471 |
| [A-8 > H, D-E switched]Rev-4F | Ac-FADKFKDHVKEYFAKFWE-NH$_2$ | 472 |
| [A-8 > H, D > E]Rev-4F | Ac-FAEKFKEHVKEYFAKFWE-NH$_2$ | 473 |
| [A-8 > H, E > D]Rev-4F | Ac-FADKFKDHVKDYFAKFWD-NH$_2$ | 474 |
| [A-8 > H, E-3 > D]Rev-4F | Ac-FADKFKEHVKDYFAKFWD-NH$_2$ | 475 |
| [A-8 > H, E-7 > D]Rev-4F | Ac-FAEKFKDHVKDYFAKFWD-NH$_2$ | 476 |
| [A-8 > H, D-11 > E]Rev-4F | Ac-FAEKFKEHVKEYFAKFWD-NH$_2$ | 477 |
| [A-8 > H, D-18 > E]Rev-4F | Ac-FAEKFKEHVKDYFAKFWE-NH$_2$ | 478 |
| [A-8 > F, F-13 > H]Rev-4F | Ac-FAEKFKEFVKDYHAKFWD-NH$_2$ | 479 |
| [A-8 > F, F-13 > H, D-E switched]Rev-4F | Ac-FADKFKDFVKEYHAKFWE-NH$_2$ | 480 |
| [A-8 > F, F-13 > H, E-3 > D]Rev-4F | Ac-FADKFKEFVKDYHAKFWD-NH$_2$ | 481 |
| [A-8 > F, F-13 > H, E-7 > D]Rev-4F | Ac-FAEKFKDFVKDYHAKFWD-NH$_2$ | 482 |
| [A-8 > F, F-13 > H, E > D]Rev-4F | Ac-FADKFKDFVKDYHAKFWD-NH$_2$ | 483 |
| [A-8 > F, F-13 > H, D > E]Rev-4F | Ac-FAEKFKEFVKEYHAKFWE-NH$_2$ | 484 |
| [A-8 > F, F-13 > H, D-11 > E]Rev-4F | Ac-FAEKFKEFVKEYHAKFWD-NH$_2$ | 485 |
| [A-8 > F, F-13 > H, D-18 > E]Rev-4F | Ac-FAEKFKEFVKDYHAKFWE-NH$_2$ | 486 |
| [A-8 > F, F16 > H]Rev-4F | Ac-FAEKFKEFVKDYFAKHWD-NH$_2$ | 487 |
| [A-8 > F, F16 > H, D-E switched]Rev-4F | Ac-FADKFKDFVKEYFAKHWE-NH$_2$ | 488 |

TABLE 5-continued

| Short Name | Peptide Sequence | SEQ ID NO. |
|---|---|---|
| [A-8 > F, F16 > H, D > E]Rev-4F | Ac-FAEKFKEFVKEYFAKHWE-NH$_2$ | 489 |
| [A-8 > F, F16 > H, E > D]Rev-4F | Ac-FADKFKDFVKDYFAKHWD-NH$_2$ | 490 |
| [A-8 > F, F16 > H, E-3 > D]Rev-4F | Ac-FADKFKEFVKDYFAKHWD-NH$_2$ | 491 |
| [A-8 > F, F16 > H, E-7 > D]Rev-4F | Ac-FAEKFKDFVKDYFAKHWD-NH$_2$ | 492 |
| [A-8 > F, F16 > H, D-11 > E]Rev-4F | Ac-FAEKFKEFVKEYFAKHWD-NH$_2$ | 493 |
| [A-8 > F, F16 > H, D-18 > E]Rev-4F | Ac-FAEKFKEFVKDYFAKHWE-NH$_2$ | 494 |

Examples of class A 4F and Rev 4F analogs with beta-Nph. Similarly, alpha-Nph analogs can be designed. Similarly to the above analogs, His can be incorporated to Nph analogs. D>E analogs, E>D analogs and D-E switch analogs are additional possibilities similarly to the above described analogs.

| | | |
|---|---|---|
| 4Nph | Ac-DWNphKANphYDKVAEKNphKEANph-NH2 | 495 |
| [D-E switched] 4Nph | Ac-EWNphKANphYEKVADKNphKDANph-NH2 | 496 |
| [D > E]4Nph | Ac-EWNphKANphYEKVAEKNphKEANph-NH2 | 497 |
| [E > D]4Nph | Ac-DWNphKANphYDKVADKNphKDANph-NH2 | 498 |
| [D-1 > E]4Nph | Ac-EWNphKANphYDKVAEKNphKEANph-NH2 | 499 |
| [D-8 > E]4Nph | Ac-DWNphKANphYEKVAEKNphKEANph-NH2 | 500 |
| [E-12 > D]4Nph | Ac-DWNphKANphYDKVADKNphKEANph-NH2 | 501 |
| [E-16 > D]4Nph | Ac-DWNphKANphYDKVAEKNphKDANph-NH2 | 502 |

As described above for 4Nph, a minimum of 7 additional analogs for each of the analogs given below.

| | | |
|---|---|---|
| [F-3, 6, > Nph]4F | Ac-DWNphKANphYDKVAEKFKEAF-NH2 | 503 |
| [F-14, 18 > Nph]4F | Ac-DWFKAFYDKVAEKNphKEANph-NH2 | 504 |
| [[F-3 > Nph]4F | Ac-DWNphKAFYDKVAEKFKEAF-NH2 | 505 |
| [F-6 > Nph]4F | Ac-DWFKANphYDKVAEKFKEAF-NH2 | 506 |
| [F-14 > Nph]4F | Ac-DWFKAFYDKVAEKNphKEAF-NH2 | 507 |
| [F-18 > Nph]4F | Ac-DWFKAFYDKVAEKFKEANph-NH2 | 508 |

For each of the analog described below, a minimum of 7 additional analogs are possible as described above by switching D-E, D>E and E>D and single D or E analogs.

| | | |
|---|---|---|
| Rev-4Nph | Ac-NphAEKNphKEAVKDYNphAKNphWD-NH2 | 509 |
| [F-3, 6 > Nph]Rev 4F | Ac-NphAEKNphKEAVKDYFAKFWD-NH2 | 510 |
| [F-13, 16]Rev-4F | Ac-FAEKFKEAVKDYNphAKNphWD-NH2 | 511 |
| [F-3 > Nph]Rev-4F | Ac-NphAEKFKEAVKDYFAKFWD-NH2 | 512 |
| [F-6 > Nph]Rev-4F | Ac-FAEKNphKEAVKDYFAKFWD-NH2 | 513 |
| [F-13 > Nph]Rev-4F | Ac-FAEKFKEAVKDYNphAKFWD-NH2 | 514 |
| [F-16 > Nph]Rev-4F | Ac-FAEKFKEAVKDYFAKNphWD-NH2 | 515 |

For the analogs described below, additional analogs are possible by incorporating His or alpha-Nph and beta-Nph

| Name | Sequence | SEQ ID |
|---|---|---|
| Rev-[D > E]-4F | Ac-FAEKFKEAVKEYFAKFWE-NH2 | 516 |
| Rev-[E > D]4F | Ac-FADKFKDAVKDYFAKFWD-NH2 | 517 |
| Rev-R4-4F | Ac-FAERFREAVKDYFAKFWD-NH2 | 518 |
| Rev-R6-4F | Ac-FAEKFREAVKDYFAKFWD-NH2 | 519 |
| Rev-R10-4F | Ac-FAEKFKEAVRDYFAKFWD-NH2 | 520 |
| Rev-R14-4F | Ac-FAEKFKEAVKDYFARFWD-NH2 | 521 |
| Rev-[D > E]-4F | Ac-FAEKFKEAVKEYFAKFWE-NH2 | 522 |
| Rev-[E > D]4F | Ac-FADKFKDAVKDYFAKFWD-NH2 | 523 |
| Rev-R4-4F | Ac-FAERFREAVKDYFAKFWD-NH2 | 524 |
| Rev-R6-4F | Ac-FAEKFREAVKDYFAKFWD-NH2 | 525 |
| Rev-R10-4F | Ac-FAEKFKEAVRDYFAKFWD-NH2 | 526 |
| Rev-R14-4F | Ac-FAEKFKEAVKDYFARFWD-NH2 | 527 |
| Rev-[D > E]-4F | Ac-FAEKFKEAVKEYFAKFWE-NH2 | 528 |
| Rev-[E > D]4F | Ac-FADKFKDAVKDYFAKFWD-NH2 | 529 |
| Rev-R4-4F | Ac-FAERFREAVKDYFAKFWD-NH2 | 530 |
| Rev-R6-4F | Ac-FAEKFREAVKDYFAKFWD-NH2 | 531 |
| Rev-R10-4F | Ac-FAEKFKEAVRDYFAKFWD-NH2 | 532 |
| Rev-R14-4F | Ac-FAEKFKEAVKDYFARFWD-NH2 | 533 |
| Rev-R4-4F | Ac-FAERFREAVKDYFAKFWD-NH2 | 534 |
| Rev-R6-4F | Ac-FAEKFREAVKDYEAKFWD-NH2 | 535 |
| Rev-R10-4F | Ac-FAEKFKEAVRDYFAKFWD-NH2 | 536 |
| Rev-R14-4F | Ac-FAEKFKEAVKDYFARFWD-NH2 | 537 |
| Rev-[D > E]-4F | Ac-FAEKFKEAVKEYFAKFWE-NH2 | 538 |
| Rev-[E > D]4F | Ac-FADKFKDAVKDYFAKFWD-NH2 | 539 |
| Rev-R4-4F | Ac-FAERFREAVKDYFAKFWD-NH2 | 540 |
| Rev-R6-4F | Ac-FAEKFREAVKDYFAKFWD-NH2 | 541 |
| Rev-R10-4F | Ac-FAEKFKEAVRDYFAKFWD-NH2 | 542 |
| Rev-R14-4F | Ac-FAEKFKEAVKDYFARFWD-NH2 | 543 |

For each of the analogs below, additional H and Nph analogs are possible using the examples described above. Each analog can yield 7 analogs with the changes described in the examples given above.

| Name | Sequence | SEQ ID |
|---|---|---|
| Rev3F-2 | Ac-LFEKFAEAFKDYVAKWKD-NH2 | 544 |
| RevR4-3F-2 | Ac-LFERFAEAFKDYVAKWKD-NH2 | 545 |
| RevR10-3F2 | Ac-LFEKFAEAFRDYVAKWKD-NH2 | 546 |
| RevR15-3F-2 | Ac-LFEKFAEAFKDYVARWKD-NH2 | 547 |
| RevR17-3F-2 | Ac-LFEKFAEAFKDYVAKWRD-NH2 | 548 |
| Rev[D > E]3F2 | Ac-LFEKFAEAFKEYVAKWE-NH2 | 549 |
| Rev[E > D]3F-2 | Ac-LFDKFADAFKDYVAKWKD-NH2 | 550 |
| Rev-[E3 > D]-3F-2 | Ac-LFDKFAEAFKDYVAKWKD-NH2 | 551 |
| Rev-[E7 > D]-3F-2 | Ac-LFEKFADAFKDYVAKWKD-NH2 | 552 |
| Rev[D11 > E]3F-2 | Ac-LFEKFAEAFKEYVAKWKD-NH2 | 553 |
| Rev-[D18 > E]3F-2 | Ac-LFEKFAEAFKDYVAKWKE-NH2 | 554 |
| Rev3F-1 | Ac-FAEKAWEFVKDYFAKLKD-NH2 | 555 |
| RevR4-3F-1 | Ac-FAERAWEFVKDYFAKLKD-NH2 | 556 |
| RevR10-3F-1 | Ac-FAEKAWEFVKDYFAKLKD-NH2 | 557 |
| RevR15-3F-1 | Ac-FAEKAWEFVKDYFAKLKD-NH2 | 558 |
| RevR17-3F-1 | Ac-FAEKAWEFVKDYFAKLRD-NH2 | 559 |
| Rev[D > E]3F-1 | Ac-FAEKAWEFVKEYFAKLKE-NH2 | 560 |
| Rev[E > D}3F-1 | Ac-FADKAWDFVKDYFAKLKD-NH2 | 561 |
| Rev[E3 > D]-3F-1 | Ac-FADKAWEFVKDYFAKLKD-NH2 | 562 |
| Rev[E7 > D]3F-1 | Ac-FAEKAWDFVKDYFAKLKD-NH2 | 563 |
| Rev-[D11 > E]3F-1 | Ac-FAEKAWEFVKEYFAKLKD-NH2 | 564 |
| Rev-[D18 > E]3F-1 | Ac-FAEKAWEFVKDYFAKLKE-NH2 | 565 |
| Rev-5F | Ac-FFEKFKEFVKDYFAKLWD-NH2 | 566 |
| Rev-[D > E]5F | Ac-FFEKFKEFVKEYFAKLWE-NH2 | 567 |
| Rev-[E > D]5F | Ac-FFDKFKDFVKDYFAKLWD-NH2 | 568 |
| Rev-R4-5F | Ac-FFERFKEFVKDYFAKLWD-NH2 | 569 |
| Rev-R6-5F | Ac-FFEKFREFVKDYFAKLWD-NH2 | 570 |
| Rev-R10-5F | Ac-FFEKFKEFVRDYFAKLWD-NH2 | 571 |
| Rev-R15-5F | Ac-FFEKFKEFVKDYFARLWD-NH2 | 572 |
| Rev-[E3 > D]-5F | Ac-FFDKFKEFVKDYFAKLWD-NH2 | 573 |
| Rev-[E7 > D]5F | Ac-FFEKFKDFVKDYFAKLWD-NH2 | 574 |
| Rev-[D11 > E]-5F | Ac-FFEKFKEFVKEYFAKLWD-NH2 | 575 |
| Rev-[D18 > E]-5F | Ac-FFEKFKEFVKDYFAKLWE-NH2 | 576 |
| Rev-5F-2 | Ac-FLEKFKEFVKDYFAKFWD-NH2 | 577 |
| Rev-[D > E]-5F-2 | Ac-FLEKFKEFVKEYFAKFWE-NH2 | 578 |
| Rev-[E > D]-5F-2 | Ac-FLDKFKEFVKDYFAKFWD-NH2 | 579 |
| Rev-[E3 > D]-5F-2 | Ac-FLDKFKEFVKDYFAKFWD-NH2 | 580 |
| Rev-[E7 > D]-5F-2 | Ac-FLEKFKDFVKDYFAKFWD-NH2 | 581 |
| Rev-[D11 > E]-5F-2 | Ac-FLEKFKEFVKEYFAKFWD-NH2 | 582 |
| Rev-[D18 > E]-5F-2 | Ac-FLEKFKEFVKDYFAKFWE-NH2 | 583 |
| Rev-R4-5F-2 | Ac-FLERFKEFVKDYFAKFWD-NH2 | 584 |
| Rev-R6-5F-2 | Ac-FLEKFREFVKDYFAKFWD-NH2 | 585 |
| RevR10-5F-2 | Ac-FLEKFKEFVRDYFAKFWD-NH2 | 586 |
| Rev-R16-5F-2 | Ac-FLEKFKEFVKDYFARFWD-NH2 | 587 |
| Rev-6F | Ac-FFEKFKEFFKDYFAKLWD-NH2 | 588 |
| Rev-[D > E]-6F | Ac-FFEKFKEFFKEYFAKLWE-NH2 | 589 |
| Rev-[E > D]-6F | Ac-FFDKFKDFFKDYFAKLWD-NH2 | 590 |

| Name | Sequence | SEQ ID NO |
|---|---|---|
| Rev-R4-6F | Ac-FFERFKEFFKDYFAKLWD-NH2 | 591 |
| Rev-R6-6F | Ac-FFEKFREFFKDYFAKLWD-NH2 | 592 |
| Rev-R10-6F | Ac-FFEKFKEFFRDYFAKLWD-NH2 | 593 |
| Rev-R14-6F | Ac-FFERFKEFFKDYFARLWD-NH2 | 594 |
| Rev-[E3 > D]-6F | Ac-FFDKFKEFFKDYFAKLWD-NH2 | 595 |
| Rev-[E7 > D]-6F | Ac-FFEKEKDFFKDYFAKLWD-NH2 | 596 |
| Rev-[D11 > E]-6F | Ac-FFEKFKEFFKEYFAKLWD-NH2 | 597 |
| Rev-[D18 > E]-6F | Ac-FFEKFKEFFKDYFAKLWE-NH2 | 598 |
| Rev-4F | Ac-FAEKFKEAVKDYFAKFWD-NH2 | 599 |
| Rev-[D > E]-4F | Ac-FAEKFKEAVKEYFAKFWE-NH2 | 600 |
| Rev-[E > D]4F | Ac-FADKFKDAVKDYFAKFWD-NH2 | 601 |
| Rev-R4-4F | Ac-FAERFREAVKDYFAKFWD-NH2 | 602 |
| Rev-R6-4F | Ac-FAEKFREAVKDYFAKFWD-NH2 | 603 |
| Rev-R10-4F | Ac-FAEKFKEAVRDYFAKFWD-NH2 | 604 |
| Rev-R14-4F | Ac-FAEKFKEAVKDYFARFWD-NH2 | 605 |
| 4F-2 | Ac-DKWKAVYDKFAEAFKEFF-NH2 | 606 |
| [D > E]-4F-2 | Ac-EKWKAVYEKFAEAFKEFF-NH2 | 607 |
| [E > D]-4F-2 | Ac-DKWKAVYDKFADAFKDFF-NH2 | 608 |
| R2-4F-2 | Ac-DRWKAVYDKFAEAFKEFF-NH2 | 609 |
| R4-4F-2 | Ac-DKWRAVYDKFAEAFKEFF-NH2 | 610 |
| R9-4F-2 | Ac-DKWKAVYDRFAEAFKEFF-NH2 | 611 |
| R14-4F-2 | Ac-DKWKAVYDKFAEAFREFF-NH2 | 612 |
| Rev4F-2 | Ac-FFEKFAEAFKDYVAKWKD-NH2 | 613 |
| Rev-[D > E]-4F-2 | Ac-FFEKFAEAFKEYVAKWKE-NH2 | 614 |
| Rev-[E > D]-3F-2 | Ac-FFDKFADAFKDYVAKWKD-NH2 | 615 |
| Rev-R4-4F-2 | Ac-FFERFAEAFKDYVAKWKD-NH2 | 616 |
| Rev-R10-4F-2 | Ac-EFERFAEAFRDYVAKWKD-NH2 | 617 |
| Rev-R15-4F-2 | Ac-FFEKFAEAFKDYVARWKD-NH2 | 618 |
| Rev-R17-4F-2 | Ac-FFERFAEAFKDYVAKWRD-NH2 | 619 |
| Rev-[E3 > D]-4F-2 | Ac-FFDKFAEAFKDYVAKWKD-NH2 | 620 |
| Rev-[E7 > D]-4F-2 | Ac-FFEKFADAFKDYVAKWKD-NH2 | 621 |
| Rev-[D11 > E]-4F-2 | Ac-FFERFAEAFKEYVAKWKD-NH2 | 622 |
| Rev-[D18 > E]-4F-2 | Ac-FFERFAEAFKDYVAKWKE-NH2 | 623 |
| Rev-7F | Ac-FFEKFKEFFKDYFAKFWD-NH2 | 624 |
| Rev-[E > D]-7F | Ac-FFDKFKDFFKDYFAKEWD-NH2 | 625 |
| Rev-[D > E]-7F | Ac-FFEKFKEFFKEYFAKFWE-NH2 | 626 |
| Rev-R4-7F | Ac-FFERFKEFFKDYFAKFWD-NH2 | 627 |
| Rev-R6-7F | Ac-FFEKFREFFKDYFAKFWD-NH2 | 628 |
| Rev-R10-7F | Ac-FFEKFKEFFRDYFAKFWD-NH2 | 629 |
| Rev-R14-7F | Ac-FFEKFKEFFKDYFARFWD-NH2 | 630 |
| Rev-[E3 > D]-7F | Ac-FFDKFKEFFKDYFAKFWD-NH2 | 631 |
| Rev-[E7 > D]7F | Ac-FFEKFKDFFKDYFAKFWD-NH2 | 632 |
| Rev-[D11 > E]-7F | Ac-FFEKFKEFFKEYFAKFWD-NH2 | 633 |
| Rev-[D18 > E]-7F | Ac-FFEKFKEFFKDYFAKFWE-NH2 | 634 |

It is also noted that any of the peptides described herein can comprise non-natural amino acids in addition to or instead of the corresponding the natural amino acids identified herein. Such modifications include, but are not limited to acetylation, amidation, formylation, methylation, sulfation, and the like. Illustrative non-natural amino acids include, but are not limited to Ornithine, norleucine, norvaline, N-methylvaline, 6-N-methyllysine, N-methylisoleucine, N-methylglycine, sarcosine, inosine, allo-isoleucine, isodesmolysine, 4-hydroxyproline, 3-hydroxyproline, allo-hydroxylysine, hydroxylisine, N-ethylasparagine, N-ethylglycine, 2,3-diaminopropionic acid, 2,2'-diaminopropionic acid, desmosine, 2,4-diaminobutyric acid, 2-aminopimelic acid, 3-aminoisobutyric acid, 2-aminoisobutyric acid, 2-aminoheptanoic acid, 6-aminocaproic acid, 4-aminobutyric acid, 2-aminobutyric acid, beta-alanine, 3-aminoadipic acid, 2-aminoadipic acid, and the like. In certain embodiments and one or more of the "natural" amino acids of the peptides described herein, can be substituted with the corresponding non-natural amino acid (e.g. as describe above).

In certain embodiments, this invention contemplates particularly the use of modified lysines. Such modifications include, but are not limited to, biotin modification of epsilon lysines and/or methylation of the epsilon lysines. Illustrative peptide comprising epsilon methylated lysines include, but are not limited to: Ac-D-W-F-K($eCH_3$)$_2$-A-F-Y-D-K($eCH_3$)$_2$-V-A-E-K($eCH_3$)-$_2$-F-K($eCH_3$)$_2$-E-A-F-NH(CH$_3$)$_2$ (SEQ ID NO:635) and: Ac-DWFK($eCH_3$)$_2$AFYDK($eCH_3$)$_2$VAEK($eCH_3$)$_2$FK($eCH_3$)$_2$EAF-NH(CH$_3$) (SEQ ID NO:636). Other modified amino acids include but are not limited to ornithine analogs and homoaminoalanine analogs (instead of $(CH_2)_4$—NH$_2$ for Lys it can be —$(CH_2)_2$—NH$_2$ for Haa and —$(CH_2)_3$—NH$_2$ for Orn] and the like. It is noted that these modifications are illustrative and not intended to be limiting. Illustrative 4F analogues that possess modified amino acids are shown in Table 6.

TABLE 6

Illustrative 4F analogs that comprise modified amino acids.

| εN-Dimethyl-Lys derivative of 4F (εN-Dime) | |
|---|---|
| Ac-D-W-F-K(εN-Dime)-A-F-Y-D-K(εN-Dime)-V-A-E-K(εN-Dime)-F-K(εN-Dime)-E-A-F-NH$_2$ | 637 |
| Ac-D-W-F-K-(εN-Dime)-A-F-Y-D-K(εN-Dime)-V-A-E-K(εN-Dime)-F-K((εN-Dime)-E-A-F-NH-Me | 638 |
| Ac-D-W-F-K-(EN-Dime)-A-F-Y-D-K(EN-Dime)-V-A-E-K(EN-Dime)-F-K(EN-Dime)-E-A-F-N-(Me)$_2$ | 639 |

TABLE 6-continued

Illustrative 4F analogs that comprise modified amino acids.

εN-Diethyl-Lys derivatives of 4F (εN-Diet)

| Sequence | No. |
|---|---|
| Ac-D-W-F-K(εN-Diet)-A-F-Y-D-K(εN-Diet)-V-A-E-K(εN-Diet)-F-K(εN-Diet)-E-A-F-NH$_2$ | 640 |
| Ac-D-W-F-K(εN-Diet)-A-F-Y-D-K(εN-Diet)-V-A-E-K(εN-Diet)-F-K(εN-Diet)-E-A-F-NH-Et | 641 |
| Ac-D-W-F-K(εN-Diet)-A-F-Y-D-K(εN-Diet)-V-A-E-K(εN-Diet)-F-K(εN-Diet)-E-A-F-NH-(Et)$_2$ | 642 |

εN-Monomethyl-Lys derivative of 4F (εN-Me)

| Sequence | No. |
|---|---|
| Ac-D-W-F-K(εN-Me)-A-F-Y-D-K(εN-Me)-V-A-E-K(εN-Me)-F-K(εN-Me)-E-A-F-NH$_2$ | 643 |
| Ac-D-W-F-K(εN-Me)-A-F-Y-D-K(εN-Me)-V-A-E-K(εN-Me)-F-K(εN-Me)-E-A-F-NH-Me | 644 |
| Ac-D-W-F-K(εN-Me)-A-F-Y-D-K(εN-Me)-V-A-E-K(εN-Me)-F-K(εN-Me)-E-A-F-N-(Me)$_2$ | 645 |

εN-ethylLys derivative of 4F (εN-Et)

| Sequence | No. |
|---|---|
| Ac-D-W-F-K(εN-Et)-A-F-Y-D-K(εN-E0-V-A-E-K(εN-Et)-F-K(εN-Et)-E-A-F-NH$_2$ | 646 |
| Ac-D-W-F-K(εN-Et)-A-F-Y-D-K(εN-E0-V-A-E-K(εN-Et)-F-K(εN-E0-E-A-F-NH-Et | 647 |
| Ac-D-W-F-K(εN-Et)-A-F-Y-D-K(εN-Et)-V-A-E-K(εN-Et)-F-K(εN-Et)-E-A-F-NH-(Et)$_2$ | 648 |

HomoLys analogs of 4F (hK) (—CH$_2$)$_5$—NH$_2$

| Sequence | No. |
|---|---|
| Ac-D-W-F-hK-A-F-Y-D-hK-V-A-E-hK-F-hK-E-A-F-NH$_2$ | 649 |
| Ac-D-W-F-hK(εN-Dime)-A-F-Y-D-hK(εN-Dime)-V-A-E-hK(εN-Dime)-F-hK(εN-Dime)-E-A-F-NH$_2$ | 650 |
| Ac-D-W-F-hK(εN-Dime)-A-F-Y-D-hK(εN-Dime)-V-A-E-hK(εN-Dime)-F-hK(εN-Dime)-E-A-F-N-(Me)$_2$ | 651 |
| Ac-D-W-F-hK(εN-Dime)-A-F-Y-D-hK(εN-Dime)-V-A-E-hK(εN-Dime)-F-hK(εN-Dime)-E-A-F-NH-Me | 652 |
| Ac-D-W-F-hK(εN-Diet)-A-F-Y-D-hK(εN-Diet)-V-A-E-hK(εN-Diet)-F-hK(εN-Diet)-E-A-F-NH-Et | 653 |
| Ac-D-W-F-hK(εN-Me)-A-F-Y-D-hK(εN-Me)-V-A-E-hK(εN-Me)-F-hK(εN-Me)-E-A-F-NH$_2$ | 654 |
| Ac-D-W-F-hK(εN-Me)-A-F-Y-D-hK(εN-Me)-V-A-E-hK(εN-Me)-F-hK(εN-Me)-E-A-F-NH-Me | 655 |
| Ac-D-W-F-hK(εN-Me)-A-F-Y-D-hK(εN-Me)-V-A-E-hK(εN-Me)-F-hK(εN-Me)-E-A-F-N-(Me)$_2$ | 656 |
| Ac-D-W-F-hK(εN-Et)-A-F-Y-D-hK(εN-Et)-V-A-E-hK(εN-Et)-F-hK(εN-Et)-E-A-F-NH$_2$ | 657 |
| Ac-D-W-F-hK(εN-Et)-A-F-Y-D-hK(εN-Et)-V-A-E-hK(εN-Et)-F-hK(εN-Et)-E-A-F-NH-Et | 658 |
| Ac-D-W-F-hK(εN-Et)-A-F-Y-D-hK(εN-Et)-V-A-E-hK(εN-Et)-F-hK(εN-Et)-E-A-F-NH-(Et)$_2$ | 659 |

4F analogs in which K is replaced O (O = Ornithine, —(CH$_2$)$_3$—NH$_2$)

| Sequence | No. |
|---|---|
| Ac-D-W-F-O-A-F-Y-D-O-V-A-E-O-F-O-E-A-F-NH$_2$ | 661 |
| Ac-D-W-F-O(δN-Dime)-A-F-Y-D-O(δN-Dime)-V-A-E-O(δN-Dime)-F-O(δN-Dime)-E-A-F-NH$_2$ | 662 |
| Ac-D-W-F-O(δN-Dime)-A-F-Y-D-)(δN-Dime)-V-A-E-O(δN-Dime)-F-O(δN-Dime)-E-A-F-N-(Me)$_2$ | 663 |
| Ac-D-W-F-O(δN-Dime)-A-F-Y-D-O(δN-Dime)-V-A-E-O(δN-Dime)-F-O(δN-Dime)-E-A-F-NH-Me | 664 |
| Ac-D-W-F-O(δN-Diet)-A-F-Y-D-O(δN-Diet)-V-A-E-O(δN-Diet)-F-O(δN-Diet)-E-A-F-NH-Et | 665 |
| Ac-D-W-F-O(δN-Me)-A-F-Y-D-O(δN-Me)-V-A-E-O(δN-Me)-F-O(δN-Me)-E-A-F-NH$_2$ | 666 |
| Ac-D-W-F-O(δN-Me)-A-F-Y-D-O(δN-Me)-V-A-E-O(δN-Me)-F-O(δN-Me)-E-A-F-NH-Me | 667 |
| Ac-D-W-F-O(δN-Me)-A-F-Y-D-O(δN-Me)-V-A-E-O(δN-Me)-F-O(δN-Me)-E-A-F-N-(Me)$_2$ | 668 |
| Ac-D-W-F-O(δN-Et)-A-F-Y-D-O(δN-Et)-V-A-E-O(δN-Et)-F-O(δN-Et)-E-A-F-NH$_2$ | 669 |
| Ac-D-W-F-O(δN-Et)-A-F-Y-D-O(δN-Et)-V-A-E-O(δN-Et)-F-O(δN-Et)-E-A-F-NH-Et | 670 |
| Ac-D-W-F-O(δN-Et)-A-F-Y-D-O(δN-Et)-V-A-E-OdεN-Et)-F-O(δN-Et)-E-A-F-NH-(Et)$_2$ | 671 |

Note: row "660" corresponds to the heading "4F analogs in which K is replaced O (O = Ornithine, —(CH$_2$)$_3$—NH$_2$)".

The peptides and modifications shown above are intended to be illustrative and not limiting.

E) Smaller Peptides.

It was also a surprising discovery that certain small peptides consisting of a minimum of three amino acids preferentially (but not necessarily) with one or more of the amino acids being the D-stereoisomer of the amino acid, and possessing hydrophobic domains to permit lipid protein interactions, and hydrophilic domains to permit a degree of water solubility also possess significant anti-inflammatory properties and are useful in treating one or more of the pathologies described herein. The "small peptides" typically range in length from 2 amino acids to about 15 amino acids, more preferably from about 3 amino acids to about 10 or 11 amino acids, and most preferably from about 4 to about 8 or 10 amino acids. In various embodiments the peptides are typically characterized by having hydrophobic terminal amino acids or terminal amino acids rendered hydrophobic by the attachment of one or more hydrophobic "protecting" groups. Various "small peptides" are described in copending applications U.S. Ser. No. 10/649,378, filed Aug. 26, 2003, and in U.S. Ser. No. 10/913,800, filed on Aug. 6, 2004, and in PCT Application PCT/US2004/026288.

In certain embodiments, the peptides can be characterized by Formula I, below: $X^1$-$X^2$-$X^3_n$-$X^4$ I where, n is 0 or 1, $X^1$ is a hydrophobic amino acid and/or bears a hydrophobic protecting group, $X^4$ is a hydrophobic amino acid and/or bears a hydrophobic protecting group; and when n is 0 $X^2$ is an acidic or a basic amino acid; when n is 1: $X^2$ and $X^3$ are independently an acidic amino acid, a basic amino acid, an aliphatic amino acid, or an aromatic amino acid such that when $X^2$ is an acidic amino acid; $X^3$ is a basic amino acid, an aliphatic amino acid, or an aromatic amino acid; when $X^2$ is a basic amino acid; $X^3$ is an acidic amino acid, an aliphatic amino acid, or an aromatic amino acid; and when $X^2$ is an aliphatic or aromatic amino acid, $X^3$ is an acidic amino acid, or a basic amino acid.

Longer peptides (e.g., up to 10, 11, or 15 amino acids) are also contemplated within the scope of this invention. Typically where the shorter peptides (e.g., peptides according to formula I) are characterized by an acidic, basic, aliphatic, or aromatic amino acid, the longer peptides are characterized by acidic, basic, aliphatic, or aromatic domains comprising two or more amino acids of that type.

1) Functional Properties of Active Small Peptides.

It was a surprising finding of this invention that a number of physical properties predict the ability of small peptides (e.g., less than 10 amino acids, preferably less than 8 amino acids, more preferably from about 3 to about 5 or 6 amino acids) of this invention to render HDL more anti-inflammatory and to mitigate atherosclerosis and/or other pathologies characterized by an inflammatory response in a mammal. The physical properties include high solubility in ethyl acetate (e.g., greater than about 4 mg/mL), and solubility in aqueous buffer at pH 7.0. Upon contacting phospholipids such as 1,2-Dimyristoyl-sn-glycero-3-phosphocholine (DMPC), in an aqueous environment, the particularly effective small peptides induce or participate in the formation of particles with a diameter of approximately 7.5 nm (±0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm). In certain preferred embodiments, the small peptides have a molecular weight of less than about 900 Da.

Thus, in certain embodiments, this invention contemplates small peptides that ameliorate one or more symptoms of an indication/pathology described herein, e.g., an inflammatory condition, where the peptide(s): ranges in length from about 3 to about 8 amino acids, preferably from about 3 to about 6, or 7 amino acids, and more preferably from about 3 to about 5 amino acids; are soluble in ethyl acetate at a concentration greater than about 4 mg/mL; are soluble in aqueous buffer at pH 7.0; when contacted with a phospholipid in an aqueous environment, form particles with a diameter of approximately 7.5 nm and/or form stacked bilayers with a bilayer dimension on the order of 3.4 to 4.1 nm with spacing between the bilayers in the stack of approximately 2 nm; have a molecular weight less than about 900 daltons; convert pro-inflammatory HDL to anti-inflammatory HDL or make anti-inflammatory HDL more anti-inflammatory; and do not have the amino acid sequence Lys-Arg-Asp-Ser (SEQ ID NO:801), especially in which Lys-Arg-Asp and Ser are all L amino acids. In certain embodiments, these small peptides protect a phospholipid against oxidation by an oxidizing agent.

While these small peptides need not be so limited, in certain embodiments, these small peptides can include the small peptides described below.

2) Tripeptides.

It was discovered that certain tripeptides (3 amino acid peptides) can be synthesized that show desirable properties as described herein (e.g., the ability to convert pro-inflammatory HDL to anti-inflammatory HDL, the ability to decrease LDL-induced monocyte chemotactic activity generated by artery wall cells, the ability to increase pre-beta HDL, etc.). In certain embodiments, the peptides are characterized by formula I, wherein N is zero, shown below as Formula II: $X^1$-$X^2$-$X^4$ II where the end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, nicotinyl-, etc., and the C-terminus blocked with (tBu)-OtBu, etc.). In certain embodiments, the $X^2$ amino acid is either acidic (e.g., aspartic acid, glutamic acid, etc.) or basic (e.g., histidine, arginine, lysine, etc.). The peptide can be all L-amino acids or include one or more or all D-amino acids.

Certain preferred tripeptides of this invention include, but are not limited to the peptides shown in Table 7.

TABLE 7

Examples of certain preferred tripeptides bearing hydrophobic blocking groups and acidic, basic, or histidine central amino acids.

| $X^1$ | $X^2$ | $X^3$ | $X^4$ | SEQ ID NO |
|---|---|---|---|---|
| Boc-Lys(EBoc) | Arg | | Ser(tBu)-OtBu | 672 |
| Boc-Lys(EBoc) | Arg | | Thr(tBu)-OtBu | 673 |
| Boc-Trp | Arg | | Ile-OtBu | 674 |
| Boc-Trp | Arg | | Leu-OtBu | 675 |
| Boc-Phe | Arg | | Ile-OtBu | 676 |
| Boc-Phe | Arg | | Leu-OtBu | 677 |
| Boc-Lys(EBoc) | Glu | | Ser(tBu)-OtBu | 678 |
| Boc-Lys(EBoc) | Glu | | Thr(tBu)-OtBu | 679 |
| Boc-Lys(EBoc) | Asp | | Ser(tBu)-OtBu | 680 |
| Boc-Lys(EBoc) | Asp | | Thr(tBu)-OtBu | 681 |
| Boc-Lys(EBoc) | Arg | | Ser(tBu)-OtBu | 682 |
| Boc-Lys(EBoc) | Arg | | Thr(tBu)-0tBu | 683 |
| Boc-Leu | Glu | | Ser(tBu)-OtBu | 684 |
| Boc-Leu | Glu | | Thr(tBu)-0tBu | 685 |
| Fmoc-Trp | Arg | | Ser(tBu)-OtBu | 686 |
| Fmoc-Trp | Asp | | Ser(tBu)-0tBu | 687 |
| Fmoc-Trp | Glu | | Ser(tBu)-OtBu | 688 |
| Fmoc-Trp | Arg | | Ser(tBu)-OtBu | 689 |
| Boc-Lys(EBoc) | Glu | | Leu-OtBu | 690 |
| Fmoc-Leu | Arg | | Ser(tBu)-OtBu | 691 |
| Fmoc-Leu | Asp | | Ser(tBu)-OtBu | 692 |
| Fmoc-Leu | Glu | | Ser(tBu)-OtBu | 693 |
| Fmoc-Leu | Arg | | Ser(tBu)-OtBu | 694 |
| Fmoc-Leu | Arg | | Thr(tBu)-OtBu | 695 |
| Boc-Glu | Asp | | Tyr(tBu)-OtBu | 696 |
| Fmoc-Lys(eFmoc) | Arg | | Ser(tBu)-OtBu | 697 |
| Fmoc-Trp | Arg | | Ile-OtBu | 698 |
| Fmoc-Trp | Arg | | Leu-OtBu | 699 |
| Fmoc-Phe | Arg | | Ile-OtBu | 700 |
| Fmoc-Phe | Arg | | Leu-OtBu | 701 |
| Boc-Trp | Arg | | Phe-OtBu | 702 |
| Boc-Trp | Arg | | Tyr-OtBu | 703 |
| Fmoc-Trp | Arg | | Phe-OtBu | 704 |
| Fmoc-Trp | Arg | | Tyr-OtBu | 705 |
| Boc-Orn(OBoc) | Arg | | Ser(tBu)-OtBu | 706 |

TABLE 7-continued

Examples of certain preferred tripeptides bearing hydrophobic blocking groups and acidic, basic, or histidine central amino acids.

| X¹ | X² | X³ | X⁴ | SEQ ID NO |
|---|---|---|---|---|
| Nicotinyl Lys(sBoc) | Arg | | Ser(tBu)-OtBu | 707 |
| Nicotinyl Lys(EBoc) | Arg | | Thr(tBu)-0tBu | 708 |
| Fmoc-Leu | Asp | | Thr(tBu)-OtBu | 709 |
| Fmoc-Leu | Glu | | Thr(tBu)-OtBu | 710 |
| Fmoc-Leu | Arg | | Thr(tBu)-0tBu | 711 |
| Fmoc-norLeu | Arg | | Ser(tBu)-OtBu | 712 |
| Fmoc-norLeu | Asp | | Ser(tBu)-OtBu | 713 |
| Fmoc-norLeu | Glu | | Ser(tBu)-0tBu | 714 |
| Fmoc-Lys(cBoc) | Arg | | Ser(tBu)-OtBu | 715 |
| Fmoc-Lys(EBoc) | Arg | | Thr(tBu)-OtBu | 716 |
| Fmoc-Lys(EBoc) | Glu | | Ser(tBu)-0tBu | 717 |
| Fmoc-Lys(EBoc) | Glu | | Thr(tBu)-OtBu | 718 |
| Fmoc-Lys(cBoc) | Asp | | Ser(tBu)-OtBu | 719 |
| Fmoc-Lys(EBoc) | Asp | | Thr(tBu)-0tBu | 720 |
| Fmoc-Lys(eBoc) | Glu | | Leu-OtBu | 721 |
| Fmoc-Lys(EBoc) | Arg | | Leu-OtBu | 722 |
| Fmoc-Lys(cFmoc) | Arg | | Thr(tBu)-0tBu | 723 |
| Fmoc-Lys(EFmoc) | Glu | | Ser(tBu)-0tBu | 724 |
| Fmoc-Lys(EFmoc) | Glu | | Thr(tBu)-OtBu | 725 |
| Fmoc-Lys(cFmoc) | Asp | | Ser(tBu)-OtBu | 726 |
| Fmoc-Lys(EFmoc) | Asp | | Thr(tBu)-OtBu | 727 |
| Fmoc-Lys(EFmoc) | Arg | | Ser(tBu)-0tBu | 728 |
| Fmoc-Lys(EFmoc)) | Glu | | Leu-OtBu | 729 |
| Boc-Lys(EFmoc) | Asp | | Ser(tBu)-OtBu | 730 |
| Boc-Lys(EFmoc) | Asp | | Thr(tBu)-OtBu | 731 |
| Boc-Lys(EFmoc) | Arg | | Thr(tBu)-OtBu | 732 |
| Boc-Lys(EFmoc) | Glu | | Leu-OtBu | 733 |
| Boc-Orn(8Fmoc) | Glu | | Ser(tBu)-0tBu | 734 |
| Boc-Orn(8Fmoc) | Asp | | Ser(tBu)-OtBu | 735 |
| Boc-Orn(6Fmoc) | Asp | | Thr(tBu)-OtBu | 736 |
| Boc-Orn(OFmoc) | Arg | | Thr(tBu)-OtBu | 737 |
| Boc-Orn(6Fmoc) | Glu | | Thr(tBu)-OtBu | 738 |
| Fmoc-Trp | Asp | | Ile-OtBu | 739 |
| Fmoc-Trp | Arg | | Ile-OtBu | 740 |
| Fmoc-Trp | Glu | | Ile-OtBu | 741 |
| Fmoc-Trp | Asp | | Leu-OtBu | 742 |
| Fmoc-Trp | Glu | | Leu-OtBu | 743 |
| Fmoc-Phe | Asp | | Ile-OtBu | 744 |
| Fmoc-Phe | Asp | | Leu-OtBu | 745 |
| Fmoc-Phe | Glu | | Leu-OtBu | 746 |
| Fmoc-Trp | Arg | | Phe-OtBu | 747 |
| Fmoc-Trp | Glu | | Phe-OtBu | 748 |
| Fmoc-Trp | Asp | | Phe-OtBu | 749 |
| Fmoc-Trp | Asp | | Tyr-OtBu | 750 |
| Fmoc-Trp | Arg | | Tyr-OtBu | 751 |
| Fmoc-Trp | Glu | | Tyr-OtBu | 752 |
| Fmoc-Trp | Arg | | Thr(tBu)-OtBu | 753 |
| Fmoc-Trp | Asp | | Thr(tBu)-OtBu | 754 |
| Fmoc-Trp | Glu | | Thr(tBu)-OtBu | 755 |
| Boc-Phe | Arg | | norLeu-OtBu | 756 |
| Boc-Phe | Glu | | norLeu-OtBu | 757 |
| Fmoc-Phe | Asp | | norLeu-OtBu | 758 |
| Boc-Glu | His | | Tyr(tBu)-OtBu | 759 |
| Boc-Leu | His | | Ser(tBu)-OtBu | 760 |
| Boc-Leu | His | | Thr(tBu)-OtBu | 761 |
| Boc-Lys(EBoc) | His | | Ser(tBu)-OtBu | 762 |
| Boc-Lys(EBoc) | His | | Thr(tBu)-0tBu | 763 |
| Boc-Lys(EBoc) | His | | Leu-OtBu | 764 |
| Boc-Lys(EFmoc) | His | | Ser(tBu)-OtBu | 765 |
| Boc-Lys(eFmoc) | His | | Thr(tBu)-OtBu | 766 |
| Boc-Lys(EFmoc) | His | | Leu-OtBu | 767 |
| Boc-Orn(OBoc) | His | | Ser(tBu)-OtBu | 768 |
| Boc-Orn(6Fmoc) | His | | Thr(tBu)-OtBu | 769 |
| Boc-Phe | His | | De-OtBu | 770 |
| Boc-Phe | His | | Leu-OtBu | 771 |
| Boc-Phe | His | | norLeu-OtBu | 772 |
| Boc-Phe | Lys | | Leu-OtBu | 773 |
| Boc-Trp | His | | Ile-OtBu | 774 |
| Boc-Trp | His | | Leu-OtBu | 775 |
| Boc-Trp | His | | Phe-OtBu | 776 |
| Boc-Trp | His | | Tyr-OtBu | 777 |
| Boc-Phe | Lys | | Leu-OtBu | 778 |
| Fmoc-Lys(EFmoc) | His | | Ser(tBu)-OtBu | 779 |
| Fmoc-Lys(EFmoc) | His | | Thr(tBu)-OtBu | 780 |
| Fmoc-Lys(EFmoc) | His | | Leu-OtBu | 781 |
| Fmoc-Leu | His | | Ser(tBu)-OtBu | 782 |
| Fmoc-Leu | His | | Thr(tBu)-OtBu | 783 |
| Fmoc-Lys(EBoc) | His | | Ser(tBu)-OtBu | 784 |
| Fmoc-Lys(EBoc) | His | | Thr(tBu)-OtBu | 785 |
| Fmoc-Lys(eBoc) | His | | Leu-OtBu | 786 |
| Fmoc-Lys(EFmoc) | His | | Ser(tBu)-OtBu | 787 |
| Fmoc-Lys(EFmoc) | His | | Thr(tBu)-OtBu | 788 |
| Fmoc-norLeu | His | | Ser(tBu)-OtBu | 789 |
| Fmoc-Phe | His | | Ile-OtBu | 790 |
| Fmoc-Phe | His | | Leu-OtBu | 791 |
| Fmoc-Phe | His | | norLeu-OtBu | 792 |
| Fmoc-Trp | His | | Ser(tBu)-OtBu | 793 |
| Fmoc-Trp | His | | Ile-OtBu | 794 |
| Fmoc-Trp | His | | Leu-OtBu | 795 |
| Fmoc-Trp | His | | Phe-OtBu | 796 |
| Fmoc-Trp | His | | Tyr-OtBu | 797 |
| Fmoc-Trp | His | | Thr(tBu)-OtBu | 798 |
| Nicotinyl Lys(eBoc) | His | | Ser(tBu)-0tBu | 799 |
| Nicotinyl Lys(EBoc) | His | | Thr(tBu)-0tBu | 800 |

While the peptides of Table 7 are illustrated with particular protecting groups, it is noted that these groups may be substituted with other protecting groups as described herein and/or one or more of the shown protecting group can be eliminated.

3) Small Peptides with Central Acidic and Basic Amino Acids.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic amino acid and an acidic amino acid (e.g., in a 4 mer) or a basic domain and/or an acidic domain in a longer molecule.

These four-mers can be represented by Formula I in which $X^1$ and $X^4$ are hydrophobic and/or bear hydrophobic protecting group(s) as described herein and $X^2$ is acidic while $X^3$ is basic or $X^2$ is basic while $X^3$ is acidic. The peptide can be all L-amino acids or include one or more or all D-amino acids.

Certain preferred peptides of this invention include, but are not limited to the peptides shown in Table 8.

TABLE 8

Illustrative examples of small peptides with central acidic and basic amino acids.

| X¹ | X² | X³ | X⁴ | SEQ ID NO |
|---|---|---|---|---|
| Boc-Lys(EBoc) | Arg | Asp | Ser(tBu)-OtBu | 801 |
| Boc-Lys(EBoc) | Arg | Asp | Thr(tBu)-OtBu | 802 |
| Boc-Trp | Arg | Asp | Ile-OtBu | 803 |
| Boc-Trp | Arg | Asp | Leu-OtBu | 804 |

TABLE 8-continued

Illustrative examples of small peptides with central acidic and basic amino acids.

| X$^1$ | X$^2$ | X$^3$ | X$^4$ | SEQ ID NO |
|---|---|---|---|---|
| Boc-Phe | Arg | Asp | Leu-OtBu | 805 |
| Boc-Phe | Arg | Asp | Ile-OtBu | 806 |
| Boc-Phe | Arg | Asp | norLeu-OtBu | 807 |
| Boc-Phe | Arg | Glu | norLeu-OtBu | 808 |
| Boc-Phe | Arg | Glu | Ile-OtBu | 809 |
| Boc-Phe | Asp | Arg | Ile-OtBu | 810 |
| Boc-Phe | Glu | Arg | Ile-OtBu | 811 |
| Boc-Phe | Asp | Arg | Leu-OtBu | 812 |
| Boc-Phe | Arg | Glu | Leu-OtBu | 813 |
| Boc-Phe | Glu | Arg | Leu-OtBu | 814 |
| Boc-Phe | Asp | Arg | norLeu-OtBu | 815 |
| Boc-Phe | Glu | Arg | norLeu-OtBu | 816 |
| Boc-Lys(EBoc) | Glu | Arg | Ser(tBu)-OtBu | 817 |
| Boc-Lys(EBoc) | Glu | Arg | Thr(tBu)-OtBu | 818 |
| Boc-Lys(EBoc) | Asp | Arg | Ser(tBu)-OtBu | 819 |
| Boc-Lys(EBoc) | Asp | Arg | Thr(tBu)-OtBu | 820 |
| Boc-Lys(eBoc) | Arg | Glu | Ser(tBu)-OtBu | 821 |
| Boc-Lys(eBoc) | Arg | Glu | Thr(tBu)-OtBu | 822 |
| Boc-Leu | Glu | Arg | Ser(tBu)-OtBu | 823 |
| Boc-Leu | Glu | Arg | Thr(tBu)-OtBu | 824 |
| Fmoc-Trp | Arg | Asp | Ser(tBu)-OtBu | 825 |
| Fmoc-Trp | Asp | Arg | Ser(tBu)-OtBu | 826 |
| Fmoc-Trp | Glu | Arg | Ser(tBu)-OtBu | 827 |
| Fmoc-Trp | Arg | Glu | Ser(tBu)-OtBu | 828 |
| Boc-Lys(eBoc) | Glu | Arg | Leu-OtBu | 829 |
| Fmoc-Leu | Arg | Asp | Ser(tBu)-OtBu | 830 |
| Fmoc-Leu | Asp | Arg | Ser(tBu)-OtBu | 831 |
| Fmoc-Leu | Glu | Arg | Ser(tBu)-OtBu | 832 |
| Fmoc-Leu | Arg | Glu | Ser(tBu)-OtBu | 833 |
| Fmoc-Leu | Arg | Asp | Thr(tBu)-OtBu | 834 |
| Boc-Glu | Asp | Arg | Tyr(tBu)-OtBu | 835 |
| Fmoc-Lys(EFmoc) | Arg | Asp | Ser(tBu)-OtBu | 836 |
| Fmoc-Trp | Arg | Asp | Ile-OtBu | 837 |
| Fmoc-Trp | Arg | Asp | Leu-OtBu | 838 |
| Fmoc-Phe | Arg | Asp | Ile-OtBu | 839 |
| Fmoc-Phe | Arg | Asp | Leu-OtBu | 840 |
| Boc-Trp | Arg | Asp | Phe-OtBu | 841 |
| Boc-Trp | Arg | Asp | Tyr-OtBu | 842 |
| Fmoc-Trp | Arg | Asp | Phe-OtBu | 843 |
| Fmoc-Trp | Arg | Asp | Tyr-OtBu | 844 |
| Boc-Orn(8Boc) | Arg | Glu | Ser(tBu)-OtBu | 845 |
| Nicotinyl Lys(eBoc) | Arg | Asp | Ser(tBu)-OtBu | 846 |
| Nicotinyl Lys(EBoc) | Arg | Asp | Thr(tBu)-OtBu | 847 |
| Fmoc-Leu | Asp | Arg | Thr(tBu)-OtBu | 848 |
| Fmoc-Leu | Glu | Arg | Thr(tBu)-OtBu | 849 |
| Fmoc-Leu | Arg | Glu | Thr(tBu)-OtBu | 850 |
| Fmoc-norLeu | Arg | Asp | Ser(tBu)-OtBu | 851 |
| Fmoc-norLeu | Asp | Arg | Ser(tBu)-OtBu | 852 |
| Fmoc-norLeu | Glu | Arg | Ser(tBu)-OtBu | 853 |
| Fmoc-norLeu | Arg | Glu | Ser(tBu)-OtBu | 854 |
| Fmoc-Lys(EBoc) | Arg | Asp | Ser(tBu)-OtBu | 855 |
| Fmoc-Lys(EBoc) | Arg | Asp | Thr(tBu)-OtBu | 856 |
| Fmoc-Lys(EBoc) | Glu | Arg | Ser(tBu)-OtBu | 857 |
| Fmoc-Lys(EBoc) | Glu | Arg | Thr(tBu)-OtBu | 858 |
| Fmoc-Lys(eBoc) | Asp | Arg | Ser(tBu)-OtBu | 859 |
| Fmoc-Lys(EBoc) | Asp | Arg | Thr(tBu)-0tBu | 860 |
| Fmoc-Lys(EBoc) | Arg | Glu | Ser(tBu)-OtBu | 861 |
| Fmoc-Lys(EBoc) | Arg | Glu | Thr(tBu)-OtBu | 862 |
| Fmoc-Lys(EBoc) | Glu | Arg | Leu-OtBu | 863 |
| Fmoc-Lys(EBoc) | Arg | Glu | Leu-OtBu | 864 |
| Fmoc-Lys(EFmoc) | Arg | Asp | Thr(tBu)-OtBu | 865 |
| Fmoc-Lys(EFmoc) | Glu | Arg | Ser(tBu)-OtBu | 866 |
| Fmoc-Lys(EFmoc) | Glu | Arg | Thr(tBu)-OtBu | 867 |
| Fmoc-Lys(EFmoc) | Asp | Arg | Ser(tBu)-0tBu | 868 |
| Fmoc-Lys(cFmoc) | Asp | Arg | Thr(tBu)-0tBu | 869 |
| Fmoc-Lys(EFmoc) | Arg | Glu | Ser(tBu)-OtBu | 870 |
| Fmoc-Lys(EFmoc) | Arg | Glu | Thr(tBu)-OtBu | 871 |
| Fmoc-Lys(EFmoc)) | Glu | Arg | Leu-OtBu | 872 |
| Boc-Lys(eFmoc) | Arg | Asp | Ser(tBu)-0tBu | 873 |
| Boc-Lys(EFmoc) | Arg | Asp | Thr(tBu)-OtBu | 874 |
| Boc-Lys(EFmoc) | Glu | Arg | Ser(tBu)-OtBu | 875 |
| Boc-Lys(eFmoc) | Glu | Arg | Thr(tBu)-OtBu | 876 |
| Boc-Lys(EFmoc) | Asp | Arg | Ser(tBu)-0tBu | 877 |
| Boc-Lys(eFmoc) | Asp | Arg | Thr(tBu)-OtBu | 878 |
| Boc-Lys(EFmoc) | Arg | Glu | Ser(tBu)-0tBu | 879 |
| Boc-Lys(EFmoc) | Arg | Glu | Thr(tBu)-OtBu | 880 |
| Boc-Lys(EFmoc) | Glu | Arg | Leu-OtBu | 881 |
| Boc-Orn(OFmoc) | Arg | Glu | Ser(tBu)-OtBu | 882 |
| Boc-Orn(8Fmoc) | Glu | Arg | Ser(tBu)-OtBu | 883 |
| Boc-Orn(8Fmoc) | Arg | Asp | Ser(tBu)-OtBu | 884 |
| Boc-Orn(8Fmoc) | Asp | Arg | Ser(tBu)-OtBu | 885 |
| Boc-Orn(OFmoc) | Asp | Arg | Thr(tBu)-OtBu | 886 |
| Boc-Orn(8Fmoc) | Arg | Asp | Thr(tBu)-OtBu | 887 |
| Boc-Orn(8Fmoc) | Glu | Arg | Thr(tBu)-OtBu | 888 |
| Boc-Orn(OFmoc) | Arg | Glu | Thr(tBu)-OtBu | 889 |
| Fmoc-Trp | Asp | Arg | Ile-OtBu | 890 |
| Fmoc-Trp | Arg | Glu | Ile-OtBu | 891 |
| Fmoc-Trp | Glu | Arg | Ile-OtBu | 892 |
| Fmoc-Trp | Asp | Arg | Leu-OtBu | 893 |
| Fmoc-Trp | Arg | Glu | Leu-OtBu | 894 |
| Fmoc-Trp | Glu | Arg | Leu-OtBu | 895 |
| Fmoc-Phe | Asp | Arg | Ile-OtBu | 896 |
| Fmoc-Phe | Arg | Glu | Ile-OtBu | 897 |
| Fmoc-Phe | Glu | Arg | Ile-OtBu | 898 |
| Fmoc-Phe | Asp | Arg | Leu-OtBu | 899 |
| Fmoc-Phe | Arg | Glu | Leu-OtBu | 900 |
| Fmoc-Phe | Glu | Arg | Leu-OtBu | 901 |
| Fmoc-Trp | Arg | Asp | Phe-OtBu | 902 |
| Fmoc-Trp | Arg | Glu | Phe-OtBu | 903 |
| Fmoc-Trp | Glu | Arg | Phe-OtBu | 904 |
| Fmoc-Trp | Asp | Arg | Tyr-OtBu | 905 |
| Fmoc-Trp | Arg | Glu | Tyr-OtBu | 906 |
| Fmoc-Trp | Glu | Arg | Tyr-OtBu | 907 |
| Fmoc-Trp | Arg | Asp | Thr(tBu)-OtBu | 908 |
| Fmoc-Trp | Asp | Arg | Thr(tBu)-OtBu | 909 |
| Fmoc-Trp | Arg | Glu | Thr(tBu)-OtBu | 910 |
| Fmoc-Trp | Glu | Arg | Thr(tBu)-OtBu | 911 |
| Fmoc-Phe | Arg | Asp | norLeu-OtBu | 912 |
| Fmoc-Phe | Arg | Glu | norLeu-OtBu | 913 |
| Boc-Phe | Lys | Asp | Leu-OtBu | 914 |
| Boc-Phe | Asp | Lys | Leu-OtBu | 915 |
| Boc-Phe | Lys | Glu | Leu-OtBu | 916 |
| Boc-Phe | Glu | Lys | Leu-OtBu | 917 |
| Boc-Phe | Lys | Asp | Ile-OtBu | 918 |
| Boc-Phe | Asp | Lys | Ile-OtBu | 919 |
| Boc-Phe | Lys | Glu | Ile-OtBu | 920 |
| Boc-Phe | Glu | Lys | Ile-OtBu | 921 |
| Boc-Phe | Lys | Asp | norLeu-OtBu | 922 |
| Boc-Phe | Asp | Lys | norLeu-OtBu | 923 |
| Boc-Phe | Lys | Glu | norLeu-OtBu | 924 |
| Boc-Phe | Glu | Lys | norLeu-OtBu | 925 |
| Boc-Phe | His | Asp | Leu-OtBu | 926 |
| Boc-Phe | Asp | His | Leu-OtBu | 927 |
| Boc-Phe | His | Glu | Leu-OtBu | 928 |
| Boc-Phe | Glu | His | Leu-OtBu | 929 |
| Boc-Phe | His | Asp | Ile-OtBu | 930 |
| Boc-Phe | Asp | His | Ile-OtBu | 931 |
| Boc-Phe | His | Glu | Ile-OtBu | 932 |
| Boc-Phe | Glu | His | Ile-OtBu | 933 |
| Boc-Phe | His | Asp | norLeu-OtBu | 934 |
| Boc-Phe | Asp | His | norLeu-OtBu | 935 |
| Boc-Phe | His | Glu | norLeu-OtBu | 936 |
| Boc-Phe | Glu | His | norLeu-OtBu | 937 |
| Boc-Lys(eBoc) | Lys | Asp | Ser(tBu)-OtBu | 938 |
| Boc-Lys(EBoc) | Asp | Lys | Ser(tBu)-OtBu | 939 |
| Boc-Lys(eBoc) | Lys | Glu | Ser(tBu)-OtBu | 940 |
| Boc-Lys(eBoc) | Glu | Lys | Ser(tBu)-OtBu | 941 |
| Boc-Lys(eBoc) | His | Asp | Ser(tBu)-OtBu | 942 |
| Boc-Lys(eBoc) | Asp | His | Ser(tBu)-OtBu | 943 |
| Boc-Lys(eBoc) | His | Glu | Ser(tBu)-OtBu | 944 |
| Boc-Lys(EBoc) | Glu | His | Ser(tBu)-OtBu | 945 |

While the peptides of Table 8 are illustrated with particular protecting groups, it is noted that these groups may be substituted with other protecting groups as described herein and/or one or more of the shown protecting group can be eliminated.

4) Small Peptides Having Either an Acidic or Basic Amino Acid in the Center Together with a Central Aliphatic Amino Acid.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups. End amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aliphatic amino acid (e.g., in a 4 mer) or a basic domain or an acidic domain and an aliphatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aliphatic or $X^2$ is aliphatic while $X^3$ is acidic or basic. The peptide can be all L-amino acids or include one, or more, or all D-amino acids.

Certain preferred peptides of this invention include, but are not limited to the peptides shown in Table 9.

TABLE 9

Examples of certain preferred peptides having either an acidic or basic amino acid in the center together with a central aliphatic amino acid.

| X¹ | X² | X³ | X⁴ | SEQ ID NO |
|---|---|---|---|---|
| Fmoc-Lys(εBoc) | Leu | Arg | Ser(tBu)-OtBu | 946 |
| Fmoc-Lys(εBoc) | Arg | Leu | Ser(tBu)-OtBu | 947 |
| Fmoc-Lys(εBoc) | Leu | Arg | Thr(tBu)-OtBu | 948 |
| Fmoc-Lys(εBoc) | Arg | Leu | Thr(tBu)-OtBu | 949 |
| Fmoc-Lys(εBoc) | Glu | Leu | Ser(tBu)-OtBu | 950 |
| Fmoc-Lys(εBoc) | Leu | Glu | Ser(tBu)-OtBu | 951 |
| Fmoc-Lys(εBoc) | Glu | Leu | Thr(tBu)-OtBu | 952 |
| Fmoc-Lys(εBoc) | Leu | Glu | Thr(tBu)-OtBu | 953 |
| Fmoc-Lys(εFmoc) | Leu | Arg | Ser(tBu)-OtBu | 954 |
| Fmoc-Lys(εFmoc) | Leu | Arg | Thr(tBu)-OtBu | 955 |
| Fmoc-Lys(εFmoc) | Glu | Leu | Ser(tBu)-OtBu | 956 |
| Fmoc-Lys(εFmoc) | Glu | Leu | Thr(tBu)-OtBu | 957 |
| Boc-Lys(εFmoc) | Glu | Ile | Thr(tBu)-OtBu | 958 |
| Boc-Lys(εFmoc) | Leu | Arg | Ser(tBu)-OtBu | 959 |
| Boc-Lys(εFmoc) | Leu | Arg | Thr(tBu)-OtBu | 960 |
| Boc-Lys(εFmoc) | Glu | Leu | Ser(tBu)-OtBu | 961 |
| Boc-Lys(εFmoc) | Glu | Leu | Thr(tBu)-OtBu | 962 |
| Boc-Lys(εBoc) | Leu | Arg | Ser(tBu)-OtBu | 963 |
| Boc-Lys(εBoc) | Arg | Phe | Thr(tBu)-OtBu | 964 |
| Boc-Lys(εBoc) | Leu | Arg | Thr(tBu)-OtBu | 965 |
| Boc-Lys(εBoc) | Glu | Ile | Thr(tBu) | 966 |
| Boc-Lys(εBoc) | Glu | Val | Thr(tBu) | 967 |
| Boc-Lys(εBoc) | Glu | Ala | Thr(tBu) | 968 |
| Boc-Lys(εBoc) | Glu | Gly | Thr(tBu) | 969 |
| Boc--Lys(εBoc) | Glu | Leu | Ser(tBu)-0tBu | 970 |
| Boc-Lys(εBoc) | Glu | Leu | Thr(tBu)-OtBu | 971 |

While the peptides of Table 9 are illustrated with particular protecting groups, it is noted that these groups may be substituted with other protecting groups as described herein and/or one or more of the shown protecting group can be eliminated.

5) Small Peptides Having Either an Acidic or Basic Amino Acid in the Center Together with a Central Aromatic Amino Acid.

In certain embodiments, the "small" peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aromatic amino acid (e.g., in a 4 mer) or a basic domain or an acidic domain and an aromatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aromatic or $X^2$ is aromatic while $X^3$ is acidic or basic. The peptide can be all L-amino acids or include one, or more, or all D-amino acids. Five-mers can be represented by a minor modification of Formula I in which $X^5$ is inserted as shown in Table 10 and in which $X^5$ is typically an aromatic amino acid.

Certain preferred peptides of this invention include, but are not limited to the peptides shown in Table 10.

TABLE 10

Examples of certain preferred peptides having either an acidic or basic amino acid in the center together with a central aromatic amino acid.

| X¹ | X² | X³ | X⁵ | X⁴ | SEQ ID NO |
|---|---|---|---|---|---|
| Fmoc-Lys(εBoc) | Arg | Trp | | Tyr(tBu)-0tBu | 972 |
| Fmoc-Lys(εBoc) | Trp | Arg | | Tyr(tBu)-OtBu | 973 |
| Fmoc-Lys(εBoc) | Arg | Tyr | | Trp-OtBu | 974 |
| Fmoc-Lys(εBoc) | Tyr | Arg | | Trp-OtBu | 975 |
| Fmoc-Lys(εBoc) | Arg | Tyr | Trp | Thr(tBu)-OtBu | 976 |
| Fmoc-Lys(εBoc) | Arg | Tyr | | Thr(tBu)-OtBu | 977 |
| Fmoc-Lys(εBoc) | Arg | Trp | | Thr(tBu)-OtBu | 978 |
| Fmoc-Lys(εFmoc) | Arg | Trp | | Tyr(tBu)-OtBu | 979 |
| Fmoc-Lys(εFmoc) | Arg | Tyr | | Trp-OtBu | 980 |
| Fmoc-Lys(εFmoc) | Arg | Tyr | Trp | Thr(tBu)-OtBu | 981 |
| Fmoc-Lys(εFmoc) | Arg | Tyr | | Thr(tBu)-OtBu | 982 |
| Fmoc-Lys(εFmoc) | Arg | Trp | | Thr(tBu)-OtBu | 983 |
| Boc-Lys(εFmoc) | Arg | Trp | | Tyr(tBu)-OtBu | 984 |
| Boc-Lys(εFmoc) | Arg | Tyr | | Trp-OtBu | 985 |
| Boc-Lys(εFmoc) | Arg | Tyr | Trp | Thr(tBu)-OtBu | 986 |
| Boc-Lys(εFmoc) | Arg | Tyr | | Thr(tBu)-OtBu | 987 |
| Boc-Lys(εFmoc) | Arg | Trp | | Thr(tBu)-OtBu | 988 |
| Boc-Glu | Lys(εFmoc) | Arg | | Tyr(tBu)-OtBu | 989 |
| Boc-Lys(εBoc) | Arg | Trp | | Tyr(tBu)-OtBu | 990 |
| Boc-Lys(εBoc) | Arg | Tyr | | Trp-OtBu | 991 |
| Boc-Lys(εBoc) | Arg | Tyr | Trp | Thr(tBu)-OtBu | 992 |
| Boc-Lys(εBoc) | Arg | Tyr | | Thr(tBu)-OtBu | 993 |
| Boc-Lys(εBoc) | Arg | Phe | | Thr(tBu)-OtBu | 994 |
| Boc-Lys(εBoc) | Arg | Trp | | Thr(tBu)-OtBu | 995 |

While the peptides of Table 10 are illustrated with particular protecting groups, it is noted that these groups may be substituted with other protecting groups as described herein and/or one or more of the shown protecting group can be eliminated.

6) Small Peptides Having Aromatic Amino Acids or Aromatic Amino Acids Separated by Histidine(s) at the Center.

In certain embodiments, the peptides of this invention are characterized by n electrons that are exposed in the center of the molecule which allow hydration of the particle and that allow the peptide particles to trap pro-inflammatory oxidized lipids such as fatty acid hydroperoxides and phospholipids that contain an oxidation product of arachidonic acid at the sn-2 position.

In certain embodiments, these peptides consist of a minimum of 4 amino acids and a maximum of about 10 amino acids, preferentially (but not necessarily) with one or more of the amino acids being the D-sterioisomer of the amino acid, with the end amino acids being hydrophobic either because of a hydrophobic side chain or because the terminal amino acid(s) bear one or more hydrophobic blocking group(s), (e.g., an N-terminus blocked with Boc-, Fmoc-, Nicotinyl-, and the like, and a C-terminus blocked with (tBu)-OtBu groups and the like). Instead of having an acidic or basic amino acid in the center, these peptides generally have an aromatic amino acid at the center or have aromatic amino acids separated by histidine in the center of the peptide.

Certain preferred peptides of this invention include, but are not limited to the peptides shown in Table 11.

TABLE 11

Examples of peptides having aromatic amino acids in the center or aromatic amino acids or aromatic domains separated by one or more histidines.

| $X^1$ | $X^2$ | $X^3$ | $X^4$ | $X^5$ | SEQ ID NO |
|---|---|---|---|---|---|
| Boc-Lys(εBoc) | Phe | Trp | Phe | Ser(tBu)-OtBu | 996 |
| Boc-Lys(εBoc) | Phe | Trp | Phe | Thr(tBu)-OtBu | 997 |
| Boc-Lys(εBoc) | Phe | Tyr | Phe | Ser(tBu)-OtBu | 998 |
| Boc-Lys(εBoc) | Phe | Tyr | Phe | Thr(tBu)-OtBu | 999 |
| Boc-Lys(εBoc) | Phe | His | Phe | Ser(tBu)-OtBu | 1000 |
| Boc-Lys(εBoc) | Phe | His | Phe | Thr(tBu)-OtBu | 1001 |
| Boc-Lys(εBoc) | Val | Phe | Phe-Tyr | Ser(tBu)-OtBu | 1002 |
| Nicotinyl-Lys(εBoc) | Phe | Trp | Phe | Ser(tBu)-OtBu | 1003 |
| Nicotinyl-Lys(εBoc) | Phe | Trp | Phe | Thr(tBu)-OtBu | 1004 |
| Nicotinyl-Lys(εBoc) | Phe | Tyr | Phe | Ser(tBu)-OtBu | 1005 |
| Nicotinyl-Lys(εBoc) | Phe | Tyr | Phe | Thr(tBu)-OtBu | 1006 |
| Nicotinyl-Lys(εBoc) | Phe | His | Phe | Ser(tBu)-OtBu | 1007 |
| Nicotinyl-Lys(εBoc) | Phe | His | Phe | Thr(tBu)-OtBu | 1008 |
| Boc-Leu | Phe | Trp | Phe | Thr(tBu)-OtBu | 1009 |
| Boc-Leu | Phe | Trp | Phe | Ser(tBu)-OtBu | 1010 |

While the peptides of Table 11 are illustrated with particular protecting groups, it is noted that these groups may be substituted with other protecting groups as described herein and/or one or more of the shown protecting group can be eliminated.

7) Summary of Tripeptides and Tetrapeptides.

For the sake of clarity, a number of tripeptides and tetrapeptides of this invention are generally summarized below in Table 12.

TABLE 12

General structure of certain peptides of this invention.

| $X^1$ | $X^2$ | $X^3$ | $X^4$ |
|---|---|---|---|
| hydrophobic side chain or hydrophobic | Acidic or Basic | — | hydrophobic side chain or hydrophobic protecting group(s) |
| hydrophobic side chain or hydrophobic protecting group(s) | Basic | Acidic | hydrophobic side chain or hydrophobic protecting group(s) |
| hydrophobic side chain or hydrophobic protecting group(s) | Acidic | Basic | hydrophobic side chain or hydrophobic protecting group(s) |
| hydrophobic side chain or hydrophobic protecting group(s) | Acidic or Basic | Aliphatic | hydrophobic side chain or hydrophobic protecting group(s) |
| hydrophobic side chain or hydrophobic protecting group(s) | Aliphatic | Acidic or Basic | hydrophobic side chain or hydrophobic protecting group(s) |
| hydrophobic side chain or hydrophobic protecting group(s) | Acidic or Basic | Aromatic | hydrophobic side chain or hydrophobic protecting group(s) |
| hydrophobic side chain or hydrophobic protecting group(s) | Aromatic | Acidic or Basic | hydrophobic side chain or hydrophobic protecting group(s) |
| hydrophobic side chain or hydrophobic protecting group(s) | Aromatic | His Aromatic | hydrophobic side chain or hydrophobic protecting group(s) |

Where longer peptides are desired, $X^2$ and $X^3$ can represent domains (e.g., regions of two or more amino acids of the specified type) rather than individual amino acids. Table 12 is intended to be illustrative and not limiting. Using the teaching provided herein, other suitable peptides can readily be identified.

8) Paired Amino Acids and Dipeptides.

In certain embodiments, this invention pertains to the discovery that certain pairs of amino acids, administered in conjunction with each other or linked to form a dipeptide have one or more of the properties described herein. Thus, without being bound to a particular theory, it is believed that when the pairs of amino acids are administered in conjunction with each other, as described herein, they are capable participating in or inducing the formation of micelles in vivo.

Similar to the other small peptides described herein, it is believed that the pairs of peptides will associate in vivo, and demonstrate physical properties including high solubility in ethyl acetate (e.g., greater than about 4 mg/mL), solubility in aqueous buffer at pH 7.0. Upon contacting phospholipids such as 1,2-Dimyristoyl-sn-glycero-3-phosphocholine (DMPC), in an aqueous environment, it is believed the pairs of amino acids induce or participate in the formation of particles with a diameter of approximately 7.5 nm (.+−.0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm).

Moreover, it is further believed that the pairs of amino acids can display one or more of the following physiologically relevant properties:

1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-β HDL;
4. They raise HDL cholesterol; and/or
5. They increase HDL paraoxonase activity.

The pairs of amino acids can be administered as separate amino acids (administered sequentially or simultaneously, e.g. in a combined formulation) or they can be covalently coupled directly or through a linker (e.g. a PEG linker, a carbon linker, a branched linker, a straight chain linker, a heterocyclic linker, a linker formed of derivatized lipid, etc.). In certain embodiments, the pairs of amino acids are covalently linked through a peptide bond to form a dipeptide. In various embodiments while the dipeptides will typically comprise two amino acids each bearing an attached protecting group, this invention also contemplates dipeptides wherein only one of the amino acids bears one or more protecting groups.

The pairs of amino acids typically comprise amino acids where each amino acid is attached to at least one protecting group (e.g., a hydrophobic protecting group as described herein). The amino acids can be in the D or the L form. In certain embodiments, where the amino acids comprising the pairs are not attached to each other, each amino acid bears two protecting groups (e.g., such as molecules 1 and 2 in Table 13).

TABLE 13

Illustrative amino acid pairs of this invention.

| | Amino Acid Pair/dipeptide |
|---|---|
| 1. | Boc-Arg-OtBu* |
| 2. | Boc-Glu-OtBu* |
| 3. | Boc-Phe-Arg-OtBu** |
| 4. | Boc-Glu-Leu-OtBu** |
| 5. | Boc-Arg-Glu-OtBu*** |

*This would typically be administered in conjunction with a second amino acid.
**In certain embodiments, these dipeptides would be administered in conjunction with each other.
***In certain embodiments, this peptide would be administered either alone or in combination with one of the other peptides described herein.

Suitable pairs of amino acids can readily be identified by providing the pair of protected amino acids and/or a dipeptide and then screening the pair of amino acids/dipeptide for one or more of the physical and/or physiological properties described above. In certain embodiments, this invention excludes pairs of amino acids and/or dipeptides comprising aspartic acid and phenylalanine. In certain embodiments, this invention excludes pairs of amino acids and/or dipeptides in which one amino acid is (−)-N-[(trans-4-isopropylcyclohexane)carbonyl]-D-phenylalanine (nateglinide).

In certain embodiments, the amino acids comprising the pair are independently selected from the group consisting of an acidic amino acid (e.g., aspartic acid, glutamic acid, etc.), a basic amino acid (e.g., lysine, arginine, histidine, etc.), and a non-polar amino acid (e.g., alanine, valine, leucine, isoleucine, proline, phenylalanine, tryptophan, methionine, etc.). In certain embodiments, where the first amino acid is acidic or basic, the second amino acid is non-polar and where the second amino acid is acidic or basic, the first amino acid is non-polar. In certain embodiments, where the first amino acid is acidic, the second amino acid is basic, and vice versa. (see, e.g., Table 14).

Similar combinations can be obtained by administering pairs of dipeptides. Thus, for example in certain embodiments, molecules 3 and 4 in Table 13 would be administered in conjunction with each other.

TABLE 14

Certain generalized amino acid pairs/dipeptides.

| | First Amino acid | Second Amino acid |
|---|---|---|
| 1. | Acidic | Basic |
| 2. | Basic | Acidic |
| 3. | Acidic | Non-polar |
| 4. | Non-polar | Acidic |
| 5. | Basic | Non-polar |
| 6. | Non-polar | Basic |

It is noted that these amino acid pairs/dipeptides are intended to be illustrative and not limiting. Using the teaching provided herein other suitable amino acid pairs/dipeptides can readily be determined.

E) Apo-J (G* Peptides).

It was a discovery of this invention that peptides that mimicking the amphipathic helical domains of apo J are capable of mitigating one or more symptoms of atherosclerosis and/or other pathologies described herein. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A number of suitable G* amphipathic peptides are described in copending applications U.S. Ser. No. 10/120,508, filed Apr. 5, 2002, U.S. Ser. No. 10/520,207, filed Apr. 1, 2003, and PCT Application PCT/US03/09988, filed Apr. 1, 2003. In addition, a variety of suitable peptides of this invention that are related to G* amphipathic helical domains of apo J are illustrated in Table 15.

TABLE 15

Certain illustrative peptides for use in this invention related to G* amphipathic helical domains of apo J.

| Amino Acid Sequence | SEQ ID NO |
|---|---|
| LLEQLNEQFNWVSRLANLTQGE | 1011 |
| LLEQLNEQFNWVSRLANL | 1012 |
| NELQEMSNQGSKYVNKEIQNAVNGV | 1013 |
| IQNAVNGVKQIKTLIEKTNEE | 1014 |
| RKTLLSNLEEAKKKKEDALNETRESETKLKEL | 1015 |
| PGVCNETMMALWEECK | 1016 |
| PCLKQTCMKFYARVCR | 1017 |
| ECKPCLKQTCMKFYARVCR | 1018 |
| LVGRQLEEFL | 1019 |
| MNGDRIDSLLEN | 1020 |
| QQTHMLDVMQD | 1021 |
| FSRASSIIDELFQD | 1022 |
| PFLEMIHEAQQAMDI | 1023 |
| PTEFIREGDDD | 1024 |
| RMKDQCDKCREILSV | 1025 |
| PSQAKLRRELDESLQVAERLTRKYNELLKSYQ | 1026 |
| LLEQLNEQFNWVSRLANLTEGE | 1027 |
| DQYYLRVTTVA | 1028 |

TABLE 15-continued

Certain illustrative peptides for use in this invention related to G* amphipathic helical domains of apo J.

| Amino Acid Sequence | SEQ ID NO |
|---|---|
| PSGVTEVVVKLFDS | 1029 |
| PKFMETVAEKALQEYRKKHRE | 1030 |

The peptides of this invention, however, are not limited to G* variants of apo J. Generally speaking G* domains from essentially any other protein preferably apo proteins are also suitable. The particular suitability of such proteins can readily be determined using assays for protective activity (e.g., protecting LDL from oxidation, and the like), e.g. as illustrated herein in the Examples. Some particularly preferred proteins include G* amphipathic helical domains or variants thereof (e.g., conservative substitutions, and the like) of proteins including, but not limited to apo AI, apo AIV, apo E, apo CII, apo CIII, and the like.

Certain preferred peptides for related to G* amphipathic helical domains related to apoproteins other than apo J are illustrated in Table 16.

TABLE 16

Peptides for use in this invention related to G* amphipathic helical domains related to apoproteins other than apo J.

| Amino Acid Sequence | SEQ ID NO |
|---|---|
| WDRVKDLATVYVDVLKDSGRDYVSQF (Related to the 8 to 33 region of apo AI) | 1031 |
| VATVMWDYFSQLSNNAKEAVEHLQK (Related to the 7 to 31 region of apo AIV) | 1032 |
| RWELALGRFWDYLRWVQTLSEQVQEEL (Related to the 25 to 51 region of apo E) | 1033 |
| LSSQVTQELRALMDETMKELKELKAYKSELEEQLT (Related to the 52 to 83 region of apo E) | 1034 |
| ARLSKELQAAQARLGADMEDVCGRLV (Related to the 91 to 116 region of apo E) | 1035 |
| VRLASHLRKLRKRLLRDADDLQKRLA (Related to the 135 to 160 region of apo E) | 1036 |
| PLVEDMQRQWAGLVEKVQA (267 to 285 of apo E.27) | 1037 |
| MSTYTGIFTDQVLSVLK (Related to the 60 to 76 region of apo CII) | 1038 |
| LLSFMQGYMKHATKTAKDALSS (Related to the 8 to 29 region of apoCIII) | 1039 |

Additional illustrative G* peptides are shown in Table 17.

TABLE 17

Additional illustrative G* peptides.

| Peptide | SEQ ID NO |
|---|---|
| Ac-Lys-Trp-Ile-Tyr-His-Leu-Thr-Glu-Gly-Ser-Thr-Asp-Leu-Arg-Thr-Glu-Gly-NH$_2$ | 1040 |
| Ac-Lys-Trp-Phe-Tyr-His-Leu-Thr-Glu-Gly-Ser-Thr-Asp-Leu-Arg-Thr-Glu-Gly-NH$_2$ | 1041 |
| Ac-Lys-Trp-Leu-Tyr-His-Leu-Thr-Glu-Gly-Ser-Thr-Asp-Leu-Arg-Thr-Glu-Gly-NH$_2$ | 1042 |
| Ac-Lys-Trp-Val-Tyr-His-Leu-Thr-Glu-Gly-Ser-Thr-Asp-Leu-Arg-Thr-Glu-Gly-NH$_2$ | 1043 |
| Ac-Lys-Tyr-Ile-Trp-His-Leu-Thr-Glu-Gly-Ser-Thr-Asp-Leu-Arg-Thr-Glu-Gly-NH$_2$ | 1044 |
| Ac-Lys-Trp-Ile-Tyr-His-Phe-Thr-Glu-Gly-Ser-Thr-Asp-Leu-Arg-Thr-Glu-Gly-NH$_2$ | 1045 |
| Ac-Lys-Trp-Phe-Tyr-His-Ile-Thr-Glu-Gly-Ser-Thr-Asp-Leu-Arg-Thr-Glu-Gly-NH$_2$ | 1046 |
| Ac-Lys-Trp-Leu-Tyr-His-Val-Thr-Glu-Gly-Ser-Thr-Asp-Leu-Arg-Thr-Glu-Gly-NH$_2$ | 1047 |
| Ac-Lys-Trp-Val-Tyr-His-Tyr-Thr-Glu-Gly-Ser-Thr-Asp-Leu-Arg-Thr-Glu-Gly-NH$_2$ | 1048 |
| Ac-Lys-Tyr-Ile-Trp-His-Phe-Thr-Glu-Gly-Ser-Thr-Asp-Leu-Arg-Thr-Glu-Gly-NH$_2$ | 1049 |
| Ac-Lys-Tyr-Ile-Trp-His-Ile-Thr-Glu-Gly-Ser-Thr-Asp-Leu-Arg-Thr-Glu-Gly-NH$_2$ | 1050 |
| Ac-Lys-Tyr-Ile-Trp-His-Val-Thr-Glu-Gly-Ser-Thr-Asp-Leu-Arg-Thr-Glu-Gly-NH$_2$ | 1051 |
| Ac-Lys-Tyr-Ile-Trp-His-Tyr-Thr-Glu-Gly-Ser-Thr-Asp-Leu-Arg-Thr-Glu-Gly-NH$_2$ | 1052 |
| Ac-Lys-Phe-Ile-Trp-His-Leu-Thr-Glu-Gly-Ser-Thr-Asp-Leu-Arg-Thr-Glu-Gly-NH$_2$ | 1053 |
| Ac-Lys-Leu-Ile-Trp-His-Leu-Thr-Glu-Gly-Ser-Thr-Asp-Leu-Arg-Thr-Glu-Gly-NH$_2$ | 1054 |
| Ac-Lys-Ile-Ile-Trp-His-Leu-Thr-Glu-Gly-Ser-Thr-Asp-Leu-Arg-Thr-Glu-Gly-NH$_2$ | 1055 |
| Ac-Lys-Tyr-Ile-Trp-Phe-Leu-Thr-Glu-Gly-Ser-Thr-Asp-Leu-Arg-Thr-Glu-Gly-NH$_2$ | 1056 |
| Ac-Lys-Trp-Ile-Tyr-Phe-Leu-Thr-Glu-Gly-Ser-Thr-Asp-Leu-Arg-Thr-Glu-Gly-NH$_2$ | 1057 |
| Ac-Lys-Trp-Ile-Tyr-Leu-Leu-Thr-Glu-Gly-Ser-Thr-Asp-Leu-Arg-Thr-Glu-Gly-NH$_2$ | 1058 |
| Ac-Lys-Trp-Ile-Tyr-His-Phe-Thr-Glu-Gly-Ser-Thr-Asp-Leu-Arg-Thr-Glu-Gly-NH$_2$ | 1059 |
| Ac-Lys-Trp-Ile-Tyr-His-Tyr-Thr-Glu-Gly-Ser-Thr-Asp-Leu-Arg-Thr-Glu-Gly-NH$_2$ | 1060 |
| Ac-Lys-Trp-Ile-Tyr-His-Ile-Thr-Glu-Gly-Ser-Thr-Asp-Leu-Arg-Thr-Glu-Gly-NH$_2$ | 1061 |
| Ac-Lys-Trp-Ile-Tyr-His-Leu-Ser-Glu-Gly-Ser-Thr-Asp-Leu-Arg-Thr-Glu-Gly-NH$_2$ | 1062 |
| Ac-Lys-Trp-Ile-Tyr-His-Leu-Thr-Asp-Gly-Ser-Thr-Asp-Leu-Arg-Thr-Glu-Gly-NH$_2$ | 1063 |
| Ac-Lys-Trp-Ile-Tyr-His-Leu-Thr-Glu-Gly-Thr-Ser-Asp-Leu-Arg-Thr-Glu-Gly-NH$_2$ | 1064 |
| Ac-Lys-Trp-Ile-Tyr-His-Leu-Thr-Glu-Gly-Ser-Thr-Glu-Leu-Arg-Thr-Glu-Gly-NH$_2$ | 1065 |
| Ac-Lys-Trp-Ile-Tyr-His-Leu-Thr-Glu-Gly-Ser-Thr-Asp-Phe-Arg-Thr-Glu-Gly-NH$_2$ | 1066 |
| Ac-Lys-Trp-Ile-Tyr-His-Leu-Thr-Glu-Gly-Ser-Thr-Asp-Tyr-Arg-Thr-Glu-Gly-NH$_2$ | 1067 |
| Ac-Lys-Trp-Ile-Tyr-His-Leu-Thr-Glu-Gly-Ser-Thr-Asp-Ile-Arg-Thr-Glu-Gly-NH$_2$ | 1068 |
| Ac-Lys-Trp-Ile-Tyr-His-Leu-Thr-Glu-Gly-Ser-Thr-Asp-Val-Arg-Thr-Glu-Gly-NH$_2$ | 1069 |
| Ac-Lys-Trp-Ile-Tyr-His-Leu-Thr-Glu-Gly-Ser-Thr-Asp-Leu-Lys-Thr-Glu-Gly-NH$_2$ | 1070 |
| Ac-Lys-Trp-Ile-Tyr-His-Leu-Thr-Glu-Gly-Ser-Thr-Asp-Leu-Arg-Ser-Glu-Gly-NH$_2$ | 1071 |
| Ac-Lys-Trp-Ile-Tyr-His-Leu-Thr-Glu-Gly-Ser-Thr-Asp-Leu-Arg-Thr-Asp-Gly-NH$_2$ | 1072 |
| Ac-Lys-Trp-Ile-Tyr-His-Leu-Thr-Glu-Gly-Ser-Thr-Asp-Ile-Lys-Thr-Glu-Gly-NH$_2$ | 1073 |
| Ac-Lys-Trp-Ile-Tyr-His-Leu-Thr-Glu-Gly-Ser-Thr-Asp-Ile-Arg-Ser-Glu-Gly-NH$_2$ | 1074 |
| Ac-Lys-Trp-Ile-Tyr-His-Leu-Thr-Glu-Gly-Ser-Thr-Asp-Ile-Lys-Ser-Glu-Gly-NH$_2$ | 1075 |
| Ac-Lys-Trp-Ile-Tyr-His-Leu-Thr-Glu-Gly-Ser-Thr-Asp-Ile-Lys-Ser-Asp-Gly-NH$_2$ | 1076 |
| Ac-Arg-Trp-Ile-Tyr-His-Leu-Thr-Glu-Gly-Ser-Thr-Asp-Leu-Arg-Thr-Glu-Gly-NH$_2$ | 1077 |

TABLE 17-continued

Additional illustrative G* peptides.

| Peptide | SEQ ID NO |
|---|---|
| Ac-Arg-Tyr-Ile-Trp-His-Leu-Thr-Glu-Gly-Ser-Thr-Asp-Ile-Arg-Thr-Glu-Gly-NH$_2$ | 1078 |
| Ac-Arg-Trp-Ile-Tyr-His-Leu-Thr-Glu-Gly-Ser-Thr-Asp-Ile-Arg-Thr-Asp-Gly-NH$_2$ | 1079 |
| Ac-Arg-Trp-Ile-Phe-His-Leu-Thr-Glu-Gly-Ser-Thr-Asp-Ile-Arg-Thr-Glu-Gly-NH$_2$ | 1080 |
| Ac-Arg-Trp-Ile-Tyr-His-Leu-Thr-Glu-Gly-Ser-Thr-Asp-Leu-Lys-Thr-Glu-Gly-NH$_2$ | 1081 |
| Ac-Arg-Trp-Ile-Tyr-His-Leu-Thr-Asp-Gly-Ser-Thr-Asp-Ile-Arg-Thr-Glu-Gly-NH$_2$ | 1082 |
| Ac-Arg-Trp-Ile-Tyr-His-Leu-Thr-Asp-Gly-Ser-Thr-Asp-Leu-Arg-Thr-Glu-Gly-NH$_2$ | 1083 |
| Ac-Arg-Trp-Ile-Tyr-Phe-Leu-Thr-Glu-Gly-Ser-Thr-Asp-Ile-Arg-Thr-Glu-Gly-NH$_2$ | 1084 |
| Ac-Arg-Trp-Ile-Tyr-Phe-Leu-Thr-Glu-Gly-Ser-Thr-Asp-Leu-Arg-Thr-Glu-Gly-NH$_2$ | 1085 |
| Ac-Lys-Trp-Phe-Tyr-His-Leu-Thr-Glu-Gly-Ser-Thr-Asp-Phe-Arg-Thr-Glu-Gly-NH$_2$ | 1086 |
| Ac-Arg-Trp-Phe-Tyr-His-Leu-Thr-Glu-Gly-Ser-Thr-Asp-Leu-Arg-Thr-Glu-Gly-NH$_2$ | 1087 |
| Ac-Lys-Trp-Ile-Phe-His-Leu-Thr-Glu-Gly-Ser-Thr-Asp-Ile-Arg-Thr-Asp-Gly-NH$_2$ | 1088 |
| Ac-Arg-Trp-Ile-Tyr-His-Leu-Thr-Glu-Gly-Ser-Thr-Asp-Ile-Arg-Thr-Asp-Gly-NH$_2$ | 1089 |
| Ac-Arg-Trp-Ile-Tyr-His-Leu-Thr-Glu-Gly-Ser-Thr-Asp-Leu-Arg-Thr-Asp-Gly-NH$_2$ | 1090 |
| Ac-Lys-Trp-Ile-Tyr-His-Leu-Thr-Glu-Gly-Ser-Thr-Asp-Ile-Lys-Thr-Glu-Gly-NH$_2$ | 1091 |
| Ac-Lys-Trp-Ile-Tyr-His-Leu-Thr-Glu-Gly-Ser-Thr-Asp-Ile-Lys-Thr-Asp-Gly-NH$_2$ | 1092 |
| Ac-Lys-Trp-Ile-Tyr-His-Leu-Thr-Glu-Gly-Ser-Thr-Asp-Phe-Lys-Thr-Glu-Gly-NH$_2$ | 1093 |
| Ac-Lys-Trp-Ile-Tyr-His-Leu-Thr-Glu-Gly-Ser-Thr-Asp-Tyr-Lys-Thr-Glu-Gly-NH$_2$ | 1094 |
| Ac-Lys-Trp-Ile-Tyr-His-Leu-Thr-Glu-Gly-Ser-Thr-Asp-Ile-Arg-Thr-Glu-Gly-NH$_2$ | 1095 |
| Ac-Lys-Trp-Phe-Tyr-His-Phe-Thr-Glu-Gly-Ser-Thr-Asp-Leu-Arg-Thr-Glu-Gly-NH$_2$ | 1096 |
| Ac-Arg-Trp-Phe-Tyr-His-Phe-Thr-Glu-Gly-Ser-Thr-Asp-Leu-Arg-Thr-Glu-Gly-NH$_2$ | 1097 |
| Ac-Lys-Trp-Phe-Tyr-His-Phe-Thr-Glu-Gly-Ser-Thr-Asp-Phe-Arg-Thr-Glu-Gly-NH$_2$ | 1098 |
| Ac-Lys-Trp-Phe-Tyr-His-Phe-Thr-Asp-Gly-Ser-Thr-Asp-Ile-Arg-Thr-Glu-Gly-NH$_2$ | 1099 |
| Ac-Arg-Trp-Phe-Tyr-His-Phe-Thr-Glu-Gly-Ser-Thr-Asp-Leu-Arg-Thr-Glu-Gly-NH$_2$ | 1100 |
| Ac-Arg-Trp-Phe-Tyr-His-Phe-Thr-Glu-Gly-Ser-Thr-Asp-Phe-Arg-Thr-Glu-Gly-NH$_2$ | 1101 |
| Ac-Arg-Trp-Phe-Tyr-His-Phe-Thr-Glu-Gly-Ser-Thr-Asp-Phe-Arg-Thr-Asp-Gly-NH$_2$ | 1102 |
| Ac-Glu-Lys-Cys-Val-Glu-Glu-Phe-Lys-Ser-Leu-Thr-Ser-Cys-Leu-Asp-Ser-Lys-Ala-Phe-NH$_2$ | 1103 |
| Ac-Asp-Lys-Cys-Val-Glu-Glu-Phe-Lys-Ser-Leu-Thr-Ser-Cys-Leu-Asp-Ser-Lys-Ala-Phe-NH$_2$ | 1104 |
| Ac-Glu-Lys-Cys-Val-Asp-Glu-Phe-Lys-Ser-Leu-Thr-Ser-Cys-Leu-Asp-Ser-Lys-Ala-Phe-NH$_2$ | 1105 |
| Ac-Glu-Lys-Cys-Val-Glu-Asp-Phe-Lys-Ser-Leu-Thr-Ser-Cys-Leu-Asp-Ser-Lys-Ala-Phe-NH$_2$ | 1106 |
| Ac-Glu-Arg-Cys-Val-Glu-Glu-Phe-Lys-Ser-Leu-Thr-Ser-Cys-Leu-Asp-Ser-Lys-Ala-Phe-NH$_2$ | 1107 |
| Ac-Asp-Lys-Cys-Val-Asp-Asp-Phe-Lys-Ser-Leu-Thr-Ser-Cys-Leu-Asp-Ser-Lys-Ala-Phe-NH$_2$ | 1108 |
| Ac-Asp-Arg-Cys-Val-Glu-Glu-Phe-Lys-Ser-Leu-Thr-Ser-Cys-Leu-Asp-Ser-Lys-Ala-Phe-NH$_2$ | 1109 |
| Ac-Glu-Arg-Cys-Val-Asp-Asp-Phe-Lys-Ser-Leu-Thr-Ser-Cys-Leu-Asp-Ser-Lys-Ala-Phe-NH$_2$ | 1110 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1111 |
| Ac-Glu-Lys-Cys-Val-Glu-Glu-Phe-Lys-Ser-Ile-Thr-Ser-Cys-Leu-Asp-Ser-Lys-Ala-Phe-NH$_2$ | 1112 |
| Ac-Glu-Lys-Cys-Val-Glu-Glu-Phe-Lys-Ser-Val-Thr-Ser-Cys-Leu-Asp-Ser-Lys-Ala-Phe-NH$_2$ | 1113 |
| Ac-Glu-Arg-Cys-Val-Glu-Glu-Phe-Lys-Ser-Tyr-Thr-Ser-Cys-Leu-Asp-Ser-Lys-Ala-Phe-NH$_2$ | 1114 |
| Ac-Glu-Arg-Cys-Val-Glu-Glu-Phe-Lys-Ser-Phe-Thr-Ser-Cys-Leu-Asp-Ser-Lys-Ala-Phe-NH$_2$ | 1115 |
| Ac-Glu-Arg-Cys-Val-Glu-Glu-Phe-Lys-Ser-Ile-Thr-Ser-Cys-Leu-Asp-Ser-Lys-Ala-Phe-NH$_2$ | 1116 |
| Ac-Glu-Arg-Cys-Val-Glu-Glu-Phe-Lys-Ser-Val-Thr-Ser-Cys-Leu-Asp-Ser-Lys-Ala-Phe-NH$_2$ | 1117 |
| Ac-Glu-Arg-Cys-Val-Glu-Glu-Phe-Lys-Ser-Tyr-Thr-Ser-Cys-Leu-Asp-Ser-Lys-Ala-Phe-NH$_2$ | 1118 |
| Ac-Glu-Lys-Cys-Val-Glu-Glu-Phe-Lys-Ser-Phe-Thr-Thr-Cys-Leu-Asp-Ser-Lys-Ala-Phe-NH$_2$ | 1119 |
| Ac-Glu-Lys-Cys-Val-Glu-Glu-Phe-Lys-Ser-Ile-Ser-Ser-Cys-Leu-Asp-Ser-Lys-Ala-Phe-NH$_2$ | 1120 |
| Ac-Glu-Lys-Cys-Val-Glu-Glu-Phe-Lys-Ser-Val-Ser-Thr-Cys-Leu-Asp-Ser-Lys-Ala-Phe-NH$_2$ | 1121 |
| Ac-Glu-Lys-Cys-Val-Glu-Glu-Phe-Lys-Ser-Tyr-Thr-Ser-Cys-Leu-Asp-Ser-Lys-Ala-Phe-NH$_2$ | 1122 |
| Ac-Glu-Lys-Cys-Val-Glu-Glu-Phe-Lys-Ser-Phe-Thr-Thr-Cys-Leu-Asp-Ser-Lys-Ala-Phe-NH$_2$ | 1123 |
| Ac-Glu-Lys-Cys-Val-Glu-Glu-Phe-Lys-Ser-Phe-Ser-Ser-Cys-Leu-Asp-Ser-Lys-Ala-Phe-NH$_2$ | 1124 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1125 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1126 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 1127 |
| Ac-Glu-Lys-Cys-Val-Glu-Glu-Phe-Lys-Ser-Phe-Thr-Ser-Cys-Phe-Asp-Ser-Lys-Ala-Phe-NH$_2$ | 1128 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 1129 |
| Ac-Glu-Lys-Cys-Val-Glu-Glu-Phe-Lys-Ser-Phe-Thr-Ser-Cys-Leu-Glu-Ser-Lys-Ala-Phe-NH$_2$ | 1130 |
| Ac-Glu-Lys-Cys-Val-Glu-Glu-Phe-Lys-Ser-Phe-Thr-Ser-Cys-Ile-Asp-Ser-Lys-Ala-Phe-NH$_2$ | 1131 |
| Ac-Glu-Lys-Cys-Val-Glu-Glu-Leu-Lys-Ser-Phe-Thr-Ser-Cys-Phe-Asp-Ser-Lys-Ala-Phe-NH$_2$ | 1132 |
| Ac-Asp-Lys-Cys-Val-Glu-Glu-Phe-Lys-Ser-Phe-Thr-Ser-Cys-Phe-Asp-Ser-Lys-Ala-Phe-NH$_2$ | 1133 |
| Ac-Asp-Lys-Cys-Val-Glu-Glu-Phe-Lys-Ser-Phe-Thr-Ser-Cys-Phe-Glu-Ser-Lys-Ala-Phe-NH$_2$ | 1134 |
| Ac-Glu-Lys-Cys-Val-Glu-Glu-Phe-Lys-Ser-Phe-Thr-Ser-Cys-Phe-Asp-Ser-Lys-Ala-Phe-NH$_2$ | 1135 |
| Ac-Glu-Lys-Cys-Phe-Glu-Glu-Phe-Lys-Ser-Phe-Thr-Ser-Cys-Phe-Asp-Ser-Lys-Ala-Phe-NH$_2$ | 1136 |
| Ac-Glu-Lys-Cys-Phe-Glu-Glu-Phe-Lys-Ser-Phe-Thr-Ser-Cys-Phe-Glu-Ser-Lys-Ala-Phe-NH$_2$ | 1137 |
| Ac-Glu-Lys-Cys-Val-Glu-Glu-Phe-Lys-Ser-Phe-Ser-Ser-Cys-Phe-Glu-Ser-Lys-Ala-Phe-NH$_2$ | 1138 |
| Ac-Glu-Lys-Cys-Val-Glu-Glu-Phe-Lys-Ser-Phe-Gln-Ser-Cys-Phe-Asp-Ser-Lys-Ala-Phe-NH$_2$ | 1139 |
| Ac-Glu-Lys-Cys-Phe-Glu-Glu-Phe-Lys-Ser-Phe-Gln-Ser-Cys-Phe-Asp-Ser-Lys-Ala-Phe-NH$_2$ | 1140 |
| Ac-Glu-Lys-Cys-Val-Glu-Glu-Phe-Lys-Ser-Gln-Thr-Ser-Cys-Phe-Asp-Ser-Lys-Ala-Phe-NH$_2$ | 1141 |
| Ac-Glu-Lys-Cys-Val-Glu-Glu-Phe-Lys-Gln-Leu-Thr-Ser-Cys-Leu-Asp-Ser-Lys-Ala-Phe-NH$_2$ | 1142 |
| Ac-Glu-Lys-Cys-Phe-Glu-Glu-Phe-Lys-Ser-Phe-Gln-Ser-Cys-Leu-Asp-Ser-Lys-Ala-Phe-NH$_2$ | 1143 |
| Ac-Glu-Lys-Cys-Val-Glu-Glu-Phe-Lys-Gln-Phe-Thr-Ser-Cys-Phe-Asp-Ser-Lys-Ala-Phe-NH$_2$ | 1144 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 1145 |
| Ac-Glu-Arg-Cys-Phe-Glu-Glu-Phe-Lys-Ser-Phe-Thr-Ser-Cys-Phe-Asp-Ser-Lys-Ala-Phe-NH$_2$ | 1146 |
| Ac-Asp-Lys-Cys-Phe-Glu-Glu-Phe-Lys-Ser-Phe-Thr-Ser-Cys-Phe-Asp-Ser-Lys-Ala-Phe-NH$_2$ | 1147 |
| Ac-Glu-Arg-Cys-Val-Glu-Glu-Phe-Lys-Ser-Leu-Thr-Ser-Cys-Leu-Glu-Ser-Lys-Ala-Phe-NH$_2$ | 1148 |
| Ac-Glu-Lys-Cys-Val-Glu-Glu-Phe-Lys-Ser-Leu-Thr-Ser-Cys-Leu-Asp-Ser-Lys-Phe-Phe-NH$_2$ | 1149 |
| Ac-Glu-Lys-Cys-Phe-Glu-Glu-Phe-Lys-Ser-Phe-Thr-Ser-Cys-Phe-Asp-Ser-Lys-Phe-Phe-NH$_2$ | 1150 |
| Ac-Asp-Lys-Cys-Phe-Glu-Glu-Phe-Lys-Ser-Phe-Thr-Ser-Cys-Leu-Asp-Ser-Lys-Phe-Phe-NH$_2$ | 1151 |

TABLE 17-continued

Additional illustrative G* peptides.

| Peptide | SEQ ID NO |
|---|---|
| Ac-Asp-Lys-Cys-Phe-Glu-Glu-Phe-Lys-Ser-Phe-Thr-Ser-Cys-Leu-Glu-Ser-Lys-Phe-Phe-NH$_2$ | 1152 |
| Ac-Asp-Lys-Cys-Phe-Glu-Glu-Leu-Lys-Ser-Phe-Thr-Ser-Cys-Leu-Asp-Ser-Lys-Phe-Phe-NH$_2$ | 1153 |
| Ac-Glu-Arg-Cys-Phe-Glu-Glu-Phe-Lys-Ser-Phe-Thr-Ser-Cys-Leu-Asp-Ser-Lys-Phe-Phe-NH$_2$ | 1154 |
| Ac-Glu-Lys-Ala-Val-Glu-Glu-Phe-Lys-Ser-Phe-Thr-Ser-Cys-Leu-Asp-Ser-Lys-Ala-Phe-NH$_2$ | 1155 |
| Ac-Asp-Lys-Ala-Val-Glu-Glu-Phe-Lys-Ser-Phe-Thr-Ser-Cys-Leu-Asp-Ser-Lys-Phe-Phe-NH$_2$ | 1156 |
| Ac-Glu-Lys-Ala-Val-Glu-Glu-Phe-Lys-Ser-Phe-Thr-Ser-Ala-Leu-Asp-Ser-Lys-Ala-Phe-NH$_2$ | 1157 |
| Ac-Asp-Lys-Ala-Val-Glu-Glu-Phe-Lys-Ser-Phe-Thr-Ser-Ala-Leu-Asp-Ser-Lys-Ala-Phe-NH$_2$ | 1158 |
| Ac-Asp-Arg-Ala-Phe-Glu-Glu-Phe-Lys-Ser-Phe-Thr-Ser-Cys-Leu-Asp-Ser-Lys-Phe-Phe-NH$_2$ | 1159 |
| Ac-Asp-Arg-Ala-Phe-Glu-Glu-Phe-Lys-Ser-Phe-Thr-Ser-Ala-Leu-Asp-Ser-Lys-Phe-Phe-NH$_2$ | 1160 |
| Ac-Asp-Lys-Cys-Phe-Glu-Glu-Phe-Lys-Ser-Phe-Thr-Ser-Cys-Phe-Glu-Ser-Lys-Phe-Phe-NH$_2$ | 1161 |
| Ac-Glu-Lys-Cys-Tyr-Glu-Glu-Phe-Lys-Ser-Phe-Thr-Ser-Cys-Leu-Asp-Ser-Lys-Phe-Phe-NH$_2$ | 1162 |
| Ac-Asp-Lys-Cys-Trp-Glu-Glu-Phe-Lys-Ser-Phe-Thr-Ser-Cys-Leu-Asp-Ser-Lys-Phe-Phe-NH$_2$ | 1163 |
| Ac-Glu-Lys-Cys-Phe-Glu-Glu-Phe-Lys-Ser-Tyr-Thr-Ser-Cys-Leu-Asp-Ser-Lys-Phe-Phe-NH$_2$ | 1164 |
| Ac-Glu-Lys-Cys-Phe-Glu-Glu-Phe-Lys-Ser-Trp-Thr-Ser-Cys-Leu-Asp-Ser-Lys-Phe-Phe-NH$_2$ | 1165 |
| Ac-Glu-Lys-Cys-Val-Glu-Glu-Phe-Lys-Ser-Trp-Thr-Ser-Cys-Leu-Asp-Ser-Lys-Ala-Phe-NH$_2$ | 1166 |
| Ac-Asp-Lys-Cys-Phe-Glu-Glu-Phe-Lys-Ser-Trp-Thr-Ser-Cys-Leu-Asp-Ser-Lys-Ala-Phe-NH$_2$ | 1167 |

Other suitable peptides include, but are not limited to the peptides of Table 18.

TABLE 18

Illustrative peptides having an improved hydrophobic phase.

| Name | Sequence | SEQ ID NO |
|---|---|---|
| V2W3A5F10,17-D-4F | Ac-Asp-Val-Trp-Lys-Ala-Ala-Tyr-Asp-Lys-Phe-Ala-Glu-Lys-Phe-Lys-Glu-Phe-Phe-NH2 | 1168 |
| V2W3F10-D-4F | Ac-Asp-Val-Trp-Lys-Ala-Phe-Tyr-Asp-Lys-Phe-Ala-Glu-Lys-Phe-Lys-Glu-Ala-Phe-NH2 | 1169 |
| W3-D-4F | Ac-Asp-Phe-Trp-Lys-Ala-Phe-Tyr-Asp-Lys-Val-Ala-Glu-Lys-Phe-Lys-Glu-Ala-Phe-NH2 | 1170 |

The peptides described here (V2W3A5F10,17-D-4F; V2W3F10-D-4F; W3-D-4F) may be more potent than the original D-4F.

Still other suitable peptides include, but are not limited to: P'-Dimethyltyrosine-D-Arg-Phe-Lys-P$^2$ (SEQ ID NO: 1171) and P$^1$-Dimethyltyrosine-Arg-Glu-Leu-P$^2$ (SEQ ID NO: 1206) where P1 and P2 are protecting groups as described herein. In certain embodiments, these peptides include, but are not limited to BocDimethyltyrosine-D-Arg-Phe-Lys (OtBu) (SEQ ID NO: 1207) and BocDimethyltyrosine-Arg-Glu-Leu(OtBu) (SEQ ID NO: 1208).

In certain embodiments, the peptides of this invention include peptides comprising or consisting of the amino acid sequence LAEYHAK (SEQ ID NO:1172) comprising at least one D amino acid and/or at least one or two terminal protecting groups. In certain embodiments, this invention includes a peptide that ameliorates one or more symptoms of an inflammatory condition, wherein the peptide: ranges in length from about 3 to about 10 amino acids; comprises an amino acid sequence where the sequence comprises acidic or basic amino acids alternating with aromatic or hydrophobic amino acids; comprises hydrophobic terminal amino acids or terminal amino acids bearing a hydrophobic protecting group; is not the sequence LAEYHAK (SEQ ID NO:1173) comprising all L amino acids; where the peptide converts pro-inflammatory HDL to anti-inflammatory HDL and/or makes anti-inflammatory HDL more anti-inflammatory.

It is also noted that the peptides listed in the Tables herein are not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos:1011-1039.

Longer peptides are also suitable. Such longer peptides may entirely form a class G or G* amphipathic helix, or the G amphipathic helix (helices) can form one or more domains of the peptide. In addition, this invention contemplates multimeric versions of the peptides. Thus, for example, the peptides illustrated in the tables herein can be coupled together (directly or through a linker (e.g. a carbon linker, or one or more amino acids) with one or more intervening amino acids). Suitable linkers include, but are not limited to Proline (-Pro-), Gly$_4$Ser$_3$ (SEQ ID NO:1174), and the like. Thus, one illustrative multimeric peptide according to this invention is (D-J336)-P-(D-J336) (i.e. Ac-L-L-E-Q-L-N-E-Q-F-N-W-V-S-R-L-A-N-L-T-Q-G-E-P-L-L-E-Q-L-N-E-Q-F-N-W-V-S-R-L-A-N-L-T-Q-G-E-NH$_2$, SEQ ID NO:1175).

This invention also contemplates the use of "hybrid" peptides comprising a one or more G or G* amphipathic helical domains and one or more class A amphipathic helices. Suitable class A amphipathic helical peptides are described in PCT publication WO 02/15923. Thus, by way of illustration, one such "hybrid" peptide is (D-J336)-Pro-4F (i.e. Ac-L-L-E-Q-L-N-E-Q-F-N-W-V-S-R-L-A-N-L-T-Q-G-E-P-D-W-F-K-A-F-Y-D-K-V-A-E-K-F-K-E-A-F-NH$_2$, SEQ ID NO: 1176), and the like.

Using the teaching provided herein, one of skill can routinely modify the illustrated amphipathic helical peptides to produce other suitable apo J variants and/or amphipathic G and/or A helical peptides of this invention. For example, routine conservative or semi-conservative substitutions (e.g., E for D) can be made of the existing amino acids. The effect of various substitutions on lipid affinity of the resulting peptide can be predicted using the computational method described by Palgunachari et al. (1996) Arteriosclerosis, Thrombosis, & Vascular Biology 16: 328-338. The peptides can be lengthened or shortened as long as the class helix structure(s) are preserved. In addition, substitutions can be made to render the resulting peptide more similar to peptide(s) endogenously produced by the subject species.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

New peptides can be designed and/or evaluated using computational methods. Computer programs to identify and classify amphipathic helical domains are well known to those of skill in the art and many have been described by Jones et al. (1992) J. Lipid Res. 33: 287-296). Such programs include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

F) Blocking Groups and D Residues.

While the various peptides and/or amino acid pairs described herein may be shown with no protecting groups, in certain embodiments (e.g. particularly for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g. an acetyl group protecting the amino terminus and/or an amide group protecting the carboxyl terminus. One example of such a "dual protected peptide is Ac-L-L-E-Q-L-N-E-Q-F-N-W-V-S-R-L-A-N-L-T-Q-G-E-NH$_2$ (SEQ ID NO:1011 with blocking groups), either or both of these protecting groups can be eliminated and/or substituted with another protecting group as described herein.

Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3—(CH_2)_n—CO—$ where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) Protective Groups in Organic Synthesis, 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

In certain particularly preferred embodiments, the peptides comprise one or more D-form (dextro rather than levo) amino acids as described herein. In certain embodiments at least two enantiomeric amino acids, more preferably at least 4 enantiomeric amino acids and most preferably at least 8 or 10 enantiomeric amino acids are "D" form amino acids. In certain embodiments every other, or even every amino acid (e.g. every enantiomeric amino acid) of the peptides described herein is a D-form amino acid.

In certain embodiments at least 50% of the enantiomeric amino acids are "D" form, more preferably at least 80% of the enantiomeric amino acids are "D" form, and most preferably at least 90% or even all of the enantiomeric amino acids are "D" form amino acids.

G) Peptide Mimetics.

In addition to the peptides described herein, peptidomimetics are also contemplated. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) Adv. Drug Res. 15: 29; Veber and Freidinger (1985) TINS p. 392; and Evans et al. (1987) J. Med. Chem. 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (e.g. SEQ ID NO:5 shown in Table 1), but have one or more peptide linkages optionally replaced by a linkage selected from the group consisting of: $—CH_2NH—$, $—CH_2S—$, $—CH_2—CH_2—$, $—CH=CH—$(cis and trans), $—COCH_2—$, $—CH(OH)CH_2—$, $—CH_2SO—$, etc. by methods known in the art and further described in the following references: Spatola (1983) p. 267 in Chemistry and Biochemistry of Amino Acids, Peptides, and Proteins, B. Weinstein, eds., Marcel Dekker, New York; Spatola (1983) Vega Data 1(3) Peptide Backbone Modifications. (general review); Morley (1980) Trends Pharm Sci pp. 463-468 (general review); Hudson et al. (1979) Int J Pept Prot Res 14:177-185 (—CH$_2$NH—, CH$_2$CH$_2$—); Spatola et al. (1986) Life Sci 38:1243-1249 (—CH$_2$—S); Hann, (1982) J Chem Soc Perkin Trans 1307-314 (—CH═CH—, cis and trans); Almquist et al. (1980) J. Med. Chem. 23:1392-1398 (—COCH$_2$—); Jennings-White et al. (1982) Tetrahedron Lett. 23:2533 (—COCH$_2$—); Szelke et al., European Appln. EP 45665 (1982) CA: 97:39405 (1982) (—CH(OH)CH2-); Holladay et al. (1983) Tetrahedron Lett 24:4401-4404 (—C(OH)CH$_2$—); and Hruby (1982) Life Sci., 31:189-199 (—CH$_2$—S—)).

One particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) Ann. Rev. Biochem. 61: 387); for example, by adding internal cysteine residues capable of forming intramolecular disulfide bridges which cyclize the peptide.

H) Small Organic Molecules.

In certain embodiments, the active agents of this invention include small organic molecules, e.g. as described in copending application U.S. Ser. No. 60/600,925, filed Aug. 11, 2004. In various embodiments the small organic molecules are similar to, and in certain cases, mimetics of the tetra- and penta-peptides described in copending application U.S. Ser. No. 10/649,378, filed on Aug. 26, 2003 and U.S. Ser. No. 60/494,449, filed on August 11.

The small organic molecules of this invention typically have molecular weights less than about 900 Daltons. Typically the molecules are highly soluble in ethyl acetate (e.g., at concentrations equal to or greater than 4 mg/mL), and also are soluble in aqueous buffer at pH 7.0.

Contacting phospholipids such as 1,2-dimyristoyl-sn-glycero-3-phosphocholine (DMPC), with the small organic molecules of this invention in an aqueous environment typically results in the formation of particles with a diameter of approximately 7.5 nm (.+−.0.1 nm). In addition, stacked bilayers are often formed with a bilayer dimension on the order of 3.4 to 4.1 nm with spacing between the bilayers in the stack of approximately 2 nm. Vesicular structures of approximately 38 nm are also often formed. Moreover, when the molecules of this invention are administered to a mammal they render HDL more anti-inflammatory and mitigate one or more symptoms of atherosclerosis and/or other conditions characterized by an inflammatory response.

Thus, in certain embodiments, the small organic molecule is one that ameliorates one or more symptoms of a pathology characterized by an inflammatory response in a mammal (e.g. atherosclerosis), where the small molecule is soluble in ethyl acetate at a concentration greater than 4 mg/mL, is soluble in aqueous buffer at pH 7.0, and, when contacted with a phospholipid in an aqueous environment, forms particles with a diameter of approximately 7.5 nm and forms stacked bilayers with a bilayer dimension on the order of 3.4 to 4.1 nm with spacing between the bilayers in the stack of approximately 2 nm, and has a molecular weight less than 900 daltons.

In certain embodiment, the molecule has the formula:

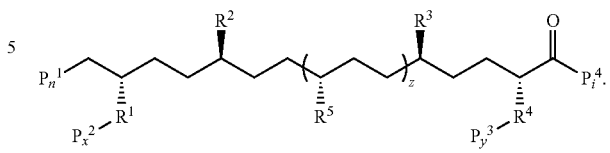

where $P^1$, $P^2$, $P^3$, and $P^4$ are independently selected hydrophobic protecting groups; $R^1$ and $R^4$ are independently selected amino acid R groups; n, i, x, y, and z are independently zero or 1 such that when n and x are both zero, $R^1$ is a hydrophobic group and when y and i are both zero, $R^4$ is a hydrophobic group; $R^2$ and $R^3$ are acidic or basic groups at pH 7.0 such that when $R^2$ is acidic, $R^3$ is basic and when $R^2$ is basic, $R^3$ is acidic; and $R^5$, when present is selected from the group consisting of an aromatic group, an aliphatic group, a positively charged group, or a negatively charged group. In certain embodiments, $R^2$ or $R^3$ is —(CH$_2$)$_j$—COOH where j=1, 2, 3, or 4 and/or —(CH$_2$)—NH$_2$ where j=1, 2, 3, 4, or 5, or —(CH$_2$)$_j$—NH—C(═NH)—NH$_2$ where n=1, 2, 3 or 4. In certain embodiments, $R^2$, $R^3$, and $R^5$, when present, are amino acid R groups. Thus, for example, In various embodiments $R^2$ and $R^3$ are independently an aspartic acid R group, a glutamic acid R group, a lysine R group, a histidine R group, or an arginine R group (e.g., as illustrated in Table 1).

In certain embodiments, $R^1$ is selected from the group consisting of a Lys R group, a Trp R group, a Phe R group, a Leu R group, an Orn R group, pr a norLeu R group. In certain embodiments, $R^4$ is selected from the group consisting of a Ser R group, a Thr R group, an Ile R group, a Leu R group, a norLeu R group, a Phe R group, or a Tyr R group.

In various embodiments x is 1, and $R^5$ is an aromatic group (e.g., a Trp R group).

In various embodiments at least one of n, x, y, and i is 1 and $P^1$, $P^2$, $P^3$, and $P^4$ when present, are independently selected from the group consisting of polyethylene glycol (PEG), an acetyl, amide, a 3 to 20 carbon alkyl group, fmoc, 9-fluorenacetyl group, 1-fluorenecarboxylic group, 9-fluorenecarboxylic, 9-fluorenone-1-carboxylic group, benzyloxycarbonyl, xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and trifluoroacetyl (TFA). In certain embodiments, $P^1$ when present and/or $P^2$ when present are independently selected from the group consisting of Boc-, Fmoc-, and Nicotinyl- and/or $P^3$ when present and/or $P^4$ when present are independently selected from the group consisting of tBu, and OtBu.

While a number of protecting groups (P', $P^2$, $P^3$, $P^4$) are illustrated above, this list is intended to be illustrative and not limiting. In view of the teachings provided herein, a number of other protecting/blocking groups will also be known to one of skill in the art. Such blocking groups can be selected to minimize digestion (e.g., for oral pharmaceutical delivery), and/or to increase uptake/bioavailability (e.g., through mucosal surfaces in nasal delivery, inhalation therapy, rectal administration), and/or to increase serum/plasma half-life. In certain embodiments, the protecting groups can be provided as an excipient or as a component of an excipient.

In certain embodiments, z is zero and the molecule has the formula:

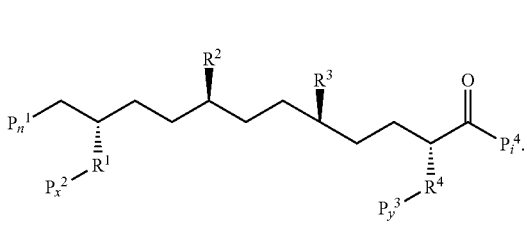

where $P^1$, $P^2$, $P^3$, $P^4$, $R^1$, $R^2$, $R^3$, $R^4$, n, x, y, and i are as described above.

In certain embodiments, z is zero and the molecule has the formula:

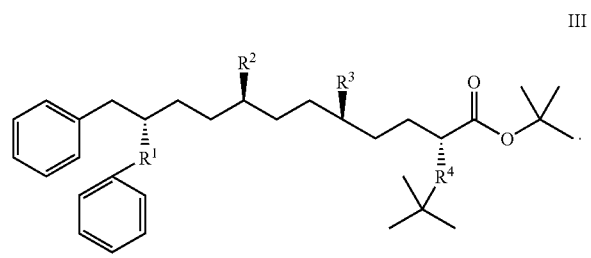

where $R^1$, $R^2$, $R^3$, and $R^4$ are as described above.
In one embodiment, the molecule has the formula:

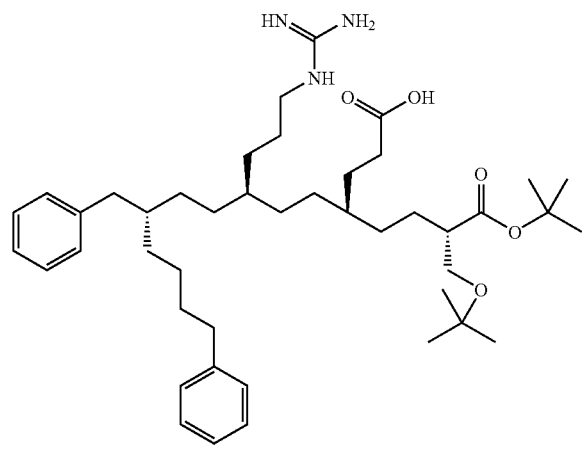 [SMILES: CC(C)(C)OC[C@H](CC[C@@H](CCC(=O)O)CC[C@H](CCCNC(=N)N)CC[C@H](CCCCc1ccccc1)Cc1ccccc1)C(=O)OC(C)(C)C]

In certain embodiments, this invention contemplates small molecules having one or more of the physical and/or functional properties described herein and having the formula:

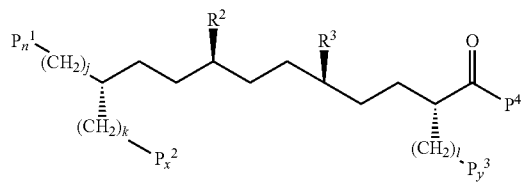

where $P^1$, $P^2$, $P^3$, and $P^4$ are independently selected hydrophobic protecting groups as described above, n, x, and y are independently zero or 1; j, k, and l are independently zero, 1, 2, 3, 4, or 5; and $R^2$ and $R^3$ are acidic or basic groups at pH 7.0 such that when $R^2$ is acidic, $R^3$ is basic and when $R^2$ is basic, $R^3$ is acidic. In certain preferred embodiments, the small molecule is soluble in water; and the small molecule has a molecular weight less than about 900 Daltons. In certain embodiments, n, x, y, j, and l are 1; and k is 4.

In certain embodiments, $P^1$ and/or $P^2$ are aromatic protecting groups. In certain embodiments, $R^2$ and $R^3$ are amino acid R groups, e.g., as described above. In various embodiments least one of n, x, and y, is 1 and $P^1$, $P^2$, $P^3$ and $P^4$ when present, are independently protecting groups, e.g. as described above. In certain embodiments the protecting groups, when present, are independently selected from the group consisting of polyethylene glycol (PEG), an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-penta.

III. Functional Assays of Active Agents

Certain active agents for use in the methods of this invention are described herein by various formulas (e.g., Formula I, above) and/or by particular sequences. In certain embodiments, preferred active agents of this invention are characterized by one or more of the following functional properties:

1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-β HDL;
4. They raise HDL cholesterol; and/or
5. They increase HDL paraoxonase activity.

The specific agents disclosed herein, and/or agents corresponding to the various formulas described herein can readily be tested for one or more of these activities as desired.

Methods of screening for each of these functional properties are well known to those of skill in the art. In particular, it is noted that assays for monocyte chemotactic activity, HDL cholesterol, and HDL paraoxonase activity are illustrated in PCT/US01/26497 (WO 2002/15923).

IV. Peptide Preparation

The peptides used in this invention can be chemically synthesized using standard chemical peptide synthesis techniques or, particularly where the peptide does not comprise "D" amino acid residues, can be recombinantly expressed. In certain embodiments, even peptides comprising "D" amino acid residues are recombinantly expressed. Where the polypeptides are recombinantly expressed, a host organism (e.g. bacteria, plant, fungal cells, etc.) in cultured in an environment where one or more of the amino acids is provided to the organism exclusively in a D form. Recombinantly expressed peptides in such a system then incorporate those D amino acids.

In preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc., 85: 2149-2156, and Stewart et al. (1984) Solid Phase Peptide Synthesis, 2nd ed. Pierce Chem. Co., Rockford, Ill.

In certain embodiments, the peptides are synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are described in a miniprint supplement accompanying Anantharamaiah et al. (1985) J. Biol. Chem., 260(16): 10248-10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

V. Pharmaceutical Formulations and Devices

A) Pharmaceutical Formulations.

In order to carry out the methods of the invention, one or more active agents of this invention are administered, e.g. to an individual diagnosed as having one or more symptoms of atherosclerosis, or as being at risk for atherosclerosis and or the various other pathologies described herein. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of Esters Typically Involves Functionalization of Hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or eye disease and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The active agents of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of the one or more pathologies described herein, or at risk for one or more of the pathologies described herein in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects. For example, the concentration for treating an eye disease can be selected to provide dosages ranging from 200 ug/ml to 800 ug/ml of fluid.

In certain preferred embodiments, the active agents of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

In addition, the active agents of this invention can be administered via intraocular injection (e.g. intravitreal injection) in accordance with standard methods well known to those of skill in the art.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) Biotechnol. Prog., 14: 108; Johnson et al. (1996) Nature Med. 2: 795; Herbert et al. (1998), Pharmaceut. Res. 15, 357) a dry powder composed of biodegradable polymeric microspheres containing the active agent in a polymer matrix that can be compounded as a dry formulation with or without other agents.

The ProLease microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

B) Lipid-Based Formulations.

In certain embodiments, the active agents of this invention are administered in conjunction with one or more lipids. The lipids can be formulated as an excipient to protect and/or enhance transport/uptake of the active agents or they can be administered separately.

Without being bound by a particular theory, it was discovered of this invention that administration (e.g. oral administration) of certain phospholipids can significantly increase HDL/LDL ratios. In addition, it is believed that certain medium-length phospholipids are transported by a process different than that involved in general lipid transport. Thus, co-administration of certain medium-length phospholipids with the active agents of this invention confer a number of advantages: They protect the active agents from digestion or hydrolysis, they improve uptake, and they improve HDL/LDL ratios.

The lipids can be formed into liposomes that encapsulate the active agents of this invention and/or they can be complexed/admixed with the active agents and/or they can be covalently coupled to the active agents. Methods of making liposomes and encapsulating reagents are well known to those of skill in the art (see, e.g., Martin and Papahadjopoulos (1982) J. Biol. Chem., 257: 286-288; Papahadjopoulos et al. (1991) Proc. Natl. Acad. Sci. USA, 88: 11460-11464; Huang et al. (1992) Cancer Res., 52:6774-6781; Lasic et al. (1992) FEBS Lett., 312: 255-258., and the like).

Preferred phospholipids for use in these methods have fatty acids ranging from about 4 carbons to about 24 carbons in the sn-1 and sn-2 positions. In certain preferred embodiments, the fatty acids are saturated. In other preferred embodiments, the fatty acids can be unsaturated. Various preferred fatty acids are illustrated in Table 19.

TABLE 19

Suitable fatty acids in the sn-1 and/or sn-2 position of the preferred phospholipids for administration of active agents described herein.

| Carbon No. | Common Name | IUPAC Name |
| --- | --- | --- |
| 3:0 | Propionoyl | Trianoic |
| 4:0 | Butanoyl | Tetranoic |
| 5:0 | Pentanoyl | Pentanoic |
| 6:0 | Caproyl | Hexanoic |
| 7:0 | Heptanoyl | Heptanoic |
| 8:0 | Capryloyl | Octanoic |

TABLE 19-continued

Suitable fatty acids in the sn-1 and/or sn-2 position of the preferred phospholipids for administration of active agents described herein.

| Carbon No. | Common Name | IUPAC Name |
| --- | --- | --- |
| 9:0 | Nonanoyl | Nonanoic |
| 10:0 | Capryl | Decanoic |
| 11:0 | Undcanoyl | Undecanoic |
| 12:0 | Lauroyl | Dodecanoic |
| 13:0 | Tridecanoyl | Tridecanoic |
| 14:0 | Myristoyl | Tetradecanoic |
| 15:0 | Pentadecanoyl | Pentadecanoic |
| 16:0 | Palmitoyl | Hexadecanoic |
| 17:0 | Heptadecanoyl | Heptadecanoic |
| 18:0 | Stearoyl | Octadecanoic |
| 19:0 | Nonadecanoyl | Nonadecanoic |
| 20:0 | Arachidoyl | Eicosanoic |
| 21:0 | Heniecosanoyl | Heniecosanoic |
| 22:0 | Behenoyl | Docosanoic |
| 23:0 | Trucisanoyl | Trocosanoic |
| 24:0 | Lignoceroyl | Tetracosanoic |
| 14:1 | Myristoleoyl (9-cis) | |
| 14:1 | Myristelaidoyl (9-trans) | |
| 16:1 | Palmitoleoyl (9-cis) | |
| 16:1 | Palmitelaidoyl (9-trans) | |

The fatty acids in these positions can be the same or different. Particularly preferred phospholipids have phosphorylcholine at the sn-3 position.

C) Specialized Delivery/Devices.

1. Drug-Eluting Stents.

Restenosis, the reclosure of a previously stenosed and subsequently dilated peripheral or coronary vessel occurs at a significant rate (e.g., 20-50% for these procedures) and is dependent on a number of clinical and morphological variables. Restenosis may begin shortly following an angioplasty procedure, but usually ceases at the end of approximately six (6) months.

A recent technology that has been developed to address the problem of restenosis in intravascular stents. Stents are typically devices that are permanently implanted (expanded) in coronary and peripheral vessels. The goal of these stents is to provide a long-term "scaffolding" or support for the diseased (stenosed) vessels. The theory being, if the vessel is supported from the inside, it will not close down or restenose.

Known stent designs include, but are not limited to monofilament wire coil stents (see, e.g., U.S. Pat. No. 4,969,458 which is incorporated herein by reference); welded metal cages (see, e.g., U.S. Pat. Nos. 4,733,665 and 4,776,337 which are incorporated herein by reference), thin-walled metal cylinders with axial slots formed around the circumference (see, e.g., U.S. Pat. Nos. 4,733,665, 4,739,762, 4,776,337 which are incorporated herein by reference). Known construction materials for use in stents include, but are not limited to polymers, organic fabrics and biocompatible metals, such as, stainless steel, gold, silver, tantalum, titanium, and shape memory alloys such as Nitinol.

To further prevent restenosis, stents can be covered and/or impregnated with one or more pharmaceutical, e.g., in controlled release formulations to inhibit cell proliferation associated with restenosis. Most commonly such "drug-eluting" stents are designed to deliver various cancer drugs (cytotoxins).

However, because of their activity in mitigating inflammatory responses, reducing and/or eliminated oxidized lipids and/or other oxidized species, inhibiting macrophage chemotactic activity and the like, the active agents described herein are well suited to prevent restenosis. Thus, in certain embodiments, this invention contemplates stents having one or more of the active agents described herein coated on the surface and/or retained within cavities or microcavities in the surface of the stent.

In certain embodiments the active agents are contained within biocompatible matrices (e.g. biocompatible polymers such as urethane, silicone, and the like). Suitable biocompatible materials are described, for example, in U.S. Patent Publications 2005/0084515, 2005/00791991, 2005/0070996, and the like which are incorporated herein by reference. In various embodiments the polymers include, but are not limited to silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer Thus, in certain embodiments this invention provides a stent for delivering drugs to a vessel in a body. The stent typically comprises stent framework including a plurality of reservoirs formed therein. The reservoirs typically include an active agent and/or active agent-containing polymer positioned in the reservoir and/or coated on the surface of the stent. In various embodiments the stent is a metallic base or a polymeric base. Certain preferred stent materials include, but are not limited to stainless steel, nitinol, tantalum, MP35N alloy, platinum, titanium, a suitable biocompatible alloy, a suitable biocompatible polymer, and/or a combination thereof.

In various embodiments where the stent comprises pores (e.g. reservoirs), the pores can include micropores (e.g., having a diameter that ranges from about 10 to about 50 μm, preferably about 20 μm or less). In various embodiments the micropores have a depth in the range of about 10 μm to about 50 μm. In various embodiments the micropores extend through the stent framework having an opening on an interior surface of the stent and an opening on an exterior surface of the stent. In certain embodiments the stent can, optionally comprise a cap layer disposed on the interior surface of the stent framework, the cap layer covering at least a portion of the through-holes and providing a barrier characteristic to control an elution rate of the active agent(s) in the polymer from the interior surface of the stent framework. In various embodiments the reservoirs comprise channels along an exterior surface of the stent framework. The stent can optionally have multiple layers of polymer where different layers of polymer carry different active agent(s) and/or other drugs.

In certain embodiments the stent comprises: an adhesion layer positioned between the stent framework and the polymer. Suitable adhesion layers include, but are not limited to a polyurethane, a phenoxy, poly(lactide-co-glycolide)-, polylactide, polysulfone, polycaprolactone, an adhesion promoter, and/or a combination thereof.

In addition to stents, the active agents can be coated on or contained within essentially any implantable medical device configured for implantation in a extravascular and/or intravascular location.

Also provided are methods of manufacturing a drug-polymer stent, comprising. The methods involve providing a stent framework; cutting a plurality of reservoirs in the stent framework, e.g., using a high power laser; applying one or more of the active agents and/or a drug polymer to at least one reservoir; drying the drug polymer; applying a polymer layer to the dried drug polymer; and drying the polymer layer. The active agent(s) and/or polymer(s) can be applied by any convenient method including but not limited to spraying, dipping, painting, brushing and dispensing.

Also provided are methods of treating a vascular condition and/or a condition characterized by an inflammatory response and/or a condition characterized by the formation of oxidized reactive species. The methods typically involve positioning a stent or other implantable device as described above within the body (e.g. within a vessel of a body) and eluting at least active agent from at least one surface of the implant.

2. Impregnated Grafts and Transplants.

Vascular grafts can be classified as either biological or synthetic. There are two commonly used types of biological grafts. An autograft is one taken from another site in the patient. In peripheral vascular surgery by far the most commonly used such graft is the long saphenous vein. This can be used in situ with the valves surgically destroyed with an intraluminal cutting valvutome.

Alternatively, the vein can be removed and reversed but this typically produces a discrepancy between the anastomotic size of the artery and vein. In thoracic surgery the use of internal mammary artery for coronary artery bypass surgery is another example of an autograft. An allograft is one taken from another animal of the same species. Externally supported umbilical vein is rarely used but is an example of such a graft.

Synthetic grafts are most commonly made from Dacron or polytetrafluoroethylene (PTFE). Dacron grafts are frequently used in aortic and aorto-iliac surgery. Below the inguinal ligament the results of all synthetic grafts are inferior to those obtained with the use of vein grafts. Suitable vein is not always available and in this situation PTFE is typically used. It can be used in conjunction with vein as a composite graft. Neointimal hyperplasia at the distal anastomosis can be reduced by the incorporation of a segment of vein as either a Millar Cuff or Taylor Patch to improve the long-term patency of the grafts.

The commonest complications associated with the use of vascular grafts include Graft occlusion, Graft infection, true and false aneurysms at the site of anastomosis, distal embolization, and erosion in to adjacent structures—e.g. Aorto-enteric fistulae. Many of these conditions are associated with an inflammatory response, macrophage migration into the site, and/or the formation of reactive oxygen species (e.g., oxidized lipids). To reduce such complications, the graft (synthetic or biological can be soaked, or otherwise coated, with one or more of the active agents described herein.

In addition, it is contemplated that other implantable tissues or materials can similarly be impregnated or coated with one or more active agents of this invention. Thus, for example, in certain embodiments this invention contemplates the use of impregnated sutures to minimize inflammation and/or infection and/or tissue rejection.

3. Subcutaneous Matrices.

In certain embodiments, one or more active agents described herein are administered alone or in combination with other therapeutics as described herein in implantable (e.g., subcutaneous) matrices.

A major problem with standard drug dosing is that typical delivery of drugs results in a quick burst of medication at the time of dosing, followed by a rapid loss of the drug from the body. Most of the side effects of a drug occur during the burst phase of its release into the bloodstream. Secondly, the time the drug is in the bloodstream at therapeutic levels is very short, most is used and cleared during the short burst.

Drugs (e.g., the active agents described herein) imbedded in various matrix materials for sustained release provides some solution to these problems. Drugs embedded, for example, in polymer beads or in polymer wafers have several advantages. First, most systems allow slow release of the drug, thus creating a continuous dosing of the body with small levels of drug. This typically prevents side effects associated with high burst levels of normal injected or pill based drugs. Secondly, since these polymers can be made to release over hours to months, the therapeutic span of the drug is markedly increased. Often, by mixing different ratios of the same polymer components, polymers of different degradation rates can be made, allowing remarkable flexibility depending on the agent being used. A long rate of drug release is beneficial for people who might have trouble staying on regular dosage, such as the elderly, but is also an ease of use improvement that everyone can appreciate. Most polymers can be made to degrade and be cleared by the body over time, so they will not remain in the body after the therapeutic interval.

Another advantage of polymer based drug delivery is that the polymers often can stabilize or solubilize proteins, peptides, and other large molecules that would otherwise be unusable as medications. Finally, many drug/polymer mixes can be placed directly in the disease area, allowing specific targeting of the medication where it is needed without losing drug to the "first pass" effect. This is certainly effective for treating the brain, which is often deprived of medicines that can't penetrate the blood/brain barrier.

A number of implantable matrix (sustained release) systems are know to those of skill and can readily be adapted for use with one or more of the active agents described herein. Suitable sustained release systems include, but are not limited to Re-Gel®, SQ2Gel®, and Oligosphere® by MacroMed, ProLease® and Medisorb® by Alkermes, Paclimer® and Gliadel® Wafer by Guilford pharmaceuticals, the Duros implant by Alza, acoustic bioSpheres by Point Biomedical, the Intelsite capsule by Scintipharma, Inc., and the like.

4. Other "Specialty Delivery Systems".

Other "specialty" delivery systems include, but are not limited to lipid based oral mist that allows absorption of drugs across the oral mucosa, developed by Generex Biotechnology, the oral transmucosal system (OTS™) by Anesta Corp., the inhalable dry powder and PulmoSpheres technology by Inhale Therapeutics, the AERx® Pulmonary Drug Delivery System by Aradigm, the AIR mechanism by Alkermes, and the like.

Another approach to delivery developed by Alkermes is a system targeted for elderly and pediatric use, two populations for which taking pills is often difficult is known as Drug Sipping Technology (DST). The medication is placed in a drinking straw device, prevented from falling out by filters on either end of it. The patient merely has to drink clear liquid (water, juice, soda) through the straw. The drug dissolves in the liquid as it is pulled through and is ingested by the patient. The filter rises to the top of the straw when all of the medication is taken. This method has the advantage in that it is easy to use, the liquid often masks the medication's taste, and the drug is pre-dissolved for more efficient absorption.

It is noted that these uses and delivery systems are intended to be illustrative and not limiting. Using the teachings provided herein, other uses and delivery systems will be known to those of skill in the art.

VI. Additional Pharmacologically Active Agents

Combined Active Agents

In various embodiments, the use of combinations of two or more active agents described is contemplated in the treatment of the various pathologies/indications described herein. The use of combinations of active agents can alter pharmacological activity, bioavailability, and the like.

By way of illustration, it is noted that D-4F rapidly associates with pre-beta HDL and HDL and then is rapidly cleared from the circulation (it is essentially non-detectable 6 hours after an oral dose), while D[113-122]apoJ slowly associates with pre-beta HDL and to a lesser extent with HDL but remains associated with these HDL fractions for at least 36 hours. FREL associates with HDL and only HDL but remains detectable in HDL for much longer than D-4F (i.e., it is detectable in HDL 48 hours after a single oral dose in mice). In certain embodiments this invention thus contemplates combinations of, for example, these three peptides to reduce the amount to reduce production expense, and/or to optimize dosage regimen, therapeutic profile, and the like. In certain embodiments combinations of the active agents described herein can be simply coadministered and/or added together to form a single pharmaceutical formulation. In certain embodiments the various active agent(s) can be complexed together (e.g. via hydrogen bonding) to form active agent complexes that are more effective than the parent agents.

Use with Additional Pharmacologically Active Materials.

Additional pharmacologically active materials (i.e., drugs) can be delivered in conjunction with one or more of the active agents described herein. In certain embodiments, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

It was discovered that, adding a low dosage active agent (e.g., of D-4F) (1 µg/ml) to the drinking water of apoE null mice for 24 hours did not significantly improve HDL function (see, e.g., related application U.S. Ser. No. 10/423,830, filed on Apr. 25, 2003, which is incorporated herein by reference). In addition, adding 0.05 mg/ml of atorvastatin or pravastatin alone to the drinking water of the apoE null mice for 24 hours did not improve HDL function. However, when D-4F 1 µg/ml was added to the drinking water together with 0.05 mg/ml of atorvastatin or pravastatin there was a significant improvement in HDL function). Indeed the pro-inflammatory apoE null HDL became as anti-inflammatory as 350 µg/ml of normal human HDL (h, HDL see, e.g., related application U.S. Ser. No. 10/423,830).

Thus, doses of D-4F alone, or statins alone, which by themselves had no effect on HDL function when given together acted synergistically. When D-4F and a statin were given together to apo E null mice, their pro-inflammatory HDL at 50 µg/ml of HDL-cholesterol became as effective as normal human HDL at 350 µg/ml of HDL-cholesterol in preventing the inflammatory response induced by the action of HPODE oxidizing PAPC in cocultures of human artery wall cells.

Thus, in certain embodiments this invention provides methods for enhancing the activity of statins. The methods generally involve administering one or more of the active agents described herein, as described herein in conjunction with one or more statins. The active agents achieve synergistic action between the statin and the agent(s) to ameliorate one or more symptoms of atherosclerosis. In this context statins can be administered at significantly lower dosages thereby avoiding various harmful side effects (e.g., muscle wasting) associated with high dosage statin use and/or the anti-inflammatory properties of statins at any given dose are significantly enhanced.

Suitable statins include, but are not limited to pravastatin (Pravachol/Bristol-Myers Squibb), simvastatin (Zocor/Merck), lovastatin (Mevacor/Merck), and the like.

In various embodiments the active agent(s) described herein are administered in conjunction with one or more beta blockers. Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™ Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable ace inhibitors include, but are not limited to captopril (e.g. Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g. Prinivil™ by Merck or Zestril™ by Astra-Zeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

In various embodiments, one or more agents described herein are administered with one or more of the drugs identified below.

Thus, in certain embodiments one or more active agents are administered in conjunction with cholesteryl ester transfer protein (CETP) inhibitors (e.g., torcetrapib, JTT-705. CP-529414) and/or acyl-CoA:cholesterol O-acyltransferase (ACAT) inhibitors (e.g., Avasimibe (CI-1011), CP 113818, F-1394, and the like), and/or immunomodulators (e.g., FTY720 (sphingosine-1-phosphate receptor agonist), Thalomid (thalidomide), Imuran (azathioprine), Copaxone (glatiramer acetate), Certican® (everolimus), Neoral® (cyclosporine), and the like), and/or dipeptidyl-peptidase-4 (DPP4) inhibitors (e.g., 2-Pyrrolidinecarbonitrile, 1-[[[2-[(5-cyano-2-pyridinyl)amino]ethyl]amino]acetyl], see also U.S. Patent Publication 2005-0070530), and/or calcium channel blockers (e.g., Adalat, Adalat CC, Calan, Calan SR, Cardene, Cardizem, Cardizem CD, Cardizem SR, Dilacor-XR, DynaCirc, Isoptin, Isoptin SR, Nimotop, Norvasc, Plendil, Procardia, Procardia XL, Vascor, Verelan), and/or peroxisome proliferator-activated receptor (PPAR) agonists for, e.g., α, γ; δ receptors (e.g., Azelaoyl PAF, 2-Bromohekadecanoic acid, Ciglitizone, Clofibrate, 15-Deoxy-$\delta^1$2,14-prostaglandin J$_2$, Fenofibrate, Fmoc-Leu-OH, GW1929, GW7647, 8(S)-Hydroxy-(5Z,9E,11Z,14Z)-eicosatetraenoic acid (8(S)-HETE), Leukotriene B$_4$, LY-171,883 (Tomelukast), Prostaglandin A$_2$, Prostaglandin J$_2$, Tetradecylthioacetic acid (TTA), Troglitazone (CS-045), WY-14643 (Pirinixic acid)), and the like.

In certain embodiments one or more of the active agents are administered in conjunction with fibrates (e.g., clofibrate (atromid), gemfibrozil (lopid), fenofibrate (tricor), etc.), bile acid sequestrants (e.g., cholestyramine, colestipol, etc.), cholesterol absorption blockers (e.g., ezetimibe (Zetia), etc.), Vytorin ((ezetimibe/simvastatin combination), and/or steroids, warfarin, and/or aspirin, and/or Bcr-Abl inhibitors/antagonists (e.g., Gleevec (Imatinib Mesylate), AMN$_1$O$_7$, STI571 (CGP57148B), ON 012380, PLX225, and the like), and/or renin angiotensin pathway blockers (e.g., Losartan (Cozaar®), Valsartan (Diovan®), Irbesartan (Avapro®), Candesartan (Atacand®), and the like), and/or angiotensin II receptor antagonists (e.g., losartan (Cozaar), valsartan (Diovan), irbesartan (Avapro), candesartan (Atacand) and telmisartan (Micardis), etc.), and/or PKC inhibitors (e.g., Calphostin C, Chelerythrine chloride, Chelerythrine.chloride, Copper bis-3,5-diisopropylsalicylate, Ebselen, EGF Receptor (human) (651-658) (N-Myristoylated), Go 6976, H-7.dihydrochloride, 1-O-Hexadecyl-2-O-methyl-rac-glycerol, Hexadecyl-phosphocholine (C$_{16:0}$); Miltefosine, Hypericin, Melittin (natural), Melittin (synthetic), ML-7.hydrochloride, ML-9.hydrochloride, Palmitoyl-DL-carnitine.hydrochloride, Protein Kinase C (19-31), Protein Kinase C (19-36), Quercetin.dihydrate, Quercetin.dihydrate, D-erythro-Sphingosine (isolated), D-erythro-Sphingosine (synthetic), Sphingosine, N,N-dimethyl, D-erythro-Sphingosine, Dihydro-, D-erythro-Sphingosine, N,N-Dimethyl-, D-erythro-Sphingosine chloride, N,N,N-Trimethyl-, Staurosporine, Bisindolylmaleimide I, G-6203, and the like).

In certain embodiments, one or more of the active agents are administered in conjunction with ApoAI, Apo A-I derivatives and/or agonists (e.g., ApoAI milano, see, e.g., U.S. Patent Publications 20050004082, 20040224011, 20040198662, 20040181034, 20040122091, 20040082548, 20040029807, 20030149094, 20030125559, 20030109442, 20030065195, 20030008827, and 20020071862, and U.S. Pat. Nos. 6,831,105, 6,790,953, 6,773,719, 6,713,507, 6,703,422, 6,699,910, 6,680,203, 6,673,780, 6,646,170, 6,617,134, 6,559,284, 6,506,879, 6,506,799, 6,459,003, 6,423,830, 6,410,802, 6,376,464, 6,367,479, 6,329,341, 6,287,590, 6,090,921, 5,990,081, and the like), renin inhibitors (e.g., SPP630 and SPP635, SPP100, Aliskiren, and the like), and/or MR antagonist (e.g., spironolactone, aldosterone glucuronide, and the like), and/or aldosterone synthase inhibitors, and/or alpha-adrenergic antagonists (e.g., Aldomet® (Methyldopa), Cardura® (Doxazosin), Catapres®; Catapres-TTS®; Duraclon™ (Clonidine), Dibenzyline® (Phenoxybenzamine), Hylorel® (Guanadrel), Hytrin® (Terazosin), Minipress® (Prazosin), Tenex® (Guanfacine), Guanabenz, Phentolamine, Reserpine, and the like), and/or liver X receptor (LXR) agonists (e.g., T0901317, GW3965, ATI-829, acetyl-podocarpic dimer (APD), and the like), and/or farnesoid X receptor (FXR) agonists (e.g., GW4064, 6alpha-ethyl-chenodeoxycholic acid (6-ECDCA), T0901317, and the like), and/or plasminogen activator-1 (PAI-1) inhibitors (see, e.g., oxime-based PAI-1 inhibitors, see also U.S. Pat. No. 5,639,726, and the like), and/or low molecular weight heparin, and/or AGE inhibitors/breakers (e.g., Benfotiamine, aminoguanidine, pyridoxamine, Tenilsetam, Pimagedine, and the like) and/or ADP receptor blockers (e.g., Clopidigrel, AZD6140, and the like), and/or ABCA1 agonists, and/or scavenger receptor B1 agonists, and/or Adiponectic receptor agonist or adiponectin inducers, and/or stearoyl-CoA Desaturase I (SCD1) inhibitors, and/or Cholesterol synthesis inhibitors (non-statins), and/or Diacylglycerol Acyltransferase I (DGAT1) inhibitors, and/or Acetyl CoA Carboxylase 2 inhibitors, and/or LP-PLA2 inhibitors, and/or GLP-1, and/or glucokinase activator, and/or CB-1 agonists, and/or anti-thrombotic/coagulants, and/or Factor Xa inhibitors, and/or GPIIb/IIIa inhibitors, and/or Factor VIIa inhibitors, and/or Tissue factor inhibitors, and/or anti-inflammatory drugs, and/or Probucol and derivatives (e.g. AGI-1067, etc.), and/or CCR2 antagonists, and/or CX3CR1 antagonists, and/or IL-1 antagonists, and/or nitrates and NO donors, and/or phosphodiesterase inhibitors, and the like.

In addition, other pharmacologically active materials that can be delivered in conjunction with one or more of the active agents described herein include, but are not limited to, agents that reduce the risk of eye disease events and/or complications thereof. Such agents include, but are not limited to anti-angiogenics or anti-VEGF (anti-Vascular Endothelial Growth Factor) agents. For example, the active agents described herein can be used in conjunction and/or combination with anti-angiogenic therapies for choroidal neovascularization. The net effect of the combination can result in limiting the expression of pro-angiogenic factors due to remodeled Bruch's membrane and thus result in a better metabolic situation for the retinal pigment epithelium and retina, which can limit the duration/circles of anti-angiogenic retreatments.

Angiogenesis is an important cellular event in which vascular endothelial cells proliferate, prune and reorganize to form new vessels from preexisting vascular network. There are compelling evidences that the development of a vascular supply is essential for normal and pathological proliferative processes (Folkman and Klagsbrun (1987) Science 235:442-447). Delivery of oxygen and nutrients, as well as the removal of catabolic products, represent rate-limiting steps in the majority of growth processes occurring in multicellular organisms. Thus, it has been generally assumed that the vascular compartment is necessary, not only for organ development and differentiation during embryogenesis, but also for wound healing and reproductive functions in the adult.

Angiogenesis is also implicated in the pathogenesis of a variety of disorders, including but not limited to, tumors, proliferative retinopathies, age-related macular degeneration, rheumatoid arthritis (RA), and psoriasis. Angiogenesis is essential for the growth of most primary tumors and their subsequent metastasis. Tumors can absorb sufficient nutrients and oxygen by simple diffusion up to a size of 1-2 mm, at which point their further growth requires the elaboration of vascular supply. This process is thought to involve recruitment of the neighboring host mature vasculature to begin sprouting new blood vessel capillaries, which grow towards, and subsequently infiltrate, the tumor mass. In addition, tumor angiogenesis involve the recruitment of circulating endothelial precursor cells from the bone marrow to promote neovascularization. Kerbel (2000) Carcinogenesis 21:505-515; Lynden et al. (2001) Nat. Med. 7:1194-1201.

In view of the remarkable physiological and pathological importance of angiogenesis, much work has been dedicated to the elucidation of the factors capable of regulating this process. It is suggested that the angiogenesis process is regulated by a balance between pro- and anti-angiogenic molecules, and is derailed in various diseases, especially cancer. Carmeliet and Jain (2000) Nature 407:249-257.

Vascular endothelial cell growth factor (VEGF), which is also termed VEGF-A or vascular permeability factor (VPF), has been reported as a pivotal regulator of both normal and abnormal angiogenesis. Ferrara and Davis-Smyth (1997) Endocrine Rev. 18:4-25; Ferrara (1999) J. Mol. Med. 77:527-543. Compared to other growth factors that contribute to the processes of vascular formation, VEGF is unique in its high specificity for endothelial cells within the vascular system. VEGF is essential for embryonic vasculogenesis and angiogenesis. (Carmeliet et al. (1996) Nature 380:435-439; Ferrara et al. (1996) Nature 380:439-442).

In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997), supra. Moreover, recent studies have reported mitogenic effects of VEGF on a few non-endothelial cell types, such as retinal pigment epithelial cells, pancreatic duct cells and Schwann cells. Guerrin et al. (1995) J. Cell Physiol. 164:385-394; Oberg-Welsh et al. (1997) Mol. Cell. Endocrinol. 126:125-132; Sondell et al. (1999) J. Neurosci. 19:5731-5740.

Substantial evidence also implicates VEGF's critical role in the development of conditions or diseases that involve pathological angiogenesis. The VEGF mRNA is overexpressed by the majority of human tumors examined (Berkman et al. J Clin Invest 91:153-159 (1993); Brown et al. Human Pathol. 26:86-91 (1995); Brown et al. Cancer Res. 53:4727-4735 (1993); Mattern et al. Brit. J. Cancer. 73:931-934 (1996); and Dvorak et al. Am J. Pathol. 146:1029-1039 (1995)). Also, the concentration of VEGF in eye fluids are highly correlated to the presence of active proliferation of blood vessels in patients with diabetic and other ischemia-related retinopathies (Aiello et al. N. Engl. J. Med. 331:1480-1487 (1994)). Furthermore, recent studies have demonstrated the localization of VEGF in choroidal neovascular membranes in patients affected by AMD (Lopez et al. Invest. Ophtalmo. Vis. Sci. 37:855-868 (1996)).

Given its central role in promoting tumor growth, VEGF provides an attractive target for therapeutic intervention. Indeed, a variety of therapeutic strategies aimed at blocking VEGF or its receptor signaling system are currently being developed for the treatment of neoplastic diseases. Rosen (2000) Oncologist 5:20-27; Ellis et al. (2000) Oncologist 5:11-15; Kerbel (2001) J. Clin. Oncol. 19:45 S-51S. So far, VEGF/VEGF receptor blockade by monoclonal antibodies and inhibition of receptor signaling by tyrosine kinase inhibitors are the best studied approaches. VEGFR-1 ribozymes, VEGF toxin conjugates, and soluble VEGF receptors are also being investigated.

Suitable antiangiogenics therefore include, but are not limited to pegaptanib (Macugen™ by Pfizer), ranibizumab (Lucentis™ by Genentech) bevacizumab (Avastin™ by Genentech), carboxyamidotriazole, TNP-470, CM101, IFN-α, IL-12, platelet factor 4, suramin, SU5416, thrombospondin, VEGFR antagonists, angiostatic steroids+heparin, cartilage-derived angiogenesis inhibitory factor, matrix metallopreteinase inhibitors, angiostatin, endostatin, 2-methoxyestradiol, tecogalan, prolactin, $\alpha_v\beta_3$ inhibitors, and linomide, VEGF-Trap (by Regeneron Pharmaceuticals), Aminosterols (Evizion® by Genera Corp.), Cortisen (Retaane® by Alcon), tyrosine kinase inhibitors, anti-angiogenic siRNA, inhibitors of the complement system, and gentherapeutic therapies (e.g. AdPEDF.11 by Genvec).

Other suitable antiangiogenics suitable for the methods described herein are described, for example, in U.S. Patent Publications 2006/0134111, 2007/0031413, 2007/0160608, and the like which are incorporated herein by reference.

One or more of the active agents can also be administered in conjunction or combination with compounds that support remodeling of Bruch's membrane and the adjacent structures (e.g. chelators for iron, calcium, zinc; metalloproteinase inhibitors etc.). As described above, the National Eye Institute and others have shown that administration of vitamin supplements with high doses of antioxidants, lutein and zeaxanthin can slow the progression of dry macular degeneration and in some patients, improve visual acuity. As such, one or more of the active agents can also be administered in conjunction or combination with vitamin supplements with high doses of antioxidants, lutein and zeaxanthin.

One or more of the active agents can also be administered in conjunction, combination, or in a preparation for cell transplants (e.g. stem cells, engineered, autologous, etc.) and biotechnical implants where cell survival and outcome of the procedure is improved by remodeled Bruch's membrane and reduced inflammation response.

IX. Kits for the Treatment of One or More Indications

In another embodiment this invention provides kits for amelioration of one or more symptoms of atherosclerosis or for the prophylactic treatment of a subject (human or animal) at risk for atherosclerosis and/or the treatment or prophylaxis of one or more of the conditions described herein. For example, also disclosed herein are kits for amelioration of one or more symptoms of atherosclerosis or for the prophylactic treatment of a subject (human or animal) at risk for eye disease.

The kits preferably comprise a container containing one or more of the active agents described herein. The active agent(s) can be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of the condition/pathology of interest. Such agents include, but are not limited to, beta blockers, vasodilators, aspirin, statins, ace inhibitors or ace receptor inhibitors (ARBs) and the like, e.g. as described above.

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to mitigate one or more symptoms of atherosclerosis (or other pathologies described herein) and/or to prevent the onset or increase of one or more of such symptoms in an individual at risk for atherosclerosis (or other pathologies described herein). The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Use of ApoJ-Related Peptides to Mediate Symptoms of Atherosclerosis

Prevention of LDL-Induced Monocyte Chemotactic Activity

FIG. 1 illustrates a comparison of the effect of D-4F (Anantharamaiah et al. (2002) Circulation, 105: 290-292) with the effect of an apoJ peptide made from D amino acids (D-J336, Ac-L-L-E-Q-L-N-E-Q-F-N-W-V-S-R-L-A-N-L-T-Q-G-E-NH$_2$, SEQ ID NO: 1177)) on the prevention of LDL-induced monocyte chemotactic activity in vitro in a co-incubation. Human aortic endothelial cells were incubated with medium alone (no addition), with control human LDL (200 µg protein/ml) or control human LDL+control human HDL (350 µg HDL protein/ml). D-J336 or D-4F was added to other wells in a concentration range as indicated plus control human LDL (200 µg protein/ml). Following overnight incubation, the supernatants were assayed for monocyte chemotactic activity. As shown in FIG. 1, the in vitro concentration of the apoJ variant peptide that prevents LDL-induced monocyte chemotactic activity by human artery wall cells is 10 to 25 times less than the concentration required for the D-4F peptide.

Prevention of LDL-Induced Monocyte Chemotactic Activity by Pre-Treatment of Artery Wall Cells with D-J336

FIG. 2 illustrates a comparison of the effect of D-4F with the effect of D-J336 on the prevention of LDL induced monocyte chemotactic activity in a pre-incubation. Human aortic endothelial cells were pre-incubated with D-J336 or D-4F at 4, 2, and 1 .mu.g/ml for DJ336 or 100, 50, 25, and 12.5 µg/ml for D-4F for 6 hrs. The cultures were then washed and were incubated with medium alone (no addition), or with control human LDL (200 µg protein/ml), or with control human LDL+control human HDL (350 µg HDL protein/ml) as assay controls. The wells that were pre-treated with peptides received the control human LDL at 200 µg protein/ml. Following overnight incubation, the supernatants were assayed for monocyte chemotactic activity.

As illustrated in FIG. 2, the ApoJ variant peptide was 10-25 times more potent in preventing LDL oxidation by artery wall cells in vitro.

The Effect of Apo J Peptide Mimetics on HDL Protective Capacity in LDL Receptor Null Mice.

D-4F designated as F, or the apoJ peptide made from D amino acids (D-J336, designated as J) was added to the drinking water of LDL receptor null mice (4 per group) at 0.25 or 0.5 mg per ml of drinking water. After 24- or 48-hrs blood was collected from the mice and their HDL was isolated and tested for its ability to protect against LDL-induced monocyte chemotactic activity. Assay controls included culture wells that received no lipoproteins (no addition), or control human LDL alone (designated as LDL, 200 .mu.g cholesterol/ml), or control LDL+control human HDL (designated as +HDL, 350 .mu.g HDL cholesterol). For testing the mouse HDL, the control LDL was added together with mouse HDL (+F HDL or +J HDL) to artery wall cell cultures. The mouse HDL was added at 100 µg cholesterol/ml respectively. After treatment with either D-4F or D-J336 the mouse HDL at 100 µg/ml was as active as 350 µg/ml of control human HDL in preventing the control LDL from inducing the artery wall cells to produce monocyte chemotactic activity. The reason for the discrepancy between the relative doses required for the D-J336 peptide relative to D-4F in vitro and in vivo may be related to the solubility of the peptides in water and we believe that when measures are taken to achieve equal solubility the D-J peptides will be much more active in vivo as they are in vitro.

Protection Against LDL-Induced Monocyte Chemotactic Activity by HDL from Apo E Null Mice Given Oral Peptides.

FIG. 4 illustrates the effect of oral apoA-1 peptide mimetic and apoJ peptide on HDL protective capacity. ApoE null mice (4 per group) were provided with D-4F (designated as F) at 50, 30, 20, 10, 5 .mu.g per ml of drinking water or apoJ peptide (designated as J) at 50, 30 or 20 .mu.g per ml of drinking water. After 24 hrs blood was collected, plasma fractionated by FPLC and fractions containing LDL (designated as mLDL for murine LDL) and fractions containing HDL (designated as mHDL) were separately pooled and HDL protective capacity against LDL oxidation as determined by LDL-induced monocyte chemotactic activity was determined. For the assay controls the culture wells received no lipoproteins (no additions), mLDL alone (at 200 μg cholesterol/ml), or mLDL+standard normal human HDL (designated as Cont. h HDL, at 350 μg HDL cholesterol/ml).

For testing the murine HDL, mLDL together with murine HDL (+F mHDL or +J mHDL) were added to artery wall cell cultures. The HDL from the mice that did not receive any peptide in their drinking water is designated as no peptide mHDL. The murine HDL was used at 100 .mu.g cholesterol/ml. After receiving D-4F or D-J336 the murine HDL at 100 μg/ml was as active as 350 .mu.g/ml of normal human HDL. As shown in FIG. 4, when added to the drinking water the D-J peptide was as potent as D-4F in enhancing HDL protective capacity in apo E null mice.

Ability of LDL Obtained from ApoE Null Mice Given Oral Peptides to Induce Monocyte Chemotactic Activity.

FIG. 5 illustrates the effect of oral apo A-1 peptide mimetic and apoJ peptide on LDL susceptibility to oxidation. ApoE null mice (4 per group) were provided, in their drinking water, with D-4F (designated as F) at 50, 30, 20, 10, 5 .mu.g per ml of drinking water or the apoJ peptide (D-J336 made from D amino acids and designated as J) at 50, 30 or 20 μg per ml of drinking water. After 24 hrs blood was collected from the mice shown in FIG. 4, plasma fractionated by FPLC and fractions containing LDL (designated as mLDL for murine LDL) were pooled and LDL susceptibility to oxidation as determined by induction of monocyte chemotactic activity was determined. For the assay controls the culture wells received no lipoproteins (no additions), mLDL alone (at 200 μg cholesterol/ml), or mLDL+standard normal human HDL (designated as Cont. h HDL, 350 μg HDL cholesterol).

Murine LDL, mLDL, from mice that received the D-4F (F mLDL) or those that received the apoJ peptide (J mLDL) were added to artery wall cell cultures. LDL from mice that did not receive any peptide in their drinking water is designated as No peptide LDL.

As shown in FIG. 5, when added to the drinking water, D-J336 was slightly more potent than D-4F in rendering the LDL from apo E null mice resistant to oxidation by human artery wall cells as determined by the induction of monocyte chemotactic activity.

Protection Against Phospholipid Oxidation and Induction of Monocyte Chemotactic Activity by HDL Obtained from Apo E Null Mice Given Oral Peptides.

Figure 6:
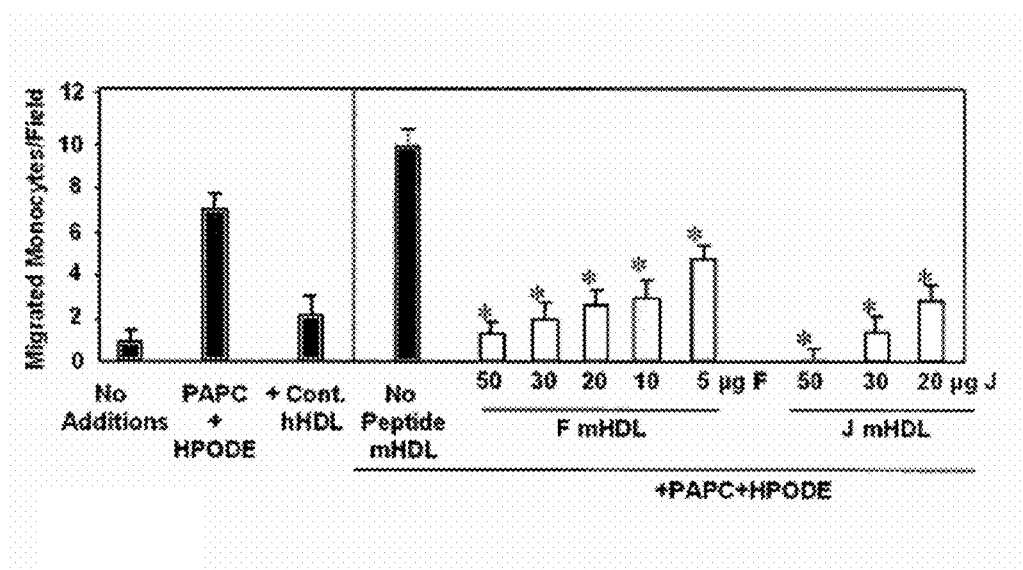
FIG. 6 illustrates the effect of oral apoA-1 peptide mimetic and apoJ peptide on HDL protective capacity. The values are the mean±SD of the number of migrated monocytes in 9 high power fields from each of quadruple assay wells. Asterisks indicate significant difference (p<0.05) as compared to No Peptide mHDL.

FIG. 6 illustrates the effect of oral apoA-1 peptide mimetic and apoJ peptide on HDL protective capacity. ApoE null mice (4 per group) were provided with D-4F (designated as F) at 50, 30, 20, 10, 5 .mu.g per ml of drinking water or apoJ peptide (D-J336 made from D amino acids and designated as J) at 50, 30 or 20 .mu.g per ml of drinking water. After 24 hrs blood was collected, plasma fractionated by FPLC and fractions containing HDL (designated as mHDL) were pooled and HDL protective capacity against PAPC oxidation as determined by the induction of monocyte chemotactic activity was determined. For the assay controls the culture wells received no lipoproteins (no additions), the phospholipid PAPC at 20 .mu.g/ml+HPODE, at 1.0 μg/ml, or PAPC+HPODE plus standard normal human HDL (at 350 μg HDL cholesterol/ml and designated as +Cont. h HDL).

For testing the murine HDL, PAPC+HPODE together with murine HDL (+F mHDL or +J mHDL) were added to artery wall cell cultures. The HDL from mice that did not receive any peptide in their drinking water is designated as "no peptide mHDL". The murine HDL was used at 100 μg cholesterol/ml.

The data shown in FIG. 6 indicates that, when added to the drinking water, D-J336 was as potent as D-4F in causing HDL to inhibit the oxidation of a phospholipid PAPC by the oxidant HPODE in a human artery wall co-culture as measured by the generation of monocyte chemotactic activity.

Effect of Oral ApoA-1 Peptide Mimetic and ApoJ Peptide on Plasma Paraoxonase Activity in Mice.

Figure 7:
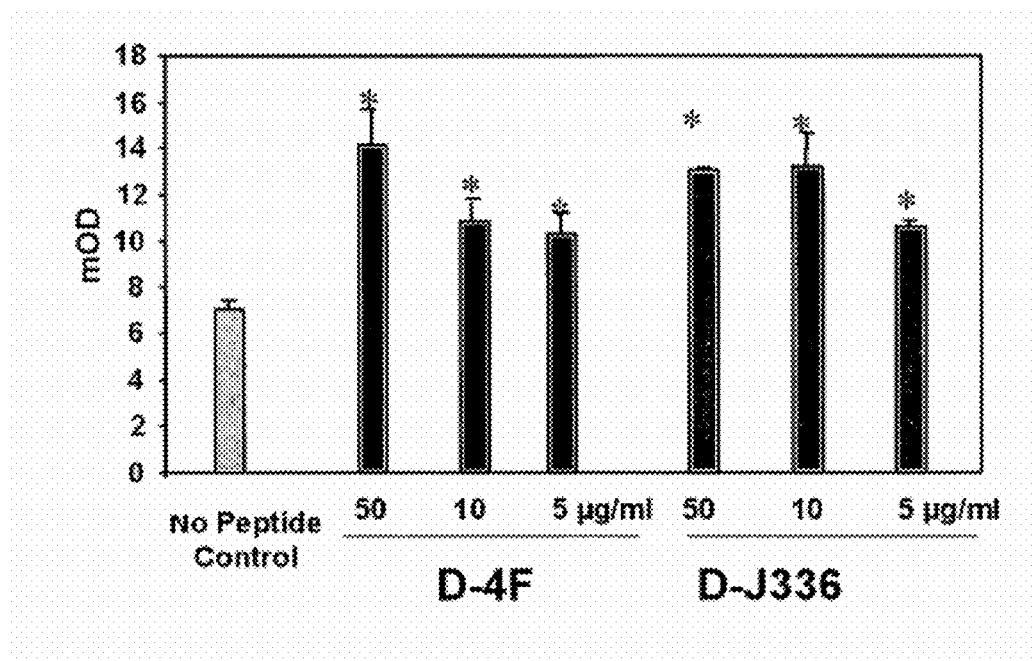
FIG. 7 illustrates the effect of oral apoA-1 peptide mimetic and apoJ peptide on plasma paraoxonase activity. The values are the mean±SD of readings from quadruple plasma aliquots. Asterisks indicate significant differences (p<0.05) as compared to No Peptide control plasma.

FIG. 7 shows the effect of oral apoA-1 peptide mimetic and apoJ peptide on plasma paraoxonase activity in mice. ApoE null mice (4 per group) were provided with D-4F designated as F at 50, 10, 5 or 0 μg per ml of drinking water or apoJ peptide (D-J336 made from D amino acids and designated as J) at 50, 10 or 5 μg per ml of drinking water. After 24 hrs blood was collected and plasma was assayed for PON1 activity. These data demonstrate that, when added to the drinking water, D-J336 was at least as potent as D-4F in increasing the paraoxonase activity of apo E null mice.

Example 2

Oral G* Peptides Increase HDL Protective Capacity in Apo E Deficient Mice

Female, 4 month old apoE deficient mice (n=4 per group) were treated with G* peptides having the following amino acid sequences. Peptide 113-122=Ac-LVGRQLEEFL-NH$_2$ (SEQ ID NO. 9), Peptide 336-357=Ac-LLEQLNEQFN-WVSRLANLTQGE-NH$_2$ (SEQ ID NO. 17), and Peptide 377-390=Ac-PSGVTEVVVKLFDS-NH$_2$ (SEQ ID NO. 19).

Figure 8:
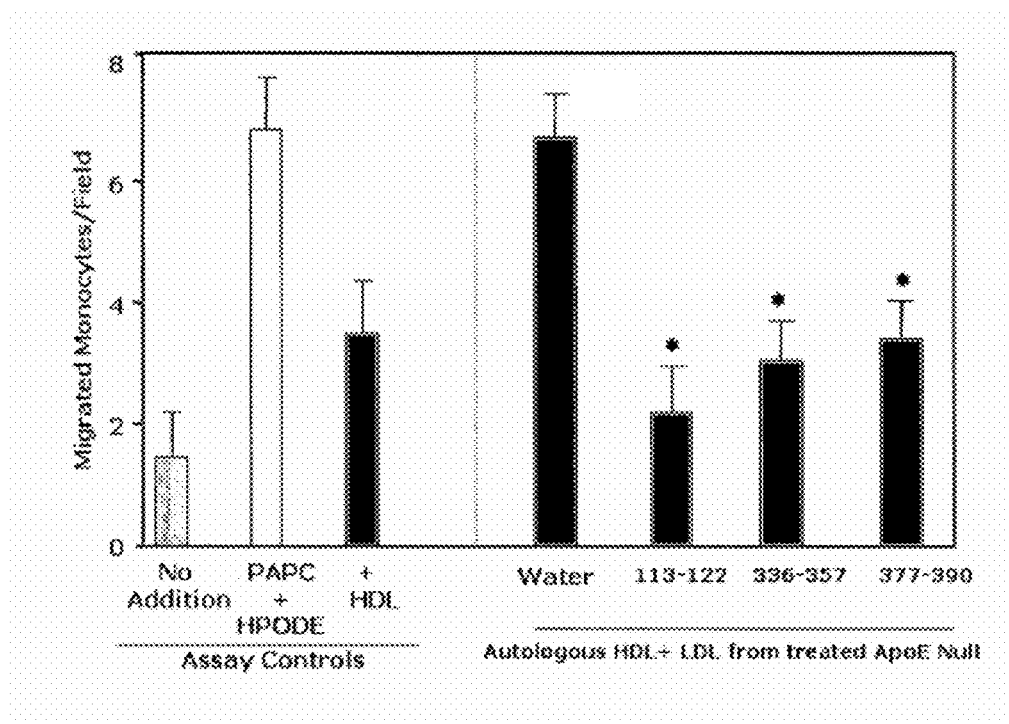
FIG. 8 shows the effect of oral G* peptides on HDL protective capacity in apoE−/− mice. The values are the mean±SD of readings from quadruple plasma aliquots. Asterisks indicate significant differences (p<0.05) as compared to no peptide control plasma.

Each mouse received 200 .mu.g of the peptide by stomach tube. Four hours later blood was obtained, plasma separated, lipoproteins fractionated and HDL (at 25 μg per ml) was assayed for protective capacity against the oxidation of LDL (at 100 μg per ml) in cultures of human artery wall cells. The data are shown in FIG. 8. The peptide afforded significant HDL-protective capacity in the mice.

Figure 9:
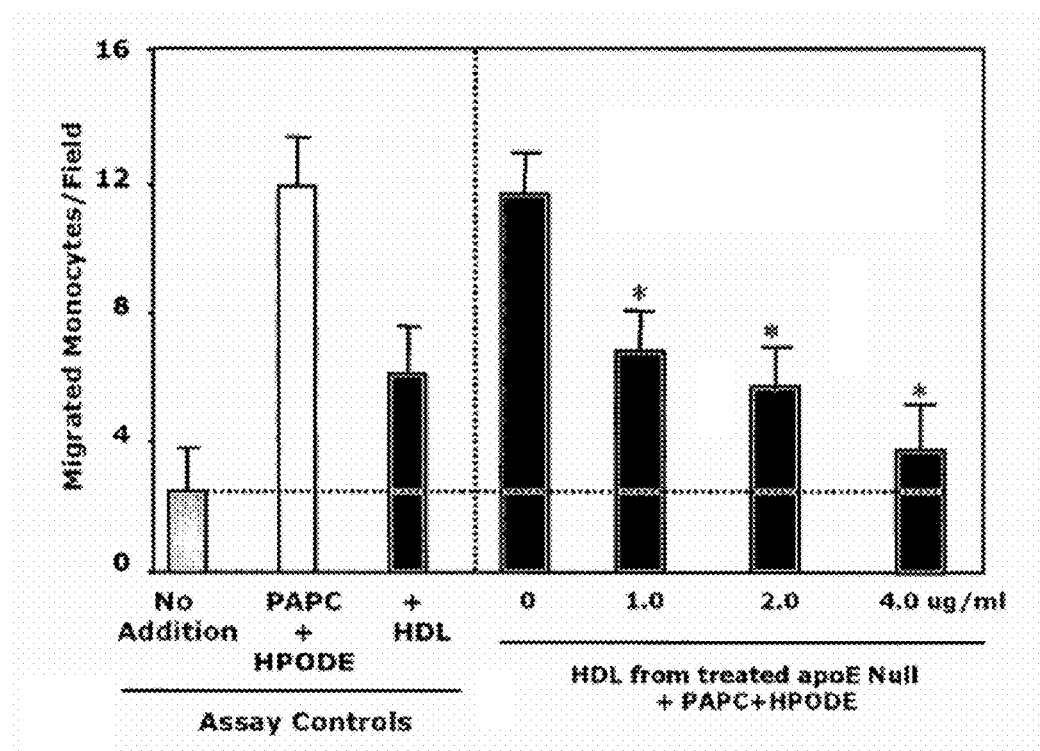
FIG. 9 shows the effect of Oral G* peptide, 146-156, on HDL protective capacity in ApoE−/− mice.
Figure 10A:
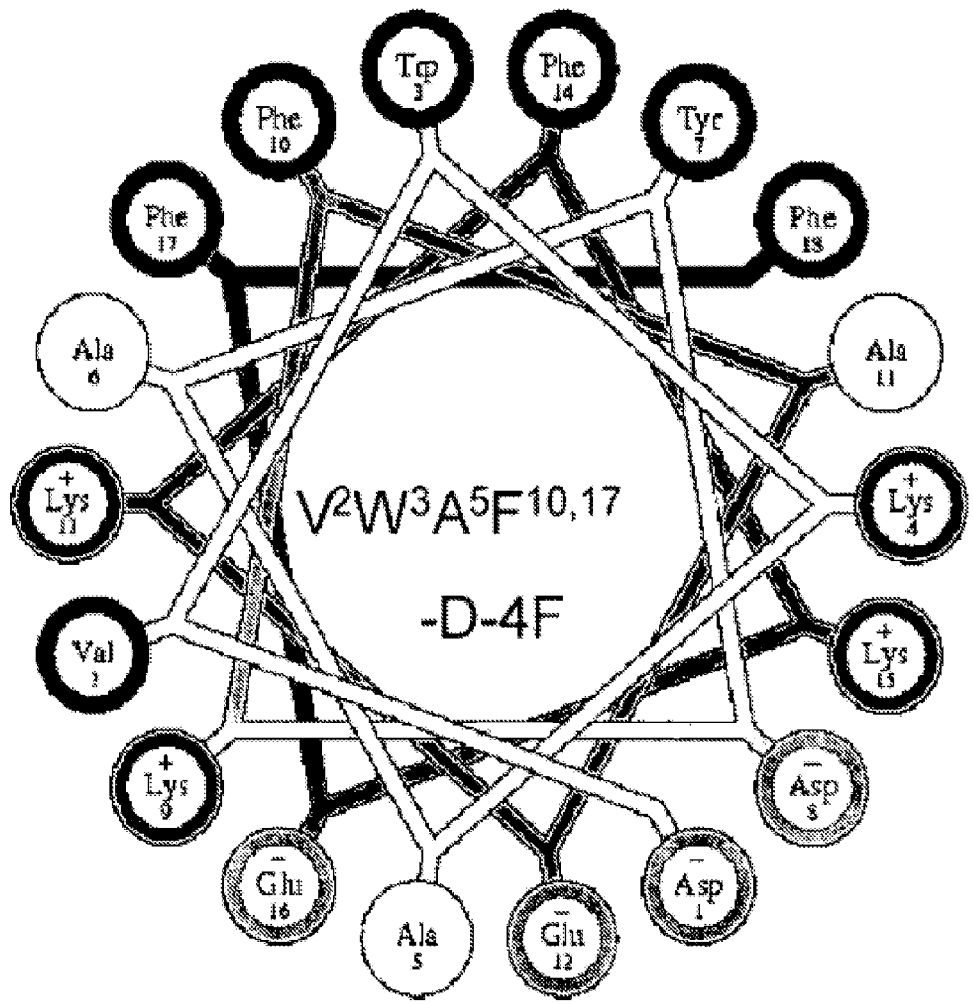
FIGS. 10A through 10C illustrate helical wheel diagrams of certain peptides of this invention.
Figure 10B:
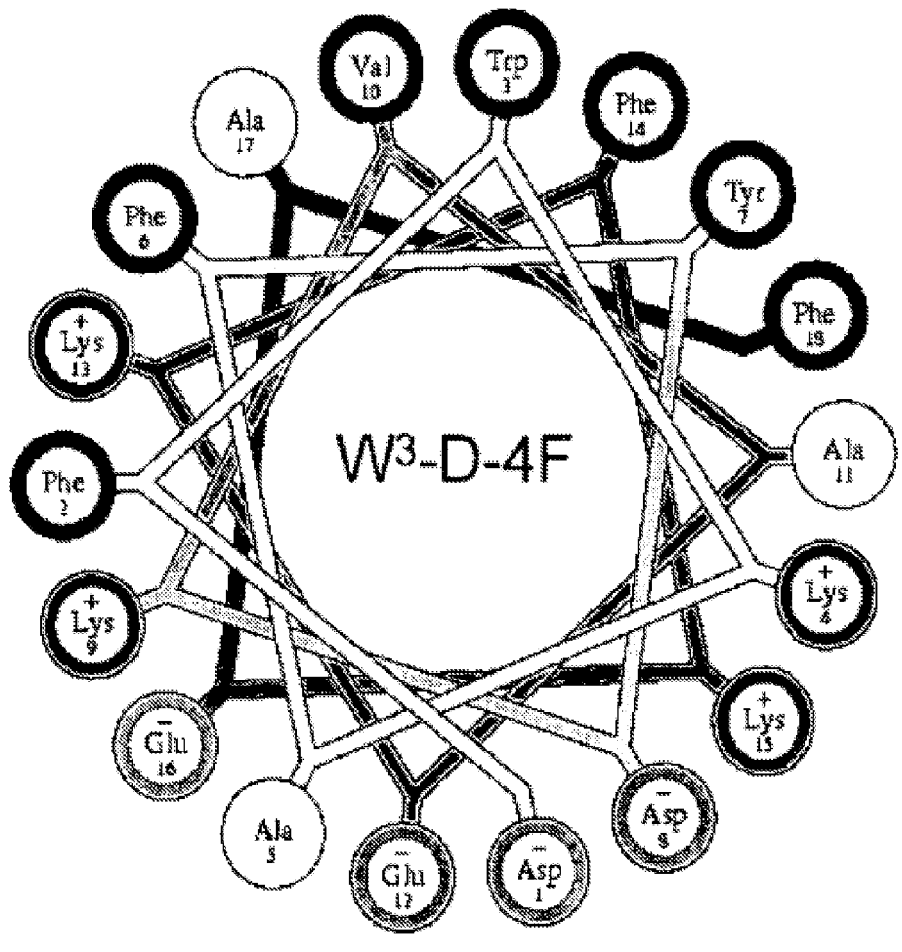
Figure 10C:
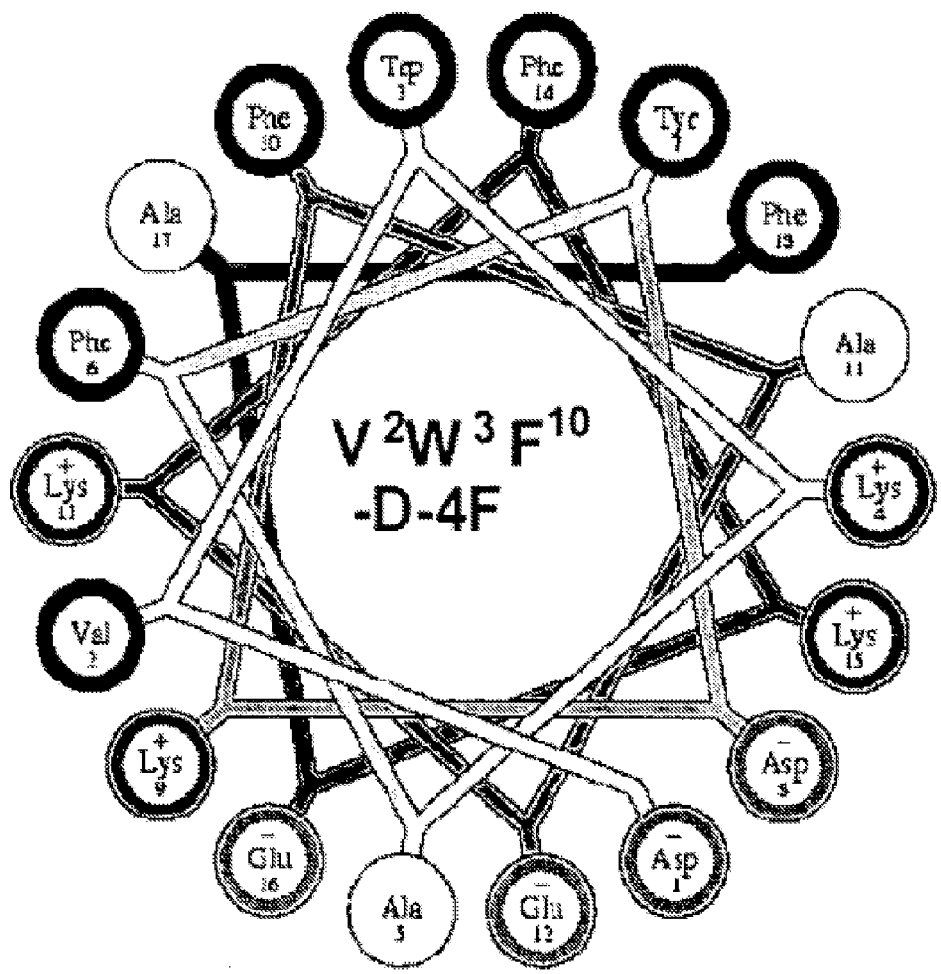
Figure 11:
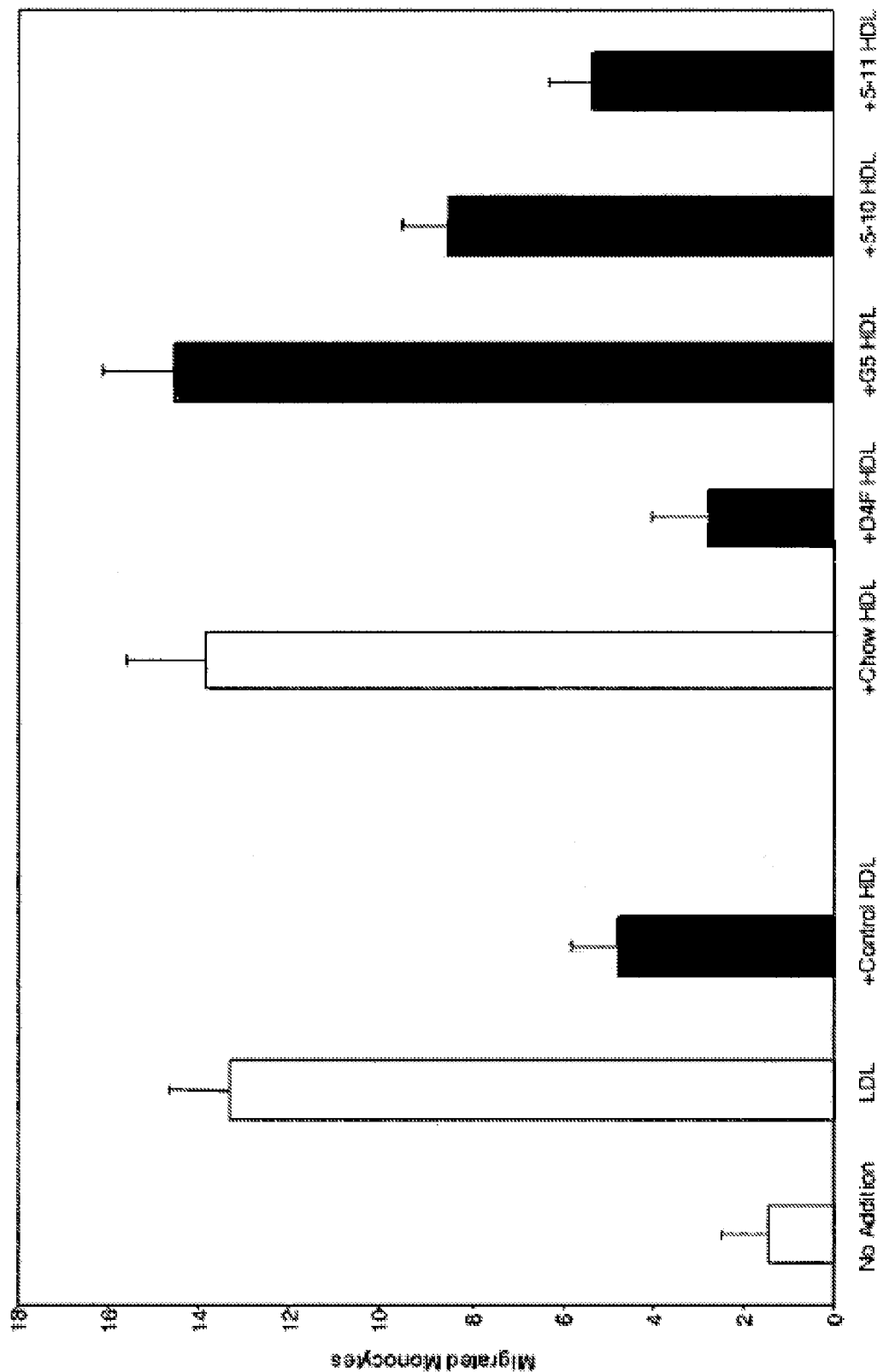
FIG. 11 A standard human LDL (LDL) was added to human artery wall cocultures without (No Addition) or with human HDL (+Control HDL) or with mouse HDL from apoE null mice given Chow overnight (+Chow HDL), or given D-4F in the chow overnight (+D4F HDL) or given G5-D-4F in the chow overnight (+G5 HDL), or given G5,10-D-4F in the chow overnight (+5-10 HDL), or given G5,11-D-4F in the chow overnight (+5-11 HDL) and the resulting monocyte chemotactic activity determined as previously described (Navab et al. (2002) Circulation, 105: 290-292).
Figure 12:
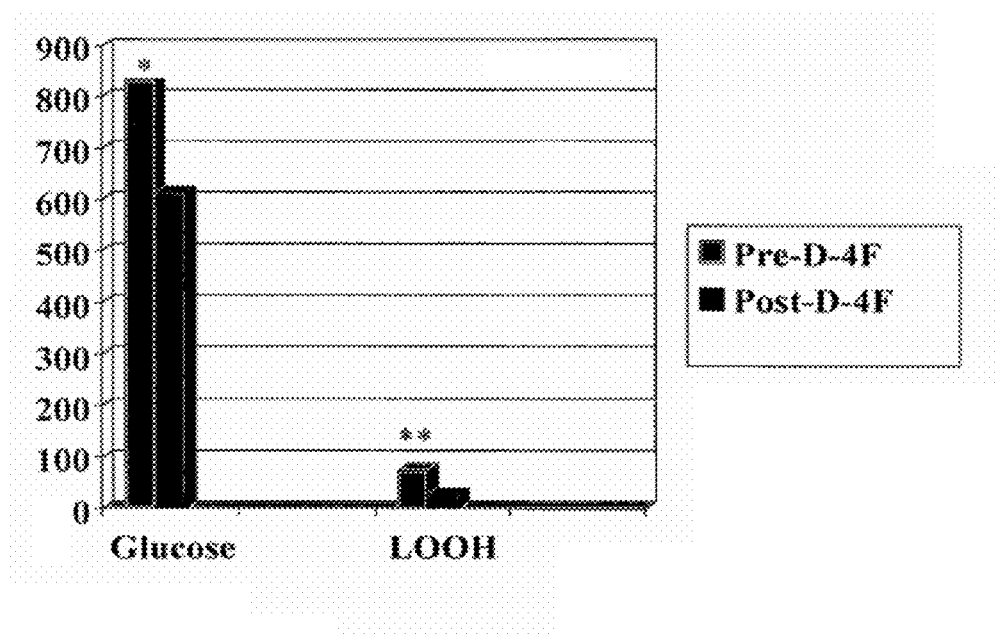
FIG. 12 shows that peptides of this invention are effective in mitigating symptoms of diabetes (e.g., blood glucose). Obese Zucker rats 26 weeks of age were bled and then treated with daily intraperitoneal injections of D-4F (5.0 mg/kg/day). After 10 days the rats were bled again plasma glucose and lipid hydroperoxides (LOOH) were determined. *p=0.027; **p=0.0017.
Figure 13A:
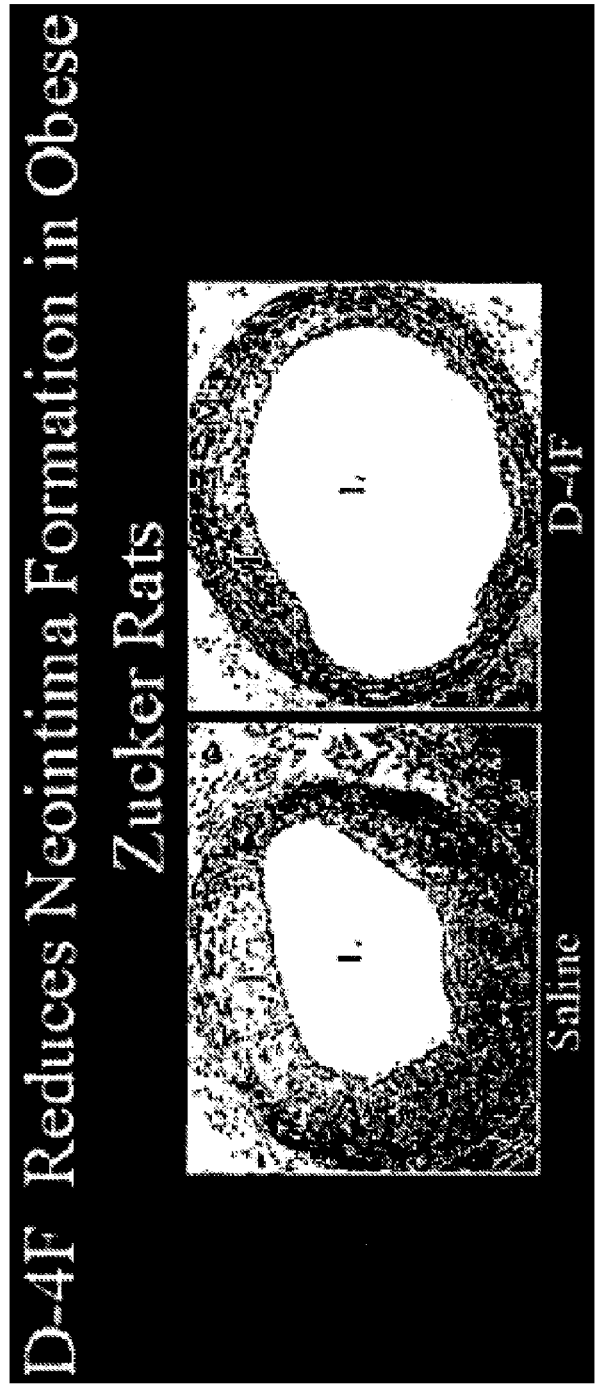
FIGS. 13A and 13B. Sixteen week old Obese Zucker Rats were injected with D-4F (5 mg/kg/daily) for 1 week at which time they underwent balloon injury of the common carotid artery. Two weeks later the rats were sacrificed and the intimal media ratio determined.
Figure 13B:
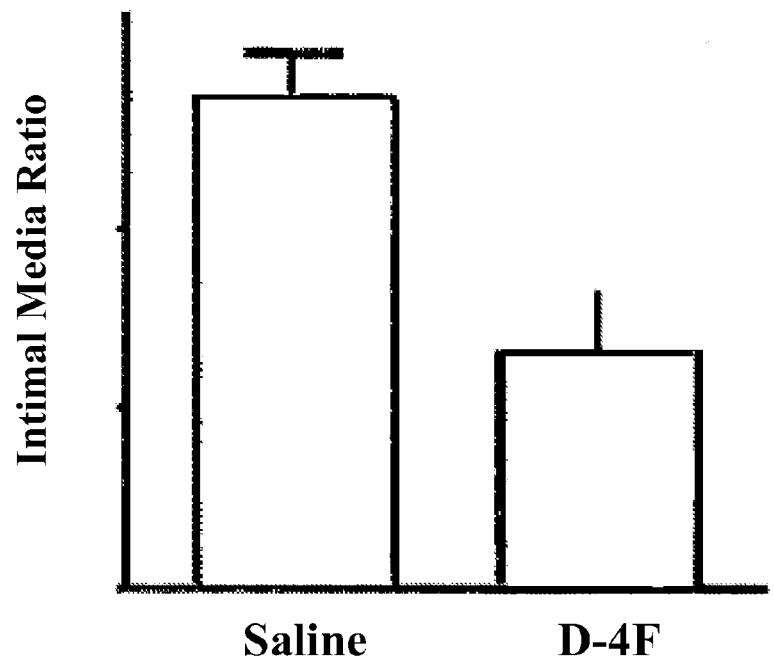

In another experiment, female, 4 month old apoE deficient mice (n=4 per group) were treated with the 11 amino acid G* peptide 146-156 with the sequence: Ac-QQTHMLDVMQD-NH$_2$. (SEQ ID NO:11). The mice received the peptide in their drinking water at the indicated concentrations (see FIG. 9). Following eighteen hrs, blood was obtained, plasma separated, lipoproteins fractionated and HDL (at 50 .mu.g cholesterol per ml) was assayed for protective capacity against the oxidation of PAPC (at 25 μg per ml)+HPODE (at 1.0 μg per ml) in cultures of human artery wall cells. Assay controls included No additions, PAPC+HPODE and PAPC+HPODE plus Control HDL (designated as +HDL). The data are mean+/−SD of the number of migrated monocytes in nine high power fields in triplicate cultures. Asterisks indicate significance at the level of p<0.05 vs. the water control (0 μg/ml).

Example 3

Solution Phase Chemistry for Peptide Synthesis

In certain embodiments, a solution-phase synthesis chemistry provides a more economical means of synthesizing peptides of this invention.

Prior to this invention synthesis was typically performed using an all-solid phase synthesis chemistry. The solid phase synthesis of peptides of less than 9 amino acids is much more economical than the solid phase synthesis of peptides of more than 9 amino acids. Synthesis of peptides of more than 9 amino acids results in a significant loss of material due to the physical dissociation of the elongating amino acid chain from the resin. The solid phase synthesis of peptides containing less than 9 amino acids is much more economical because there is relatively little loss of the elongating chain from the resin.

In certain embodiments, the solution phase synthesis functions by converting the synthesis of the 18 amino acid apoA-I mimetic peptide, 4F (and other related peptides) from an all solid phase synthesis to either an all solution phase synthesis or to a combination of solid phase synthesis of three chains each containing, e.g., 6 amino acids followed by the assembly of the three chains in solution. This provides a much more economical overall synthesis. This procedure is readily modified where the peptides are not 18 amino acids in length. Thus, for example, a 15 mer can be synthesized by solid phase synthesis of three 5 mers followed by assembly of the three chains in solution. A 14 mer can be synthesized by the solid phase synthesis of two 5 mers and one 4 mer followed by assembly of these chains in solution, and so forth.

A) Summary of Synthesis Protocol.

A scheme for the synthesis of the peptide D4F (Ac-D-W-F-K-A-F-Y-D-K-V-A-E-K-F-K-E-A-F-NH$_2$, (SEQ ID NO:5) is illustrated in Table 20. (The scheme and yields for the synthesis are shown in Table 20.

TABLE 20

Illustrative solution phase synthesis scheme.
Methods Used for D4F Synthesis

| Synthesis | Resin | Fmoc Amino Acid | Coupling Reagent | Final Wt. of Resin(gms) | Wt. of Crude Peptide (gms) Yield (%) | Wt. of Pure Peptide (mg) Yield ((%) |
|---|---|---|---|---|---|---|
| Stepwise Solid Phase | Rink Amide (1 mmole) 1.8 gms | 6 Equiv | HBTU/ HOBT | 4 | 2.0 86 | 500 25 |
| Stepwise Solid Phase | Rink Amide (1 mmole) 1.8 gms | 2 Equiv | DIC/HOBT | 3.9 | 2.0 86 | 450 22.5 |
| Fragment coupling (6 + 6 + 6) | Rink Amide (1 mmole) 1.8 gms* | | HBTU/ HOBT | 3.3 | 1.0 43 | 100 10 |

Synthesis of D4F Fragments Fragments
Fragment 1 (2HN-KFKEAF (SEQ ID NO: 1178) on rink amide resin
(K and E are properly protected)

| Fragment 2 6 residues stepwise Solid Phase | Cl-TrT-Resin (5 mmol) 6.5 gms | 6 Equiv | HBTU/ HOBT | 11 | 2.2 crude protected 32 | |

Fmoc-Y(But)-D(But)-K(Boc)-V-A-E(But)-COOH (SEQ ID NO: 1179)

| Fragment 2 6 residues stepwise Solid Phase | Cl-TrT-Resin (5 mmol) 6.5 gms | 6 Equiv | HBTU/ HOBT | 10 | 1.8 crude protected 32 | |

Ac-D(But)-W-F-K(Boc)-A-F-COOH (SEQ ID NO: 1180)

Synthesis by solution phase using fragments produced by the solid phase method. Fragment Wang resin. C-terminal hexapeptide (subjected to ammonolysis). Yield quantitative.

1. NH2-K(Boc)-F-K(Boc)-E(But)-A-F-Wang resin (SEQ ID NO: 1181) NH2-K(Boc)-F-K(Boc)-E(But)-A-F-CO—NH2 (SEQ ID NO: 1182)

Fragment 2 from above was coupled to fragment 1 in DMF using DIC/HOBT.
  Fmoc-Y(But)-D(But)-K(Bpc)-V-A-E(But)-K(Boc)-F-K(Boc)-E(But)-F-Co—NH2 (SEQ ID NO: 1183) 12 residue peptide was characterized as free peptide after removing protecting groups. Yield was 50%

Fmoc from the above-12 residue was removed by piperidine in DMF (20%. After drying the peptide was copied to Fragment 3 using DCl/HOBT in DMF.

Ac-D(But)-W-F-K(Boc)-A-F-Y(But)-D(but)-K(Boc)-V-A-E(But)-K(Boc)-F-K(Boc)-E(But)-A-FCO-NH2 (SEQ ID NO: 1184) Protected peptide yield was quantitative.

Protecting groups removed using mixture of TFA (80%), phenol (5%), thioanisole (5%). water)$_5$%), triisopropylsilane (TIS, 5%), stirred for 90 min. Precipitated by ether and purified by C-4 HPLC column. Yield 25%

B) Details of Synthesis Protocol.
1. Fragment Condensation Procedure to Synthesize D-4F
Fragments synthesized for fragment condensation on solid phase are:
  Fragment 1: Ac-D(OBut)-W-F-K($\epsilon$Boc)-A-F-COOH (SEQ ID NO:1185);
  Fragment 2: Fmoc-Y(OBut)-D(OBut)-K($\epsilon$Boc)-V-A-E(OBut)-COOH (SEQ ID NO:1186); and
  Fragment 3 Fmoc-K($\epsilon$Boc)F-K($\epsilon$Boc)-E($\epsilon$But)-A-F-Rink amide resin (SEQ ID NO:1187).

Fragment 1 was left on the resin to obtain final peptide amide after TFA treatment.

To synthesize fragment 1: Fmoc-Phe (1.2 equivalents) was added to chlorotrityl resin (Nova Biochem, 1.3 mMol/g substitution, 5 mMol or 6.5 g was used) in presence of six equivalents of DIEA in DMF:dichloromethane (1:1)) and stirred for 4 h. Excess of functionality on the resin was capped with methanol in presence of dichloromethane and DIEA. After the removal of Fmoc-Fmoc amino acid derivatives (2 equivalents) were added using HOBut/HBTU reagents as described above. Final Fmoc-D(OBut)-W-F-K($\epsilon$Boc)-A-F Chlorotrityl resin was treated with Fmoc deblocking agent and acetylated with 6 equivalents of acetic anhydride in presence of diisoprolylethyl amine. The resulting Ac-D(OBut)-W-F-K($\epsilon$Boc)-A-F-resin was treated with a mixture of trifluoroethanol-acetic acid-dichloromethane (2:2:6, 10 ml/g of resin) for 4 h at room temperature. After removal of the resin by filtration, the solvent was removed by aziotropic distillation with n-hexane under vacuum. The residue (1.8 g) was determined by mass spectral analysis to be Ac-D(OBut)-W-F-K(εBoc)-A-F-COOH (SEQ ID NO:1188).

Fragment 2, Fmoc-Y(OBut)-D(OBut)-K(εBoc)-V-A-E(OBut)-COOH (SEQ ID NO:1189), was obtained using the procedure described for Fragment 1. Final yield was 2.2 g.

Fragment 3. 0.9 g (0.5 mmol) of Rink amide resin (Nova Biochem) was used to obtain fragment Rink amide resin was treated with 20% pipetidine in dichloromethane for 5 min once and 15 min the second time (Fmoc deblocking reagents). 1.2 equivalents of Fmoc-Phe was condensed using condensing agents HOBt/HBTU (2 equivalents in presence of few drops of diisopropylethyl amine) (amino acid condensation). Deblocking and condensation of the rest of the amino acids were continued to obtain the of Fmoc-K(EBoc)F-K(εBoc)-E(OBut)-A-F-rink amide resin (SEQ ID NO:1190). Fmoc was cleaved and the peptide resin K(εBoc)F-K(εBoc)-E(OBut)-A-F-rink amide resin (SEQ ID NO:1190) was used for fragment condensation as described below.

Fragment 2 in DMF was added to Fragment 3 (1.2 equivalents) using HOBt-HBTU procedure in presence of DIEA overnight. After washing the resin with DMF and deblocking Fmoc-Fragment 1 (1.2 equivalents) was added to the dodecapeptide resin using HOBt-HBTU procedure overnight.

The final peptide resin (3.3 g) was treated with a mixture of TFA-Phenol-triisopropylsilane-thioanisole-water (80:5:5:5) for 1.5 h (10 ml of the reagent/g of the resin). The resin was filtered off and the solution was diluted with 10 volumes of ether. Precipitated peptide was isolated by centrifugation and washed twice with ether. 1 g of the crude peptide was subjected to HPLC purification to obtain 100 mg of the peptide.

2. Characterization of Peptide.

The peptide was identified by mass spectral and analytical HPLC methods.

Figure 14:
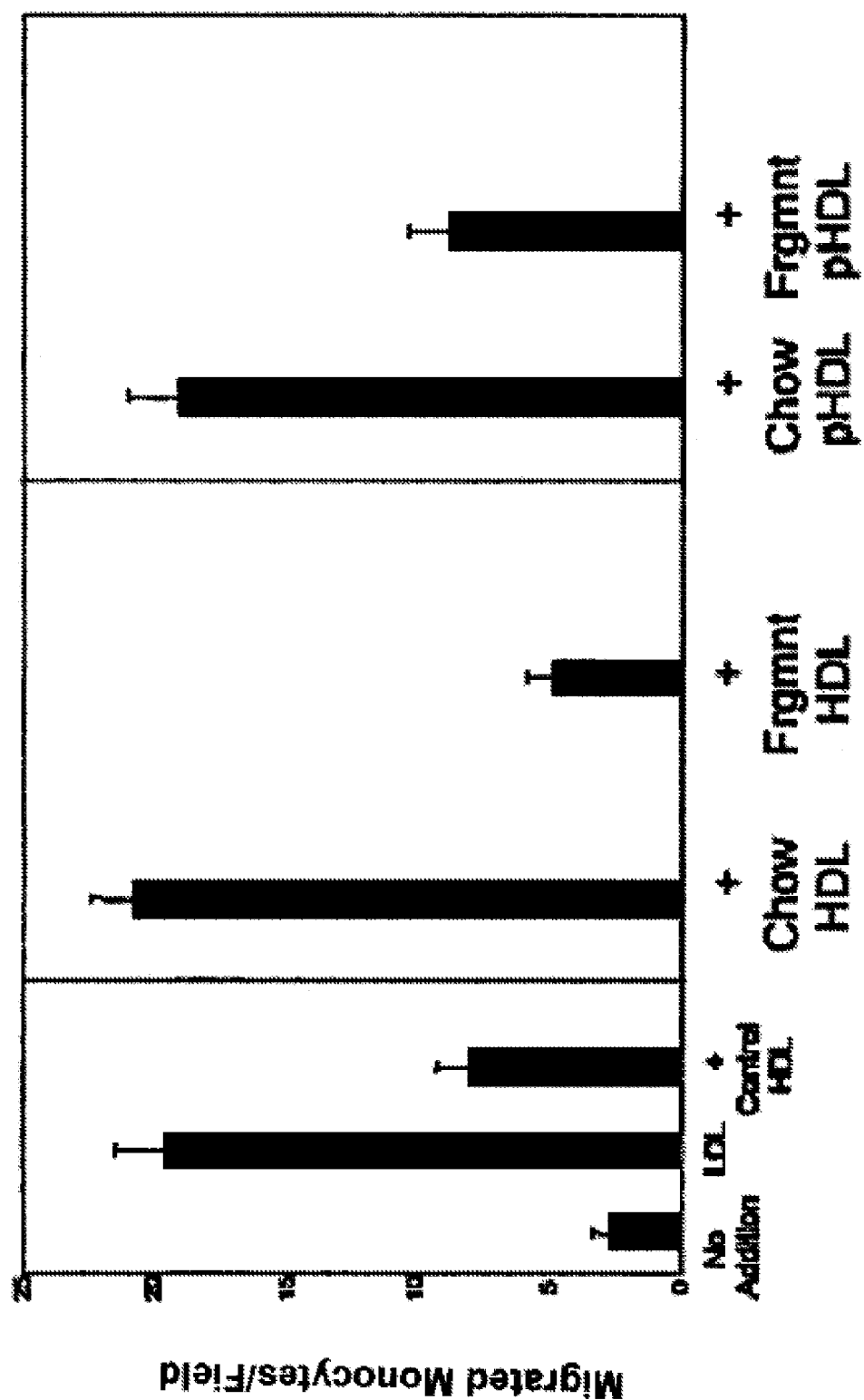
FIG. 14 demonstrates that the product of the solution phase synthesis scheme is very biologically active in producing HDL and pre-beta HDL that inhibit LDL-induced monocyte chemotaxis in apo E null mice. ApoE null mice were fed 5 micrograms of the D-4F synthesized as described above (Frgmnt) or the mice were given the same amount of mouse chow without D-4F (Chow). Twelve hours after the feeding was started, the mice were bled and their plasma was fractionated on FPLC. LDL (100 micrograms LDL-cholesterol) was added to cocultures of human artery wall cells alone (LDL) or with a control human HDL (Control HDL) or with HDL (50 micrograms HDL-cholesterol) or post-HDL (pHDL; prebeta HDL) from mice that did (Frgmnt) or did not (Chow) receive the D-4F and the monocyte chemotactic activity produced was determined

As shown in FIG. 14 the product of the solution phase synthesis scheme is very biologically active in producing HDL and pre-beta HDL that inhibit LDL-induced monocyte chemotaxis in apo E null mice. ApoE null mice were fed 5 micrograms of the D-4F synthesized as described above (Frgmnt) or the mice were given the same amount of mouse chow without D-4F (Chow). Twelve hours after the feeding was started, the mice were bled and their plasma was fractionated on FPLC. LDL (100 micrograms LDL-cholesterol) was added to cocultures of human artery wall cells alone (LDL) or with a control human HDL (Control HDL) or with HDL (50 micrograms HDL-cholesterol) or post-HDL (pHDL; prebeta HDL) from mice that did (Frgmnt) or did not (Chow) receive the D-4F and the monocyte chemotactic activity produced was determined.

Example 4

Comparison of D-4F and Reverse (Retro-) D-4F Activity

Figure 16:
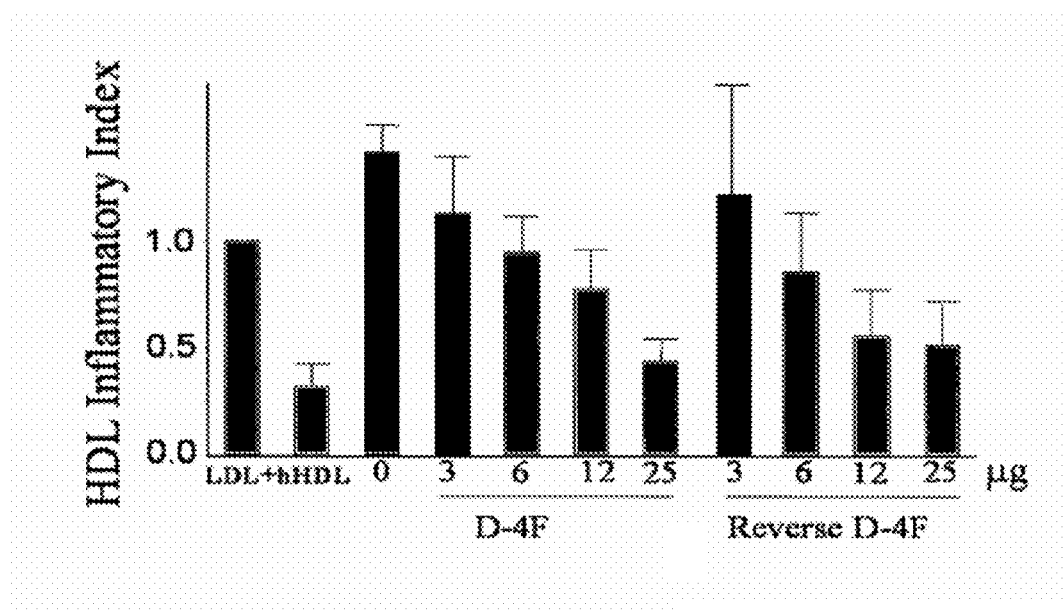
FIG. 16 shows a comparison of the HDL inflammatory index of D-4F versus reverse D-4F.
Figure 17A:
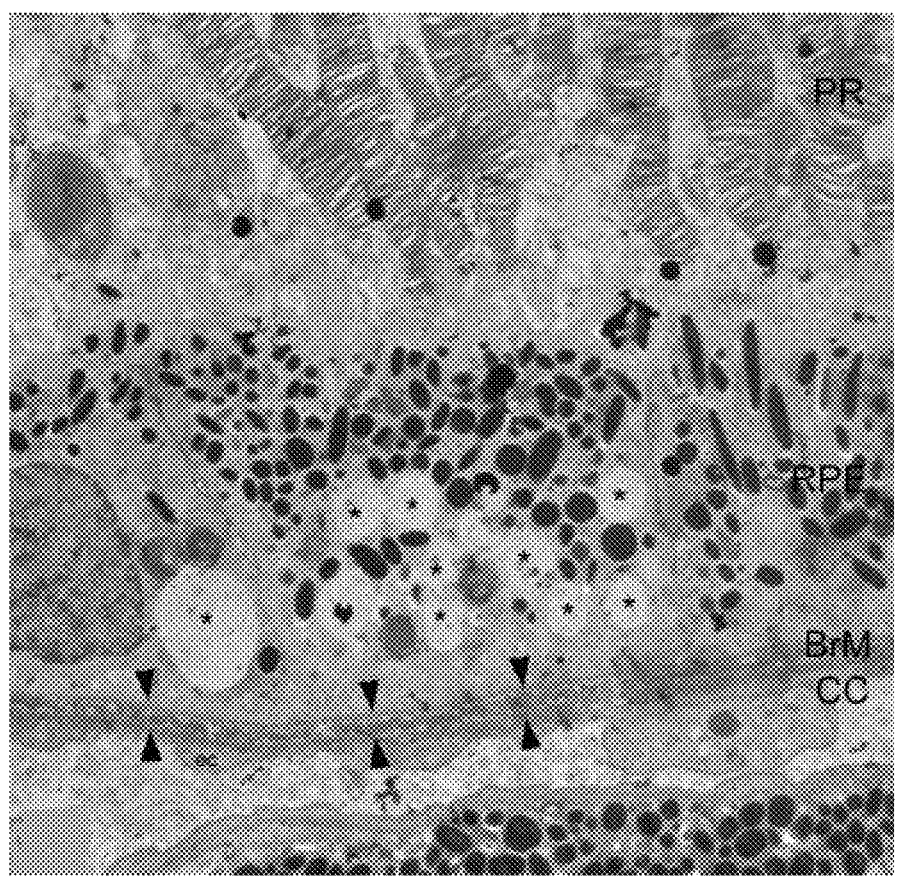
FIG. 17A (1A from Rudolf Summary) shows electron microscopy of untreated eyes (controls) at a magnification of 5,000×; Bruch's membrane (BrM, arrow heads) structure loosen up with many translucent lipid vacuoles, these degenerative changes can be observed in both control eyes in at least ¾ of the entire Bruch's membrane. In every other RPE cell big lipid vacuoles (asterisks) are found, a sign of stress and beginning degeneration. PR: photo receptors; CC: choriocapillaris: EC: vascular endothelial cell of the choriocapillaris.
Figure 17B:
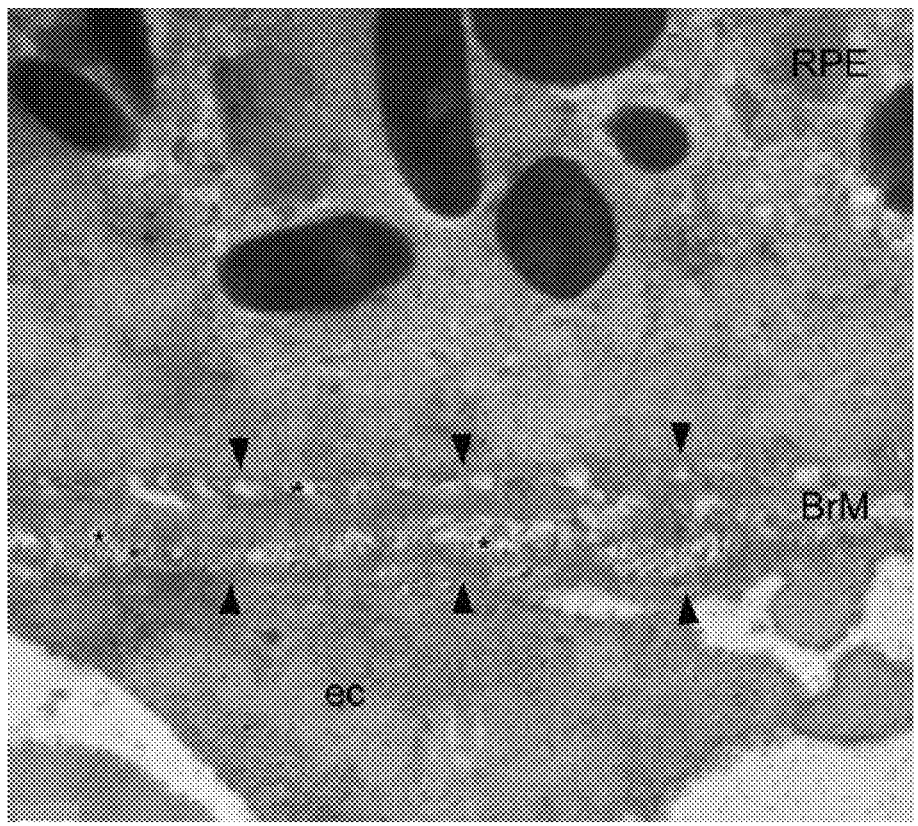
FIG. 17B (1B from Rudolf Summary) shows electron microscopy of untreated eyes (controls) at a magnification of 20,000×; Bruch's membrane (BrM, arrow heads) shows a significant compromised morphology without the regular and uniform five layer arrangement. The membrane is slightly thickened with multiple translucent lipid vacuoles. A few are marked with asterisks. EC: vascular endothelial cell of choriocapillaris.
Figure 18A:
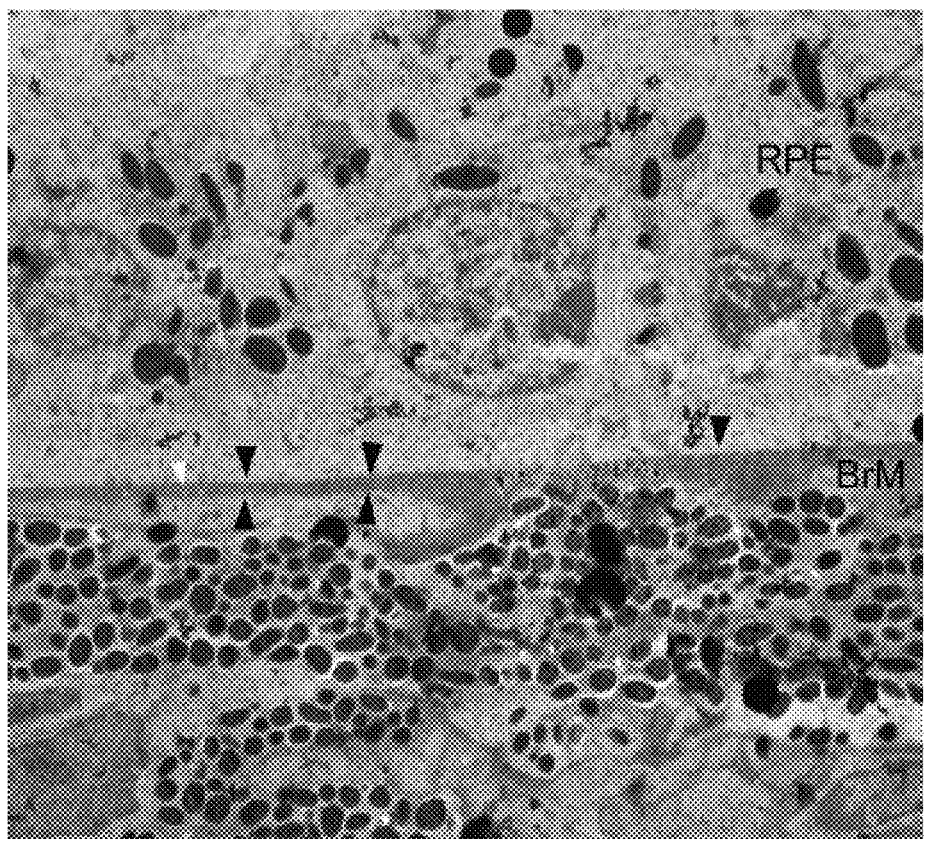
FIG. 18A (2A from Rudolf Summary) shows electron microscopy of treated eyes (Apolipoprotein mimetic peptide L-4F) at a magnification of 5,000×; regular and uniform Bruch's membrane structure (BrM, black arrow heads) which resembles Bruch's membrane in healthy wild type mice (Dithmar et al. (2000) Invest Opthalmol Vis Sci 41:2035-42); only occasionally a lipid vacuole left (white arrow head); this effect was found in the entire Bruch's membrane; none of the RPE cells showed lipid droplets.
Figure 18B:
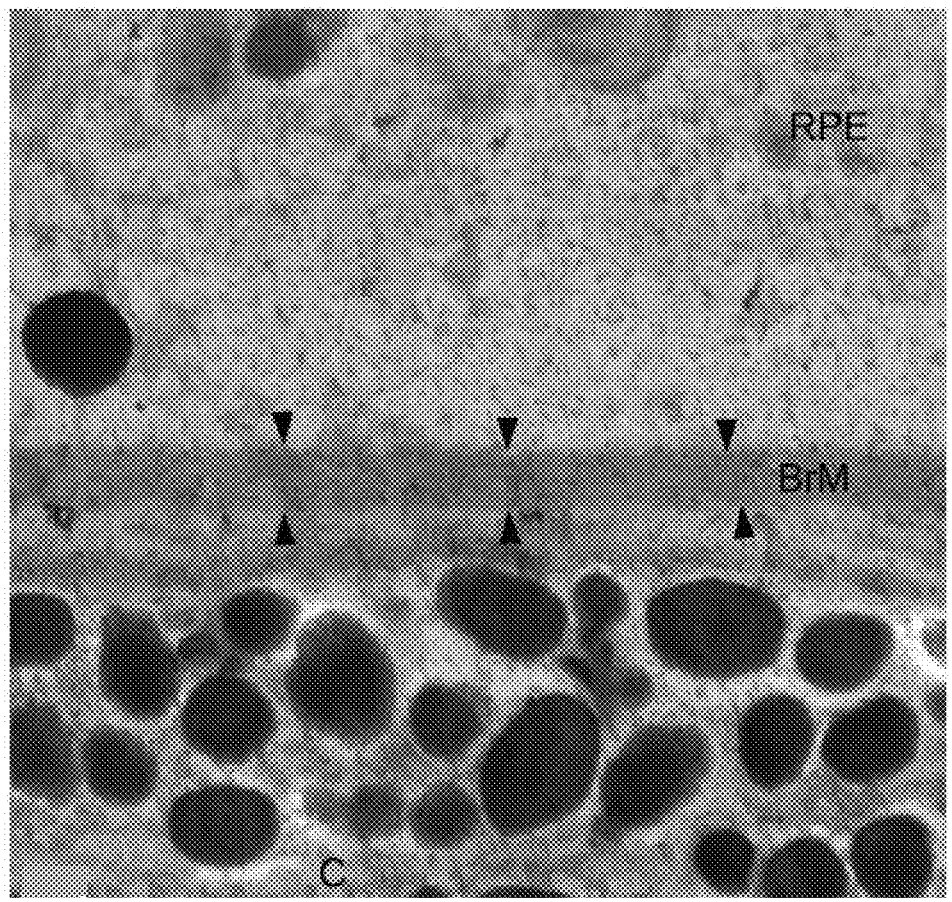
FIG. 18B (2B from Rudolf Summary) shows electron microscopy of a treated eye (Apolipoprotein mimetic peptide L-4F) at a magnification of 20,000×; regular and uniform Bruch's membrane (BrM, black arrow heads) no translucent lipid vacuoles shown.

As shown in FIG. 16, the biological activities of D-4F and reverse RD-4F are not significantly different. Female apoE null mice were administered by stomach tube 0, 3, 6, 12, or 25 micrograms of D-4F or Reverse D-4F in 100 microliters of water. Blood was obtained 7 hours later and the plasma was fractionated by FPLC. A standard control human LDL was added to human artery wall cells at a concentration of 100 micrograms of LDL-cholesterol/mL (LDL). The resulting monocyte chemotactic activity was normalized to 1.0. The same LDL at the same concentration was added to the human artery wall cells together with HDL at 50 micrograms HDL-cholesterol/mL from a normal human (hHDL) or from the apoE null mice that received the dose of D-4F or Reverse D-4F shown on the X-axis. The resulting monocyte chemotactic activity was normalized to that of the LDL added without HDL. The resulting value is the HDL Inflammatory Index. The results shown are the Mean±S.D. for the data from three separate experiments.

Example 5

Effects of L-4F on the Bruch's Membrane of Aged C57Bl/6J-apoE Null Mice

Aged C57Bl/6J-apoE null mice are a classic atherosclerosis model with significantly elevated plasma cholesterol levels even under standard diets. Previous studies demonstrated lipid accumulation in Bruch's membrane mimicking early stages of AMD in these animals (Dithmar et al. (2000) Invest Opthalmol Vis Sci 41:2035-42).

An effective clearance of this lipid debris via an ApoA-I mimetic peptide (L-4F) could prevent early AMD-like degeneration.

Study Design

L-4F was injected directly into the vitreous cavity of right eyes of 10 eight month old C57Bl/6J-apoE null mice. A single dose of 3 µl was injected with a L-4F concentration of 400 µg/ml. All left eyes were untreated throughout the study and thus bserved as controls. The animals were then sacrificed 21 days after the injection and the eyes were immediately enucleated and fixed. Eyes then were processed for electron microscopy (EM).

Results

EM of 2 mice was reviewed. The treated eyes (L-4F) showed in both cases a significant improvement in Bruch's membrane and RPE morphology as well as lipid content compared to the untreated eyes (control).

Example 6

Animal Model

Aged C57Bl/6J-apoE null mice are a classic atherosclerosis model with significantly elevated plasma cholesterol levels even under standard diets. Previous studies demonstrated lipid accumulation in Bruch's membrane mimicking early stages of AMD (Dithmar et al. (2000) Invest Opthalmol Vis Sci 41:2035-42). An effective clearance of this lipid debris via an ApoA-I/ApoE mimetic peptide will remodel Bruch's membrane structure to a state of wild type animal and restore Bruch's membrane function with improved hydraulic conductivity and increased metabolic exchange rate. In this study the ApoA-I mimetic peptides L-4F and D-4F will be analyzed.

Animals

Female C57Bl/6J-apoE null mice were purchased from Jackson Laboratories (Bar Harbor, Me.). The use of animals was conducted according to the Association for Research in Vision and Opthalmology (ARVO) Guidelines for the Care and Use of Animals. Animals can be kept in plastic cages with regular light-dark cycle and will be provided continuous free access to water and food. All animals will receive a regular rodent chow diet. At 9 months animals will be divided into 8 groups with 7 animals each.

Single intravitreal injection of 3 µl can be performed in the right eyes of all Study I animals. All left eyes will be kept uninjected and served as intra-individual negative controls. Group 1 received a concentration of 200 µg/ml L-4F, group 2 received 400 µg/ml L-4F, group 3 received 800 µg/ml L-4F and group 4 served as inter-individual negative control with sham injections (no L-4F).

In addition, single intravitreal injection of 3 µl can be performed in the right eyes of all Study II animals. All left eyes will be kept uninjected and served as intra-individual negative controls. Group 1 received a concentration of 200 µg/ml D-4F, group 2 received 400 µg/ml D-4F, group 3 received 800 µg/ml D-4F and group 4 served as inter-individual negative control with sham injections (no D-4F).

Procedure

Inhalation anesthesia was induced with 5% isofluorane. Additional topical 0.5% paracaine anesthesia eye drop were administered as well as tropicamide eye drops for pupil dilation. With continuous 3% isofluorane inhalation anesthesia mice were positioned under a surgery microscope. Eyelids were gently retracted, eyeballs manually protruded and gently fixed. A sterile 30½-gauge needle (BectonDickinson, Franklin Lakes, N.J.) were used for sclera penetration and the intraocular position of the needle tip was checked under the microscope. A volume of 3 µl of L-4F or D-4F diluted in saline solution was injected with sterilized 10 µl glass microsyringes (Hamilton, Reno, Nev.) directly into the vitreous cavity. The concentration varied between the 3 groups. Groups 1 received 200 µg/ml L-4F (Study I) or D-4F (Study II), group 2 received 400 µg/ml L-4F or D-4F and group 3 received saline without L-4F or D-4F. The needle was held in place for 1 min to allow the drug to diffuse into the vitreous cavity and to prevent retrograde efflux. After the injection is finished both eyes were treated once with antibiotic 0.3% gentamicin sulphate eye ointment (Gentak®, Akorn Inc., Buffalo Grove, Ill.). After treatment mice were daily observed for adverse events, especially relating to the eye.

After 21 days all animals were sacrificed after deep ketamine/xylazine intraperitoneal anesthesia by thoracotomy/exsanguinations followed by a whole body perfusion with 1.2% paraformaldehyde/0.8% glutaraldehyde in 0.1M phosphate buffer. Immediately all right and left eyes were enucleated and stored in the above mentioned fixative.

Transmission Electron Microscopy

The fixed eyes were bisected under a dissecting scope (SMZ-U, Nikon Instruments Inc., Melville N.Y.) for further processing for TEM. The halves used for TEM were postfixed in 2% buffered osmium tetroxide, dehydrated in a graded ethanol series, and embedded in epoxy resin according to standard protocols. One-µm thick semithin sections were stained with toluidine blue; ultrathin sections will be stained with uranyl acetate and lead citrate and examined with an electron microscope (1200 EXII; JEOL USA, Peabody, Mass.) equipped with a digital camera (Optronics, Goleta, Calif.).

From each specimen, sections including the central retina including Bruch's membrane will be investigated. Images were acquired according to a random sampling procedure using the bars of the supporting grid as points of reference, by which 5 consecutive areas adjacent to the right side of a grid bar will be imaged at a magnification of 5,000× and 20,000× and later analyzed.

Image Analysis

The investigator performing electron microscopic image evaluations and measurements will be masked regarding the origin of the specimens. With ImageJ (a public domain, Java-based image processing program developed at the National Institutes of Health) a standard grid was placed above each image. For standardization Bruch's membrane will be evaluated with point counting stereology only above capillary lumens and not in intercapillary pillar areas.

Statistical Analysis

For statistical analysis of the morphological parameters from TEM imaging, the mean±SD of the individual 30 measurements will be calculated for each eye. The mean values will be compared between groups using the non-parametric Mann-Whitney test; differences will be considered significant at $p<0.05$. The SPSS for Windows statistics program (Version 6.0.1, SPSS Inc.) will be used.

Example 7

To study the pharmacokinetics and pharmacodynamics of ApoA-I mimetic peptides in the eye both eyes of 15 ApoE null mice can be injected with 400 µg/ml of biotinylated but functional L-4F or D-4F. Animals can then be sacrificed at different time points after injection, 3 mice for each time point (1 day, 2 days, 4 days, 7 days, and 12 days after injection).

One eye of each animal can then be cryo-preserved for fluorescent labeling of the biotinylated compound and light microscopy, the second eye can then be paraformaldehyde/glutaraldehyde-fixed for electron microscopy for evaluation of structural effects as described above.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for treating a subject with eye disease, the method comprising administering to the subject in need thereof an effective amount of one or more of the active agents described in SEQ ID NOS: 1-1208 in an amount sufficient to ameliorate one or more symptoms of said condition.

2. The method of claim 1, wherein said active agent is a polypeptide comprising the amino acid sequence of 4F (SEQ ID NO:5).

3. The method of claim 1, wherein said administration is by a route selected from the group consisting of oral administration, nasal administration, rectal administration, intraperitoneal injection, and intravascular injection, intraocular injection, intravitreal injection, subconjuctival injection, peri-retrobulbar injection, subcutaneous injection, eye drops, eye gel, eye ointment, spray, emulsion, suspension, transcutaneous administration, and intramuscular injection, drug carriers, sponges, contact lenses, polymers, microspheres, implants, pellets, and genetically engineered cells.

4. The method of claim 1, wherein said active agent is administered in conjunction with a antiangiogenic agents.

5. The method of claim 1, wherein the eye disease is selected from the group consisting of macular degeneration, age related maculopathy (ARM), dry age related macular degeneration (AMD), wet age related macular degeneration, glaucoma, ocular hypertension, macular edema, retinal pigment epithelium detachments, Coat's disease, uveitis, sicca syndrome, hereditary diseases associated with increased extracellular or intracellular lipid storage or accumulation, and juvenile macular degeneration.

6. A method of ameliorating a symptom of eye disease, the method comprising a) administering to the subject an effective amount of a peptide wherein said peptide ranges in length from about 18 to 37 amino acids and comprises at least 3 alanines (A), 2 aspartates (D), 2 glutamates (E), 4 phenylalanines (F), 4 lysines (K), 1 valine (V), 1 tryptophan (W), 1 tyrosine (Y); b) wherein said peptide forms a class A amphipathic helix; c) comprises at least one "D" amino acid residue; and d) protects a phospholipid against oxidation by an oxidizing agent.

7. The method of claim 6, wherein said peptide further comprises a protecting group coupled to the amino or carboxyl terminus.

8. The method of claim 6, wherein said peptide further comprises a first protecting group coupled to the amino terminus and a second protecting group coupled to the carboxyl terminus.

9. The method of claim 7, wherein said protecting groups are independently selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

10. The method of claim 6, wherein all enantiomeric amino acids are "D" amino acids.

11. The method of claim 6, wherein said peptide is mixed with a pharmacologically acceptable excipient.

12. The method of claim 6, wherein said peptide is mixed with a pharmacologically acceptable excipient suitable for oral administration to a mammal.

13. The method of claim 6, wherein said peptide comprises an amino acid sequence selected from the group consisting of SEQ ID NO: 1191, SEQ ID NO: 1192, SEQ ID NO: 1193, SEQ ID NO: 1194, SEQ ID NO: 1195, SEQ ID NO: 1196, SEQ ID NO: 1197, and the reverse of any of these sequences.

14. The method of claim 13, wherein said peptide comprises a protecting group coupled to the amino terminal and said amino terminal protecting group is a protecting group selected from the group consisting of acetyl, propionyl, and a 3 to 20 carbon alkyl.

15. The method of claim 13, wherein said peptide comprises a protecting group coupled to the carboxyl terminal and said carboxyl terminal protecting group is an amide.

16. The method of claim 13, wherein said peptide comprises a first protecting group coupled to the amino terminus wherein said protecting group is a protecting group selected from the group consisting of acetyl, propionyl, and a 3 to 20 carbon alkyl; and a second protecting group coupled to the carboxyl terminal and said carboxyl terminal protecting group is an amide.

17. The method of claim 6, wherein said oxidizing agent is selected from the group consisting of hydrogen peroxide, 13(S)-HPODE, 15(S)-HPETE, HPODE, HPETE, HODE, and HETE.

18. The method of claim 6, wherein said phospholipid is selected from the group consisting of 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEI PE).

19. A method for treating a subject with eye disease, the method comprising administering to the subject in need thereof an effective amount of one or more of the active agents described in SEQ ID NOS: 1-1208 in an amount sufficient to ameliorate one or more symptoms of said condition in combination with an anti-angiogenic therapy.

20. The method of claim 19, wherein the anti-angiogenic therapy is selected from the group consisting of pegaptanib, ranibizumab, bevacizumab, carboxyamidotriazole, TNP-470, CM101, IFN-α, IL-12, platelet factor 4, suramin, SU5416, thrombospondin, VEGFR antagonists, angiostatic steroids and heparin, cartilage-derived angiogenesis inhibitory factor, matrix metalloproteinase inhibitors, angiostatin, endostatin, 2-methoxyestradiol, tecogalan, prolactin, $\alpha_v\beta_3$ inhibitors, linomide, VEGF-Trap, aminosterols, cortisone, tyrosine kinase inhibitors, anti-angiogenic siRNA, inhibitors of the complement system, and gentherapeutic therapies.

21. A method of ameliorating a symptom of eye disease, the method comprising administering to the subject in need thereof an effective amount of one or more of the active agents described in SEQ ID NOS: 1-1208 in an amount sufficient to ameliorate one or more symptoms of said condition in combination with an anti-angiogenic therapy.

22. The method of claim 21, wherein the anti-angiogenic therapy is selected from the group consisting of pegaptanib, ranibizumab, bevacizumab, arboxyamidotriazole, TNP-470, CM101, IFN-α, IL-12, platelet factor 4, suramin, SU5416, thrombospondin, VEGFR antagonists, angiostatic steroids and heparin, cartilage-derived angiogenesis inhibitory factor, matrix metalloproteinase inhibitors, angiostatin, endostatin, 2-methoxyestradiol, tecogalan, prolactin, $\alpha v\beta 3$ inhibitors, linomide, VEGF-Trap, aminosterols, cortisone, tyrosine kinase inhibitors, anti-angiogenic siRNA, inhibitors of the complement system, and gentherapeutic therapies.

23. The method of claim 10 wherein the symptom is selected from the group consisting of accumulation of extracellular lipids in Bruch's membranes, accumulation of lipid rich debris, vision loss, formation of choriocapillaris, thickening of the Bruch's membrane, accumulation of neutral lipids in the Bruch's membrane, formation of a diffusion barrier between the retinal pigment epithelium and choriocapillaris, deposition of debris (basal linear deposits and drusen) between the basal membrane of the RPE and the inner collagenous layer, accumulation of lipofuscin in the RPE cells, RPE atrophy, photoreceptor degeneration, choroidal neovascularization, as well as leakage, bleeding, and scarring of the eye.

24. The method of claim 10, wherein the eye disease is selected from the group consisting of macular degeneration, age related maculopathy (ARM), dry age related macular degeneration (AMD), wet age related macular degeneration, glaucoma, ocular hypertension, macular edema, retinal pigment epithelium detachments, Coat's disease, uveitis, sicca syndrome, hereditary diseases associated with increased extracellular or intracellular lipid storage or accumulation, and juvenile macular degeneration.

* * * * *

SEQUENCE LISTING

<160> NUMBER OF SEQ ID NOS: 1208

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 1

Asp Trp Leu Lys Ala Phe Tyr Asp Lys Val Ala Glu Lys Leu Lys Glu
1               5                   10                  15

Ala Phe

```
<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 3

Asp Trp Phe Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 4

Asp Trp Leu Lys Ala Phe Tyr Asp Lys Val Ala Glu Lys Phe Lys Glu
1               5                   10                  15

Ala Phe

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 5

Asp Trp Phe Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 6

Asp Trp Leu Lys Ala Phe Tyr Asp Lys Val Phe Glu Lys Phe Lys Glu
1               5                   10                  15

Phe Phe
```

```
<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 7

Asp Trp Leu Lys Ala Phe Tyr Asp Lys Phe Phe Glu Lys Phe Lys Glu
1               5                   10                  15

Phe Phe

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 8

Asp Trp Phe Lys Ala Phe Tyr Asp Lys Phe Phe Glu Lys Phe Lys Glu
1               5                   10                  15

Phe Phe

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 9

Asp Trp Leu Lys Ala Phe Tyr Asp Lys Val Ala Glu Lys Leu Lys Glu
1               5                   10                  15

Phe Phe

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 11

Asp Trp Leu Lys Ala Phe Tyr Asp Lys Val Phe Glu Lys Leu Lys Glu
1               5                   10                  15

Phe Phe
```

```
<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 12

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 13

Asp Trp Leu Lys Ala Phe Tyr Asp Lys Val Phe Glu Lys Phe Lys Glu
1               5                   10                  15

Phe Phe

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 14

Glu Trp Leu Lys Leu Phe Tyr Glu Lys Val Leu Glu Lys Phe Lys Glu
1               5                   10                  15

Ala Phe

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 15

Glu Trp Leu Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 16

Glu Trp Leu Lys Ala Phe Tyr Asp Lys Val Ala Glu Lys Leu Lys Glu
1               5                   10                  15

Phe Phe
```

```
<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 17

Glu Trp Leu Lys Ala Phe Tyr Asp Lys Val Phe Glu Lys Phe Lys Glu
1               5                   10                  15

Ala Phe

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 18

Glu Trp Leu Lys Ala Phe Tyr Asp Lys Val Phe Glu Lys Leu Lys Glu
1               5                   10                  15

Phe Phe

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 19

Glu Trp Leu Lys Ala Phe Tyr Asp Lys Val Ala Glu Lys Phe Lys Glu
1               5                   10                  15

Phe Phe

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 20

Glu Trp Leu Lys Ala Phe Tyr Asp Lys Val Phe Glu Lys Phe Lys Glu
1               5                   10                  15

Phe Phe

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 21

Ala Phe Tyr Asp Lys Val Ala Glu Lys Leu Lys Glu Ala Phe
1               5                   10

<210> SEQ ID NO 22
<211> LENGTH: 14
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 22

Ala Phe Tyr Asp Lys Val Ala Glu Lys Phe Lys Glu Ala Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 23

Ala Phe Tyr Asp Lys Val Ala Glu Lys Phe Lys Glu Ala Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 24

Ala Phe Tyr Asp Lys Phe Phe Glu Lys Phe Lys Glu Phe Phe
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 25

Ala Phe Tyr Asp Lys Phe Phe Glu Lys Phe Lys Glu Phe Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 27

Ala Phe Tyr Asp Lys Val Ala Glu Lys Leu Lys Glu Phe Phe
1               5                   10
```

```
<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 29

Ala Phe Tyr Asp Lys Val Phe Glu Lys Leu Lys Glu Phe Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 30

Ala Phe Tyr Asp Lys Val Ala Glu Lys Phe Lys Glu Phe Phe
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 31

Lys Ala Phe Tyr Asp Lys Val Phe Glu Lys Phe Lys Glu Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 32

Leu Phe Tyr Glu Lys Val Leu Glu Lys Phe Lys Glu Ala Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 35

Ala Phe Tyr Asp Lys Val Phe Glu Lys Phe Lys Glu Ala Phe
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 36

Ala Phe Tyr Asp Lys Val Phe Glu Lys Leu Lys Glu Phe Phe
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 39

Asp Trp Leu Lys Ala Leu Tyr Asp Lys Val Ala Glu Lys Leu Lys Glu
1               5                   10                  15

Ala Leu

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 40

Asp Trp Phe Lys Ala Phe Tyr Glu Lys Val Ala Glu Lys Leu Lys Glu
1               5                   10                  15

Phe Phe

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 41

Asp Trp Phe Lys Ala Phe Tyr Glu Lys Phe Phe Glu Lys Phe Lys Glu
1               5                   10                  15

Phe Phe

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 42

Glu Trp Leu Lys Ala Leu Tyr Glu Lys Val Ala Glu Lys Leu Lys Glu
1               5                   10                  15

Ala Leu

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 43

Glu Trp Leu Lys Ala Phe Tyr Glu Lys Val Ala Glu Lys Leu Lys Glu
1               5                   10                  15

Ala Phe

<210> SEQ ID NO 44
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 44

Glu Trp Phe Lys Ala Phe Tyr Glu Lys Val Ala Glu Lys Leu Lys Glu
1               5                   10                  15

Phe Phe

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 45

Glu Trp Leu Lys Ala Phe Tyr Glu Lys Val Phe Glu Lys Phe Lys Glu
1               5                   10                  15

Phe Phe

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 46

Glu Trp Leu Lys Ala Phe Tyr Glu Lys Phe Phe Glu Lys Phe Lys Glu
1               5                   10                  15

Phe Phe

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 47

Glu Trp Phe Lys Ala Phe Tyr Glu Lys Phe Phe Glu Lys Phe Lys Glu
1               5                   10                  15

Phe Phe

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 48

Asp Phe Leu Lys Ala Trp Tyr Asp Lys Val Ala Glu Lys Leu Lys Glu
1               5                   10                  15

Ala Trp

<210> SEQ ID NO 49
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 49

Glu Phe Leu Lys Ala Trp Tyr Glu Lys Val Ala Glu Lys Leu Lys Glu
1               5                   10                  15

Ala Trp

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 50

Asp Phe Trp Lys Ala Trp Tyr Asp Lys Val Ala Glu Lys Leu Lys Glu
1               5                   10                  15

Trp Trp

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 51

Glu Phe Trp Lys Ala Trp Tyr Glu Lys Val Ala Glu Lys Leu Lys Glu
1               5                   10                  15

Trp Trp

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 52

Asp Lys Leu Lys Ala Phe Tyr Asp Lys Val Phe Glu Trp Ala Lys Glu
1               5                   10                  15

Ala Phe

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 53

Asp Lys Trp Lys Ala Val Tyr Asp Lys Phe Ala Glu Ala Phe Lys Glu
1               5                   10                  15

Phe Leu

<210> SEQ ID NO 54
<211> LENGTH: 18
<212> TYPE: PRT
<213> ORGANISM: Artificial Sequence
```

```
-continued

<220> FEATURE:
<223> OTHER INFORMATION: Description of Artificial Sequence: note =
      Synthetic Construct

<400> SEQUENCE: 54

Glu Lys Leu Lys Ala Phe Tyr Glu Lys Val Phe Glu Trp Ala Lys Glu
1               5                   10                  15

Ala Phe

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 55

Glu Lys Trp Lys Ala Val Tyr Glu Lys Phe Ala Glu Ala Phe Lys Glu
1               5                   10                  15

Phe Leu

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 56

Asp Trp Leu Lys Ala Phe Val Asp Lys Phe Ala Glu Lys Phe Lys Glu
1               5                   10                  15

Ala Tyr

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 57

Glu Lys Trp Lys Ala Val Tyr Glu Lys Phe Ala Glu Ala Phe Lys Glu
1               5                   10                  15

Phe Leu

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 58

Asp Trp Leu Lys Ala Phe Val Tyr Asp Lys Val Phe Lys Leu Lys Glu
1               5                   10                  15

Phe Phe

<210> SEQ ID NO 59
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 59

Glu Trp Leu Lys Ala Phe Val Tyr Glu Lys Val Phe Lys Leu Lys Glu
1               5                   10                  15

Phe Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 60

Asp Trp Leu Arg Ala Phe Tyr Asp Lys Val Ala Glu Lys Leu Lys Glu
1               5                   10                  15

Ala Phe

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 61

Glu Trp Leu Arg Ala Phe Tyr Glu Lys Val Ala Glu Lys Leu Lys Glu
1               5                   10                  15

Ala Phe

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 62

Asp Trp Leu Lys Ala Phe Tyr Asp Arg Val Ala Glu Lys Leu Lys Glu
1               5                   10                  15

Ala Phe

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 63

Glu Trp Leu Lys Ala Phe Tyr Glu Arg Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 64

Asp Trp Leu Lys Ala Phe Tyr Asp Lys Val Ala Glu Arg Leu Lys Glu
1               5                   10                  15

Ala Phe

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 65

Glu Trp Leu Lys Ala Phe Tyr Glu Lys Val Ala Glu Arg Leu Lys Glu
1               5                   10                  15

Ala Phe

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 66

Asp Trp Leu Lys Ala Phe Tyr Asp Lys Val Ala Glu Lys Leu Arg Glu
1               5                   10                  15

Ala Phe

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 67

Glu Trp Leu Lys Ala Phe Tyr Glu Lys Val Ala Glu Lys Leu Arg Glu
1               5                   10                  15

Ala Phe

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 68

Asp Trp Leu Lys Ala Phe Tyr Asp Arg Val Ala Glu Arg Leu Lys Glu
1               5                   10                  15

Ala Phe

<210> SEQ ID NO 69
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 69

Glu Trp Leu Lys Ala Phe Tyr Glu Arg Val Ala Glu Arg Leu Lys Glu
1               5                   10                  15

Ala Phe

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 70

Asp Trp Leu Arg Ala Phe Tyr Asp Lys Val Ala Glu Lys Leu Arg Glu
1               5                   10                  15

Ala Phe

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 71

Glu Trp Leu Arg Ala Phe Tyr Glu Lys Val Ala Glu Lys Leu Arg Glu
1               5                   10                  15

Ala Phe

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 72

Asp Trp Leu Arg Ala Phe Tyr Asp Arg Val Ala Glu Lys Leu Lys Glu
1               5                   10                  15

Ala Phe

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 73

Glu Trp Leu Arg Ala Phe Tyr Glu Arg Val Ala Glu Lys Leu Lys Glu
1               5                   10                  15

Ala Phe

<210> SEQ ID NO 74
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 74

Asp Trp Leu Lys Ala Phe Tyr Asp Lys Val Ala Glu Arg Leu Arg Glu
1               5                   10                  15

Ala Phe

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 75

Glu Trp Leu Lys Ala Phe Tyr Glu Lys Val Ala Glu Arg Leu Arg Glu
1               5                   10                  15

Ala Phe

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 76

Asp Trp Leu Arg Ala Phe Tyr Asp Lys Val Ala Glu Arg Leu Lys Glu
1               5                   10                  15

Ala Phe

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 77

Glu Trp Leu Arg Ala Phe Tyr Glu Lys Val Ala Glu Arg Leu Lys Glu
1               5                   10                  15

Ala Phe

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 78

Asp Trp Leu Lys Ala Phe Tyr Asp Lys Val Ala Glu Lys Leu Lys Glu
1               5                   10                  15

Ala Phe Pro Asp Trp
            20

<210> SEQ ID NO 79
<211> LENGTH: 37
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 79

Leu Lys Ala Phe Tyr Asp Lys Val Ala Glu Lys Leu Lys Glu Ala Phe
1               5                   10                  15

Asp Trp Leu Lys Ala Phe Tyr Asp Lys Val Ala Glu Lys Leu Lys Glu
            20                  25                  30

Phe Phe Pro Asp Trp
        35

<210> SEQ ID NO 80
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 80

Leu Lys Ala Phe Tyr Asp Lys Val Ala Glu Lys Leu Lys Glu Phe Phe
1               5                   10                  15

Asp Trp Phe Lys Ala Phe Tyr Asp Lys Val Ala Glu Lys Leu Lys Glu
            20                  25                  30

Ala Phe Pro Asp Trp
        35

<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 81

Phe Lys Ala Phe Tyr Asp Lys Val Ala Glu Lys Leu Lys Glu Ala Phe
1               5                   10                  15

Asp Lys Leu Lys Ala Phe Tyr Asp Lys Val Phe Glu Trp Ala Lys Glu
            20                  25                  30

Ala Phe Pro Asp Lys
        35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 82

Leu Lys Ala Phe Tyr Asp Lys Val Phe Glu Trp Leu Lys Glu Ala Phe
1               5                   10                  15

Asp Lys Trp Lys Ala Val Tyr Asp Lys Phe Ala Glu Ala Phe Lys Glu
            20                  25                  30

Phe Leu Pro Asp Lys
        35

<210> SEQ ID NO 83
<211> LENGTH: 37
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 83

Trp Lys Ala Val Tyr Asp Lys Phe Ala Glu Ala Phe Lys Glu Phe Leu
1               5                   10                  15

Asp Trp Phe Lys Ala Phe Tyr Asp Lys Val Ala Glu Lys Phe Lys Glu
            20                  25                  30

Ala Phe Pro Asp Trp
        35

<210> SEQ ID NO 84
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 84

Phe Lys Ala Phe Tyr Asp Lys Val Ala Glu Lys Phe Lys Glu Ala Phe
1               5                   10                  15

Asp Trp Leu Lys Ala Phe Val Tyr Asp Lys Val Phe Lys Leu Lys Glu
            20                  25                  30

Phe Phe Pro Asp Trp
        35

<210> SEQ ID NO 85
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 85

Leu Lys Ala Phe Val Tyr Asp Lys Val Phe Leu Lys Glu Phe Phe
1               5                   10                  15

Asp Trp Leu Lys Ala Phe Tyr Asp Lys Phe Ala Glu Lys Phe Lys Glu
            20                  25                  30

Phe Phe Pro Asp Trp
        35

<210> SEQ ID NO 86
<211> LENGTH: 34
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 86

Leu Lys Ala Phe Tyr Asp Lys Phe Ala Glu Lys Phe Lys Glu Phe Phe
1               5                   10                  15

Glu Trp Phe Lys Ala Phe Tyr Glu Lys Val Ala Glu Lys Phe Lys Glu
            20                  25                  30

Ala Phe

<210> SEQ ID NO 87
<211> LENGTH: 14
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 87

Asp Trp Phe Lys Ala Phe Tyr Asp Lys Val Ala Glu Lys Phe
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 88

Phe Lys Ala Phe Tyr Asp Lys Val Ala Glu Lys Phe Lys Glu
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 89

Phe Lys Ala Phe Tyr Glu Lys Val Ala Glu Lys Phe Lys Glu
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 90

Phe Lys Ala Phe Tyr Asp Lys Val Ala Glu Lys Phe Lys Glu
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 91

Phe Lys Ala Phe Tyr Glu Lys Val Ala Glu Lys Phe Lys Glu
1               5                   10

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 92

Asp Trp Phe Lys Ala Phe Tyr Asp Lys Val Ala Glu Lys Phe Lys Glu
1               5                   10                  15

Ala Phe
```

```
<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 93

Glu Trp Phe Lys Ala Phe Tyr Glu Lys Val Ala Glu Lys Phe Lys Glu
1               5                   10                  15

Ala Phe

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 94

Ala Phe Tyr Asp Lys Val Ala Glu Lys Phe Lys Glu Ala Phe
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 95

Asp Trp Phe Lys Ala Phe Tyr Asp Lys Val Ala Glu Lys Phe
1               5                   10

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 96

Asp Trp Leu Lys Ala Phe Tyr Asp Lys Val Phe Glu Lys Phe Lys Glu
1               5                   10                  15

Phe Phe

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 97

Glu Trp Leu Lys Ala Phe Tyr Glu Lys Val Phe Glu Lys Phe Lys Glu
1               5                   10                  15

Phe Phe

<210> SEQ ID NO 98
<211> LENGTH: 14
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 98

Ala Phe Tyr Asp Lys Val Phe Glu Lys Phe Lys Glu Phe Phe
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 99

Ala Phe Tyr Glu Lys Val Phe Glu Lys Phe Lys Glu Phe Phe
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 100

Asp Trp Leu Lys Ala Phe Tyr Asp Lys Val Phe Glu Lys Phe
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 101

Glu Trp Leu Lys Ala Phe Tyr Glu Lys Val Phe Glu Lys Phe
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 102

Leu Lys Ala Phe Tyr Asp Lys Val Phe Glu Lys Phe Lys Glu
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 103

Leu Lys Ala Phe Tyr Glu Lys Val Phe Glu Lys Phe Lys Glu
1               5                   10
```

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 104

Phe Ala Glu Lys Phe Lys Glu Ala Val Lys Asp Tyr Phe Ala Lys Phe
1               5                   10                  15

Trp Asp

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 105

Asp Lys Trp Lys Ala Val Tyr Asp Lys Phe Ala Glu Ala Phe Lys Glu
1               5                   10                  15

Phe Leu

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 106

Asp Lys Leu Lys Ala Phe Tyr Asp Lys Val Phe Glu Trp Ala Lys Glu
1               5                   10                  15

Ala Phe

<210> SEQ ID NO 107

<400> SEQUENCE: 107

000

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 108

Glu Trp Phe Lys Ala Phe Tyr Glu Lys Val Ala Asp Lys Phe Lys Asp
1               5                   10                  15

Ala Phe

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 109

Glu Trp Phe Lys Ala Phe Tyr Asp Lys Val Ala Asp Lys Phe Lys Glu
1               5                   10                  15

Ala Phe

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 110

Asp Trp Phe Lys Ala Phe Tyr Glu Lys Val Ala Asp Lys Phe Lys Glu
1               5                   10                  15

Ala Glu

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 111

Asp Trp Phe Lys Ala Phe Tyr Glu Lys Val Ala Glu Lys Phe Lys Asp
1               5                   10                  15

Ala Phe

<210> SEQ ID NO 112

<400> SEQUENCE: 112

000

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 113

Asp Phe Trp Lys Ala Phe Tyr Asp Lys Val Ala Glu Lys Phe Lys Glu
1               5                   10                  15

Ala Phe

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 114

Glu Phe Trp Lys Ala Phe Tyr Glu Lys Val Ala Asp Lys Phe Lys Asp
1               5                   10                  15

Ala Phe

```
<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 115

Glu Phe Trp Lys Ala Phe Tyr Asp Lys Val Ala Asp Lys Phe Lys Glu
1               5                   10                  15

Ala Phe

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 116

Asp Phe Trp Lys Ala Phe Tyr Glu Lys Val Ala Asp Lys Phe Lys Glu
1               5                   10                  15

Ala Phe

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 117

Asp Phe Trp Lys Ala Phe Tyr Glu Lys Val Ala Glu Lys Phe Lys Asp
1               5                   10                  15

Ala Phe

<210> SEQ ID NO 118

<400> SEQUENCE: 118

000

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 119

Asp Trp Phe Lys Ala Tyr Phe Asp Lys Val Ala Glu Lys Phe Lys Glu
1               5                   10                  15

Ala Phe

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 120
```

```
Glu Trp Phe Lys Ala Tyr Phe Glu Lys Val Ala Asp Lys Glu Lys Asp
1               5                   10                  15

Ala Phe

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 121

Glu Trp Phe Lys Ala Tyr Phe Asp Lys Val Ala Asp Lys Phe Lys Glu
1               5                   10                  15

Ala Phe

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 122

Asp Trp Phe Lys Ala Tyr Phe Glu Lys Val Ala Asp Lys Phe Lys Glu
1               5                   10                  15

Ala Phe

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 123

Asp Trp Phe Lys Ala Tyr Phe Glu Lys Val Ala Glu Lys Phe Lys Asp
1               5                   10                  15

Ala Phe

<210> SEQ ID NO 124

<400> SEQUENCE: 124

000

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 125

Asp Trp Phe Lys Ala Phe Val Asp Lys Tyr Ala Glu Lys Phe Lys Glu
1               5                   10                  15

Ala Phe

<210> SEQ ID NO 126
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 126

Glu Trp Phe Lys Ala Phe Val Glu Lys Tyr Ala Asp Lys Phe Lys Asp
1               5                   10                  15

Ala Phe

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 127

Glu Trp Phe Lys Ala Phe Val Asp Lys Tyr Ala Asp Lys Phe Lys Glu
1               5                   10                  15

Ala Phe

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 128

Asp Trp Phe Lys Ala Phe Val Glu Lys Tyr Ala Asp Lys Phe Lys Glu
1               5                   10                  15

Ala Phe

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 129

Asp Trp Phe Lys Ala Phe Val Glu Lys Tyr Ala Glu Lys Phe Lys Asp
1               5                   10                  15

Ala Phe

<210> SEQ ID NO 130

<400> SEQUENCE: 130

000

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 131

Asp Trp Phe Lys Ala Phe Tyr Asp Lys Ala Val Glu Lys Phe Lys Glu
```

```
1               5                   10                  15
Ala Phe

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 132

Glu Trp Phe Lys Ala Phe Tyr Glu Lys Ala Val Asp Lys Phe Lys Asp
1               5                   10                  15

Ala Phe

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 133

Glu Trp Phe Lys Ala Phe Tyr Asp Lys Ala Val Asp Lys Phe Lys Glu
1               5                   10                  15

Ala Phe

<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 134

Asp Trp Phe Lys Ala Phe Tyr Glu Lys Ala Val Asp Lys Phe Lys Glu
1               5                   10                  15

Ala Phe

<210> SEQ ID NO 135
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 135

Asp Trp Phe Lys Ala Phe Tyr Glu Lys Ala Val Glu Lys Phe Lys Asp
1               5                   10                  15

Ala Phe

<210> SEQ ID NO 136

<400> SEQUENCE: 136

000

<210> SEQ ID NO 137
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 137

Asp Trp Phe Lys Ala Phe Tyr Asp Lys Val Phe Glu Lys Ala Lys Glu
1               5                   10                  15

Ala Phe

<210> SEQ ID NO 138
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 138

Glu Trp Phe Lys Ala Phe Tyr Glu Lys Val Phe Asp Lys Ala Lys Asp
1               5                   10                  15

Ala Phe

<210> SEQ ID NO 139
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 139

Glu Trp Phe Lys Ala Phe Tyr Asp Lys Val Phe Asp Lys Ala Lys Glu
1               5                   10                  15

Ala Phe

<210> SEQ ID NO 140
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 140

Asp Trp Phe Lys Ala Phe Tyr Glu Lys Val Phe Asp Lys Ala Lys Glu
1               5                   10                  15

Ala Phe

<210> SEQ ID NO 141
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 141

Asp Trp Phe Lys Ala Phe Tyr Glu Lys Val Phe Glu Lys Ala Lys Asp
1               5                   10                  15

Ala Phe

<210> SEQ ID NO 142
<211> LENGTH: 13
<212> TYPE: PRT
<213> ORGANISM: Artificial Sequence
```

-continued

```
<220> FEATURE:
<223> OTHER INFORMATION: Description of Artificial Sequence: note =
      Synthetic Construct

<400> SEQUENCE: 142

Ala Arg Thr Ile Phe Ile Cys Ile Ala Leu Ser Glu Gln
1               5                   10

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 143

Asp Trp Phe Lys Ala Phe Tyr Asp Lys Val Ala Glu Lys Ala Lys Glu
1               5                   10                  15

Phe Phe

<210> SEQ ID NO 144
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 144

Glu Trp Phe Lys Ala Phe Tyr Glu Lys Val Ala Asp Lys Ala Lys Asp
1               5                   10                  15

Phe Phe

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 145

Glu Trp Phe Lys Ala Phe Tyr Asp Lys Val Ala Asp Lys Ala Lys Glu
1               5                   10                  15

Phe Phe

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 146

Asp Trp Phe Lys Ala Phe Tyr Glu Lys Val Ala Asp Lys Ala Lys Glu
1               5                   10                  15

Phe Phe

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: note =
```

Synthetic Construct

<400> SEQUENCE: 147

Asp Trp Phe Lys Ala Phe Tyr Glu Lys Val Ala Glu Lys Ala Lys Asp
1               5                   10                  15

Phe Phe

<210> SEQ ID NO 148

<400> SEQUENCE: 148

000

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 149

Asp Trp Phe Lys Ala Phe Tyr Asp Lys Val Ala Glu Lys Phe Lys Glu
1               5                   10                  15

Phe Ala

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 150

Glu Trp Phe Lys Ala Phe Tyr Glu Lys Val Ala Asp Lys Phe Lys Asp
1               5                   10                  15

Phe Ala

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 151

Glu Trp Phe Lys Ala Phe Tyr Asp Lys Val Ala Asp Lys Phe Lys Glu
1               5                   10                  15

Phe Ala

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 152

Asp Trp Phe Lys Ala Phe Tyr Glu Lys Val Ala Asp Lys Phe Lys Glu
1               5                   10                  15

Phe Ala

```
<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 153

Asp Trp Phe Lys Ala Phe Tyr Glu Lys Val Ala Glu Lys Phe Lys Asp
1               5                   10                  15

Phe Ala

<210> SEQ ID NO 154

<400> SEQUENCE: 154

000

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 155

Asp Ala Phe Lys Ala Phe Tyr Asp Lys Val Ala Glu Lys Phe Lys Glu
1               5                   10                  15

Trp Phe

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 156

Glu Ala Phe Lys Ala Phe Tyr Glu Lys Val Ala Asp Lys Phe Lys Asp
1               5                   10                  15

Trp Phe

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 157

Glu Ala Phe Lys Ala Phe Tyr Asp Lys Val Ala Asp Lys Glu Lys Glu
1               5                   10                  15

Trp Phe

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 158

Asp Ala Phe Lys Ala Phe Tyr Glu Lys Val Ala Asp Lys Phe Lys Glu
1               5                   10                  15

Trp Phe

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 159

Asp Ala Phe Lys Ala Phe Tyr Glu Lys Val Ala Glu Lys Phe Lys Asp
1               5                   10                  15

Trp Phe

<210> SEQ ID NO 160

<400> SEQUENCE: 160

000

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 161

Asp Ala Phe Lys Ala Phe Tyr Asp Lys Val Trp Glu Lys Phe Lys Glu
1               5                   10                  15

Ala Phe

<210> SEQ ID NO 162
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 162

Glu Ala Phe Lys Ala Phe Tyr Glu Lys Val Trp Asp Lys Phe Lys Asp
1               5                   10                  15

Ala Phe

<210> SEQ ID NO 163
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 163

Glu Ala Phe Lys Ala Phe Tyr Asp Lys Val Trp Asp Lys Phe Lys Glu
1               5                   10                  15

Ala Phe

<210> SEQ ID NO 164
```

```
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 164

Asp Ala Phe Lys Ala Phe Tyr Glu Lys Val Trp Asp Lys Phe Lys Glu
1               5                   10                  15

Ala Phe

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 165

Asp Ala Phe Lys Ala Phe Tyr Glu Lys Val Trp Glu Lys Phe Lys Asp
1               5                   10                  15

Ala Phe

<210> SEQ ID NO 166

<400> SEQUENCE: 166

000

<210> SEQ ID NO 167
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 167

Asp Tyr Phe Lys Ala Phe Trp Asp Lys Val Ala Glu Lys Phe Lys Glu
1               5                   10                  15

Ala Phe

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 168

Glu Tyr Phe Lys Ala Phe Trp Glu Lys Val Ala Asp Lys Phe Lys Asp
1               5                   10                  15

Ala Phe

<210> SEQ ID NO 169
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 169
```

```
Glu Tyr Phe Lys Ala Phe Trp Asp Lys Val Ala Asp Lys Phe Lys Glu
1               5                   10                  15

Ala Phe

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 170

Asp Tyr Phe Lys Ala Phe Trp Glu Lys Val Ala Asp Lys Phe Lys Glu
1               5                   10                  15

Ala Phe

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 171

Asp Tyr Phe Lys Ala Phe Trp Glu Lys Val Ala Glu Lys Phe Lys Asp
1               5                   10                  15

Ala Phe

<210> SEQ ID NO 172

<400> SEQUENCE: 172

000

<210> SEQ ID NO 173
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 173

Asp Trp Ala Lys Ala Phe Tyr Asp Lys Val Ala Glu Lys Phe Lys Glu
1               5                   10                  15

Phe Phe

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 174

Glu Trp Ala Lys Ala Phe Tyr Glu Lys Val Ala Asp Lys Phe Lys Asp
1               5                   10                  15

Phe Phe

<210> SEQ ID NO 175
<211> LENGTH: 18
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 175

Glu Trp Ala Lys Ala Phe Tyr Asp Lys Val Ala Asp Lys Phe Lys Glu
1               5                   10                  15

Phe Phe

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 176

Asp Trp Ala Lys Ala Phe Tyr Glu Lys Val Ala Asp Lys Phe Lys Glu
1               5                   10                  15

Phe Phe

<210> SEQ ID NO 177
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 177

Asp Trp Ala Lys Ala Phe Tyr Glu Lys Val Ala Glu Lys Phe Lys Asp
1               5                   10                  15

Phe Phe

<210> SEQ ID NO 178

<400> SEQUENCE: 178

000

<210> SEQ ID NO 179
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 179

Asp Trp Phe Lys Ala Ala Tyr Asp Lys Val Ala Glu Lys Phe Lys Glu
1               5                   10                  15

Phe Phe

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 180

Glu Trp Phe Lys Ala Ala Tyr Glu Lys Val Ala Asp Lys Phe Lys Asp
1               5                   10                  15
```

Phe Phe

<210> SEQ ID NO 181
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 181

Glu Trp Phe Lys Ala Ala Tyr Asp Lys Val Ala Asp Lys Phe Lys Glu
1               5                   10                  15

Phe Phe

<210> SEQ ID NO 182
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 182

Asp Trp Phe Lys Ala Ala Tyr Glu Lys Val Ala Asp Lys Phe Lys Glu
1               5                   10                  15

Phe Phe

<210> SEQ ID NO 183
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 183

Asp Trp Phe Lys Ala Ala Tyr Glu Lys Val Ala Glu Lys Phe Lys Asp
1               5                   10                  15

Phe Phe

<210> SEQ ID NO 184

<400> SEQUENCE: 184

000

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 185

Asp Trp Phe Lys Ala Phe Ala Asp Lys Val Ala Glu Lys Phe Lys Glu
1               5                   10                  15

Tyr Phe

<210> SEQ ID NO 186
<211> LENGTH: 18
<212> TYPE: PRT
<213> ORGANISM: Artificial Sequence
<220> FEATURE:

<223> OTHER INFORMATION: Description of Artificial Sequence: note =
      Synthetic Construct

<400> SEQUENCE: 186

Glu Trp Phe Lys Ala Phe Ala Glu Lys Val Ala Asp Lys Phe Lys Asp
1               5                   10                  15

Tyr Phe

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 187

Glu Trp Phe Lys Ala Phe Ala Asp Lys Val Ala Asp Lys Phe Lys Glu
1               5                   10                  15

Tyr Phe

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 188

Asp Trp Phe Lys Ala Phe Ala Glu Lys Val Ala Asp Lys Phe Lys Glu
1               5                   10                  15

Tyr Phe

<210> SEQ ID NO 189
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 189

Asp Trp Phe Lys Ala Phe Ala Glu Lys Val Ala Glu Lys Phe Lys Asp
1               5                   10                  15

Tyr Phe

<210> SEQ ID NO 190

<400> SEQUENCE: 190

000

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 191

Asp Trp Phe Lys Ala Phe Tyr Asp Lys Ala Ala Glu Lys Phe Lys Glu
1               5                   10                  15

Val Phe

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 192

Glu Trp Phe Lys Ala Phe Tyr Glu Lys Ala Ala Asp Lys Phe Lys Asp
1               5                   10                  15

Val Phe

<210> SEQ ID NO 193
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 193

Glu Trp Phe Lys Ala Phe Tyr Asp Lys Ala Ala Asp Lys Phe Lys Glu
1               5                   10                  15

Val Phe

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 194

Asp Trp Phe Lys Ala Phe Tyr Glu Lys Ala Ala Asp Lys Phe Lys Glu
1               5                   10                  15

Val Phe

<210> SEQ ID NO 195
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 195

Asp Trp Phe Lys Ala Phe Tyr Glu Lys Ala Ala Glu Lys Phe Lys Asp
1               5                   10                  15

Val Phe

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 196

Ala Arg Thr Ile Phe Ile Cys Ile Ala Leu Ser Glu Gln
1               5                   10

```
<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 197

Asp Trp Tyr Lys Ala Phe Phe Asp Lys Val Ala Glu Lys Phe Lys Glu
1               5                   10                  15

Ala Phe

<210> SEQ ID NO 198
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 198

Glu Trp Tyr Lys Ala Phe Phe Glu Lys Val Ala Asp Lys Phe Lys Asp
1               5                   10                  15

Ala Phe

<210> SEQ ID NO 199
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 199

Glu Trp Tyr Lys Ala Phe Phe Asp Lys Val Ala Asp Lys Phe Lys Glu
1               5                   10                  15

Ala Phe

<210> SEQ ID NO 200
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 200

Asp Trp Tyr Lys Ala Phe Phe Glu Lys Val Ala Asp Lys Phe Lys Glu
1               5                   10                  15

Ala Phe

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 201

Asp Trp Tyr Lys Ala Phe Phe Glu Lys Val Ala Glu Lys Phe Lys Asp
1               5                   10                  15

Ala Phe
```

```
<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 202

Ala Arg Thr Ile Phe Ile Cys Ile Ala Leu Ser Glu Gln
1               5                   10

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 203

Asp Trp Val Lys Ala Phe Tyr Asp Lys Phe Ala Glu Lys Phe Lys Glu
1               5                   10                  15

Ala Phe

<210> SEQ ID NO 204
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 204

Glu Trp Val Lys Ala Phe Tyr Glu Lys Phe Ala Asp Lys Phe Lys Asp
1               5                   10                  15

Ala Phe

<210> SEQ ID NO 205
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 205

Glu Trp Val Lys Ala Phe Tyr Asp Lys Phe Ala Asp Lys Phe Lys Glu
1               5                   10                  15

Ala Phe

<210> SEQ ID NO 206
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 206

Asp Trp Val Lys Ala Phe Tyr Glu Lys Phe Ala Asp Lys Phe Lys Glu
1               5                   10                  15

Ala Phe

<210> SEQ ID NO 207
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 207

Asp Trp Val Lys Ala Phe Tyr Glu Lys Phe Ala Glu Lys Phe Lys Asp
1               5                   10                  15

Ala Phe

<210> SEQ ID NO 208

<400> SEQUENCE: 208

000

<210> SEQ ID NO 209
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 209

Asp Trp Phe Lys Ala Phe Phe Asp Lys Val Ala Glu Lys Tyr Lys Glu
1               5                   10                  15

Ala Phe

<210> SEQ ID NO 210
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 210

Glu Trp Phe Lys Ala Phe Phe Glu Lys Val Ala Asp Lys Tyr Lys Asp
1               5                   10                  15

Ala Phe

<210> SEQ ID NO 211
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 211

Glu Trp Phe Lys Ala Phe Phe Asp Lys Val Ala Asp Lys Tyr Lys Glu
1               5                   10                  15

Ala Phe

<210> SEQ ID NO 212
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 212

Asp Trp Phe Lys Ala Phe Phe Glu Lys Val Ala Asp Lys Tyr Lys Glu
```

```
                1               5                  10                  15
Ala Glu

<210> SEQ ID NO 213
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 213

Asp Trp Phe Lys Ala Phe Phe Glu Lys Val Ala Asp Lys Tyr Lys Glu
1               5                  10                  15

Ala Phe

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 214

Ala Arg Thr Ile Phe Ile Cys Ile Ala Leu Ser Glu Gln
1               5                  10

<210> SEQ ID NO 215
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 215

Asp Trp Phe Lys Ala Phe Phe Asp Lys Val Ala Glu Lys Phe Lys Glu
1               5                  10                  15

Ala Tyr

<210> SEQ ID NO 216
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 216

Glu Trp Phe Lys Ala Phe Phe Glu Lys Val Ala Asp Lys Phe Lys Asp
1               5                  10                  15

Ala Tyr

<210> SEQ ID NO 217
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 217

Glu Trp Phe Lys Ala Phe Phe Asp Lys Val Ala Asp Lys Phe Lys Glu
1               5                  10                  15
```

Ala Tyr

<210> SEQ ID NO 218
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 218

Asp Trp Phe Lys Ala Phe Phe Glu Lys Val Ala Asp Lys Phe Lys Glu
1               5                   10                  15

Ala Tyr

<210> SEQ ID NO 219
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 219

Asp Trp Phe Lys Ala Phe Phe Glu Lys Val Ala Glu Lys Phe Lys Asp
1               5                   10                  15

Ala Tyr

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 220

Ala Arg Thr Ile Phe Ile Cys Ile Ala Leu Ser Glu Gln
1               5                   10

<210> SEQ ID NO 221
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 221

Asp Trp Phe Lys Ala Phe Tyr Asp Lys Phe Ala Glu Lys Phe Lys Glu
1               5                   10                  15

Ala Val

<210> SEQ ID NO 222
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 222

Glu Trp Phe Lys Ala Phe Tyr Glu Lys Phe Ala Asp Lys Phe Lys Asp
1               5                   10                  15

Ala Val

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 223

Glu Trp Phe Lys Ala Phe Tyr Asp Lys Phe Ala Asp Lys Phe Lys Glu
1               5                   10                  15

Ala Val

<210> SEQ ID NO 224
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 224

Asp Trp Phe Lys Ala Glu Tyr Glu Lys Phe Ala Asp Lys Phe Lys Glu
1               5                   10                  15

Ala Val

<210> SEQ ID NO 225
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 225

Asp Trp Phe Lys Ala Phe Tyr Glu Lys Phe Ala Glu Lys Phe Lys Asp
1               5                   10                  15

Ala Val

<210> SEQ ID NO 226

<400> SEQUENCE: 226

000

<210> SEQ ID NO 227
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 227

Asp Lys Phe Lys Ala Phe Tyr Asp Lys Val Ala Glu Lys Phe Trp Glu
1               5                   10                  15

Ala Phe

<210> SEQ ID NO 228
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct -continued

```
<400> SEQUENCE: 228

Glu Lys Phe Lys Ala Phe Tyr Glu Lys Val Ala Asp Lys Phe Trp Asp
1               5                   10                  15

Ala Phe

<210> SEQ ID NO 229
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 229

Glu Lys Phe Lys Ala Phe Tyr Asp Lys Val Ala Asp Lys Phe Trp Glu
1               5                   10                  15

Ala Phe

<210> SEQ ID NO 230
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 230

Asp Lys Phe Lys Ala Phe Tyr Glu Lys Val Ala Asp Lys Phe Trp Glu
1               5                   10                  15

Ala Phe

<210> SEQ ID NO 231
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 231

Asp Lys Phe Lys Ala Phe Tyr Glu Lys Val Ala Glu Lys Phe Trp Asp
1               5                   10                  15

Ala Phe

<210> SEQ ID NO 232

<400> SEQUENCE: 232

000

<210> SEQ ID NO 233
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 233

Asp Lys Trp Lys Ala Phe Tyr Asp Lys Val Ala Glu Lys Phe Phe Glu
1               5                   10                  15

Ala Phe

<210> SEQ ID NO 234
```

```
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 234

Glu Lys Trp Lys Ala Phe Tyr Glu Lys Val Ala Asp Lys Phe Phe Asp
1               5                   10                  15

Ala Phe

<210> SEQ ID NO 235
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 235

Glu Lys Trp Lys Ala Phe Tyr Asp Lys Val Ala Asp Lys Phe Phe Glu
1               5                   10                  15

Ala Phe

<210> SEQ ID NO 236
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 236

Asp Lys Trp Lys Ala Phe Tyr Glu Lys Val Ala Asp Lys Phe Phe Glu
1               5                   10                  15

Ala Phe

<210> SEQ ID NO 237
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 237

Asp Lys Trp Lys Ala Phe Tyr Glu Lys Val Ala Glu Lys Phe Phe Asp
1               5                   10                  15

Ala Phe

<210> SEQ ID NO 238

<400> SEQUENCE: 238

000

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 239
```

```
Asp Lys Phe Lys Ala Phe Tyr Asp Lys Trp Ala Glu Val Phe Lys Glu
1               5                   10                  15

Ala Phe

<210> SEQ ID NO 240

<400> SEQUENCE: 240

000

<210> SEQ ID NO 241
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 241

Glu Lys Phe Lys Ala Phe Tyr Glu Lys Trp Ala Asp Val Phe Lys Asp
1               5                   10                  15

Ala Phe

<210> SEQ ID NO 242
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 242

Glu Lys Phe Lys Ala Phe Tyr Asp Lys Trp Ala Asp Val Phe Lys Glu
1               5                   10                  15

Ala Phe

<210> SEQ ID NO 243
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 243

Asp Lys Phe Lys Ala Phe Tyr Glu Lys Trp Ala Asp Val Phe Lys Glu
1               5                   10                  15

Ala Phe

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 244

Asp Lys Phe Lys Ala Phe Tyr Glu Lys Trp Ala Glu Val Phe Lys Asp
1               5                   10                  15

Ala Phe

<210> SEQ ID NO 245

<400> SEQUENCE: 245
```

000

<210> SEQ ID NO 246
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 246

Asp Lys Phe Lys Ala Phe Tyr Asp Lys Val Ala Glu Phe Trp Lys Glu
1               5                   10                  15

Ala Phe

<210> SEQ ID NO 247

<400> SEQUENCE: 247

000

<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 248

Glu Lys Phe Lys Ala Phe Tyr Glu Lys Val Ala Asp Phe Trp Lys Asp
1               5                   10                  15

Ala Phe

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 249

Glu Lys Phe Lys Ala Phe Tyr Asp Lys Val Ala Asp Phe Trp Lys Glu
1               5                   10                  15

Ala Phe

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 250

Asp Lys Phe Lys Ala Phe Tyr Glu Lys Val Ala Asp Phe Trp Lys Glu
1               5                   10                  15

Ala Phe

<210> SEQ ID NO 251
<211> LENGTH: 18
<212> TYPE: PRT
<213> ORGANISM: Artificial Sequence
<220> FEATURE:

```
<223> OTHER INFORMATION: Description of Artificial Sequence: note =
      Synthetic Construct

<400> SEQUENCE: 251

Asp Lys Phe Lys Ala Phe Tyr Glu Lys Val Ala Glu Phe Trp Lys Asp
1               5                   10                  15

Ala Phe

<210> SEQ ID NO 252

<400> SEQUENCE: 252

000

<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 253

Phe Ala Glu Lys Phe Lys Glu Ala Val Lys Asp Tyr Phe Ala Lys Phe
1               5                   10                  15

Trp Asp

<210> SEQ ID NO 254
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 254

Phe Ala Asp Lys Phe Lys Asp Ala Val Lys Glu Tyr Phe Ala Lys Phe
1               5                   10                  15

Trp Glu

<210> SEQ ID NO 255
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 255

Phe Ala Asp Lys Phe Lys Glu Ala Val Lys Asp Tyr Phe Ala Lys Phe
1               5                   10                  15

Trp Glu

<210> SEQ ID NO 256
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 256

Phe Ala Glu Lys Phe Lys Asp Ala Val Lys Glu Tyr Phe Ala Lys Phe
1               5                   10                  15

Trp Asp
```

```
<210> SEQ ID NO 257
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 257

Phe Ala Glu Lys Phe Lys Asp Ala Val Lys Asp Tyr Phe Ala Lys Phe
1               5                   10                  15

Trp Glu

<210> SEQ ID NO 258

<400> SEQUENCE: 258

000

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 259

Phe Trp Glu Lys Phe Lys Glu Ala Val Lys Asp Tyr Phe Ala Lys Phe
1               5                   10                  15

Ala Asp

<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 260

Phe Trp Asp Lys Phe Lys Asp Ala Val Lys Glu Tyr Phe Ala Lys Phe
1               5                   10                  15

Ala Glu

<210> SEQ ID NO 261
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 261

Phe Ala Asp Lys Phe Lys Glu Ala Val Lys Asp Tyr Phe Ala Lys Phe
1               5                   10                  15

Trp Glu

<210> SEQ ID NO 262
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 262

Phe Ala Glu Lys Phe Lys Asp Ala Val Lys Glu Tyr Phe Ala Lys Phe
 1               5                  10                  15

Trp Asp

<210> SEQ ID NO 263
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 263

Phe Ala Glu Lys Phe Lys Asp Ala Val Lys Asp Tyr Phe Ala Lys Phe
 1               5                  10                  15

Trp Glu

<210> SEQ ID NO 264

<400> SEQUENCE: 264

000

<210> SEQ ID NO 265
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 265

Phe Phe Glu Lys Phe Lys Glu Ala Val Lys Asp Tyr Phe Ala Lys Ala
 1               5                  10                  15

Trp Asp

<210> SEQ ID NO 266
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 266

Phe Phe Asp Lys Phe Lys Asp Ala Val Lys Glu Tyr Phe Ala Lys Ala
 1               5                  10                  15

Trp Glu

<210> SEQ ID NO 267
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 267

Phe Phe Asp Lys Phe Lys Glu Ala Val Lys Asp Tyr Phe Ala Lys Ala
 1               5                  10                  15

Trp Glu
```

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 268

Phe Phe Glu Lys Phe Lys Asp Ala Val Lys Glu Tyr Phe Ala Lys Ala
1               5                   10                  15

Trp Asp

<210> SEQ ID NO 269
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 269

Phe Phe Glu Lys Phe Lys Asp Ala Val Lys Asp Tyr Phe Ala Lys Ala
1               5                   10                  15

Trp Glu

<210> SEQ ID NO 270

<400> SEQUENCE: 270

000

<210> SEQ ID NO 271
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 271

Phe Ala Glu Lys Ala Lys Glu Phe Val Lys Asp Tyr Phe Ala Lys Phe
1               5                   10                  15

Trp Asp

<210> SEQ ID NO 272
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 272

Phe Ala Asp Lys Ala Lys Asp Phe Val Lys Glu Tyr Phe Ala Lys Phe
1               5                   10                  15

Trp Glu

<210> SEQ ID NO 273
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 273

Phe Ala Asp Lys Ala Lys Glu Phe Val Lys Asp Tyr Phe Ala Lys Phe
1               5                   10                  15

Trp Glu

<210> SEQ ID NO 274
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 274

Phe Ala Glu Lys Ala Lys Asp Phe Val Lys Glu Tyr Phe Ala Lys Phe
1               5                   10                  15

Trp Asp

<210> SEQ ID NO 275
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 275

Phe Ala Glu Lys Ala Lys Asp Phe Val Lys Asp Tyr Phe Ala Lys Phe
1               5                   10                  15

Trp Glu

<210> SEQ ID NO 276

<400> SEQUENCE: 276

000

<210> SEQ ID NO 277
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 277

Phe Ala Glu Lys Phe Lys Glu Val Ala Lys Asp Tyr Phe Ala Lys Phe
1               5                   10                  15

Trp Asp

<210> SEQ ID NO 278
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 278

Phe Ala Asp Lys Phe Lys Asp Val Ala Lys Glu Tyr Phe Ala Lys Phe
1               5                   10                  15

Trp Glu

<210> SEQ ID NO 279
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 279

Phe Ala Asp Lys Phe Lys Glu Val Ala Lys Asp Tyr Phe Ala Lys Phe
1               5                   10                  15

Trp Glu

<210> SEQ ID NO 280
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 280

Phe Ala Glu Lys Phe Lys Asp Val Ala Lys Glu Tyr Phe Ala Lys Phe
1               5                   10                  15

Trp Asp

<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 281

Phe Ala Glu Lys Phe Lys Asp Val Ala Lys Asp Tyr Phe Ala Lys Phe
1               5                   10                  15

Trp Glu

<210> SEQ ID NO 282

<400> SEQUENCE: 282

000

<210> SEQ ID NO 283
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 283

Phe Ala Glu Lys Phe Lys Glu Ala Tyr Lys Asp Val Phe Ala Lys Phe
1               5                   10                  15

Trp Asp

<210> SEQ ID NO 284
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 284

Phe Ala Asp Lys Phe Lys Asp Ala Tyr Lys Glu Val Phe Ala Lys Phe
```

```
<210> SEQ ID NO 285
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 285

Phe Ala Asp Lys Phe Lys Glu Ala Tyr Lys Asp Val Phe Ala Lys Phe
1               5                   10                  15

Trp Glu

<210> SEQ ID NO 286
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 286

Phe Ala Glu Lys Phe Lys Asp Ala Tyr Lys Glu Val Phe Ala Lys Phe
1               5                   10                  15

Trp Asp

<210> SEQ ID NO 287
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 287

Phe Ala Glu Lys Phe Lys Asp Ala Tyr Lys Asp Val Phe Ala Lys Phe
1               5                   10                  15

Trp Glu

<210> SEQ ID NO 288

<400> SEQUENCE: 288

000

<210> SEQ ID NO 289
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 289

Phe Ala Glu Lys Phe Lys Glu Ala Val Lys Asp Phe Tyr Ala Lys Phe
1               5                   10                  15

Trp Asp

<210> SEQ ID NO 290
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 290

Phe Ala Asp Lys Phe Lys Asp Ala Val Lys Glu Phe Tyr Ala Lys Phe
1               5                   10                  15

Trp Glu

<210> SEQ ID NO 291
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 291

Phe Ala Asp Lys Phe Lys Glu Ala Val Lys Asp Phe Tyr Ala Lys Phe
1               5                   10                  15

Trp Glu

<210> SEQ ID NO 292
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 292

Phe Ala Glu Lys Phe Lys Asp Ala Val Lys Glu Phe Tyr Ala Lys Phe
1               5                   10                  15

Trp Asp

<210> SEQ ID NO 293
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 293

Phe Ala Glu Lys Phe Lys Asp Ala Val Lys Asp Phe Tyr Ala Lys Phe
1               5                   10                  15

Trp Glu

<210> SEQ ID NO 294

<400> SEQUENCE: 294

000

<210> SEQ ID NO 295
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 295

Phe Ala Glu Lys Phe Trp Glu Ala Val Lys Asp Tyr Phe Ala Lys Phe
1               5                   10                  15
```

-continued

Lys Asp

```
<210> SEQ ID NO 296
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 296
```

Phe Ala Asp Lys Phe Trp Asp Ala Val Lys Glu Tyr Phe Ala Lys Phe
1               5                   10                  15

Lys Glu

```
<210> SEQ ID NO 297
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 297
```

Phe Ala Asp Lys Phe Trp Glu Ala Val Lys Asp Tyr Phe Ala Lys Phe
1               5                   10                  15

Lys Glu

```
<210> SEQ ID NO 298
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 298
```

Phe Ala Glu Lys Phe Trp Asp Ala Val Lys Glu Tyr Phe Ala Lys Phe
1               5                   10                  15

Lys Asp

```
<210> SEQ ID NO 299
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 299
```

Phe Ala Glu Lys Phe Trp Asp Ala Val Lys Asp Tyr Phe Ala Lys Phe
1               5                   10                  15

Lys Glu

```
<210> SEQ ID NO 300

<400> SEQUENCE: 300

000

<210> SEQ ID NO 301
<211> LENGTH: 18
<212> TYPE: PRT
<213> ORGANISM: Artificial Sequence
<220> FEATURE:
<223> OTHER INFORMATION: Description of Artificial Sequence: note =
```

```
                       Synthetic Construct

<400> SEQUENCE: 301

Ala Phe Glu Lys Phe Lys Glu Ala Val Lys Asp Tyr Phe Ala Lys Phe
1               5                   10                  15

Trp Asp

<210> SEQ ID NO 302
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 302

Ala Phe Asp Lys Phe Lys Asp Ala Val Lys Glu Tyr Phe Ala Lys Phe
1               5                   10                  15

Trp Glu

<210> SEQ ID NO 303
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 303

Ala Phe Asp Lys Phe Lys Glu Ala Val Lys Asp Tyr Phe Ala Lys Phe
1               5                   10                  15

Trp Glu

<210> SEQ ID NO 304
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 304

Ala Phe Glu Lys Phe Lys Asp Ala Val Lys Glu Tyr Phe Ala Lys Phe
1               5                   10                  15

Trp Asp

<210> SEQ ID NO 305
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 305

Ala Phe Glu Lys Phe Lys Asp Ala Val Lys Asp Tyr Phe Ala Lys Phe
1               5                   10                  15

Trp Glu

<210> SEQ ID NO 306

<400> SEQUENCE: 306

000
```

```
<210> SEQ ID NO 307
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 307

Val Ala Glu Lys Phe Lys Glu Ala Phe Lys Asp Tyr Phe Ala Lys Phe
1               5                   10                  15

Trp Asp

<210> SEQ ID NO 308
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 308

Val Ala Asp Lys Phe Lys Asp Ala Phe Lys Glu Tyr Phe Ala Lys Glu
1               5                   10                  15

Trp Glu

<210> SEQ ID NO 309
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 309

Val Ala Asp Lys Phe Lys Glu Ala Phe Lys Asp Tyr Phe Ala Lys Phe
1               5                   10                  15

Trp Glu

<210> SEQ ID NO 310
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 310

Val Ala Glu Lys Phe Lys Asp Ala Phe Lys Glu Tyr Phe Ala Lys Phe
1               5                   10                  15

Trp Asp

<210> SEQ ID NO 311
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 311

Val Ala Glu Lys Phe Lys Asp Ala Phe Lys Asp Tyr Phe Ala Lys Phe
1               5                   10                  15

Trp Glu
```

<210> SEQ ID NO 312

<400> SEQUENCE: 312

000

<210> SEQ ID NO 313
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 313

Tyr Ala Glu Lys Phe Lys Glu Ala Val Lys Asp Phe Phe Ala Lys Phe
1               5                   10                  15

Trp Asp

<210> SEQ ID NO 314
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 314

Tyr Ala Asp Lys Phe Lys Asp Ala Val Lys Glu Phe Phe Ala Lys Phe
1               5                   10                  15

Trp Glu

<210> SEQ ID NO 315
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 315

Tyr Ala Asp Lys Phe Lys Glu Ala Val Lys Asp Phe Phe Ala Lys Phe
1               5                   10                  15

Trp Glu

<210> SEQ ID NO 316
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 316

Tyr Ala Glu Lys Phe Lys Asp Ala Val Lys Glu Phe Phe Ala Lys Phe
1               5                   10                  15

Trp Asp

<210> SEQ ID NO 317
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

```
<400> SEQUENCE: 317

Tyr Ala Glu Lys Phe Lys Asp Ala Val Lys Asp Phe Phe Ala Lys Phe
1               5                  10                  15

Trp Glu

<210> SEQ ID NO 318

<400> SEQUENCE: 318

000

<210> SEQ ID NO 319
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 319

Ala Ala Glu Lys Phe Lys Glu Phe Val Lys Asp Tyr Phe Ala Lys Phe
1               5                  10                  15

Trp Asp

<210> SEQ ID NO 320
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 320

Ala Ala Asp Lys Phe Lys Asp Phe Val Lys Glu Tyr Phe Ala Lys Phe
1               5                  10                  15

Trp Glu

<210> SEQ ID NO 321
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 321

Ala Ala Asp Lys Phe Lys Glu Phe Val Lys Asp Tyr Phe Ala Lys Phe
1               5                  10                  15

Trp Glu

<210> SEQ ID NO 322
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 322

Ala Ala Glu Lys Phe Lys Asp Phe Val Lys Glu Tyr Phe Ala Lys Phe
1               5                  10                  15

Trp Asp

<210> SEQ ID NO 323
```

```
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 323

Ala Ala Glu Lys Phe Lys Asp Phe Val Lys Asp Tyr Phe Ala Lys Phe
1               5                   10                  15

Trp Glu

<210> SEQ ID NO 324

<400> SEQUENCE: 324

000

<210> SEQ ID NO 325
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 325

Phe Phe Glu Lys Ala Lys Glu Ala Val Lys Asp Tyr Phe Ala Lys Phe
1               5                   10                  15

Trp Asp

<210> SEQ ID NO 326
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 326

Phe Phe Asp Lys Ala Lys Asp Ala Val Lys Glu Tyr Phe Ala Lys Phe
1               5                   10                  15

Trp Glu

<210> SEQ ID NO 327
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 327

Phe Phe Asp Lys Ala Lys Glu Ala Val Lys Asp Tyr Phe Ala Lys Phe
1               5                   10                  15

Trp Glu

<210> SEQ ID NO 328
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 328
```

```
Phe Phe Glu Lys Ala Lys Asp Ala Val Lys Glu Tyr Phe Ala Lys Phe
1               5                   10                  15

Trp Asp

<210> SEQ ID NO 329
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 329

Phe Phe Glu Lys Ala Lys Asp Ala Val Lys Asp Tyr Phe Ala Lys Phe
1               5                   10                  15

Trp Glu

<210> SEQ ID NO 330

<400> SEQUENCE: 330

000

<210> SEQ ID NO 331
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 331

Phe Tyr Glu Lys Phe Lys Glu Ala Val Lys Asp Ala Phe Ala Lys Phe
1               5                   10                  15

Trp Asp

<210> SEQ ID NO 332
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 332

Phe Tyr Asp Lys Phe Lys Asp Ala Val Lys Glu Ala Phe Ala Lys Phe
1               5                   10                  15

Trp Glu

<210> SEQ ID NO 333
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 333

Phe Tyr Asp Lys Phe Lys Glu Ala Val Lys Asp Ala Phe Ala Lys Phe
1               5                   10                  15

Trp Glu

<210> SEQ ID NO 334
<211> LENGTH: 18
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 334

Phe Tyr Glu Lys Phe Lys Asp Ala Val Lys Glu Ala Phe Ala Lys Phe
1               5                   10                  15

Trp Asp

<210> SEQ ID NO 335
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 335

Phe Tyr Glu Lys Phe Lys Asp Ala Val Lys Asp Ala Phe Ala Lys Phe
1               5                   10                  15

Trp Glu

<210> SEQ ID NO 336

<400> SEQUENCE: 336

000

<210> SEQ ID NO 337
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 337

Phe Val Glu Lys Phe Lys Glu Ala Ala Lys Asp Tyr Phe Ala Lys Phe
1               5                   10                  15

Trp Asp

<210> SEQ ID NO 338
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 338

Phe Val Asp Lys Phe Lys Asp Ala Ala Lys Glu Tyr Phe Ala Lys Phe
1               5                   10                  15

Trp Glu

<210> SEQ ID NO 339
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 339

Phe Val Asp Lys Phe Lys Glu Ala Ala Lys Asp Tyr Phe Ala Lys Phe
1               5                   10                  15
```

Trp Glu

<210> SEQ ID NO 340
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 340

Phe Val Glu Lys Phe Lys Asp Ala Ala Lys Glu Tyr Phe Ala Lys Phe
1               5                   10                  15

Trp Asp

<210> SEQ ID NO 341
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 341

Phe Val Glu Lys Phe Lys Asp Ala Ala Lys Asp Tyr Phe Ala Lys Phe
1               5                   10                  15

Trp Glu

<210> SEQ ID NO 342

<400> SEQUENCE: 342

000

<210> SEQ ID NO 343
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 343

Phe Ala Glu Lys Tyr Lys Glu Ala Val Lys Asp Phe Phe Ala Lys Phe
1               5                   10                  15

Trp Asp

<210> SEQ ID NO 344
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 344

Phe Ala Asp Lys Tyr Lys Asp Ala Val Lys Glu Phe Phe Ala Lys Phe
1               5                   10                  15

Trp Glu

<210> SEQ ID NO 345
<211> LENGTH: 18
<212> TYPE: PRT
<213> ORGANISM: Artificial Sequence
<220> FEATURE:

<223> OTHER INFORMATION: Description of Artificial Sequence: note =
      Synthetic Construct

<400> SEQUENCE: 345

Phe Ala Asp Lys Tyr Lys Glu Ala Val Lys Asp Phe Phe Ala Lys Phe
1               5                   10                  15

Trp Glu

<210> SEQ ID NO 346
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 346

Phe Ala Glu Lys Tyr Lys Asp Ala Val Lys Glu Phe Phe Ala Lys Phe
1               5                   10                  15

Trp Asp

<210> SEQ ID NO 347
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 347

Phe Ala Glu Lys Tyr Lys Asp Ala Val Lys Asp Phe Phe Ala Lys Phe
1               5                   10                  15

Trp Glu

<210> SEQ ID NO 348

<400> SEQUENCE: 348

000

<210> SEQ ID NO 349
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 349

Phe Ala Glu Lys Val Lys Glu Ala Phe Lys Asp Tyr Phe Ala Lys Phe
1               5                   10                  15

Trp Asp

<210> SEQ ID NO 350
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 350

Phe Ala Asp Lys Val Lys Asp Ala Phe Lys Glu Tyr Phe Ala Lys Phe
1               5                   10                  15

Trp Glu

<210> SEQ ID NO 351
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 351

Phe Ala Asp Lys Val Lys Glu Ala Phe Lys Asp Tyr Phe Ala Lys Phe
1               5                   10                  15

Trp Glu

<210> SEQ ID NO 352
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 352

Phe Ala Glu Lys Val Lys Asp Ala Phe Lys Glu Tyr Phe Ala Lys Phe
1               5                   10                  15

Trp Asp

<210> SEQ ID NO 353
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 353

Phe Ala Glu Lys Val Lys Asp Ala Phe Lys Asp Tyr Phe Ala Lys Phe
1               5                   10                  15

Trp Glu

<210> SEQ ID NO 354

<400> SEQUENCE: 354

000

<210> SEQ ID NO 355
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 355

Phe Ala Glu Lys Phe Lys Glu Tyr Val Lys Asp Ala Phe Ala Lys Phe
1               5                   10                  15

Trp Asp

<210> SEQ ID NO 356
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

```
<400> SEQUENCE: 356

Phe Ala Asp Lys Phe Lys Asp Tyr Val Lys Glu Ala Phe Ala Lys Phe
1               5                   10                  15

Trp Glu

<210> SEQ ID NO 357
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 357

Phe Ala Asp Lys Phe Lys Glu Tyr Val Lys Asp Ala Phe Ala Lys Phe
1               5                   10                  15

Trp Glu

<210> SEQ ID NO 358
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 358

Phe Ala Glu Lys Phe Lys Asp Tyr Val Lys Glu Ala Phe Ala Lys Phe
1               5                   10                  15

Trp Asp

<210> SEQ ID NO 359
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 359

Phe Ala Glu Lys Phe Lys Asp Tyr Val Lys Asp Ala Phe Ala Lys Phe
1               5                   10                  15

Trp Glu

<210> SEQ ID NO 360

<400> SEQUENCE: 360

000

<210> SEQ ID NO 361
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 361

Phe Ala Glu Lys Phe Lys Glu Ala Phe Lys Asp Tyr Val Ala Lys Phe
1               5                   10                  15

Trp Asp
```

```
<210> SEQ ID NO 362
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 362

Phe Ala Asp Lys Phe Lys Asp Ala Phe Lys Glu Tyr Val Ala Lys Phe
1               5                   10                  15

Trp Glu

<210> SEQ ID NO 363
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 363

Phe Ala Asp Lys Phe Lys Glu Ala Phe Lys Asp Tyr Val Ala Lys Phe
1               5                   10                  15

Trp Glu

<210> SEQ ID NO 364
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 364

Phe Ala Glu Lys Phe Lys Asp Ala Phe Lys Glu Tyr Val Ala Lys Phe
1               5                   10                  15

Trp Asp

<210> SEQ ID NO 365
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 365

Phe Ala Glu Lys Phe Lys Asp Ala Phe Lys Asp Tyr Val Ala Lys Phe
1               5                   10                  15

Trp Glu

<210> SEQ ID NO 366

<400> SEQUENCE: 366

000

<210> SEQ ID NO 367
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 367
```

```
Phe Ala Glu Lys Phe Lys Glu Ala Phe Lys Asp Tyr Phe Ala Lys Val
1               5                   10                  15

Trp Asp

<210> SEQ ID NO 368
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 368

Phe Ala Asp Lys Phe Lys Asp Ala Phe Lys Glu Tyr Phe Ala Lys Val
1               5                   10                  15

Trp Glu

<210> SEQ ID NO 369
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 369

Phe Ala Asp Lys Phe Lys Glu Ala Phe Lys Asp Tyr Phe Ala Lys Val
1               5                   10                  15

Trp Glu

<210> SEQ ID NO 370
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 370

Phe Ala Glu Lys Phe Lys Asp Ala Phe Lys Glu Tyr Phe Ala Lys Val
1               5                   10                  15

Trp Asp

<210> SEQ ID NO 371
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 371

Phe Ala Glu Lys Phe Lys Asp Ala Phe Lys Asp Tyr Phe Ala Lys Val
1               5                   10                  15

Trp Glu

<210> SEQ ID NO 372

<400> SEQUENCE: 372

000

<210> SEQ ID NO 373
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 373

Phe Ala Glu Lys Phe Lys Glu Ala Val Lys Asp Phe Phe Ala Lys Tyr
1               5                   10                  15

Trp Asp

<210> SEQ ID NO 374
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 374

Phe Ala Asp Lys Phe Lys Asp Ala Val Lys Glu Phe Phe Asn Lys Tyr
1               5                   10                  15

Trp Glu

<210> SEQ ID NO 375
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 375

Phe Ala Asp Lys Phe Lys Glu Ala Val Lys Asp Phe Phe Ala Lys Tyr
1               5                   10                  15

Trp Glu

<210> SEQ ID NO 376
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 376

Phe Ala Glu Lys Phe Lys Asp Ala Val Lys Glu Phe Phe Ala Lys Tyr
1               5                   10                  15

Trp Asp

<210> SEQ ID NO 377
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 377

Phe Ala Glu Lys Phe Lys Asp Ala Val Lys Asp Phe Phe Ala Lys Tyr
1               5                   10                  15

Trp Glu

<210> SEQ ID NO 378
```

```
<400> SEQUENCE: 378

000

<210> SEQ ID NO 379
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 379

Trp Ala Glu Lys Phe Phe Glu Ala Val Lys Asp Tyr Phe Ala Lys Phe
1               5                   10                  15

Lys Asp

<210> SEQ ID NO 380
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 380

Trp Ala Asp Lys Phe Phe Asp Ala Val Lys Glu Tyr Phe Ala Lys Phe
1               5                   10                  15

Lys Glu

<210> SEQ ID NO 381
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 381

Trp Ala Asp Lys Phe Phe Glu Ala Val Lys Asp Tyr Phe Ala Lys Phe
1               5                   10                  15

Lys Glu

<210> SEQ ID NO 382
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 382

Trp Ala Glu Lys Phe Phe Asp Ala Val Lys Glu Tyr Phe Ala Lys Phe
1               5                   10                  15

Lys Asp

<210> SEQ ID NO 383
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 383

Trp Ala Glu Lys Phe Phe Asp Ala Val Lys Asp Tyr Phe Ala Lys Phe
```

```
<210> SEQ ID NO 384

<400> SEQUENCE: 384

000

<210> SEQ ID NO 385
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 385

Phe Ala Glu Lys Trp Phe Glu Ala Val Lys Asp Tyr Phe Ala Lys Phe
1               5                   10                  15

Lys Asp

<210> SEQ ID NO 386
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 386

Phe Ala Asp Lys Trp Phe Asp Ala Val Lys Glu Tyr Phe Ala Lys Phe
1               5                   10                  15

Lys Glu

<210> SEQ ID NO 387
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 387

Phe Ala Asp Lys Trp Phe Glu Ala Val Lys Asp Tyr Phe Ala Lys Phe
1               5                   10                  15

Lys Glu

<210> SEQ ID NO 388
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 388

Phe Ala Glu Lys Trp Phe Asp Ala Val Lys Glu Tyr Phe Ala Lys Phe
1               5                   10                  15

Lys Asp

<210> SEQ ID NO 389
<211> LENGTH: 18
<212> TYPE: PRT
<213> ORGANISM: Artificial Sequence
```

```
<220> FEATURE:
<223> OTHER INFORMATION: Description of Artificial Sequence: note =
      Synthetic Construct

<400> SEQUENCE: 389

Phe Ala Glu Lys Trp Phe Asp Ala Val Lys Asp Tyr Phe Ala Lys Phe
1               5                   10                  15

Lys Glu

<210> SEQ ID NO 390

<400> SEQUENCE: 390

000

<210> SEQ ID NO 391
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 391

Phe Ala Glu Lys Phe Val Glu Ala Trp Lys Asp Tyr Phe Ala Lys Phe
1               5                   10                  15

Lys Asp

<210> SEQ ID NO 392
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 392

Phe Ala Asp Lys Phe Val Asp Ala Trp Lys Glu Tyr Phe Ala Lys Phe
1               5                   10                  15

Lys Glu

<210> SEQ ID NO 393
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 393

Phe Ala Asp Lys Phe Val Glu Ala Trp Lys Asp Tyr Phe Ala Lys Phe
1               5                   10                  15

Lys Glu

<210> SEQ ID NO 394
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 394

Phe Ala Glu Lys Phe Val Asp Ala Trp Lys Glu Tyr Phe Ala Lys Phe
1               5                   10                  15
```

Lys Asp

```
<210> SEQ ID NO 395
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 395
```

Phe Ala Glu Lys Phe Val Asp Ala Trp Lys Asp Tyr Phe Ala Lys Phe
1               5                   10                  15

Lys Glu

```
<210> SEQ ID NO 396

<400> SEQUENCE: 396
```

000

```
<210> SEQ ID NO 397
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 397
```

Phe Tyr Glu Lys Phe Ala Glu Ala Val Lys Asp Trp Phe Ala Lys Phe
1               5                   10                  15

Lys Asp

```
<210> SEQ ID NO 398
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 398
```

Phe Tyr Asp Lys Phe Ala Asp Ala Val Lys Glu Trp Phe Ala Lys Phe
1               5                   10                  15

Lys Glu

```
<210> SEQ ID NO 399
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 399
```

Phe Tyr Asp Lys Phe Ala Glu Ala Val Lys Asp Trp Phe Ala Lys Phe
1               5                   10                  15

Lys Glu

```
<210> SEQ ID NO 400
<211> LENGTH: 18
<212> TYPE: PRT
<213> ORGANISM: Artificial Sequence
<220> FEATURE:
<223> OTHER INFORMATION: Description of Artificial Sequence: note =
```

Synthetic Construct

<400> SEQUENCE: 400

Phe Tyr Glu Lys Phe Ala Asp Ala Val Lys Glu Trp Phe Ala Lys Phe
1               5                   10                  15

Lys Asp

<210> SEQ ID NO 401
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 401

Phe Tyr Glu Lys Phe Ala Asp Ala Val Lys Asp Trp Phe Ala Lys Phe
1               5                   10                  15

Lys Glu

<210> SEQ ID NO 402
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 402

Asp Xaa Xaa Lys Tyr Xaa Xaa Asp Lys Xaa Tyr Asp Lys Xaa Lys Asp
1               5                   10                  15

Tyr Xaa

<210> SEQ ID NO 403
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 403

Asp Trp Phe Lys His Phe Tyr Asp Lys Val Ala Glu Lys Phe Lys Glu
1               5                   10                  15

Ala Phe

<210> SEQ ID NO 404
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 404

Glu Trp Phe Lys His Phe Tyr Glu Lys Val Ala Asp Lys Phe Lys Asp
1               5                   10                  15

Ala Phe

<210> SEQ ID NO 405
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 405

Glu Trp Phe Lys His Phe Tyr Asp Lys Val Ala Glu Lys Phe Lys Glu
1               5                   10                  15

Ala Phe

<210> SEQ ID NO 406
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 406

Asp Trp Phe Lys His Phe Tyr Glu Lys Val Ala Glu Lys Phe Lys Glu
1               5                   10                  15

Ala Phe

<210> SEQ ID NO 407
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 407

Asp Trp Phe Lys His Phe Tyr Asp Lys Val Ala Asp Lys Phe Lys Glu
1               5                   10                  15

Ala Phe

<210> SEQ ID NO 408
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 408

Asp Trp Phe Lys His Phe Tyr Asp Lys Val Ala Glu Lys Phe Lys Asp
1               5                   10                  15

Ala Phe

<210> SEQ ID NO 409
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 409

Asp Trp His Lys Phe Phe Tyr Asp Lys Val Ala Glu Lys Phe Lys Glu
1               5                   10                  15
Ala Phe

<210> SEQ ID NO 410
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 410

Glu Trp His Lys Phe Phe Tyr Glu Lys Val Ala Asp Lys Phe Lys Asp
1               5                   10                  15
Ala Phe

<210> SEQ ID NO 411
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 411

Glu Trp His Lys Phe Phe Tyr Asp Lys Val Ala Glu Lys Phe Lys Glu
1               5                   10                  15
Ala Phe

<210> SEQ ID NO 412
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 412

Asp Trp His Lys Phe Phe Tyr Glu Lys Val Ala Glu Lys Phe Lys Glu
1               5                   10                  15
Ala Phe

<210> SEQ ID NO 413
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 413

Asp Trp His Lys Phe Phe Tyr Asp Lys Val Ala Asp Lys Phe Lys Glu
1               5                   10                  15
Ala Phe

<210> SEQ ID NO 414
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 414

Asp Trp His Lys Phe Phe Tyr Asp Lys Val Ala Glu Lys Phe Lys Asp
1               5                   10                  15

Ala Phe

<210> SEQ ID NO 415
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 415

Asp Trp Phe Lys Phe His Tyr Asp Lys Val Ala Glu Lys Phe Lys Glu
1               5                   10                  15

Ala Phe

<210> SEQ ID NO 416
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 416

Glu Trp Phe Lys Phe His Tyr Glu Lys Val Ala Asp Lys Phe Lys Asp
1               5                   10                  15

Ala Phe

<210> SEQ ID NO 417
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 417

Glu Trp Phe Lys Phe His Tyr Asp Lys Val Ala Glu Lys Phe Lys Glu
1               5                   10                  15

Ala Phe

<210> SEQ ID NO 418
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 418

Asp Trp Phe Lys Phe His Tyr Glu Lys Val Ala Glu Lys Phe Lys Glu
1               5                   10                  15

Ala Phe

<210> SEQ ID NO 419
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 419

Asp Trp Phe Lys Phe His Tyr Asp Lys Val Ala Asp Lys Phe Lys Glu
1               5                   10                  15

Ala Phe

<210> SEQ ID NO 420
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 420

Asp Trp Phe Lys Phe His Tyr Asp Lys Val Ala Glu Lys Phe Lys Asp
1               5                   10                  15

Ala Phe

<210> SEQ ID NO 421
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 421

Asp Trp Phe Lys Val Phe Tyr Asp Lys His Ala Glu Lys Phe Lys Glu
1               5                   10                  15

Ala Phe

<210> SEQ ID NO 422
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 422

Glu Trp Phe Lys Val Phe Tyr Glu Lys His Ala Asp Lys Phe Lys Asp
1               5                   10                  15

Ala Phe

<210> SEQ ID NO 423
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 423

Glu Trp Phe Lys Val Phe Tyr Asp Lys His Ala Glu Lys Phe Lys Glu
1               5                   10                  15

Ala Phe

<210> SEQ ID NO 424
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 424

Asp Trp Phe Lys Val Phe Tyr Glu Lys His Ala Glu Lys Phe Lys Glu
1               5                   10                  15

Ala Phe

<210> SEQ ID NO 425
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 425

Asp Trp Phe Lys Val Phe Tyr Asp Lys His Ala Asp Lys Phe Lys Glu
1               5                   10                  15

Ala Phe

<210> SEQ ID NO 426
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 426

Asp Trp Phe Lys Val Phe Tyr Asp Lys His Ala Glu Lys Phe Lys Asp
1               5                   10                  15

Ala Phe

<210> SEQ ID NO 427
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 427

Asp Trp Phe Lys Ala Phe Tyr Asp Lys Val Ala Glu Lys Phe Lys Glu
1               5                   10                  15

His Phe

<210> SEQ ID NO 428
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 428

Glu Trp Phe Lys Ala Phe Tyr Glu Lys Val Ala Asp Lys Phe Lys Asp
1               5                   10                  15

His Phe

<210> SEQ ID NO 429
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 429

Glu Trp Phe Lys Ala Phe Tyr Asp Lys Val Ala Glu Lys Phe Lys Glu
1               5                   10                  15

His Phe

<210> SEQ ID NO 430
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 430

Asp Trp Phe Lys Ala Phe Tyr Glu Lys Val Ala Glu Lys Phe Lys Glu
1               5                   10                  15

His Phe

<210> SEQ ID NO 431
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 431

Asp Trp Phe Lys Ala Phe Tyr Asp Lys Val Ala Asp Lys Phe Lys Glu
1               5                   10                  15

His Phe

<210> SEQ ID NO 432
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 432

Asp Trp Phe Lys Ala Phe Tyr Asp Lys Val Ala Glu Lys Phe Lys Asp
1               5                   10                  15

His Phe

<210> SEQ ID NO 433
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 433

Asp Trp Phe Lys Ala Phe Tyr Asp Lys Val Ala Glu Lys Phe Lys Glu
1               5                   10                  15

Phe His

<210> SEQ ID NO 434
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 434

Glu Trp Phe Lys Ala Phe Tyr Glu Lys Val Ala Asp Lys Phe Lys Asp
1               5                   10                  15

Phe His

<210> SEQ ID NO 435
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 435

Glu Trp Phe Lys Ala Phe Tyr Asp Lys Val Ala Glu Lys Phe Lys Glu
1               5                   10                  15

Phe His

<210> SEQ ID NO 436
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 436

Asp Trp Phe Lys Ala Phe Tyr Asp Lys Val Ala Glu Lys Phe Lys Glu
1               5                   10                  15

Phe His

<210> SEQ ID NO 437
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 437

Asp Trp Phe Lys Ala Phe Tyr Glu Lys Val Ala Glu Lys Phe Lys Glu
1               5                   10                  15

Phe His

<210> SEQ ID NO 438
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 438

Asp Trp Phe Lys Ala Phe Tyr Asp Lys Val Ala Glu Lys Phe Lys Glu
1               5                   10                  15

Phe His

<210> SEQ ID NO 439
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 439

Asp Trp Phe Lys Ala Phe Tyr Asp Lys Val Ala Glu Lys Phe Lys Asp
1               5                   10                  15

Phe His

<210> SEQ ID NO 440
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 440

Phe Ala Glu Lys Phe Lys Glu Ala Val Lys Asp Tyr Phe Ala Lys Phe
1               5                   10                  15

Trp Asp

<210> SEQ ID NO 441
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 441

Phe His Glu Lys Phe Lys Glu Ala Val Lys Asp Tyr Phe Ala Lys Phe
1               5                   10                  15

Trp Asp

<210> SEQ ID NO 442
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 442

Phe His Glu Lys Phe Lys Glu Ala Val Lys Glu Tyr Phe Ala Lys Phe
1               5                   10                  15

Trp Glu

<210> SEQ ID NO 443
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 443

Phe His Asp Lys Phe Lys Asp Ala Val Lys Asp Tyr Phe Ala Lys Phe
1               5                   10                  15

Trp Asp

<210> SEQ ID NO 444
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 444

Phe His Asp Lys Phe Lys Asp Ala Val Lys Glu Tyr Phe Ala Lys Phe
1               5                   10                  15

Trp Glu

<210> SEQ ID NO 445
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 445

Phe His Asp Lys Phe Lys Glu Ala Val Lys Asp Tyr Phe Ala Lys Phe
1               5                   10                  15

Trp Asp

<210> SEQ ID NO 446
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 446

Phe His Glu Lys Phe Lys Asp Ala Val Lys Asp Tyr Phe Ala Lys Phe
1               5                   10                  15

Trp Asp

<210> SEQ ID NO 447
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 447

Phe His Glu Lys Phe Lys Glu Ala Val Lys Glu Tyr Phe Ala Lys Phe
1               5                   10                  15

Trp Asp

<210> SEQ ID NO 448
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 448

Phe His Glu Lys Phe Lys Glu Ala Val Lys Asp Tyr Phe Ala Lys Phe
1               5                   10                  15

Trp Glu

<210> SEQ ID NO 449
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 449

His Phe Glu Lys Phe Lys Glu Ala Val Lys Asp Tyr Phe Ala Lys Phe
1               5                   10                  15

Trp Asp

<210> SEQ ID NO 450
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 450

His Phe Asp Lys Phe Lys Asp Ala Val Lys Glu Tyr Phe Ala Lys Phe
1               5                   10                  15

Trp Glu

<210> SEQ ID NO 451
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 451

His Phe Glu Lys Phe Lys Glu Ala Val Lys Glu Tyr Phe Ala Lys Phe
1               5                   10                  15

Trp Glu

<210> SEQ ID NO 452
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 452

His Phe Asp Lys Phe Lys Glu Ala Val Lys Asp Tyr Phe Ala Lys Phe
1               5                   10                  15

Trp Asp

<210> SEQ ID NO 453
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 453

His Phe Glu Lys Phe Lys Asp Ala Val Lys Asp Tyr Phe Ala Lys Phe
1               5                   10                  15

Trp Asp

<210> SEQ ID NO 454
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 454

His Phe Glu Lys Phe Lys Glu Ala Val Lys Glu Tyr Phe Ala Lys Phe
1               5                   10                  15

Trp Asp

<210> SEQ ID NO 455
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 455

His Phe Glu Lys Phe Lys Glu Ala Val Lys Asp Tyr Phe Ala Lys Phe
1               5                   10                  15

Trp Glu

<210> SEQ ID NO 456
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 456

Phe Phe Glu Lys His Lys Glu Ala Val Lys Asp Tyr Phe Ala Lys Phe
1               5                   10                  15

Trp Asp

<210> SEQ ID NO 457
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 457

Phe Phe Asp Lys His Lys Asp Ala Val Lys Glu Tyr Phe Ala Lys Phe
1               5                   10                  15

Trp Glu

<210> SEQ ID NO 458
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 458

Phe Phe Glu Lys His Lys Glu Ala Val Lys Glu Tyr Phe Ala Lys Phe
1               5                   10                  15

Trp Glu

<210> SEQ ID NO 459
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 459

Phe Phe Asp Lys His Lys Asp Ala Val Lys Asp Tyr Phe Ala Lys Phe
1               5                   10                  15

Trp Asp

<210> SEQ ID NO 460
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 460

Phe Phe Asp Lys His Lys Glu Ala Val Lys Asp Tyr Phe Ala Lys Phe
1               5                   10                  15

Trp Asp

<210> SEQ ID NO 461
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 461

Phe Phe Glu Lys His Lys Glu Ala Val Lys Glu Tyr Phe Ala Lys Phe
1               5                   10                  15

Trp Asp

<210> SEQ ID NO 462
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 462

Phe Phe Glu Lys His Lys Glu Ala Val Lys Asp Tyr Phe Ala Lys Phe
1               5                   10                  15

Trp Glu

<210> SEQ ID NO 463
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 463

Phe Val Glu Lys Phe Lys Glu Ala His Lys Asp Tyr Phe Ala Lys Phe
1               5                   10                  15

Trp Asp

<210> SEQ ID NO 464
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 464

Phe Val Asp Lys Phe Lys Asp Ala His Lys Glu Tyr Phe Ala Lys Phe
1               5                   10                  15

Trp Glu

<210> SEQ ID NO 465
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 465

Phe Val Glu Lys Phe Lys Glu Ala His Lys Glu Tyr Phe Ala Lys Phe
1               5                   10                  15

Trp Glu

<210> SEQ ID NO 466
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 466

Phe Val Asp Lys Phe Lys Asp Ala His Lys Asp Tyr Phe Ala Lys Phe
1               5                   10                  15

Trp Asp

<210> SEQ ID NO 467
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 467

Phe Val Asp Lys Phe Lys Glu Ala His Lys Asp Tyr Phe Ala Lys Phe
1               5                   10                  15

Trp Asp

<210> SEQ ID NO 468
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 468

Phe Val Glu Lys Phe Lys Asp Ala His Lys Asp Tyr Phe Ala Lys Phe
1               5                   10                  15

Trp Asp

<210> SEQ ID NO 469
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 469

Phe Val Glu Lys Phe Lys Glu Ala His Lys Glu Tyr Phe Ala Lys Phe
1               5                   10                  15
Trp Asp

<210> SEQ ID NO 470
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 470

Phe Val Glu Lys Phe Lys Glu Ala His Lys Asp Tyr Phe Ala Lys Phe
1               5                   10                  15
Trp Glu

<210> SEQ ID NO 471
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 471

Phe Ala Glu Lys Phe Lys Glu His Val Lys Asp Tyr Phe Ala Lys Phe
1               5                   10                  15
Trp Asp

<210> SEQ ID NO 472
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 472

Phe Ala Asp Lys Phe Lys Asp His Val Lys Glu Tyr Phe Ala Lys Phe
1               5                   10                  15
Trp Glu

<210> SEQ ID NO 473
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 473

Phe Ala Glu Lys Phe Lys Glu His Val Lys Glu Tyr Phe Ala Lys Phe
1               5                   10                  15
Trp Glu

<210> SEQ ID NO 474
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 474

Phe Ala Asp Lys Phe Lys Asp His Val Lys Asp Tyr Phe Ala Lys Phe
1               5                   10                  15

Trp Asp

<210> SEQ ID NO 475
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 475

Phe Ala Asp Lys Phe Lys Glu His Val Lys Asp Tyr Phe Ala Lys Phe
1               5                   10                  15

Trp Asp

<210> SEQ ID NO 476
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 476

Phe Ala Glu Lys Phe Lys Asp His Val Lys Asp Tyr Phe Ala Lys Phe
1               5                   10                  15

Trp Asp

<210> SEQ ID NO 477
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 477

Phe Ala Glu Lys Phe Lys Glu His Val Lys Glu Tyr Phe Ala Lys Phe
1               5                   10                  15

Trp Asp

<210> SEQ ID NO 478
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 478

Phe Ala Glu Lys Phe Lys Glu His Val Lys Asp Tyr Phe Ala Lys Phe
1               5                   10                  15

Trp Glu

<210> SEQ ID NO 479
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 479

Phe Ala Glu Lys Phe Lys Glu Phe Val Lys Asp Tyr His Ala Lys Phe
1               5                   10                  15

Trp Asp

<210> SEQ ID NO 480
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 480

Phe Ala Asp Lys Phe Lys Asp Phe Val Lys Glu Tyr His Ala Lys Phe
1               5                   10                  15

Trp Glu

<210> SEQ ID NO 481
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 481

Phe Ala Asp Lys Phe Lys Glu Phe Val Lys Asp Tyr His Ala Lys Phe
1               5                   10                  15

Trp Asp

<210> SEQ ID NO 482
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 482

Phe Ala Glu Lys Phe Lys Asp Phe Val Lys Asp Tyr His Ala Lys Phe
1               5                   10                  15

Trp Asp

<210> SEQ ID NO 483
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 483

Phe Ala Asp Lys Phe Lys Asp Phe Val Lys Asp Tyr His Ala Lys Phe
1               5                   10                  15

Trp Asp

<210> SEQ ID NO 484
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 484

Phe Ala Glu Lys Phe Lys Glu Phe Val Lys Glu Tyr His Ala Lys Phe
1               5                   10                  15

Trp Glu

<210> SEQ ID NO 485
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 485

Phe Ala Glu Lys Phe Lys Glu Phe Val Lys Glu Tyr His Ala Lys Phe
1               5                   10                  15

Trp Asp

<210> SEQ ID NO 486
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 486

Phe Ala Glu Lys Phe Lys Glu Phe Val Lys Asp Tyr His Ala Lys Phe
1               5                   10                  15

Trp Glu

<210> SEQ ID NO 487
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 487

Phe Ala Glu Lys Phe Lys Glu Phe Val Lys Asp Tyr Phe Ala Lys His
1               5                   10                  15

Trp Asp

<210> SEQ ID NO 488
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 488

Phe Ala Asp Lys Phe Lys Asp Phe Val Lys Glu Tyr Phe Ala Lys His
1               5                   10                  15

Trp Glu

<210> SEQ ID NO 489
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 489

Phe Ala Glu Lys Phe Lys Glu Phe Val Lys Glu Tyr Phe Ala Lys His
1               5                   10                  15

Trp Glu

<210> SEQ ID NO 490
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 490

Phe Ala Asp Lys Phe Lys Asp Phe Val Lys Asp Tyr Phe Ala Lys His
1               5                   10                  15

Trp Asp

<210> SEQ ID NO 491
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 491

Phe Ala Asp Lys Phe Lys Glu Phe Val Lys Asp Tyr Phe Ala Lys His
1               5                   10                  15

Trp Asp

<210> SEQ ID NO 492
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 492

Phe Ala Glu Lys Phe Lys Asp Phe Val Lys Asp Tyr Phe Ala Lys His
1               5                   10                  15

Trp Asp

<210> SEQ ID NO 493
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 493

Phe Ala Glu Lys Phe Lys Glu Phe Val Lys Glu Tyr Phe Ala Lys His
1               5                   10                  15

Trp Asp

<210> SEQ ID NO 494
<211> LENGTH: 18
```

<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 494

Phe Ala Glu Lys Phe Lys Glu Phe Val Lys Asp Tyr Phe Ala Lys His
1               5                   10                  15

Trp Glu

<210> SEQ ID NO 495
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 495

Asp Trp Xaa Lys Ala Xaa Tyr Asp Lys Val Ala Glu Lys Xaa Lys Glu
1               5                   10                  15

Ala Xaa

<210> SEQ ID NO 496
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 496

Glu Trp Xaa Lys Ala Xaa Tyr Glu Lys Val Ala Asp Lys Xaa Lys Asp
1               5                   10                  15

Ala Xaa

<210> SEQ ID NO 497
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 497

Glu Trp Xaa Lys Ala Xaa Tyr Glu Lys Val Ala Glu Lys Xaa Lys Glu
1               5                   10                  15

Ala Xaa

<210> SEQ ID NO 498
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 498

Asp Trp Xaa Lys Ala Xaa Tyr Asp Lys Val Ala Asp Lys Xaa Lys Asp
1               5                   10                  15

Ala Xaa

<210> SEQ ID NO 499
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
```

-continued

```
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 499

Glu Trp Xaa Lys Ala Xaa Tyr Asp Lys Val Ala Glu Lys Xaa Lys Glu
1               5                   10                  15

Ala Xaa

<210> SEQ ID NO 500
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 500

Asp Trp Xaa Lys Ala Xaa Tyr Glu Lys Val Ala Glu Lys Xaa Lys Glu
1               5                   10                  15

Ala Xaa

<210> SEQ ID NO 501
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 501

Asp Trp Xaa Lys Ala Xaa Tyr Asp Lys Val Ala Asp Lys Xaa Lys Glu
1               5                   10                  15

Ala Xaa

<210> SEQ ID NO 502
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 502

Asp Trp Xaa Lys Ala Xaa Tyr Asp Lys Val Ala Glu Lys Xaa Lys Asp
1               5                   10                  15

Ala Xaa

<210> SEQ ID NO 503
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 503

Asp Trp Xaa Lys Ala Xaa Tyr Asp Lys Val Ala Glu Lys Phe Lys Glu
1               5                   10                  15

Ala Phe

<210> SEQ ID NO 504
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 504

Asp Trp Phe Lys Ala Phe Tyr Asp Lys Val Ala Glu Lys Xaa Lys Glu
1               5                   10                  15

Ala Xaa

<210> SEQ ID NO 505
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 505

Asp Trp Xaa Lys Ala Phe Tyr Asp Lys Val Ala Glu Lys Phe Lys Glu
1               5                   10                  15

Ala Phe

<210> SEQ ID NO 506
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 506

Asp Trp Phe Lys Ala Xaa Tyr Asp Lys Val Ala Glu Lys Phe Lys Glu
1               5                   10                  15

Ala Phe

<210> SEQ ID NO 507
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (14)..(14)
<223> OTHER INFORMATION: Xaa can be any naturally occurring amino acid

<400> SEQUENCE: 507

Asp Trp Phe Lys Ala Phe Tyr Asp Lys Val Ala Glu Lys Xaa Lys Glu
1               5                   10                  15

Ala Phe

<210> SEQ ID NO 508
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (18)..(18)
<223> OTHER INFORMATION: Xaa can be any naturally occurring amino acid

<400> SEQUENCE: 508

Asp Trp Phe Lys Ala Phe Tyr Asp Lys Val Ala Glu Lys Phe Lys Glu
1               5                   10                  15

Ala Xaa

<210> SEQ ID NO 509
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 509

Xaa Ala Glu Lys Xaa Lys Glu Ala Val Lys Asp Tyr Xaa Ala Lys Xaa
1               5                   10                  15

Trp Asp

<210> SEQ ID NO 510
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 510

Xaa Ala Glu Lys Xaa Lys Glu Ala Val Lys Asp Tyr Phe Ala Lys Phe
1               5                   10                  15

Trp Asp

<210> SEQ ID NO 511
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 511

Ala Glu Lys Phe Lys Glu Ala Val Lys Asp Tyr Xaa Ala Lys Xaa Trp
1               5                   10                  15

Asp

<210> SEQ ID NO 512
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 512

Xaa Ala Glu Lys Phe Lys Glu Ala Val Lys Asp Tyr Phe Ala Lys Phe
1               5                   10                  15

Trp Asp

<210> SEQ ID NO 513
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 513

Phe Ala Glu Lys Xaa Lys Glu Ala Val Lys Asp Tyr Phe Ala Lys Phe
1               5                   10                  15

Trp Asp

<210> SEQ ID NO 514
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (13)..(13)
<223> OTHER INFORMATION: Xaa can be any naturally occurring amino acid

<400> SEQUENCE: 514

Phe Ala Glu Lys Phe Lys Glu Ala Val Lys Asp Tyr Xaa Ala Lys Phe
1               5                   10                  15

Trp Asp

<210> SEQ ID NO 515
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (16)..(16)
<223> OTHER INFORMATION: Xaa can be any naturally occurring amino acid

<400> SEQUENCE: 515

Phe Ala Glu Lys Glu Lys Glu Ala Val Lys Asp Tyr Phe Ala Lys Xaa
1               5                   10                  15

Trp Asp

<210> SEQ ID NO 516
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 516

Phe Ala Glu Lys Phe Lys Glu Ala Val Lys Glu Tyr Phe Ala Lys Phe
1               5                   10                  15

Trp Glu

<210> SEQ ID NO 517
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 517

Phe Ala Asp Lys Phe Lys Asp Ala Val Lys Asp Tyr Phe Ala Lys Phe
1               5                   10                  15

Trp Asp

<210> SEQ ID NO 518
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 518

Phe Ala Glu Arg Phe Arg Glu Ala Val Lys Asp Tyr Phe Ala Lys Phe
1               5                   10                  15

Trp Asp

<210> SEQ ID NO 519
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 519

Phe Ala Glu Lys Phe Arg Glu Ala Val Lys Asp Tyr Phe Ala Lys Phe
1               5                   10                  15

Trp Asp

<210> SEQ ID NO 520
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 520

Phe Ala Glu Lys Phe Lys Glu Ala Val Arg Asp Tyr Phe Ala Lys Phe
1               5                   10                  15

Trp Asp

<210> SEQ ID NO 521
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 521

Phe Ala Glu Lys Phe Lys Glu Ala Val Lys Asp Tyr Phe Ala Arg Phe
1               5                   10                  15

Trp Asp

<210> SEQ ID NO 522
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 522

Phe Ala Glu Lys Phe Lys Glu Ala Val Lys Glu Tyr Phe Ala Lys Phe
1               5                   10                  15

Trp Glu

<210> SEQ ID NO 523
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 523

Phe Ala Asp Lys Phe Lys Asp Ala Val Lys Asp Tyr Phe Ala Lys Phe
1               5                   10                  15

Trp Asp

<210> SEQ ID NO 524
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 524

Phe Ala Glu Arg Phe Arg Glu Ala Val Lys Asp Tyr Phe Ala Lys Phe
1               5                   10                  15

Trp Asp

<210> SEQ ID NO 525
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 525

Phe Ala Glu Lys Phe Arg Glu Ala Val Lys Asp Tyr Phe Ala Lys Phe
1               5                   10                  15

Trp Asp

<210> SEQ ID NO 526
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 526

Phe Ala Glu Lys Phe Lys Glu Ala Val Arg Asp Tyr Phe Ala Lys Phe
1               5                   10                  15

Trp Asp

<210> SEQ ID NO 527
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 527

Phe Ala Glu Lys Phe Lys Glu Ala Val Lys Asp Tyr Phe Ala Arg Phe
1               5                   10                  15

Trp Asp

<210> SEQ ID NO 528
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 528

Phe Ala Glu Lys Phe Lys Glu Ala Val Lys Glu Tyr Phe Ala Lys Phe
1               5                   10                  15

Trp Glu

<210> SEQ ID NO 529
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 529

Phe Ala Asp Lys Phe Lys Asp Ala Val Lys Asp Tyr Phe Ala Lys Phe
1               5                   10                  15

Trp Asp

<210> SEQ ID NO 530
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 530

Phe Ala Glu Arg Phe Arg Glu Ala Val Lys Asp Tyr Phe Ala Lys Phe
1               5                   10                  15

Trp Asp

<210> SEQ ID NO 531
<211> LENGTH: 18
```

-continued

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 531

Phe Ala Glu Lys Phe Arg Glu Ala Val Lys Asp Tyr Phe Ala Lys Phe
1               5                   10                  15

Trp Asp

<210> SEQ ID NO 532
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 532

Phe Ala Glu Lys Phe Lys Glu Ala Val Arg Asp Tyr Phe Ala Lys Phe
1               5                   10                  15

Trp Asp

<210> SEQ ID NO 533
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 533

Phe Ala Glu Lys Phe Lys Glu Ala Val Lys Asp Tyr Phe Ala Arg Phe
1               5                   10                  15

Trp Asp

<210> SEQ ID NO 534
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 534

Phe Ala Glu Arg Phe Arg Glu Ala Val Lys Asp Tyr Phe Ala Lys Phe
1               5                   10                  15

Trp Asp

<210> SEQ ID NO 535
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 535

Phe Ala Glu Lys Phe Arg Glu Ala Val Lys Asp Tyr Glu Ala Lys Phe
1               5                   10                  15

Trp Asp

<210> SEQ ID NO 536
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 536

Phe Ala Glu Lys Phe Lys Glu Ala Val Arg Asp Tyr Phe Ala Lys Phe
1               5                   10                  15

Trp Asp

<210> SEQ ID NO 537
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 537

Phe Ala Glu Lys Phe Lys Glu Ala Val Lys Asp Tyr Phe Ala Arg Phe
1               5                   10                  15

Trp Asp

<210> SEQ ID NO 538
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 538

Phe Ala Glu Lys Phe Lys Glu Ala Val Lys Glu Tyr Phe Ala Lys Phe
1               5                   10                  15

Trp Glu

<210> SEQ ID NO 539
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 539

Phe Ala Asp Lys Phe Lys Asp Ala Val Lys Asp Tyr Phe Ala Lys Phe
1               5                   10                  15

Trp Asp

<210> SEQ ID NO 540
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 540

Phe Ala Glu Arg Phe Arg Glu Ala Val Lys Asp Tyr Phe Ala Lys Phe
1               5                   10                  15

Trp Asp

<210> SEQ ID NO 541
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 541

Phe Ala Glu Lys Phe Arg Glu Ala Val Lys Asp Tyr Phe Ala Lys Phe
1               5                   10                  15

Trp Asp

<210> SEQ ID NO 542
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 542

Phe Ala Glu Lys Phe Lys Glu Ala Val Arg Asp Tyr Phe Ala Lys Phe
1               5                   10                  15

Trp Asp

<210> SEQ ID NO 543
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 543

Phe Ala Glu Lys Phe Lys Glu Ala Val Lys Asp Tyr Phe Ala Arg Phe
1               5                   10                  15

Trp Asp

<210> SEQ ID NO 544
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 544

Leu Phe Glu Lys Phe Ala Glu Ala Phe Lys Asp Tyr Val Ala Lys Trp
1               5                   10                  15

Lys Asp

<210> SEQ ID NO 545
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 545

Leu Phe Glu Arg Phe Ala Glu Ala Phe Lys Asp Tyr Val Ala Lys Trp
1               5                   10                  15

Lys Asp

<210> SEQ ID NO 546
<211> LENGTH: 18
```

<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 546

Leu Phe Glu Lys Phe Ala Glu Ala Phe Arg Asp Tyr Val Ala Lys Trp
1               5                   10                  15

Lys Asp

<210> SEQ ID NO 547
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 547

Leu Phe Glu Lys Phe Ala Glu Ala Phe Lys Asp Tyr Val Ala Arg Trp
1               5                   10                  15

Lys Asp

<210> SEQ ID NO 548
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 548

Leu Phe Glu Lys Phe Ala Glu Ala Phe Lys Asp Tyr Val Ala Lys Trp
1               5                   10                  15

Arg Asp

<210> SEQ ID NO 549
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 549

Leu Phe Glu Lys Phe Ala Glu Ala Phe Lys Glu Tyr Val Ala Lys Trp
1               5                   10                  15

Lys Glu

<210> SEQ ID NO 550
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 550

Leu Phe Asp Lys Phe Ala Asp Ala Phe Lys Asp Tyr Val Ala Lys Trp
1               5                   10                  15

Lys Asp

<210> SEQ ID NO 551
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 551

Leu Phe Asp Lys Phe Ala Glu Ala Phe Lys Asp Tyr Val Ala Lys Trp
1               5                   10                  15

Lys Asp

<210> SEQ ID NO 552
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 552

Leu Phe Glu Lys Phe Ala Asp Ala Phe Lys Asp Tyr Val Ala Lys Trp
1               5                   10                  15

Lys Asp

<210> SEQ ID NO 553
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 553

Leu Phe Glu Lys Phe Ala Glu Ala Phe Lys Glu Tyr Val Ala Lys Trp
1               5                   10                  15

Lys Asp

<210> SEQ ID NO 554
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 554

Leu Phe Glu Lys Phe Ala Glu Ala Phe Lys Asp Tyr Val Ala Lys Trp
1               5                   10                  15

Lys Glu

<210> SEQ ID NO 555
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 555

Phe Ala Glu Lys Ala Trp Glu Phe Val Lys Asp Tyr Phe Ala Lys Leu
1               5                   10                  15

Lys Asp

<210> SEQ ID NO 556
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 556

Phe Ala Glu Arg Ala Trp Glu Phe Val Lys Asp Tyr Phe Ala Lys Leu
1               5                   10                  15

Lys Asp

<210> SEQ ID NO 557
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 557

Phe Ala Glu Lys Ala Trp Glu Phe Val Lys Asp Tyr Phe Ala Lys Leu
1               5                   10                  15

Lys Asp

<210> SEQ ID NO 558
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 558

Phe Ala Glu Lys Ala Trp Glu Phe Val Lys Asp Tyr Phe Ala Lys Leu
1               5                   10                  15

Lys Asp

<210> SEQ ID NO 559
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 559

Phe Ala Glu Lys Ala Trp Glu Phe Val Lys Asp Tyr Phe Ala Lys Leu
1               5                   10                  15

Arg Asp

<210> SEQ ID NO 560
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 560

Phe Ala Glu Lys Ala Trp Glu Phe Val Lys Glu Tyr Phe Ala Lys Leu
1               5                   10                  15

Lys Glu

<210> SEQ ID NO 561
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 561

Phe Ala Asp Lys Ala Trp Asp Phe Val Lys Asp Tyr Phe Ala Lys Leu
1               5                   10                  15
Lys Asp

<210> SEQ ID NO 562
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 562

Phe Ala Asp Lys Ala Trp Glu Phe Val Lys Asp Tyr Phe Ala Lys Leu
1               5                   10                  15
Lys Asp

<210> SEQ ID NO 563
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 563

Phe Ala Glu Lys Ala Trp Asp Phe Val Lys Asp Tyr Phe Ala Lys Leu
1               5                   10                  15
Lys Asp

<210> SEQ ID NO 564
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 564

Phe Ala Glu Lys Ala Trp Glu Phe Val Lys Glu Tyr Phe Ala Lys Leu
1               5                   10                  15
Lys Asp

<210> SEQ ID NO 565
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 565

Phe Ala Glu Lys Ala Trp Glu Phe Val Lys Asp Tyr Phe Ala Lys Leu
1               5                   10                  15
Lys Glu

<210> SEQ ID NO 566
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 566

Phe Phe Glu Lys Phe Lys Glu Phe Val Lys Asp Tyr Phe Ala Lys Leu
1               5                   10                  15

Trp Asp

<210> SEQ ID NO 567
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 567

Phe Phe Glu Lys Phe Lys Glu Phe Val Lys Glu Tyr Phe Ala Lys Leu
1               5                   10                  15

Trp Glu

<210> SEQ ID NO 568
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 568

Phe Phe Asp Lys Phe Lys Asp Phe Val Lys Asp Tyr Phe Ala Lys Leu
1               5                   10                  15

Trp Asp

<210> SEQ ID NO 569
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 569

Phe Phe Glu Arg Phe Lys Glu Phe Val Lys Asp Tyr Phe Ala Lys Leu
1               5                   10                  15

Trp Asp

<210> SEQ ID NO 570
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 570

Phe Phe Glu Lys Phe Arg Glu Phe Val Lys Asp Tyr Phe Ala Lys Leu
1               5                   10                  15

Trp Asp

<210> SEQ ID NO 571
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 571

Phe Phe Glu Lys Phe Lys Glu Phe Val Arg Asp Tyr Phe Ala Lys Leu
1               5                   10                  15

Trp Asp

<210> SEQ ID NO 572
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 572

Phe Phe Glu Lys Phe Lys Glu Phe Val Lys Asp Tyr Phe Ala Arg Leu
1               5                   10                  15

Trp Asp

<210> SEQ ID NO 573
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 573

Phe Phe Asp Lys Phe Lys Glu Phe Val Lys Asp Tyr Phe Ala Lys Leu
1               5                   10                  15

Trp Asp

<210> SEQ ID NO 574
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 574

Phe Phe Glu Lys Phe Lys Asp Phe Val Lys Asp Tyr Phe Ala Lys Leu
1               5                   10                  15

Trp Asp

<210> SEQ ID NO 575
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 575

Phe Phe Glu Lys Phe Lys Glu Phe Val Lys Glu Tyr Phe Ala Lys Leu
1               5                   10                  15

Trp Asp

<210> SEQ ID NO 576
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 576

Phe Phe Glu Lys Phe Lys Glu Phe Val Lys Asp Tyr Phe Ala Lys Leu
1               5                   10                  15

Trp Glu

<210> SEQ ID NO 577
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 577

Phe Leu Glu Lys Phe Lys Glu Phe Val Lys Asp Tyr Phe Ala Lys Phe
1               5                   10                  15

Trp Asp

<210> SEQ ID NO 578
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 578

Phe Leu Glu Lys Phe Lys Glu Phe Val Lys Gly Tyr Phe Ala Lys Phe
1               5                   10                  15

Trp Glu

<210> SEQ ID NO 579
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 579

Phe Leu Asp Lys Phe Lys Glu Phe Val Lys Asp Tyr Phe Ala Lys Phe
1               5                   10                  15

Trp Asp

<210> SEQ ID NO 580
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 580

Phe Leu Asp Lys Phe Lys Glu Phe Val Lys Asp Tyr Phe Ala Lys Phe
1               5                   10                  15

Trp Asp

<210> SEQ ID NO 581
<211> LENGTH: 18
```

<210> SEQ ID NO 581
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 581

Phe Leu Glu Lys Phe Lys Asp Phe Val Lys Asp Tyr Phe Ala Lys Phe
1               5                   10                  15

Trp Asp

<210> SEQ ID NO 582
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 582

Phe Leu Glu Lys Phe Lys Glu Phe Val Lys Glu Tyr Phe Ala Lys Phe
1               5                   10                  15

Trp Asp

<210> SEQ ID NO 583
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 583

Phe Leu Glu Lys Phe Lys Glu Phe Val Lys Asp Tyr Phe Ala Lys Phe
1               5                   10                  15

Trp Glu

<210> SEQ ID NO 584
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 584

Phe Leu Glu Arg Phe Lys Glu Phe Val Lys Asp Tyr Phe Ala Lys Phe
1               5                   10                  15

Trp Asp

<210> SEQ ID NO 585
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 585

Phe Leu Glu Lys Phe Arg Glu Phe Val Lys Asp Tyr Phe Ala Lys Phe
1               5                   10                  15

Trp Asp

<210> SEQ ID NO 586
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 586

Phe Leu Glu Lys Phe Lys Glu Phe Val Arg Asp Tyr Phe Ala Lys Phe
1               5                   10                  15

Trp Asp

<210> SEQ ID NO 587
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 587

Phe Leu Glu Lys Phe Lys Glu Phe Val Lys Asp Tyr Phe Ala Arg Phe
1               5                   10                  15

Trp Asp

<210> SEQ ID NO 588
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 588

Phe Phe Glu Lys Phe Lys Glu Phe Phe Lys Asp Tyr Phe Ala Lys Leu
1               5                   10                  15

Trp Asp

<210> SEQ ID NO 589
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 589

Phe Phe Glu Lys Phe Lys Glu Phe Phe Lys Glu Tyr Phe Ala Lys Leu
1               5                   10                  15

Trp Glu

<210> SEQ ID NO 590
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 590

Phe Phe Asp Lys Phe Lys Asp Phe Phe Lys Asp Tyr Phe Ala Lys Leu
1               5                   10                  15

Trp Asp

<210> SEQ ID NO 591
<211> LENGTH: 18
```

-continued

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 591

Phe Phe Glu Arg Phe Lys Glu Phe Phe Lys Asp Tyr Phe Ala Lys Leu
1               5                   10                  15

Trp Asp

<210> SEQ ID NO 592
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 592

Phe Phe Glu Lys Phe Arg Glu Phe Phe Lys Asp Tyr Phe Ala Lys Leu
1               5                   10                  15

Trp Asp

<210> SEQ ID NO 593
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 593

Phe Phe Glu Lys Phe Lys Glu Phe Phe Arg Asp Tyr Phe Ala Lys Leu
1               5                   10                  15

Trp Asp

<210> SEQ ID NO 594
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 594

Phe Phe Glu Arg Phe Lys Glu Phe Phe Lys Asp Tyr Phe Ala Arg Leu
1               5                   10                  15

Trp Asp

<210> SEQ ID NO 595
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 595

Phe Phe Asp Lys Phe Lys Glu Phe Phe Lys Asp Tyr Phe Ala Lys Leu
1               5                   10                  15

Trp Asp

<210> SEQ ID NO 596
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 596

Phe Phe Glu Lys Glu Lys Asp Phe Phe Lys Asp Tyr Phe Ala Lys Leu
1               5                   10                  15

Trp Asp

<210> SEQ ID NO 597
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 597

Phe Phe Glu Lys Phe Lys Glu Phe Phe Lys Glu Tyr Phe Ala Lys Leu
1               5                   10                  15

Trp Asp

<210> SEQ ID NO 598
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 598

Phe Phe Glu Lys Phe Lys Glu Phe Phe Lys Asp Tyr Phe Ala Lys Leu
1               5                   10                  15

Trp Glu

<210> SEQ ID NO 599
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 599

Phe Ala Glu Lys Phe Lys Glu Ala Val Lys Asp Tyr Phe Ala Lys Phe
1               5                   10                  15

Trp Asp

<210> SEQ ID NO 600
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 600

Phe Ala Glu Lys Phe Lys Glu Ala Val Lys Glu Tyr Phe Ala Lys Phe
1               5                   10                  15

Trp Glu

<210> SEQ ID NO 601
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 601

Phe Ala Asp Lys Phe Lys Asp Ala Val Lys Asp Tyr Phe Ala Lys Phe
1               5                   10                  15

Trp Asp

<210> SEQ ID NO 602
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 602

Phe Ala Glu Arg Phe Arg Glu Ala Val Lys Asp Tyr Phe Ala Lys Phe
1               5                   10                  15

Trp Asp

<210> SEQ ID NO 603
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 603

Phe Ala Glu Lys Phe Arg Glu Ala Val Lys Asp Tyr Phe Ala Lys Phe
1               5                   10                  15

Trp Asp

<210> SEQ ID NO 604
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 604

Phe Ala Glu Lys Phe Lys Glu Ala Val Arg Asp Tyr Phe Ala Lys Phe
1               5                   10                  15

Trp Asp

<210> SEQ ID NO 605
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 605

Phe Ala Glu Lys Phe Lys Glu Ala Val Lys Asp Tyr Phe Ala Arg Phe
1               5                   10                  15

Trp Asp

<210> SEQ ID NO 606
<211> LENGTH: 18
```

<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 606

Asp Lys Trp Lys Ala Val Tyr Asp Lys Phe Ala Glu Ala Phe Lys Glu
1               5                   10                  15

Phe Phe

<210> SEQ ID NO 607
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 607

Glu Lys Trp Lys Ala Val Tyr Glu Lys Phe Ala Glu Ala Phe Lys Glu
1               5                   10                  15

Phe Phe

<210> SEQ ID NO 608
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 608

Asp Lys Trp Lys Ala Val Tyr Asp Lys Phe Ala Asp Ala Phe Lys Asp
1               5                   10                  15

Phe Phe

<210> SEQ ID NO 609
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 609

Asp Arg Trp Lys Ala Val Tyr Asp Lys Phe Ala Glu Ala Phe Lys Glu
1               5                   10                  15

Phe Phe

<210> SEQ ID NO 610
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 610

Asp Lys Trp Arg Ala Val Tyr Asp Lys Phe Ala Glu Ala Phe Lys Glu
1               5                   10                  15

Phe Phe

<210> SEQ ID NO 611
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 611

Asp Lys Trp Lys Ala Val Tyr Asp Arg Phe Ala Glu Ala Phe Lys Glu
1               5                   10                  15

Phe Phe

<210> SEQ ID NO 612
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 612

Asp Lys Trp Lys Ala Val Tyr Asp Lys Phe Ala Glu Ala Phe Arg Glu
1               5                   10                  15

Phe Phe

<210> SEQ ID NO 613
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 613

Phe Phe Glu Lys Phe Ala Glu Ala Phe Lys Asp Tyr Val Ala Lys Trp
1               5                   10                  15

Lys Asp

<210> SEQ ID NO 614
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 614

Phe Phe Glu Lys Phe Ala Glu Ala Phe Lys Glu Tyr Val Ala Lys Trp
1               5                   10                  15

Lys Glu

<210> SEQ ID NO 615
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 615

Phe Phe Asp Lys Phe Ala Asp Ala Phe Lys Asp Tyr Val Ala Lys Trp
1               5                   10                  15

Lys Asp

<210> SEQ ID NO 616
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 616

Phe Phe Glu Arg Phe Ala Glu Ala Phe Lys Asp Tyr Val Ala Lys Trp
1               5                   10                  15

Lys Asp

<210> SEQ ID NO 617
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 617

Glu Phe Glu Arg Phe Ala Glu Ala Phe Arg Asp Tyr Val Ala Lys Trp
1               5                   10                  15

Lys Asp

<210> SEQ ID NO 618
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 618

Phe Phe Glu Lys Phe Ala Glu Ala Phe Lys Asp Tyr Val Ala Arg Trp
1               5                   10                  15

Lys Asp

<210> SEQ ID NO 619
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 619

Phe Phe Glu Arg Phe Ala Glu Ala Phe Lys Asp Tyr Val Ala Lys Trp
1               5                   10                  15

Arg Asp

<210> SEQ ID NO 620
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 620

Phe Phe Asp Lys Phe Ala Glu Ala Phe Lys Asp Tyr Val Ala Lys Trp
1               5                   10                  15

Lys Asp

<210> SEQ ID NO 621
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 621

Phe Phe Glu Lys Phe Ala Asp Ala Phe Lys Asp Tyr Val Ala Lys Trp
1               5                   10                  15

Lys Asp

<210> SEQ ID NO 622
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 622

Phe Phe Glu Arg Phe Ala Glu Ala Phe Lys Glu Tyr Val Ala Lys Trp
1               5                   10                  15

Lys Asp

<210> SEQ ID NO 623
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 623

Phe Phe Glu Arg Phe Ala Glu Ala Phe Lys Asp Tyr Val Ala Lys Trp
1               5                   10                  15

Lys Glu

<210> SEQ ID NO 624
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 624

Phe Phe Glu Lys Phe Lys Glu Phe Phe Lys Asp Tyr Phe Ala Lys Phe
1               5                   10                  15

Trp Asp

<210> SEQ ID NO 625
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 625

Phe Phe Asp Lys Phe Lys Asp Phe Phe Lys Asp Tyr Phe Ala Lys Phe
1               5                   10                  15

Trp Asp

<210> SEQ ID NO 626
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 626

Phe Phe Glu Lys Phe Lys Glu Phe Phe Lys Glu Tyr Phe Ala Lys Phe
1               5                   10                  15
Trp Glu

<210> SEQ ID NO 627
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 627

Phe Phe Glu Arg Phe Lys Glu Phe Phe Lys Asp Tyr Phe Ala Lys Phe
1               5                   10                  15
Trp Asp

<210> SEQ ID NO 628
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 628

Phe Phe Glu Lys Phe Arg Glu Phe Phe Lys Asp Tyr Phe Ala Lys Phe
1               5                   10                  15
Trp Asp

<210> SEQ ID NO 629
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 629

Phe Phe Glu Lys Phe Lys Glu Phe Phe Arg Asp Tyr Phe Ala Lys Phe
1               5                   10                  15
Trp Asp

<210> SEQ ID NO 630
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 630

Phe Phe Glu Lys Phe Lys Glu Phe Phe Lys Asp Tyr Phe Ala Arg Phe
1               5                   10                  15
Trp Asp

<210> SEQ ID NO 631
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 631

Phe Phe Asp Lys Phe Lys Glu Phe Phe Lys Asp Tyr Phe Ala Lys Phe
1               5                   10                  15

Trp Asp

<210> SEQ ID NO 632
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 632

Phe Phe Glu Lys Phe Lys Asp Phe Phe Lys Asp Tyr Phe Ala Lys Phe
1               5                   10                  15

Trp Asp

<210> SEQ ID NO 633
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 633

Phe Phe Glu Lys Phe Lys Glu Phe Phe Lys Glu Tyr Phe Ala Lys Phe
1               5                   10                  15

Trp Asp

<210> SEQ ID NO 634
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 634

Phe Phe Glu Lys Phe Lys Glu Phe Phe Lys Asp Tyr Phe Ala Lys Phe
1               5                   10                  15

Trp Glu

<210> SEQ ID NO 635
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
```

<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 635

Asp Trp Phe Xaa Ala Phe Tyr Asp Xaa Val Ala Glu Xaa Phe Xaa Glu
1               5                   10                  15

Ala Phe

<210> SEQ ID NO 636
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 636

Asp Trp Phe Xaa Ala Phe Tyr Asp Xaa Val Ala Glu Xaa Phe Xaa Glu
1               5                   10                  15

Ala Phe

<210> SEQ ID NO 637
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 637

Asp Trp Phe Xaa Ala Phe Tyr Asp Xaa Val Ala Glu Xaa Phe Xaa Glu
1               5                   10                  15

Ala Phe

<210> SEQ ID NO 638
<211> LENGTH: 18

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 638

Asp Trp Phe Xaa Ala Phe Tyr Asp Xaa Val Ala Glu Xaa Phe Xaa Glu
1               5                   10                  15

Ala Phe

<210> SEQ ID NO 639
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 639

Asp Trp Phe Xaa Ala Phe Tyr Asp Xaa Val Ala Glu Xaa Phe Xaa Glu
1               5                   10                  15

Ala Phe Asn

<210> SEQ ID NO 640
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
```

-continued

```
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 640

Asp Trp Phe Xaa Ala Phe Tyr Asp Xaa Val Ala Glu Xaa Phe Xaa Glu
1               5                   10                  15
Ala Phe

<210> SEQ ID NO 641
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 641

Asp Trp Phe Xaa Ala Phe Tyr Asp Xaa Val Ala Glu Xaa Phe Xaa Glu
1               5                   10                  15
Ala Phe

<210> SEQ ID NO 642
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 642

Asp Trp Phe Xaa Ala Phe Tyr Asp Xaa Val Ala Glu Xaa Phe Xaa Glu
1               5                   10                  15
Ala Phe

<210> SEQ ID NO 643
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 643

Asp Trp Phe Xaa Ala Phe Tyr Asp Xaa Val Ala Glu Xaa Phe Xaa Glu
1               5                   10                  15

Ala Phe

<210> SEQ ID NO 644
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 644

Asp Trp Phe Xaa Ala Phe Tyr Asp Xaa Val Ala Glu Xaa Phe Xaa Glu
1               5                   10                  15

Ala Phe

<210> SEQ ID NO 645
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
```

```
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 645

Asp Trp Phe Xaa Ala Phe Tyr Asp Xaa Val Ala Glu Xaa Phe Xaa Glu
1               5                   10                  15

Ala Phe Asn

<210> SEQ ID NO 646
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 646

Asp Trp Phe Xaa Ala Phe Tyr Asp Xaa Val Ala Glu Xaa Phe Xaa Glu
1               5                   10                  15

Ala Phe

<210> SEQ ID NO 647
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 647

Asp Trp Phe Xaa Ala Phe Tyr Asp Xaa Val Ala Glu Xaa Phe Xaa Glu
1               5                   10                  15

Ala Phe

<210> SEQ ID NO 648
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 648

Asp Trp Phe Xaa Ala Phe Tyr Asp Xaa Val Ala Glu Xaa Phe Xaa Glu
1               5                   10                  15

Ala Phe

<210> SEQ ID NO 649
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 649

Asp Trp Phe Xaa Ala Phe Tyr Asp Xaa Val Ala Glu Xaa Phe Xaa Glu
1               5                   10                  15

Ala Phe

<210> SEQ ID NO 650
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
```

```
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 650

Asp Trp Phe Xaa Ala Phe Tyr Asp Xaa Val Ala Glu Xaa Phe Xaa Glu
1               5                   10                  15

Ala Phe

<210> SEQ ID NO 651
<211> LENGTH: 19
<212> TYPE: PRT
<213> ORGANISM: artificial sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 651

Asp Trp Phe Xaa Ala Phe Tyr Asp Xaa Val Ala Glu Xaa Phe Xaa Glu
1               5                   10                  15

Ala Phe Asn

<210> SEQ ID NO 652
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 652

Asp Trp Phe Xaa Ala Phe Tyr Asp Xaa Val Ala Glu Xaa Phe Xaa Glu
1               5                   10                  15

Ala Phe

<210> SEQ ID NO 653
<211> LENGTH: 18
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 653

Asp Trp Phe Xaa Ala Phe Tyr Asp Xaa Val Ala Glu Xaa Phe Xaa Glu
1               5                   10                  15

Ala Phe

<210> SEQ ID NO 654
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 654

Asp Trp Phe Xaa Ala Phe Tyr Asp Xaa Val Ala Glu Xaa Phe Xaa Glu
1               5                   10                  15

Ala Phe

<210> SEQ ID NO 655
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
```

```
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 655

Asp Trp Phe Xaa Ala Phe Tyr Asp Xaa Val Ala Glu Xaa Phe Xaa Glu
1               5                   10                  15

Ala Phe

<210> SEQ ID NO 656
<211> LENGTH: 20
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 656

Asp Trp Phe Xaa Ala Phe Tyr Asp Xaa Val Ala Glu Xaa Phe Xaa Glu
1               5                   10                  15

Ala Phe Asn Xaa
            20

<210> SEQ ID NO 657
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 657

Asp Trp Phe Xaa Ala Phe Tyr Asp Xaa Val Ala Glu Xaa Phe Xaa Glu
1               5                   10                  15
```

Ala Phe

<210> SEQ ID NO 658
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 658

Asp Trp Phe Xaa Ala Phe Tyr Asp Xaa Val Ala Glu Xaa Phe Xaa Glu
1               5                   10                  15

Ala Phe

<210> SEQ ID NO 659
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 659

Asp Trp Phe Xaa Ala Phe Tyr Asp Xaa Val Ala Glu Xaa Phe Xaa Glu
1               5                   10                  15

Ala Phe

<210> SEQ ID NO 660
<211> LENGTH: 13
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 660

Ala Arg Thr Ile Phe Ile Cys Ile Ala Leu Ser Glu Gln
1               5                   10

```
<210> SEQ ID NO 661
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 661

Asp Trp Phe Xaa Ala Phe Tyr Asp Xaa Val Ala Glu Xaa Phe Xaa Glu
1               5                   10                  15

Ala Phe

<210> SEQ ID NO 662
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 662

Asp Trp Phe Xaa Ala Phe Tyr Asp Xaa Val Ala Glu Xaa Phe Xaa Glu
1               5                   10                  15

Ala Phe

<210> SEQ ID NO 663
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
```

```
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 663

Asp Trp Phe Xaa Ala Phe Tyr Asp Xaa Val Ala Glu Xaa Phe Xaa Glu
1               5                   10                  15

Ala Phe Asn

<210> SEQ ID NO 664
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 664

Asp Trp Phe Xaa Ala Phe Tyr Asp Xaa Val Ala Glu Xaa Phe Xaa Glu
1               5                   10                  15

Ala Phe

<210> SEQ ID NO 665
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 665

Asp Trp Phe Xaa Ala Phe Tyr Asp Xaa Val Ala Glu Xaa Phe Xaa Glu
1               5                   10                  15

Ala Phe
```

```
<210> SEQ ID NO 666
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 666

Asp Trp Phe Xaa Ala Phe Tyr Asp Xaa Val Ala Glu Xaa Phe Xaa Glu
1               5                   10                  15

Ala Phe

<210> SEQ ID NO 667
<211> LENGTH: 20
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 667

Asp Trp Phe Xaa Ala Phe Tyr Asp Xaa Val Ala Glu Xaa Phe Xaa Glu
1               5                   10                  15

Ala Phe Xaa Xaa
            20

<210> SEQ ID NO 668
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
```

```
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 668

Asp Trp Phe Xaa Ala Phe Tyr Asp Xaa Val Ala Glu Xaa Phe Xaa Glu
1               5                   10                  15

Ala Phe Asn

<210> SEQ ID NO 669
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 669

Asp Trp Phe Xaa Ala Phe Tyr Asp Xaa Val Ala Glu Xaa Phe Xaa Glu
1               5                   10                  15

Ala Phe

<210> SEQ ID NO 670
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 670
```

```
Asp Trp Phe Xaa Ala Phe Tyr Asp Xaa Val Ala Glu Xaa Phe Xaa Glu
1               5                   10                  15

Ala Phe

<210> SEQ ID NO 671
<211> LENGTH: 20
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 671

Asp Trp Phe Xaa Ala Phe Tyr Asp Xaa Val Ala Glu Xaa Phe Xaa Glu
1               5                   10                  15

Ala Phe Xaa Xaa
            20

<210> SEQ ID NO 672
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 672

Lys Arg Ser
1

<210> SEQ ID NO 673
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 673

Lys Arg Thr
1

<210> SEQ ID NO 674
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 674
```

Trp Arg Ile
1

<210> SEQ ID NO 675
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 675

Trp Arg Leu
1

<210> SEQ ID NO 676
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 676

Phe Arg Ile
1

<210> SEQ ID NO 677
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 677

Phe Arg Leu
1

<210> SEQ ID NO 678
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 678

Lys Glu Ser
1

<210> SEQ ID NO 679
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 679

Lys Glu Thr
1

<210> SEQ ID NO 680
<211> LENGTH: 3
<212> TYPE: PRT
<213> ORGANISM: Artificial Sequence
<220> FEATURE:

```
<223> OTHER INFORMATION: Description of Artificial Sequence: note =
      Synthetic Construct

<400> SEQUENCE: 680

Lys Asp Ser
1

<210> SEQ ID NO 681
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 681

Lys Asp Thr
1

<210> SEQ ID NO 682
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 682

Lys Arg Ser
1

<210> SEQ ID NO 683
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 683

Lys Arg Thr
1

<210> SEQ ID NO 684
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 684

Leu Glu Ser
1

<210> SEQ ID NO 685
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 685

Leu Glu Thr
1

<210> SEQ ID NO 686
```

```
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 686

Trp Arg Ser
1

<210> SEQ ID NO 687
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 687

Trp Asp Ser
1

<210> SEQ ID NO 688
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 688

Trp Glu Ser
1

<210> SEQ ID NO 689
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 689

Trp Arg Ser
1

<210> SEQ ID NO 690
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 690

Lys Glu Leu
1

<210> SEQ ID NO 691
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 691

Leu Arg Ser
```

<210> SEQ ID NO 692
<211> LENGTH: 3
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 692

Leu Asp Ser
1

<210> SEQ ID NO 693
<211> LENGTH: 3
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 693

Leu Glu Ser
1

<210> SEQ ID NO 694
<211> LENGTH: 3
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 694

Leu Arg Ser
1

<210> SEQ ID NO 695
<211> LENGTH: 3
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 695

Leu Arg Thr
1

<210> SEQ ID NO 696
<211> LENGTH: 3
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 696

Glu Asp Tyr
1

<210> SEQ ID NO 697
<211> LENGTH: 3
<212> TYPE: PRT
<213> ORGANISM: Artificial Sequence
<220> FEATURE:
<223> OTHER INFORMATION: Description of Artificial Sequence: note = Synthetic Construct

```
<400> SEQUENCE: 697

Lys Arg Ser
1

<210> SEQ ID NO 698
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 698

Trp Arg Ile
1

<210> SEQ ID NO 699
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 699

Trp Arg Leu
1

<210> SEQ ID NO 700
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 700

Phe Arg Ile
1

<210> SEQ ID NO 701
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 701

Phe Arg Leu
1

<210> SEQ ID NO 702
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 702

Trp Arg Phe
1

<210> SEQ ID NO 703
<211> LENGTH: 3
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 703

Trp Arg Tyr
1

<210> SEQ ID NO 704
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 704

Trp Arg Phe
1

<210> SEQ ID NO 705
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 705

Trp Arg Tyr
1

<210> SEQ ID NO 706
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 706

Xaa Arg Ser
1

<210> SEQ ID NO 707
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 707

Lys Arg Ser
1

<210> SEQ ID NO 708
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 708
```

Lys Arg Thr
1

<210> SEQ ID NO 709
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 709

Leu Asp Thr
1

<210> SEQ ID NO 710
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 710

Leu Glu Thr
1

<210> SEQ ID NO 711
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 711

Leu Arg Thr
1

<210> SEQ ID NO 712
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 712

Xaa Arg Ser
1

<210> SEQ ID NO 713
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 713

Xaa Asp Ser

-continued

<210> SEQ ID NO 714
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 714

Xaa Glu Ser
1

<210> SEQ ID NO 715
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 715

Lys Arg Ser
1

<210> SEQ ID NO 716
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 716

Lys Arg Thr
1

<210> SEQ ID NO 717
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 717

Lys Glu Ser
1

<210> SEQ ID NO 718
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 718

Lys Glu Thr
1

<210> SEQ ID NO 719
<211> LENGTH: 3
<212> TYPE: PRT

```
<213> ORGANISM: Artificial Sequence
<220> FEATURE:
<223> OTHER INFORMATION: Description of Artificial Sequence: note =
      Synthetic Construct

<400> SEQUENCE: 719

Lys Asp Ser
1

<210> SEQ ID NO 720
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 720

Lys Asp Thr
1

<210> SEQ ID NO 721
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 721

Lys Glu Leu
1

<210> SEQ ID NO 722
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 722

Lys Arg Leu
1

<210> SEQ ID NO 723
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 723

Lys Arg Thr
1

<210> SEQ ID NO 724
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 724

Lys Glu Ser
1
```

```
<210> SEQ ID NO 725
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 725

Lys Glu Thr
1

<210> SEQ ID NO 726
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 726

Lys Asp Ser
1

<210> SEQ ID NO 727
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 727

Lys Asp Thr
1

<210> SEQ ID NO 728
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 728

Lys Arg Ser
1

<210> SEQ ID NO 729
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 729

Lys Glu Leu
1

<210> SEQ ID NO 730
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 730
```

Lys Asp Ser
1

<210> SEQ ID NO 731
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 731

Lys Asp Thr
1

<210> SEQ ID NO 732
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 732

Lys Arg Thr
1

<210> SEQ ID NO 733
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 733

Lys Glu Leu
1

<210> SEQ ID NO 734
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 734

Xaa Glu Ser
1

<210> SEQ ID NO 735
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 735

Xaa Asp Ser

```
<210> SEQ ID NO 736
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 736

Xaa Asp Thr
1

<210> SEQ ID NO 737
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 737

Xaa Arg Thr
1

<210> SEQ ID NO 738
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 738

Xaa Glu Thr
1

<210> SEQ ID NO 739
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 739

Trp Asp Ile
1

<210> SEQ ID NO 740
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 740
```

Trp Arg Ile
1

<210> SEQ ID NO 741
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 741

Trp Glu Ile
1

<210> SEQ ID NO 742
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 742

Trp Asp Leu
1

<210> SEQ ID NO 743
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 743

Trp Glu Leu
1

<210> SEQ ID NO 744
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 744

Phe Asp Ile
1

<210> SEQ ID NO 745
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 745

Phe Asp Leu
1

<210> SEQ ID NO 746
<211> LENGTH: 3
<212> TYPE: PRT
<213> ORGANISM: Artificial Sequence
<220> FEATURE:

```
<223> OTHER INFORMATION: Description of Artificial Sequence: note =
      Synthetic Construct

<400> SEQUENCE: 746

Phe Glu Leu
1

<210> SEQ ID NO 747
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 747

Trp Arg Phe
1

<210> SEQ ID NO 748
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 748

Trp Glu Phe
1

<210> SEQ ID NO 749
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 749

Trp Asp Phe
1

<210> SEQ ID NO 750
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 750

Trp Asp Tyr
1

<210> SEQ ID NO 751
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 751

Trp Arg Tyr
1

<210> SEQ ID NO 752
```

```
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 752

Trp Glu Tyr
1

<210> SEQ ID NO 753
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 753

Trp Arg Thr
1

<210> SEQ ID NO 754
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 754

Trp Asp Thr
1

<210> SEQ ID NO 755
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 755

Trp Glu Thr
1

<210> SEQ ID NO 756
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 756

Phe Arg Xaa
1

<210> SEQ ID NO 757
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 757

Phe Glu Xaa
1

<210> SEQ ID NO 758
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 758

Phe Asp Xaa
1

<210> SEQ ID NO 759
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 759

Glu His Tyr
1

<210> SEQ ID NO 760
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 760

Leu His Ser
1

<210> SEQ ID NO 761
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 761

Leu His Thr
1

<210> SEQ ID NO 762
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 762
```

Lys His Ser
1

<210> SEQ ID NO 763
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 763

Lys His Thr
1

<210> SEQ ID NO 764
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 764

Lys His Leu
1

<210> SEQ ID NO 765
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 765

Lys His Ser
1

<210> SEQ ID NO 766
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 766

Lys His Thr
1

<210> SEQ ID NO 767
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 767

Lys His Leu
1

<210> SEQ ID NO 768
<211> LENGTH: 3
<212> TYPE: PRT
<213> ORGANISM: Artificial Sequence
<220> FEATURE:

-continued

```
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 768

Xaa His Ser
1

<210> SEQ ID NO 769
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 769

Xaa His Thr
1

<210> SEQ ID NO 770
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 770

Phe His Ile
1

<210> SEQ ID NO 771
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 771

Phe His Leu
1

<210> SEQ ID NO 772
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 772

Phe His Xaa
1

<210> SEQ ID NO 773
<211> LENGTH: 3
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 773

Phe Lys Leu
1

<210> SEQ ID NO 774
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 774

Trp His Ile
1

<210> SEQ ID NO 775
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 775

Trp His Leu
1

<210> SEQ ID NO 776
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 776

Trp His Phe
1

<210> SEQ ID NO 777
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 777

Trp His Tyr
1

<210> SEQ ID NO 778
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 778

Phe Lys Leu
1
```

<210> SEQ ID NO 779
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 779

Lys His Ser
1

<210> SEQ ID NO 780
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 780

Lys His Thr
1

<210> SEQ ID NO 781
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 781

Lys His Leu
1

<210> SEQ ID NO 782
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 782

Leu His Ser
1

<210> SEQ ID NO 783
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 783

Leu His Thr
1

<210> SEQ ID NO 784
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 784

```
Lys His Ser
1

<210> SEQ ID NO 785
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 785

Lys His Thr
1

<210> SEQ ID NO 786
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 786

Lys His Leu
1

<210> SEQ ID NO 787
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 787

Lys His Ser
1

<210> SEQ ID NO 788
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 788

Lys His Thr
1

<210> SEQ ID NO 789
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 789

Xaa His Ser
1

<210> SEQ ID NO 790
```

```
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 790

Phe His Ile
1

<210> SEQ ID NO 791
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 791

Phe His Leu
1

<210> SEQ ID NO 792
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 792

Phe His Xaa
1

<210> SEQ ID NO 793
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 793

Trp His Ser
1

<210> SEQ ID NO 794
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 794

Trp His Ile
1

<210> SEQ ID NO 795
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 795

Trp His Leu
1

<210> SEQ ID NO 796
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 796

Trp His Phe
1

<210> SEQ ID NO 797
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 797

Trp His Tyr
1

<210> SEQ ID NO 798
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 798

Trp His Thr
1

<210> SEQ ID NO 799
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 799

Lys His Ser
1

<210> SEQ ID NO 800
<211> LENGTH: 3
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 800

Lys His Thr
1

<210> SEQ ID NO 801
<211> LENGTH: 4
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 801

Lys Arg Asp Ser
1

<210> SEQ ID NO 802
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 802

Lys Arg Asp Thr
1

<210> SEQ ID NO 803
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 803

Trp Arg Asp Ile
1

<210> SEQ ID NO 804
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 804

Trp Arg Asp Leu
1

<210> SEQ ID NO 805
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 805

Phe Arg Asp Leu
1

<210> SEQ ID NO 806
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 806

Phe Arg Asp Ile
1
```

```
<210> SEQ ID NO 807
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 807

Phe Arg Asp Xaa
1

<210> SEQ ID NO 808
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 808

Phe Arg Glu Xaa
1

<210> SEQ ID NO 809
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 809

Phe Arg Glu Ile
1

<210> SEQ ID NO 810
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 810

Phe Asp Arg Ile
1

<210> SEQ ID NO 811
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 811

Phe Glu Arg Ile
1

<210> SEQ ID NO 812
```

```
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 812

Phe Asp Arg Leu
1

<210> SEQ ID NO 813
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 813

Phe Arg Glu Leu
1

<210> SEQ ID NO 814
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 814

Phe Glu Arg Leu
1

<210> SEQ ID NO 815
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 815

Phe Asp Arg Xaa
1

<210> SEQ ID NO 816
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 816

Phe Glu Arg Xaa
1

<210> SEQ ID NO 817
<211> LENGTH: 4
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 817

Lys Glu Arg Ser
1

<210> SEQ ID NO 818
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 818

Lys Glu Arg Thr
1

<210> SEQ ID NO 819
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 819

Lys Asp Arg Ser
1

<210> SEQ ID NO 820
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 820

Lys Asp Arg Thr
1

<210> SEQ ID NO 821
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 821

Lys Arg Glu Ser
1

<210> SEQ ID NO 822
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 822

Lys Arg Glu Thr
1
```

```
<210> SEQ ID NO 823
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 823

Leu Glu Arg Ser
1

<210> SEQ ID NO 824
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 824

Leu Glu Arg Thr
1

<210> SEQ ID NO 825
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 825

Trp Arg Asp Ser
1

<210> SEQ ID NO 826
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 826

Trp Asp Arg Ser
1

<210> SEQ ID NO 827
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 827

Trp Glu Arg Ser
1

<210> SEQ ID NO 828
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 828
```

Trp Arg Glu Ser
1

<210> SEQ ID NO 829
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 829

Lys Glu Arg Leu
1

<210> SEQ ID NO 830
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 830

Leu Arg Asp Ser
1

<210> SEQ ID NO 831
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 831

Leu Asp Arg Ser
1

<210> SEQ ID NO 832
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 832

Leu Glu Arg Ser
1

<210> SEQ ID NO 833
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 833

Leu Arg Glu Ser
1

<210> SEQ ID NO 834
<211> LENGTH: 4
<212> TYPE: PRT
<213> ORGANISM: Artificial Sequence
<220> FEATURE:

```
<223> OTHER INFORMATION: Description of Artificial Sequence: note =
      Synthetic Construct

<400> SEQUENCE: 834

Leu Arg Asp Thr
1

<210> SEQ ID NO 835
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 835

Glu Asp Arg Tyr
1

<210> SEQ ID NO 836
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 836

Lys Arg Asp Ser
1

<210> SEQ ID NO 837
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 837

Trp Arg Asp Ile
1

<210> SEQ ID NO 838
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 838

Trp Arg Asp Leu
1

<210> SEQ ID NO 839
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 839

Phe Arg Asp Ile
1

<210> SEQ ID NO 840
```

```
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 840

Phe Arg Asp Leu
1

<210> SEQ ID NO 841
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 841

Trp Arg Asp Phe
1

<210> SEQ ID NO 842
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 842

Trp Arg Asp Tyr
1

<210> SEQ ID NO 843
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 843

Trp Arg Asp Phe
1

<210> SEQ ID NO 844
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 844

Trp Arg Asp Tyr
1

<210> SEQ ID NO 845
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid
```

```
<400> SEQUENCE: 845

Xaa Arg Glu Ser
1

<210> SEQ ID NO 846
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 846

Lys Arg Asp Ser
1

<210> SEQ ID NO 847
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 847

Lys Arg Asp Thr
1

<210> SEQ ID NO 848
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 848

Leu Asp Arg Thr
1

<210> SEQ ID NO 849
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 849

Leu Glu Arg Thr
1

<210> SEQ ID NO 850
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 850

Leu Arg Glu Thr
1

<210> SEQ ID NO 851
<211> LENGTH: 4
<212> TYPE: PRT
```

-continued

```
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 851

Xaa Arg Asp Ser
1

<210> SEQ ID NO 852
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 852

Xaa Asp Arg Ser
1

<210> SEQ ID NO 853
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 853

Xaa Glu Arg Ser
1

<210> SEQ ID NO 854
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 854

Xaa Arg Glu Ser
1

<210> SEQ ID NO 855
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 855

Lys Arg Asp Ser
```

```
<210> SEQ ID NO 856
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 856

Lys Arg Asp Thr
1

<210> SEQ ID NO 857
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 857

Lys Glu Arg Ser
1

<210> SEQ ID NO 858
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 858

Lys Glu Arg Thr
1

<210> SEQ ID NO 859
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 859

Lys Asp Arg Ser
1

<210> SEQ ID NO 860
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 860

Lys Asp Arg Thr
1

<210> SEQ ID NO 861
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 861

Lys Arg Glu Ser
1

<210> SEQ ID NO 862
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 862

Lys Arg Glu Thr
1

<210> SEQ ID NO 863
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 863

Lys Glu Arg Leu
1

<210> SEQ ID NO 864
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 864

Lys Arg Glu Leu
1

<210> SEQ ID NO 865
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 865

Lys Arg Asp Thr
1

<210> SEQ ID NO 866
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 866

Lys Glu Arg Ser
1

<210> SEQ ID NO 867
<211> LENGTH: 4
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 867

Lys Glu Arg Thr
1

<210> SEQ ID NO 868
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 868

Lys Asp Arg Ser
1

<210> SEQ ID NO 869
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 869

Lys Asp Arg Thr
1

<210> SEQ ID NO 870
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 870

Lys Arg Glu Ser
1

<210> SEQ ID NO 871
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 871

Lys Arg Glu Thr
1

<210> SEQ ID NO 872
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 872

Lys Glu Arg Leu
1
```

<210> SEQ ID NO 873
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 873

Lys Arg Asp Ser
1

<210> SEQ ID NO 874
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 874

Lys Arg Asp Thr
1

<210> SEQ ID NO 875
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 875

Lys Glu Arg Ser
1

<210> SEQ ID NO 876
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 876

Lys Glu Arg Thr
1

<210> SEQ ID NO 877
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 877

Lys Asp Arg Ser
1

<210> SEQ ID NO 878
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 878

Lys Asp Arg Thr
1

<210> SEQ ID NO 879
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 879

Lys Arg Glu Ser
1

<210> SEQ ID NO 880
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 880

Lys Arg Glu Thr
1

<210> SEQ ID NO 881
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 881

Lys Glu Arg Leu
1

<210> SEQ ID NO 882
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 882

Xaa Arg Glu Ser
1

<210> SEQ ID NO 883
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 883

Xaa Glu Arg Ser

```
<210> SEQ ID NO 884
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 884

Xaa Arg Asp Ser
1

<210> SEQ ID NO 885
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 885

Xaa Asp Arg Ser
1

<210> SEQ ID NO 886
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 886

Xaa Asp Arg Thr
1

<210> SEQ ID NO 887
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 887

Xaa Arg Asp Thr
1

<210> SEQ ID NO 888
<211> LENGTH: 4
<212> TYPE: PRT
<213> ORGANISM: Artificial Sequence
<220> FEATURE:
```

```
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 888

Xaa Glu Arg Thr
1

<210> SEQ ID NO 889
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 889

Xaa Arg Glu Thr
1

<210> SEQ ID NO 890
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 890

Trp Asp Arg Ile
1

<210> SEQ ID NO 891
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 891

Trp Arg Glu Ile
1

<210> SEQ ID NO 892
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 892

Trp Glu Arg Ile
1

<210> SEQ ID NO 893
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 893

Trp Asp Arg Leu
1

<210> SEQ ID NO 894
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 894

Trp Arg Glu Leu
1

<210> SEQ ID NO 895
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 895

Trp Glu Arg Leu
1

<210> SEQ ID NO 896
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 896

Phe Asp Arg Ile
1

<210> SEQ ID NO 897
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 897

Phe Arg Glu Ile
1

<210> SEQ ID NO 898
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 898

Phe Glu Arg Ile
1

<210> SEQ ID NO 899
<211> LENGTH: 4
<212> TYPE: PRT
```

-continued

```
<213> ORGANISM: Artificial Sequence
<220> FEATURE:
<223> OTHER INFORMATION: Description of Artificial Sequence: note =
      Synthetic Construct

<400> SEQUENCE: 899

Phe Asp Arg Leu
1

<210> SEQ ID NO 900
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 900

Phe Arg Glu Leu
1

<210> SEQ ID NO 901
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 901

Phe Glu Arg Leu
1

<210> SEQ ID NO 902
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 902

Trp Arg Asp Phe
1

<210> SEQ ID NO 903
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 903

Trp Arg Glu Phe
1

<210> SEQ ID NO 904
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 904

Trp Glu Arg Phe
1
```

```
<210> SEQ ID NO 905
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 905

Trp Asp Arg Tyr
1

<210> SEQ ID NO 906
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 906

Trp Arg Glu Tyr
1

<210> SEQ ID NO 907
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 907

Trp Glu Arg Tyr
1

<210> SEQ ID NO 908
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 908

Trp Arg Asp Thr
1

<210> SEQ ID NO 909
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 909

Trp Asp Arg Thr
1

<210> SEQ ID NO 910
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 910
```

Trp Arg Glu Thr
1

<210> SEQ ID NO 911
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 911

Trp Glu Arg Thr
1

<210> SEQ ID NO 912
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 912

Phe Arg Asp Xaa
1

<210> SEQ ID NO 913
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 913

Phe Arg Glu Xaa
1

<210> SEQ ID NO 914
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 914

Phe Lys Asp Leu
1

<210> SEQ ID NO 915
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 915

Phe Asp Lys Leu

```
<210> SEQ ID NO 916
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 916

Phe Lys Glu Leu
1

<210> SEQ ID NO 917
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 917

Phe Glu Lys Leu
1

<210> SEQ ID NO 918
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 918

Phe Lys Asp Ile
1

<210> SEQ ID NO 919
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 919

Phe Asp Lys Ile
1

<210> SEQ ID NO 920
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 920

Phe Lys Glu Ile
1

<210> SEQ ID NO 921
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 921

Phe Glu Lys Ile
1

<210> SEQ ID NO 922
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 922

Phe Lys Asp Xaa
1

<210> SEQ ID NO 923
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 923

Phe Asp Lys Xaa
1

<210> SEQ ID NO 924
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 924

Phe Lys Glu Xaa
1

<210> SEQ ID NO 925
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 925

Phe Glu Lys Xaa
1

<210> SEQ ID NO 926
```

```
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 926

Phe His Asp Leu
1

<210> SEQ ID NO 927
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 927

Phe Asp His Leu
1

<210> SEQ ID NO 928
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 928

Phe His Glu Leu
1

<210> SEQ ID NO 929
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 929

Phe Glu His Leu
1

<210> SEQ ID NO 930
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 930

Phe His Asp Ile
1

<210> SEQ ID NO 931
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 931

Phe Asp His Ile
```

```
<210> SEQ ID NO 932
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 932

Phe His Glu Ile
1

<210> SEQ ID NO 933
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 933

Phe Glu His Ile
1

<210> SEQ ID NO 934
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 934

Phe His Asp Xaa
1

<210> SEQ ID NO 935
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 935

Phe Asp His Xaa
1

<210> SEQ ID NO 936
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 936
```

Phe His Glu Xaa
1

<210> SEQ ID NO 937
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 937

Phe Glu His Xaa
1

<210> SEQ ID NO 938
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 938

Lys Lys Asp Ser
1

<210> SEQ ID NO 939
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 939

Lys Asp Lys Ser
1

<210> SEQ ID NO 940
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 940

Lys Lys Glu Ser
1

<210> SEQ ID NO 941
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 941

Lys Glu Lys Ser
1

<210> SEQ ID NO 942

```
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 942

Lys His Asp Ser
1

<210> SEQ ID NO 943
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 943

Lys Asp His Ser
1

<210> SEQ ID NO 944
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 944

Lys His Glu Ser
1

<210> SEQ ID NO 945
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 945

Lys Glu His Ser
1

<210> SEQ ID NO 946
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 946

Lys Leu Arg Ser
1

<210> SEQ ID NO 947
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 947

Lys Arg Leu Ser
```

```
<210> SEQ ID NO 948
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 948

Lys Leu Arg Thr
1

<210> SEQ ID NO 949
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 949

Lys Arg Leu Thr
1

<210> SEQ ID NO 950
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 950

Lys Glu Leu Ser
1

<210> SEQ ID NO 951
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 951

Lys Leu Glu Ser
1

<210> SEQ ID NO 952
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 952

Lys Glu Leu Thr
1

<210> SEQ ID NO 953
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 953

Lys Leu Glu Thr
1

<210> SEQ ID NO 954
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 954

Lys Leu Arg Ser
1

<210> SEQ ID NO 955
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 955

Lys Leu Arg Thr
1

<210> SEQ ID NO 956
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 956

Lys Glu Leu Ser
1

<210> SEQ ID NO 957
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 957

Lys Glu Leu Thr
1

<210> SEQ ID NO 958
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 958

Lys Glu Ile Thr
1

<210> SEQ ID NO 959
<211> LENGTH: 4
<212> TYPE: PRT
```

-continued

```
<213> ORGANISM: Artificial Sequence
<220> FEATURE:
<223> OTHER INFORMATION: Description of Artificial Sequence: note =
      Synthetic Construct

<400> SEQUENCE: 959

Lys Leu Arg Ser
1

<210> SEQ ID NO 960
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 960

Lys Leu Arg Thr
1

<210> SEQ ID NO 961
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 961

Lys Glu Leu Ser
1

<210> SEQ ID NO 962
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 962

Lys Glu Leu Thr
1

<210> SEQ ID NO 963
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 963

Lys Leu Arg Ser
1

<210> SEQ ID NO 964
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 964

Lys Arg Phe Thr
1
```

```
<210> SEQ ID NO 965
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 965

Lys Leu Arg Thr
1

<210> SEQ ID NO 966
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 966

Lys Glu Ile Thr
1

<210> SEQ ID NO 967
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 967

Lys Glu Val Thr
1

<210> SEQ ID NO 968
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 968

Lys Glu Ala Thr
1

<210> SEQ ID NO 969
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 969

Lys Glu Gly Thr
1

<210> SEQ ID NO 970
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 970
```

Lys Glu Leu Ser
1

<210> SEQ ID NO 971
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 971

Lys Glu Leu Thr
1

<210> SEQ ID NO 972
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 972

Lys Arg Trp Tyr
1

<210> SEQ ID NO 973
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 973

Lys Trp Arg Tyr
1

<210> SEQ ID NO 974
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 974

Lys Arg Tyr Trp
1

<210> SEQ ID NO 975
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 975

Lys Tyr Arg Trp
1

<210> SEQ ID NO 976
<211> LENGTH: 5
<212> TYPE: PRT
<213> ORGANISM: Artificial Sequence
<220> FEATURE:

<223> OTHER INFORMATION: Description of Artificial Sequence: note = Synthetic Construct

<400> SEQUENCE: 976

Lys Arg Tyr Trp Thr
1               5

<210> SEQ ID NO 977
<211> LENGTH: 4
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 977

Lys Arg Tyr Thr
1

<210> SEQ ID NO 978
<211> LENGTH: 4
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 978

Lys Arg Trp Thr
1

<210> SEQ ID NO 979
<211> LENGTH: 4
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 979

Lys Arg Trp Tyr
1

<210> SEQ ID NO 980
<211> LENGTH: 4
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 980

Lys Arg Tyr Trp
1

<210> SEQ ID NO 981
<211> LENGTH: 5
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 981

Lys Arg Tyr Trp Thr
1               5

<210> SEQ ID NO 982

```
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 982

Lys Arg Tyr Thr
1

<210> SEQ ID NO 983
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 983

Lys Arg Trp Thr
1

<210> SEQ ID NO 984
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 984

Lys Arg Trp Tyr
1

<210> SEQ ID NO 985
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 985

Lys Arg Tyr Trp
1

<210> SEQ ID NO 986
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 986

Lys Arg Tyr Trp Thr
1               5

<210> SEQ ID NO 987
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 987

Lys Arg Tyr Thr
```

<210> SEQ ID NO 988
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 988

Lys Arg Trp Thr
1

<210> SEQ ID NO 989
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 989

Glu Lys Arg Tyr
1

<210> SEQ ID NO 990
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 990

Lys Arg Trp Tyr
1

<210> SEQ ID NO 991
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 991

Lys Arg Tyr Trp
1

<210> SEQ ID NO 992
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 992

Lys Arg Tyr Trp Thr
1               5

<210> SEQ ID NO 993
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

```
<400> SEQUENCE: 993

Lys Arg Tyr Thr
1

<210> SEQ ID NO 994
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 994

Lys Arg Phe Thr
1

<210> SEQ ID NO 995
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 995

Lys Arg Trp Thr
1

<210> SEQ ID NO 996
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 996

Lys Phe Trp Phe Ser
1               5

<210> SEQ ID NO 997
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 997

Lys Phe Trp Phe Thr
1               5

<210> SEQ ID NO 998
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 998

Lys Phe Tyr Phe Ser
1               5

<210> SEQ ID NO 999
<211> LENGTH: 5
<212> TYPE: PRT
```

```
<213> ORGANISM: Artificial Sequence
<220> FEATURE:
<223> OTHER INFORMATION: Description of Artificial Sequence: note =
      Synthetic Construct

<400> SEQUENCE: 999

Lys Phe Tyr Phe Thr
1               5

<210> SEQ ID NO 1000
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1000

Lys Phe His Phe Ser
1               5

<210> SEQ ID NO 1001
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1001

Lys Phe His Phe Thr
1               5

<210> SEQ ID NO 1002
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1002

Lys Val Phe Phe Tyr Ser
1               5

<210> SEQ ID NO 1003
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1003

Lys Phe Trp Phe Ser
1               5

<210> SEQ ID NO 1004
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1004

Lys Phe Trp Phe Thr
1               5
```

```
<210> SEQ ID NO 1005
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1005

Lys Phe Tyr Phe Ser
1               5

<210> SEQ ID NO 1006
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1006

Lys Phe Tyr Phe Thr
1               5

<210> SEQ ID NO 1007
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1007

Lys Phe His Phe Ser
1               5

<210> SEQ ID NO 1008
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1008

Lys Phe His Phe Thr
1               5

<210> SEQ ID NO 1009
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1009

Leu Phe Trp Phe Thr
1               5

<210> SEQ ID NO 1010
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1010
```

```
Leu Phe Trp Phe Ser
1               5

<210> SEQ ID NO 1011
<211> LENGTH: 22
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1011

Leu Leu Glu Gln Leu Asn Glu Gln Phe Asn Trp Val Ser Arg Leu Ala
1               5                   10                  15

Asn Leu Thr Gln Gly Glu
            20

<210> SEQ ID NO 1012
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1012

Leu Leu Glu Gln Leu Asn Glu Gln Phe Asn Trp Val Ser Arg Leu Ala
1               5                   10                  15

Asn Leu

<210> SEQ ID NO 1013
<211> LENGTH: 25
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1013

Asn Glu Leu Gln Glu Met Ser Asn Gln Gly Ser Lys Tyr Val Asn Lys
1               5                   10                  15

Glu Ile Gln Asn Ala Val Asn Gly Val
            20                  25

<210> SEQ ID NO 1014
<211> LENGTH: 21
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1014

Ile Gln Asn Ala Val Asn Gly Val Lys Gln Ile Lys Thr Leu Ile Glu
1               5                   10                  15

Lys Thr Asn Glu Glu
            20

<210> SEQ ID NO 1015
<211> LENGTH: 32
<212> TYPE: PRT
<213> ORGANISM: Artificial Sequence
<220> FEATURE:
<223> OTHER INFORMATION: Description of Artificial Sequence: note =
      Synthetic Construct
```

-continued

```
<400> SEQUENCE: 1015

Arg Lys Thr Leu Leu Ser Asn Leu Glu Glu Ala Lys Lys Lys Glu
1               5                   10                  15
Asp Ala Leu Asn Glu Thr Arg Glu Ser Glu Thr Lys Leu Lys Glu Leu
            20                  25                  30

<210> SEQ ID NO 1016
<211> LENGTH: 16
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1016

Pro Gly Val Cys Asn Glu Thr Met Met Ala Leu Trp Glu Glu Cys Lys
1               5                   10                  15

<210> SEQ ID NO 1017
<211> LENGTH: 16
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1017

Pro Cys Leu Lys Gln Thr Cys Met Lys Phe Tyr Ala Arg Val Cys Arg
1               5                   10                  15

<210> SEQ ID NO 1018
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1018

Glu Cys Lys Pro Cys Leu Lys Gln Thr Cys Met Lys Phe Tyr Ala Arg
1               5                   10                  15
Val Cys Arg

<210> SEQ ID NO 1019
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1019

Leu Val Gly Arg Gln Leu Glu Glu Phe Leu
1               5                   10

<210> SEQ ID NO 1020
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1020

Met Asn Gly Asp Arg Ile Asp Ser Leu Leu Glu Asn
1               5                   10
```

<210> SEQ ID NO 1021
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1021

Gln Gln Thr His Met Leu Asp Val Met Gln Asp
1               5                   10

<210> SEQ ID NO 1022
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1022

Phe Ser Arg Ala Ser Ser Ile Ile Asp Glu Leu Phe Gln Asp
1               5                   10

<210> SEQ ID NO 1023
<211> LENGTH: 15
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1023

Pro Phe Leu Glu Met Ile His Glu Ala Gln Gln Ala Met Asp Ile
1               5                   10                  15

<210> SEQ ID NO 1024
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1024

Pro Thr Glu Phe Ile Arg Glu Gly Asp Asp Asp
1               5                   10

<210> SEQ ID NO 1025
<211> LENGTH: 15
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1025

Arg Met Lys Asp Gln Cys Asp Lys Cys Arg Glu Ile Leu Ser Val
1               5                   10                  15

<210> SEQ ID NO 1026
<211> LENGTH: 32
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1026

```
Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
            20                  25                  30

<210> SEQ ID NO 1027
<211> LENGTH: 22
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1027

Leu Leu Glu Gln Leu Asn Glu Gln Phe Asn Trp Val Ser Arg Leu Ala
1               5                   10                  15

Asn Leu Thr Glu Gly Glu
            20

<210> SEQ ID NO 1028
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1028

Asp Gln Tyr Tyr Leu Arg Val Thr Thr Val Ala
1               5                   10

<210> SEQ ID NO 1029
<211> LENGTH: 25
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1029

Asp Gln Tyr Tyr Leu Arg Val Thr Thr Val Ala Pro Ser Gly Val Thr
1               5                   10                  15

Glu Val Val Val Lys Leu Phe Asp Ser
            20                  25

<210> SEQ ID NO 1030
<211> LENGTH: 21
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1030

Pro Lys Phe Met Glu Thr Val Ala Glu Lys Ala Leu Gln Glu Tyr Arg
1               5                   10                  15

Lys Lys His Arg Glu
            20

<210> SEQ ID NO 1031
<211> LENGTH: 26
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 1031

Trp Asp Arg Val Lys Asp Leu Ala Thr Val Tyr Val Asp Val Leu Lys
1               5                   10                  15

Asp Ser Gly Arg Asp Tyr Val Ser Gln Phe
            20                  25

<210> SEQ ID NO 1032
<211> LENGTH: 25
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1032

Val Ala Thr Val Met Trp Asp Tyr Phe Ser Gln Leu Ser Asn Asn Ala
1               5                   10                  15

Lys Glu Ala Val Glu His Leu Gln Lys
            20                  25

<210> SEQ ID NO 1033
<211> LENGTH: 27
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1033

Arg Trp Glu Leu Ala Leu Gly Arg Phe Trp Asp Tyr Leu Arg Trp Val
1               5                   10                  15

Gln Thr Leu Ser Glu Gln Val Gln Glu Glu Leu
            20                  25

<210> SEQ ID NO 1034
<211> LENGTH: 35
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1034

Leu Ser Ser Gln Val Thr Gln Glu Leu Arg Ala Leu Met Asp Glu Thr
1               5                   10                  15

Met Lys Glu Leu Lys Glu Leu Lys Ala Tyr Lys Ser Glu Leu Glu Glu
            20                  25                  30

Gln Leu Thr
        35

<210> SEQ ID NO 1035
<211> LENGTH: 26
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1035

Ala Arg Leu Ser Lys Glu Leu Gln Ala Ala Gln Ala Arg Leu Gly Ala
1               5                   10                  15

Asp Met Glu Asp Val Cys Gly Arg Leu Val
            20                  25
```

<210> SEQ ID NO 1036
<211> LENGTH: 26
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 1036

```
Val Arg Leu Ala Ser His Leu Arg Lys Leu Arg Lys Arg Leu Leu Arg
1               5                   10                  15

Asp Ala Asp Asp Leu Gln Lys Arg Leu Ala
            20                  25
```

<210> SEQ ID NO 1037
<211> LENGTH: 19
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 1037

```
Pro Leu Val Glu Asp Met Gln Arg Gln Trp Ala Gly Leu Val Glu Lys
1               5                   10                  15

Val Gln Ala
```

<210> SEQ ID NO 1038
<211> LENGTH: 17
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 1038

```
Met Ser Thr Tyr Thr Gly Ile Phe Thr Asp Gln Val Leu Ser Val Leu
1               5                   10                  15

Lys
```

<210> SEQ ID NO 1039
<211> LENGTH: 22
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 1039

```
Leu Leu Ser Phe Met Gln Gly Tyr Met Lys His Ala Thr Lys Thr Ala
1               5                   10                  15

Lys Asp Ala Leu Ser Ser
            20
```

<210> SEQ ID NO 1040
<211> LENGTH: 17
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 1040

```
Lys Trp Ile Tyr His Leu Thr Glu Gly Ser Thr Asp Leu Arg Thr Glu
1               5                   10                  15

Gly
```

```
<210> SEQ ID NO 1041
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1041

Lys Phe Phe Tyr His Leu Thr Glu Gly Ser Thr Asp Leu Arg Thr Glu
1               5                   10                  15

Gly

<210> SEQ ID NO 1042
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1042

Lys Trp Leu Tyr His Leu Thr Glu Gly Ser Thr Asp Leu Arg Thr Glu
1               5                   10                  15

Gly

<210> SEQ ID NO 1043
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1043

Lys Trp Val Tyr His Leu Thr Glu Gly Ser Thr Asp Leu Arg Thr Glu
1               5                   10                  15

Gly

<210> SEQ ID NO 1044
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1044

Lys Tyr Ile Trp His Leu Thr Glu Gly Ser Thr Asp Leu Arg Thr Glu
1               5                   10                  15

Gly

<210> SEQ ID NO 1045
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1045

Lys Trp Ile Tyr His Phe Thr Glu Gly Ser Thr Asp Leu Arg Thr Glu
1               5                   10                  15

Gly
```

```
<210> SEQ ID NO 1046
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1046

Lys Trp Phe Tyr His Ile Thr Glu Gly Ser Thr Asp Leu Arg Thr Glu
1               5                   10                  15
Gly

<210> SEQ ID NO 1047
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1047

Lys Trp Leu Tyr His Val Thr Glu Gly Ser Thr Asp Leu Arg Thr Glu
1               5                   10                  15
Gly

<210> SEQ ID NO 1048
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1048

Lys Trp Val Tyr His Tyr Thr Glu Gly Ser Thr Asp Leu Arg Thr Glu
1               5                   10                  15
Gly

<210> SEQ ID NO 1049
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1049

Lys Tyr Ile Trp His Phe Thr Glu Gly Ser Thr Asp Leu Arg Thr Glu
1               5                   10                  15
Gly

<210> SEQ ID NO 1050
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1050

Lys Tyr Ile Trp His Ile Thr Glu Gly Ser Thr Asp Leu Arg Thr Glu
1               5                   10                  15
Gly
```

```
<210> SEQ ID NO 1051
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1051

Lys Tyr Ile Trp His Val Thr Glu Gly Ser Thr Asp Leu Arg Thr Glu
1               5                   10                  15

Gly

<210> SEQ ID NO 1052
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1052

Lys Tyr Ile Trp His Tyr Thr Glu Gly Ser Thr Asp Leu Arg Thr Glu
1               5                   10                  15

Gly

<210> SEQ ID NO 1053
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1053

Lys Phe Ile Trp His Leu Thr Glu Gly Ser Thr Asp Leu Arg Thr Glu
1               5                   10                  15

Gly

<210> SEQ ID NO 1054
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1054

Lys Leu Ile Trp His Leu Thr Glu Gly Ser Thr Asp Leu Arg Thr Glu
1               5                   10                  15

Gly

<210> SEQ ID NO 1055
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1055

Lys Ile Ile Trp His Leu Thr Glu Gly Ser Thr Asp Leu Arg Thr Glu
1               5                   10                  15

Gly
```

<210> SEQ ID NO 1056
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1056

Lys Tyr Ile Trp Phe Leu Thr Glu Gly Ser Thr Asp Leu Arg Thr Glu
1               5                   10                  15

Gly

<210> SEQ ID NO 1057
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1057

Lys Trp Ile Tyr Phe Leu Thr Glu Gly Ser Thr Asp Leu Arg Thr Glu
1               5                   10                  15

Gly

<210> SEQ ID NO 1058
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1058

Lys Trp Ile Tyr Leu Leu Thr Glu Gly Ser Thr Asp Leu Arg Thr Glu
1               5                   10                  15

Gly

<210> SEQ ID NO 1059
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1059

Lys Trp Ile Tyr His Phe Thr Glu Gly Ser Thr Asp Leu Arg Thr Glu
1               5                   10                  15

Gly

<210> SEQ ID NO 1060
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1060

Lys Trp Ile Tyr His Tyr Thr Glu Gly Ser Thr Asp Leu Arg Thr Glu
1               5                   10                  15

Gly

<210> SEQ ID NO 1061
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1061

Lys Trp Ile Tyr His Ile Thr Glu Gly Ser Thr Asp Leu Arg Thr Glu
1               5                   10                  15

Gly

<210> SEQ ID NO 1062
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1062

Lys Trp Ile Tyr His Leu Ser Glu Gly Ser Thr Asp Leu Arg Thr Glu
1               5                   10                  15

Gly

<210> SEQ ID NO 1063
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1063

Lys Trp Ile Tyr His Leu Thr Asp Gly Ser Thr Asp Leu Arg Thr Glu
1               5                   10                  15

Gly

<210> SEQ ID NO 1064
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1064

Lys Trp Ile Tyr His Leu Thr Glu Gly Thr Ser Asp Leu Arg Thr Glu
1               5                   10                  15

Gly

<210> SEQ ID NO 1065
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1065

Lys Trp Ile Tyr His Leu Thr Glu Gly Ser Thr Glu Leu Arg Thr Glu
1               5                   10                  15

Gly

```
<210> SEQ ID NO 1066
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1066

Lys Trp Ile Tyr His Leu Thr Glu Gly Ser Thr Asp Phe Arg Thr Glu
1               5                   10                  15

Gly

<210> SEQ ID NO 1067
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1067

Lys Trp Ile Tyr His Leu Thr Glu Gly Ser Thr Asp Tyr Arg Thr Glu
1               5                   10                  15

Gly

<210> SEQ ID NO 1068
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1068

Lys Trp Ile Tyr His Leu Thr Glu Gly Ser Thr Asp Ile Arg Thr Glu
1               5                   10                  15

Gly

<210> SEQ ID NO 1069
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1069

Lys Trp Ile Tyr His Leu Thr Glu Gly Ser Thr Asp Val Arg Thr Glu
1               5                   10                  15

Gly

<210> SEQ ID NO 1070
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1070

Lys Trp Ile Tyr His Leu Thr Glu Gly Ser Thr Asp Leu Lys Thr Glu
1               5                   10                  15

Gly
```

```
<210> SEQ ID NO 1071
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1071

Lys Trp Ile Tyr His Leu Thr Glu Gly Ser Thr Asp Leu Arg Ser Glu
1               5                   10                  15

Gly

<210> SEQ ID NO 1072
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1072

Lys Trp Ile Tyr His Leu Thr Glu Gly Ser Thr Asp Leu Arg Thr Asp
1               5                   10                  15

Gly

<210> SEQ ID NO 1073
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1073

Lys Trp Ile Tyr His Leu Thr Glu Gly Ser Thr Asp Ile Lys Thr Glu
1               5                   10                  15

Gly

<210> SEQ ID NO 1074
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1074

Lys Trp Ile Tyr His Leu Thr Glu Gly Ser Thr Asp Ile Arg Ser Glu
1               5                   10                  15

Gly

<210> SEQ ID NO 1075
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1075

Lys Trp Ile Tyr His Leu Thr Glu Gly Ser Thr Asp Ile Lys Ser Glu
1               5                   10                  15

Gly
```

<210> SEQ ID NO 1076
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1076

Lys Trp Ile Tyr His Leu Thr Glu Gly Ser Thr Asp Ile Lys Ser Asp
1               5                   10                  15

Gly

<210> SEQ ID NO 1077
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1077

Arg Trp Ile Tyr His Leu Thr Glu Gly Ser Thr Asp Leu Arg Thr Glu
1               5                   10                  15

Gly

<210> SEQ ID NO 1078
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1078

Arg Tyr Ile Trp His Leu Thr Glu Gly Ser Thr Asp Ile Arg Thr Glu
1               5                   10                  15

Gly

<210> SEQ ID NO 1079
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1079

Arg Trp Ile Tyr His Leu Thr Glu Gly Ser Thr Asp Ile Arg Thr Asp
1               5                   10                  15

Gly

<210> SEQ ID NO 1080
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1080

Arg Trp Ile Phe His Leu Thr Glu Gly Ser Thr Asp Ile Arg Thr Glu
1               5                   10                  15

Gly

<210> SEQ ID NO 1081
<211> LENGTH: 17
<212> TYPE: PRT
<213> ORGANISM: Artificial Sequence
<220> FEATURE:
<223> OTHER INFORMATION: Description of Artificial Sequence: note =
    Synthetic Construct

<400> SEQUENCE: 1081

Arg Trp Ile Tyr His Leu Thr Glu Gly Ser Thr Asp Leu Lys Thr Glu
1               5                   10                  15

Gly

<210> SEQ ID NO 1082
<211> LENGTH: 17
<212> TYPE: PRT
<213> ORGANISM: Artificial Sequence
<220> FEATURE:
<223> OTHER INFORMATION: Description of Artificial Sequence: note =
    Synthetic Construct

<400> SEQUENCE: 1082

Arg Trp Ile Tyr His Leu Thr Asp Gly Ser Thr Asp Ile Arg Thr Glu
1               5                   10                  15

Gly

<210> SEQ ID NO 1083
<211> LENGTH: 17
<212> TYPE: PRT
<213> ORGANISM: Artificial Sequence
<220> FEATURE:
<223> OTHER INFORMATION: Description of Artificial Sequence: note =
    Synthetic Construct

<400> SEQUENCE: 1083

Arg Trp Ile Tyr His Leu Thr Asp Gly Ser Thr Asp Leu Arg Thr Glu
1               5                   10                  15

Gly

<210> SEQ ID NO 1084
<211> LENGTH: 17
<212> TYPE: PRT
<213> ORGANISM: Artificial Sequence
<220> FEATURE:
<223> OTHER INFORMATION: Description of Artificial Sequence: note =
    Synthetic Construct

<400> SEQUENCE: 1084

Arg Trp Ile Tyr Phe Leu Thr Glu Gly Ser Thr Asp Ile Arg Thr Glu
1               5                   10                  15

Gly

<210> SEQ ID NO 1085
<211> LENGTH: 17
<212> TYPE: PRT
<213> ORGANISM: Artificial Sequence
<220> FEATURE:
<223> OTHER INFORMATION: Description of Artificial Sequence: note =
    Synthetic Construct

<400> SEQUENCE: 1085

Arg Trp Ile Tyr Phe Leu Thr Glu Gly Ser Thr Asp Leu Arg Thr Glu
1               5                   10                  15

Gly

```
<210> SEQ ID NO 1086
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1086

Lys Trp Phe Tyr His Leu Thr Glu Gly Ser Thr Asp Phe Arg Thr Glu
1               5                   10                  15

Gly

<210> SEQ ID NO 1087
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1087

Arg Trp Phe Tyr His Leu Thr Glu Gly Ser Thr Asp Leu Arg Thr Glu
1               5                   10                  15

Gly

<210> SEQ ID NO 1088
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1088

Lys Trp Ile Phe His Leu Thr Glu Gly Ser Thr Asp Ile Arg Thr Asp
1               5                   10                  15

Gly

<210> SEQ ID NO 1089
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1089

Arg Trp Ile Tyr His Leu Thr Glu Gly Ser Thr Asp Ile Arg Thr Asp
1               5                   10                  15

Gly

<210> SEQ ID NO 1090
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1090

Arg Trp Ile Tyr His Leu Thr Glu Gly Ser Thr Asp Leu Arg Thr Asp
1               5                   10                  15

Gly
```

```
<210> SEQ ID NO 1091
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1091

Lys Trp Ile Tyr His Leu Thr Glu Gly Ser Thr Asp Ile Lys Thr Glu
1               5                   10                  15

Gly

<210> SEQ ID NO 1092
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1092

Lys Trp Ile Tyr His Leu Thr Glu Gly Ser Thr Asp Ile Lys Thr Asp
1               5                   10                  15

Gly

<210> SEQ ID NO 1093
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1093

Lys Trp Ile Tyr His Leu Thr Glu Gly Ser Thr Asp Phe Lys Thr Glu
1               5                   10                  15

Gly

<210> SEQ ID NO 1094
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1094

Lys Trp Ile Tyr His Leu Thr Glu Gly Ser Thr Asp Tyr Lys Thr Glu
1               5                   10                  15

Gly

<210> SEQ ID NO 1095
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1095

Lys Trp Ile Tyr His Leu Thr Glu Gly Ser Thr Asp Ile Arg Thr Glu
1               5                   10                  15

Gly
```

<210> SEQ ID NO 1096
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1096

Lys Trp Phe Tyr His Phe Thr Glu Gly Ser Thr Asp Leu Arg Thr Glu
1               5                   10                  15

Gly

<210> SEQ ID NO 1097
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1097

Arg Trp Phe Tyr His Phe Thr Glu Gly Ser Thr Asp Leu Arg Thr Glu
1               5                   10                  15

Gly

<210> SEQ ID NO 1098
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1098

Lys Trp Phe Tyr His Phe Thr Glu Gly Ser Thr Asp Phe Arg Thr Glu
1               5                   10                  15

Gly

<210> SEQ ID NO 1099
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1099

Lys Trp Phe Tyr His Phe Thr Asp Gly Ser Thr Asp Ile Arg Thr Glu
1               5                   10                  15

Gly

<210> SEQ ID NO 1100
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1100

Arg Trp Phe Tyr His Phe Thr Glu Gly Ser Thr Asp Leu Arg Thr Glu
1               5                   10                  15

Gly

<210> SEQ ID NO 1101
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1101

Arg Trp Phe Tyr His Phe Thr Glu Gly Ser Thr Asp Phe Arg Thr Glu
1               5                   10                  15

Gly

<210> SEQ ID NO 1102
<211> LENGTH: 17
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1102

Arg Trp Phe Tyr His Phe Thr Glu Gly Ser Thr Asp Phe Arg Thr Asp
1               5                   10                  15

Gly

<210> SEQ ID NO 1103
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1103

Glu Lys Cys Val Glu Glu Phe Lys Ser Leu Thr Ser Cys Leu Asp Ser
1               5                   10                  15

Lys Ala Phe

<210> SEQ ID NO 1104
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1104

Asp Lys Cys Val Glu Glu Phe Lys Ser Leu Thr Ser Cys Leu Asp Ser
1               5                   10                  15

Lys Ala Phe

<210> SEQ ID NO 1105
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1105

Glu Lys Cys Val Asp Glu Phe Lys Ser Leu Thr Ser Cys Leu Asp Ser
1               5                   10                  15

Lys Ala Phe

```
<210> SEQ ID NO 1106
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1106

Glu Lys Cys Val Glu Asp Phe Lys Ser Leu Thr Ser Cys Leu Asp Ser
1               5                   10                  15

Lys Ala Phe

<210> SEQ ID NO 1107
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1107

Glu Arg Cys Val Glu Glu Phe Lys Ser Leu Thr Ser Cys Leu Asp Ser
1               5                   10                  15

Lys Ala Phe

<210> SEQ ID NO 1108
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1108

Asp Lys Cys Val Asp Asp Phe Lys Ser Leu Thr Ser Cys Leu Asp Ser
1               5                   10                  15

Lys Ala Phe

<210> SEQ ID NO 1109
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1109

Asp Arg Cys Val Glu Glu Phe Lys Ser Leu Thr Ser Cys Leu Asp Ser
1               5                   10                  15

Lys Ala Phe

<210> SEQ ID NO 1110
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1110

Glu Arg Cys Val Asp Asp Phe Lys Ser Leu Thr Ser Cys Leu Asp Ser
1               5                   10                  15

Lys Ala Phe
```

```
<210> SEQ ID NO 1111
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1111

Glu Lys Cys Val Glu Glu Phe Lys Ser Phe Thr Ser Cys Leu Asp Ser
1               5                   10                  15

Lys Ala Phe

<210> SEQ ID NO 1112
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1112

Glu Lys Cys Val Glu Glu Phe Lys Ser Ile Thr Ser Cys Leu Asp Ser
1               5                   10                  15

Lys Ala Phe

<210> SEQ ID NO 1113
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1113

Glu Lys Cys Val Glu Glu Phe Lys Ser Val Thr Ser Cys Leu Asp Ser
1               5                   10                  15

Lys Ala Phe

<210> SEQ ID NO 1114
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1114

Glu Arg Cys Val Glu Glu Phe Lys Ser Tyr Thr Ser Cys Leu Asp Ser
1               5                   10                  15

Lys Ala Phe

<210> SEQ ID NO 1115
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1115

Glu Arg Cys Val Glu Glu Phe Lys Ser Phe Thr Ser Cys Leu Asp Ser
1               5                   10                  15

Lys Ala Phe
```

<210> SEQ ID NO 1116
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1116

Glu Arg Cys Val Glu Glu Phe Lys Ser Ile Thr Ser Cys Leu Asp Ser
1               5                   10                  15

Lys Ala Phe

<210> SEQ ID NO 1117
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1117

Glu Arg Cys Val Glu Glu Phe Lys Ser Val Thr Ser Cys Leu Asp Ser
1               5                   10                  15

Lys Ala Phe

<210> SEQ ID NO 1118
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1118

Glu Arg Cys Val Glu Glu Phe Lys Ser Tyr Thr Ser Cys Leu Asp Ser
1               5                   10                  15

Lys Ala Phe

<210> SEQ ID NO 1119
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1119

Glu Lys Cys Val Glu Glu Phe Lys Ser Phe Thr Thr Cys Leu Asp Ser
1               5                   10                  15

Lys Ala Phe

<210> SEQ ID NO 1120
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1120

Glu Lys Cys Val Glu Glu Phe Lys Ser Ile Ser Ser Cys Leu Asp Ser
1               5                   10                  15

Lys Ala Phe

```
<210> SEQ ID NO 1121
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1121

Glu Lys Cys Val Glu Glu Phe Lys Ser Val Ser Thr Cys Leu Asp Ser
1               5                   10                  15

Lys Ala Phe

<210> SEQ ID NO 1122
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1122

Glu Lys Cys Val Glu Glu Phe Lys Ser Tyr Thr Ser Cys Leu Asp Ser
1               5                   10                  15

Lys Ala Phe

<210> SEQ ID NO 1123
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1123

Glu Lys Cys Val Glu Glu Phe Lys Ser Phe Thr Thr Cys Leu Asp Ser
1               5                   10                  15

Lys Ala Phe

<210> SEQ ID NO 1124
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1124

Glu Lys Cys Val Glu Glu Phe Lys Ser Phe Ser Ser Cys Leu Asp Ser
1               5                   10                  15

Lys Ala Phe

<210> SEQ ID NO 1125
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1125

Glu Lys Cys Val Glu Glu Phe Lys Ser Phe Thr Ser Cys Leu Asp Ser
1               5                   10                  15

Lys Ala Phe
```

<210> SEQ ID NO 1126
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1126

Glu Lys Cys Val Glu Glu Phe Lys Ser Phe Thr Ser Cys Leu Asp Ser
1               5                   10                  15

Lys Ala Phe

<210> SEQ ID NO 1127
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1127

Glu Lys Cys Val Glu Glu Phe Lys Ser Phe Thr Ser Cys Leu Asp Ser
1               5                   10                  15

Lys Ala Phe

<210> SEQ ID NO 1128
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1128

Glu Lys Cys Val Glu Glu Phe Lys Ser Phe Thr Ser Cys Phe Asp Ser
1               5                   10                  15

Lys Ala Phe

<210> SEQ ID NO 1129
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1129

Glu Lys Cys Val Glu Glu Phe Lys Ser Phe Thr Ser Cys Phe Glu Ser
1               5                   10                  15

Lys Ala Phe

<210> SEQ ID NO 1130
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1130

Glu Lys Cys Val Glu Glu Phe Lys Ser Phe Thr Ser Cys Leu Glu Ser
1               5                   10                  15

Lys Ala Phe

```
<210> SEQ ID NO 1131
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1131

Glu Lys Cys Val Glu Glu Phe Lys Ser Phe Thr Ser Cys Ile Asp Ser
1               5                   10                  15

Lys Ala Phe

<210> SEQ ID NO 1132
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1132

Glu Lys Cys Val Glu Glu Leu Lys Ser Phe Thr Ser Cys Phe Asp Ser
1               5                   10                  15

Lys Ala Phe

<210> SEQ ID NO 1133
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1133

Asp Lys Cys Val Glu Glu Phe Lys Ser Phe Thr Ser Cys Phe Asp Ser
1               5                   10                  15

Lys Ala Phe

<210> SEQ ID NO 1134
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1134

Asp Lys Cys Val Glu Glu Phe Lys Ser Phe Thr Ser Cys Phe Glu Ser
1               5                   10                  15

Lys Ala Phe

<210> SEQ ID NO 1135
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1135

Glu Arg Cys Val Glu Glu Phe Lys Ser Phe Thr Ser Cys Phe Asp Ser
1               5                   10                  15

Lys Ala Phe
```

```
<210> SEQ ID NO 1136
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1136

Glu Lys Cys Phe Glu Glu Phe Lys Ser Phe Thr Ser Cys Phe Asp Ser
1               5                   10                  15

Lys Ala Phe

<210> SEQ ID NO 1137
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1137

Glu Lys Cys Phe Glu Glu Phe Lys Ser Phe Thr Ser Cys Phe Glu Ser
1               5                   10                  15

Lys Ala Phe

<210> SEQ ID NO 1138
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1138

Glu Lys Cys Val Glu Glu Phe Lys Ser Phe Ser Ser Cys Phe Glu Ser
1               5                   10                  15

Lys Ala Phe

<210> SEQ ID NO 1139
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1139

Glu Lys Cys Val Glu Glu Phe Lys Ser Phe Gln Ser Cys Phe Asp Ser
1               5                   10                  15

Lys Ala Phe

<210> SEQ ID NO 1140
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1140

Glu Lys Cys Phe Glu Glu Phe Lys Ser Phe Gln Ser Cys Phe Asp Ser
1               5                   10                  15

Lys Ala Phe
```

```
<210> SEQ ID NO 1141
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1141

Glu Lys Cys Val Glu Glu Phe Lys Gln Phe Thr Ser Cys Phe Asp Ser
1               5                   10                  15

Lys Ala Phe

<210> SEQ ID NO 1142
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1142

Glu Lys Cys Val Glu Glu Phe Lys Gln Leu Thr Ser Cys Leu Asp Ser
1               5                   10                  15

Lys Ala Phe

<210> SEQ ID NO 1143
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1143

Glu Lys Cys Phe Glu Glu Phe Lys Ser Phe Gln Ser Cys Leu Asp Ser
1               5                   10                  15

Lys Ala Phe

<210> SEQ ID NO 1144
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1144

Glu Lys Cys Val Glu Glu Phe Lys Gln Phe Thr Ser Cys Phe Asp Ser
1               5                   10                  15

Lys Ala Phe

<210> SEQ ID NO 1145
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1145

Glu Lys Cys Val Glu Glu Phe Lys Ser Phe Thr Ser Cys Phe Glu Ser
1               5                   10                  15

Lys Ala Phe
```

```
<210> SEQ ID NO 1146
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1146

Glu Arg Cys Phe Glu Glu Phe Lys Ser Phe Thr Ser Cys Phe Asp Ser
1               5                   10                  15

Lys Ala Phe

<210> SEQ ID NO 1147
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1147

Asp Lys Cys Phe Glu Glu Phe Lys Ser Phe Thr Ser Cys Phe Asp Ser
1               5                   10                  15

Lys Ala Phe

<210> SEQ ID NO 1148
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1148

Glu Arg Cys Val Glu Glu Phe Lys Ser Leu Thr Ser Cys Leu Glu Ser
1               5                   10                  15

Lys Ala Phe

<210> SEQ ID NO 1149
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1149

Glu Lys Cys Val Glu Glu Phe Lys Ser Leu Thr Ser Cys Leu Asp Ser
1               5                   10                  15

Lys Phe Phe

<210> SEQ ID NO 1150
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1150

Glu Lys Cys Phe Glu Glu Phe Lys Ser Phe Thr Ser Cys Phe Asp Ser
1               5                   10                  15

Lys Phe Phe
```

<210> SEQ ID NO 1151
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1151

Asp Lys Cys Phe Glu Glu Phe Lys Ser Phe Thr Ser Cys Leu Asp Ser
1               5                   10                  15

Lys Phe Phe

<210> SEQ ID NO 1152
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1152

Asp Lys Cys Phe Glu Glu Phe Lys Ser Phe Thr Ser Cys Leu Glu Ser
1               5                   10                  15

Lys Phe Phe

<210> SEQ ID NO 1153
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1153

Asp Lys Cys Phe Glu Glu Leu Lys Ser Phe Thr Ser Cys Leu Asp Ser
1               5                   10                  15

Lys Phe Phe

<210> SEQ ID NO 1154
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1154

Glu Arg Cys Phe Glu Glu Phe Lys Ser Phe Thr Ser Cys Leu Asp Ser
1               5                   10                  15

Lys Phe Phe

<210> SEQ ID NO 1155
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1155

Glu Lys Ala Val Glu Glu Phe Lys Ser Phe Thr Ser Cys Leu Asp Ser
1               5                   10                  15

Lys Ala Phe

```
<210> SEQ ID NO 1156
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1156

Asp Lys Ala Val Glu Glu Phe Lys Ser Phe Thr Ser Cys Leu Asp Ser
1               5                   10                  15

Lys Phe Phe

<210> SEQ ID NO 1157
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1157

Glu Lys Ala Val Glu Glu Phe Lys Ser Phe Thr Ser Ala Leu Asp Ser
1               5                   10                  15

Lys Ala Phe

<210> SEQ ID NO 1158
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1158

Asp Lys Ala Val Glu Glu Phe Lys Ser Phe Thr Ser Ala Leu Asp Ser
1               5                   10                  15

Lys Ala Phe

<210> SEQ ID NO 1159
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1159

Asp Arg Ala Phe Glu Glu Phe Lys Ser Phe Thr Ser Cys Leu Asp Ser
1               5                   10                  15

Lys Phe Phe

<210> SEQ ID NO 1160
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1160

Asp Arg Ala Phe Glu Glu Phe Lys Ser Phe Thr Ser Ala Leu Asp Ser
1               5                   10                  15

Lys Phe Phe
```

<210> SEQ ID NO 1161
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1161

Asp Lys Cys Phe Glu Glu Phe Lys Ser Phe Thr Ser Cys Phe Glu Ser
1               5                   10                  15

Lys Phe Phe

<210> SEQ ID NO 1162
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1162

Glu Lys Cys Tyr Glu Glu Phe Lys Ser Phe Thr Ser Cys Leu Asp Ser
1               5                   10                  15

Lys Phe Phe

<210> SEQ ID NO 1163
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1163

Asp Lys Cys Trp Glu Glu Phe Lys Ser Phe Thr Ser Cys Leu Asp Ser
1               5                   10                  15

Lys Phe Phe

<210> SEQ ID NO 1164
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1164

Glu Lys Cys Phe Glu Glu Phe Lys Ser Tyr Thr Ser Cys Leu Asp Ser
1               5                   10                  15

Lys Phe Phe

<210> SEQ ID NO 1165
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1165

Glu Lys Cys Phe Glu Glu Phe Lys Ser Trp Thr Ser Cys Leu Asp Ser
1               5                   10                  15

Lys Phe Phe

```
<210> SEQ ID NO 1166
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1166

Glu Lys Cys Val Glu Glu Phe Lys Ser Trp Thr Ser Cys Leu Asp Ser
1               5                   10                  15

Lys Ala Phe

<210> SEQ ID NO 1167
<211> LENGTH: 19
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1167

Asp Lys Cys Phe Glu Glu Phe Lys Ser Trp Thr Ser Cys Leu Asp Ser
1               5                   10                  15

Lys Ala Phe

<210> SEQ ID NO 1168
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1168

Asp Val Trp Lys Ala Ala Tyr Asp Lys Phe Ala Glu Lys Phe Lys Glu
1               5                   10                  15

Phe Phe

<210> SEQ ID NO 1169
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1169

Asp Val Trp Lys Ala Phe Tyr Asp Lys Phe Ala Glu Lys Phe Lys Glu
1               5                   10                  15

Ala Phe

<210> SEQ ID NO 1170
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1170

Asp Phe Trp Lys Ala Phe Tyr Asp Lys Val Ala Glu Lys Phe Lys Glu
1               5                   10                  15

Ala Phe
```

```
<210> SEQ ID NO 1171
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1171

Xaa Arg Phe Lys
1

<210> SEQ ID NO 1172
<211> LENGTH: 7
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1172

Leu Ala Glu Tyr His Ala Lys
1               5

<210> SEQ ID NO 1173
<211> LENGTH: 7
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1173

Leu Ala Glu Tyr His Ala Lys
1               5

<210> SEQ ID NO 1174
<211> LENGTH: 8
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1174

Pro Gly Gly Gly Gly Ser Ser Ser
1               5

<210> SEQ ID NO 1175
<211> LENGTH: 45
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1175

Leu Leu Glu Gln Leu Asn Glu Gln Phe Asn Trp Val Ser Arg Leu Ala
1               5                   10                  15

Asn Leu Thr Gln Gly Glu Pro Leu Leu Glu Gln Leu Asn Glu Gln Phe
            20                  25                  30

Asn Trp Val Ser Arg Leu Ala Asn Leu Thr Gln Gly Glu
        35                  40                  45
```

```
<210> SEQ ID NO 1176
<211> LENGTH: 41
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1176

Leu Leu Glu Gln Leu Asn Glu Gln Phe Asn Trp Val Ser Arg Leu Ala
1               5                   10                  15

Asn Leu Thr Gln Gly Glu Pro Asp Trp Phe Lys Ala Phe Tyr Asp Lys
            20                  25                  30

Val Ala Glu Lys Phe Lys Glu Ala Phe
        35                  40

<210> SEQ ID NO 1177
<211> LENGTH: 22
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1177

Leu Leu Glu Gln Leu Asn Glu Gln Phe Asn Trp Val Ser Arg Leu Ala
1               5                   10                  15

Asn Leu Thr Gln Gly Glu
            20

<210> SEQ ID NO 1178
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1178

Lys Phe Lys Glu Ala Phe
1               5

<210> SEQ ID NO 1179
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1179

Tyr Asp Lys Val Ala Glu
1               5

<210> SEQ ID NO 1180
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1180

Asp Trp Phe Lys Ala Phe
1               5
```

```
<210> SEQ ID NO 1181
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1181

Lys Phe Lys Glu Ala Phe
1               5

<210> SEQ ID NO 1182
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1182

Lys Phe Lys Glu Ala Phe
1               5

<210> SEQ ID NO 1183
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1183

Tyr Asp Lys Val Ala Glu Lys Phe Lys Glu Phe
1               5                   10

<210> SEQ ID NO 1184
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1184

Asp Trp Phe Lys Ala Phe Tyr Asp Lys Val Ala Glu Lys Phe Lys Glu
1               5                   10                  15

Ala Phe

<210> SEQ ID NO 1185
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1185

Asp Trp Phe Lys Ala Phe
1               5

<210> SEQ ID NO 1186
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 1186

Tyr Asp Lys Val Ala Glu
1               5

<210> SEQ ID NO 1187
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1187

Lys Phe Lys Glu Ala Phe
1               5

<210> SEQ ID NO 1188
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1188

Asp Trp Phe Lys Ala Phe
1               5

<210> SEQ ID NO 1189
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1189

Tyr Asp Lys Val Ala Glu
1               5

<210> SEQ ID NO 1190
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1190

Lys Phe Lys Glu Ala Phe
1               5

<210> SEQ ID NO 1191
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1191

Asp Trp Phe Lys Ala Phe Tyr Asp Lys Val Ala Glu Lys Phe Lys Glu
1               5                   10                  15

Ala Phe
```

```
<210> SEQ ID NO 1192
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1192

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
            35

<210> SEQ ID NO 1193
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1193

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
            35

<210> SEQ ID NO 1194
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1194

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
                20                  25                  30

Leu Lys Glu Ala Phe
            35

<210> SEQ ID NO 1195
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1195

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
                20                  25                  30

Leu Lys Glu Ala Phe
            35
```

```
<210> SEQ ID NO 1196
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1196

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
        35

<210> SEQ ID NO 1197
<211> LENGTH: 37
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1197

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
        35

<210> SEQ ID NO 1198
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1198

Asp Trp Leu Lys Ala Phe Tyr Asp Lys Val Phe Glu Lys Phe Lys Glu
1               5                   10                  15

Phe Phe

<210> SEQ ID NO 1199
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1199

Glu Trp Leu Lys Ala Phe Tyr Glu Lys Val Phe Glu Lys Phe Lys Glu
1               5                   10                  15

Phe Phe

<210> SEQ ID NO 1200
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct
```

```
<400> SEQUENCE: 1200

Ala Phe Tyr Asp Lys Val Phe Glu Lys Phe Lys Glu Phe Phe
1               5                   10

<210> SEQ ID NO 1201
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1201

Ala Phe Tyr Glu Lys Val Phe Glu Lys Phe Lys Glu Phe Phe
1               5                   10

<210> SEQ ID NO 1202
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1202

Asp Trp Leu Lys Ala Phe Tyr Asp Lys Val Phe Glu Lys Phe
1               5                   10

<210> SEQ ID NO 1203
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1203

Glu Trp Leu Lys Ala Phe Tyr Glu Lys Val Phe Glu Lys Phe
1               5                   10

<210> SEQ ID NO 1204
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1204

Leu Lys Ala Phe Tyr Asp Lys Val Phe Glu Lys Phe Lys Glu
1               5                   10

<210> SEQ ID NO 1205
<211> LENGTH: 14
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 1205

Leu Lys Ala Phe Tyr Glu Lys Val Phe Glu Lys Phe Lys Glu
1               5                   10

<210> SEQ ID NO 1206
<211> LENGTH: 4
<212> TYPE: PRT
<213> ORGANISM: Artificial Sequence
```

```
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1206

Xaa Arg Glu Leu
1

<210> SEQ ID NO 1207
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1207

Xaa Arg Phe Lys
1

<210> SEQ ID NO 1208
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1208

Xaa Arg Glu Lys
1
```